(12) United States Patent
Burt et al.

(10) Patent No.: US 9,561,278 B2
(45) Date of Patent: *Feb. 7, 2017

(54) DERIVATIZED HYPERBRANCHED POLYGLYCEROLS

(71) Applicants: THE UNIVERSITY OF BRITISH COLUMBIA, Vancouver (CA); Centre for Drug Research and Development, Vancouver (CA)

(72) Inventors: Helen M. Burt, Vancouver (CA); Donald E. Brooks, Vancouver (CA); Jayachandran N. Kizhakkedathu, New Westminster (CA); Richard Liggins, Coquitlam (CA); Dechi Guan, Vancouver (CA); Lu Ye, Richmond (CA); Clement Mugabe, Vancouver (CA); Alan So, Vancouver (CA); Martin E. Gleave, Vancouver (CA); John K. Jackson, Vancouver (CA); Rajesh Kumar Kainthan, Tappan, NY (US)

(73) Assignees: The University of British Columbia, Vancouver (CA); Centre for Drug Research and Development, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/868,148

(22) Filed: Sep. 28, 2015

(65) Prior Publication Data
US 2016/0114040 A1  Apr. 28, 2016

Related U.S. Application Data

(63) Continuation of application No. 13/581,463, filed as application No. PCT/CA2011/000225 on Mar. 1, 2011, now Pat. No. 9,186,410.

(60) Provisional application No. 61/309,304, filed on Mar. 1, 2010.

(51) Int. Cl.

| | | |
|---|---|---|
| A61K 47/10 | (2006.01) | |
| A61K 31/337 | (2006.01) | |
| A61K 31/407 | (2006.01) | |
| A61K 9/51 | (2006.01) | |
| A61K 47/34 | (2006.01) | |
| C08G 65/34 | (2006.01) | |
| C08G 65/48 | (2006.01) | |
| C08G 83/00 | (2006.01) | |
| C08G 65/333 | (2006.01) | |
| A61K 33/24 | (2006.01) | |
| A61K 9/00 | (2006.01) | |

(52) U.S. Cl.
CPC ............ *A61K 47/10* (2013.01); *A61K 9/5146* (2013.01); *A61K 31/337* (2013.01); *A61K 31/407* (2013.01); *A61K 33/24* (2013.01); *A61K 47/34* (2013.01); *C08G 65/33306* (2013.01); *C08G 65/33337* (2013.01); *C08G 65/34* (2013.01); *C08G 65/48* (2013.01); *C08G 83/005* (2013.01); *C08G 83/006* (2013.01); *A61K 9/006* (2013.01); *A61K 9/0034* (2013.01); *C08G 2650/54* (2013.01)

(58) Field of Classification Search
IPC ................. A61K 31/337,47/10, 33/24, 31/407
See application file for complete search history.

(56) References Cited

U.S. PATENT DOCUMENTS

| | | | |
|---|---|---|---|
| 4,814,470 | A | 3/1989 | Colin et al. |
| 5,112,876 | A | 5/1992 | Tairaka et al. |
| 5,407,528 | A | 4/1995 | McGrath et al. |
| 5,688,977 | A | 11/1997 | Sisti et al. |
| 5,830,948 | A | 11/1998 | Frechet et al. |
| 6,039,967 | A | 3/2000 | Ottoboni et al. |
| 6,207,180 | B1 | 3/2001 | Ottoboni et al. |

(Continued)

FOREIGN PATENT DOCUMENTS

| | | |
|---|---|---|
| JP | 2007503514 | 2/2007 |
| WO | 0077070 | 12/2000 |

(Continued)

OTHER PUBLICATIONS

Go et al. Oncolink—Abramson Cancer of University of Pennsylvania (2001), 1-3.*
Knischaka & Lutz (2000) "Funtional Poly(ethylene oxide) Multiarm Star Polymers: Core-First Synthesis Using Hyperbranched Polyglycerol Initiators" Macromolecules, 33:315-320.
Ofek et al. (2010) "In Vivo Delivery of Smal Interfering RNA to Tumors and Their Vasculature by Novel Dendritic Nanocarriers" FASEB J 2415(9):3122-3231.

(Continued)

*Primary Examiner* — Shirley V Gembeh
(74) *Attorney, Agent, or Firm* — Rudy J. Ng; Carol L. Francis; Bozicevic, Field & Francis LLP

(57) ABSTRACT

Herein are provided derivatized hyperbranched polyglycerols ("dHPGs"). The dHPG comprises a core comprising a hyperbranched polyglycerol derivatized with $C_1C_{20}$ alkyl chains and a shell comprising at least one hydrophilic substituent bound to hydroxyl groups of the core, wherein the hyperbranched polyglycerol comprises from about 1 to about 200 moles of the at least one hydrophilic substituent. The dHPGs are for use as agents for the delivery of a drug or other biologically active moiety to the urinary tract, the digestive tract, the airways, the vaginal cavity and cervix and the peritoneal cavity to treat indications such as cancer, which may be useful in the treatment of or the manufacture of a medicament, in the preparation, of a pharmaceutical composition for the treatment of cancer, as a pre-treatment or co-treatment to improve drug uptake in a tissue. Furthermore, there are provided methods of making dHPGs.

38 Claims, 50 Drawing Sheets

(56) References Cited

U.S. PATENT DOCUMENTS

| | | | |
|---|---|---|---|
| 6,469,218 | B1 | 10/2002 | Rexin et al. |
| 6,524,608 | B2 | 2/2003 | Ottoboni et al. |
| 6,730,334 | B2 | 5/2004 | Zhao |
| 6,765,082 | B2 | 7/2004 | Sunder et al. |
| 6,822,068 | B2 | 11/2004 | Sunder et al. |
| 6,838,528 | B2 | 1/2005 | Zhao |
| 6,862,167 | B1 | 3/2005 | Banno et al. |
| 6,894,071 | B2 | 5/2005 | Nuijen et al. |
| 6,897,266 | B2 | 5/2005 | Kenig-Dodiuk |
| 6,949,335 | B2 | 9/2005 | Fahy et al. |
| 7,063,860 | B2 | 6/2006 | Chancellor et al. |
| 7,265,186 | B2 | 9/2007 | Zhao |
| 7,320,963 | B2 | 1/2008 | Esuvaranathan et al. |
| 7,393,841 | B2 | 7/2008 | Sommermeyer |
| 7,396,861 | B2 | 7/2008 | Loccufier et al. |
| 7,550,255 | B2 | 6/2009 | Fahy et al. |
| 7,550,446 | B2 | 6/2009 | Henning |
| 7,709,457 | B2 | 5/2010 | Esuvaranathan et al. |
| 7,875,698 | B2 | 1/2011 | Vanmaele et al. |
| 7,977,369 | B2 | 7/2011 | Nuijen et al. |
| 8,354,549 | B2 | 1/2013 | Zhang |
| 8,519,189 | B2 | 8/2013 | Kizhakkedathu et al. |
| 8,637,008 | B2 | 1/2014 | Kizhakkedathu et al. |
| 9,186,410 | B2 | 11/2015 | Burt et al. |
| 2005/0042293 | A1 | 2/2005 | Jackson et al. |
| 2006/0127420 | A1 | 6/2006 | Chung et al. |
| 2008/0108693 | A1 | 5/2008 | Liao et al. |
| 2008/0292579 | A1 | 11/2008 | Brooks et al. |
| 2009/0105351 | A1 | 4/2009 | Jackson et al. |
| 2010/0324150 | A1 | 12/2010 | Allard et al. |
| 2011/0060036 | A1 | 3/2011 | Nie et al. |
| 2013/0122112 | A1 | 5/2013 | Burt et al. |
| 2014/0127312 | A1 | 5/2014 | Kizhakkedathu et al. |

FOREIGN PATENT DOCUMENTS

| | | |
|---|---|---|
| WO | 2005028539 | 3/2005 |
| WO | 2005037911 | 4/2005 |
| WO | 2005079856 | 9/2005 |
| WO | 2006130978 | 12/2006 |
| WO | 2008066902 | 6/2008 |
| WO | 2008074154 | 6/2008 |
| WO | 2008123751 | 10/2008 |
| WO | 2009055935 | 7/2009 |
| WO | 2009141170 | 11/2009 |
| WO | 2012031245 | 5/2012 |
| WO | 2012162789 | 12/2012 |
| WO | 2013159188 | 10/2013 |

OTHER PUBLICATIONS

Tziveleka et al. (2008) "Synthesis and Evaluation of Functional Hyperbranched Polyether Polyols as Prospected Gene Carriers" Int J Pharm 356(1-2):314-324.
Brooks & Keevil (1997) "A simple artificial urine for the growth of urinary pathogens" Lett. Appl. Microbiol. 24(3):203-206.
Dalbagni (2007) "The management of superficial bladder cancer" Nat. Clin. Pract. Urol. 4(5):254-260.
Dordunoo & Burt (1996) "Solubility and Stability of Taxol: Effects of Buffers and Cyclodextrins" Int. J. Pharm. 133(1-2):191-201.
Du et al. (2007) "Synthesis and evaluation of water-soluble docetaxel prodrugs-docetaxel esters of malic acid" Bioorg. Med. Chem. 15(18):6323-6330.
Fischer et al. (2010) "Hyperbranched Polyamines for Transfection" Top Curr Chem 296: 95-129.
Gao & Yan (2004) "Hyperbranched Polymers: From Synthesis to Applications" Prog. Polym Sci. 29:183-275.
Grabnar et al. (2003) "Influence of chitosan and polycarbophil on permeation of a model hydrophilic drug into the urinary bladder wall" Int J Pharm 256(1-2):167-173.
Haag et al. (2000) "An Approach to Core-Shell-Type Architectures in Hyperbranched Polyglycerols by Selective Chemical Differentiation" Macromolecules 33(22):8158-8166.

Haag et al. (2002) "Dendritic aliphatic polyethers as high-loading soluble supports for carbonyl compounds and parallel membrane separation techniques" J. Comb. Chem. 4(2):112-119.
Hadaschik et al. (2007) "A validated mouse model for orthotopic bladder cancer using transurethral tumour inoculation and bioluminescence imaging" BJU Int. 100(6):1377-1384.
Hadaschik et al. (2008) "Intravesical chemotherapy of high-grade bladder cancer with HTI-286, a synthetic analogue of the marine sponge product hemiasterlin" Clin Cancer Res. 14(5):1510-1518.
Hadaschik et al. (2008) "Oncolytic vesicular stomatitis viruses are potent agents for intravesical treatment of high-risk bladder cancer" Cancer Res. 68(12):4506-4510.
Hadaschik et al. (2008) "Paclitaxel and cisplatin as intravesical agents against non-muscle-invasive bladder cancer" BJU Int. 101(11):1347-1355.
Haxton & Burt (2008) "Hyperbranched polymers for controlled release of cisplatin" Dalton Trans.(43):5872-5875. Epub Sep. 25, 2008.
Henni et al. (2007) "Enhancement of the solubility and efficacy of poorly water-soluble drugs by hydrophobically-modified polysaccharide derivatives" Pharm Res 24(12):2317-2326.
Huang et al. (2003) "Involvement of endocytic organelles in the subcellular trafficking and localization of riboflavin" J. Pharmacol. Exp. Ther. 306(2):681-687.
Iwase et al. (2004) "Cremophor EL Augments the Cytotoxicity of Hydrogen Peroxide in Lymphocytes Dissociated from Rat Thymus Glands" Toxicol Lett, 154(1-2) 143-148.
Jackson et al. (2004) "Characterization of perivascular poly(lactic-co-glycolic acid) films containing paclitaxel" Int. J. Pharma. 283(1-2):97-109.
Jasti et al. (2003) "Recent advances in Mucoadhesive Drug Delivery Systems" Business Briefing Pharmatech 194-196.
Kainthan & Brooks (2008) "Unimolecular micelles based on hydrophobically derivatized hyperbranched polyglycerols: biodistribution studies" Bioconjugate Chemistry, 19(11):2231-2238. Epub Oct. 11, 2008.
Kainthan et al. (2008) "Hydrophobically derivatized hyperbranched polyglycerol as a human serum albumin substitute" Biomaterials, 29(11):1693-1704. Epub Jan. 14, 2008 Epub Oct. 11, 2008.
Kainthan et al. (2008) "Unimolecular micelles based on hydrophobically derivatized hyperbranched polyglycerols: ligand binding properties" Biomacromolecules 9(3):886-895. Epub Feb. 2, 2008.
Karger-Kocsis et al. (2004) "Synthesis of Reactive Hyperbranched and Star-Like Polyethers and their use for toughening of Vinylester-Urethane Hybrid Resins" Polymer, 45:1185-1195.
Khandare et al. (2010) "Structure-biocompatibility relationship of dendritic polyglycerol derivatives" Biomaterials 31(15): 4268-4277.
Liggins et al. (1997) "Solid-state characterization of paclitaxel" Pharm. Sci. 86(12):1458-1463.
Meise (2009) "Modular Synthesis of Hyperbranched Polyglycerol Supported N-Heterocyclic Carbene Ligands for Application in Catalysis" Freie Universitat Berlin, Dissertation. 150 pages.
Mugabe et al. (2011) "Development and in vitro characterization of paclitaxel and docetaxel loaded into hydrophobically derivatized hyperbranched polyglycerols" Int J. Pharm. 404(1-2):238-249. Epub Nov. 17, 2010.
Mugabe et al. (2011) "In vitro and in vivo evaluation of intravesical docetaxel loaded hydrophobically derivatized hyperbranched polyglycerols in an orthotopic model of bladder cancer" Biomacromolecules 12(4):949-960. Epub Mar. 1, 2011.
Mugabe et al. (2011) "In vivo efficacy of intravesical paclitaxel and docetaxel loaded hydrophobically derivatized hyperbranched polyglycerols" Nanomedicine in press DOI: 10.2217NNM.11. 37 pages.
Mugabe et al. (2011) "In vivo evaluation of mucoadhesive nanoparticulate docetaxel for intravesicl treatment of non-muscle-invasive bladder cancer" Clin Cancer Res. 17(9): 2788-2798. Epub Feb. 28, 2011.
Roller et al. (2005) "High-loading polyglycerol supported reagents for Mitsunobu- and acylation-reactions and other useful polyglycerol derivatives" Mol Divers 9(4):305-316.

(56) References Cited

OTHER PUBLICATIONS

Savic et al. (2003) "Micellar nanocontainers distribute to defined cytoplasmic organe" Science 300(5619):615-618.
Sunder et al. (1999) "Controlled Synthesis of Hyperbranched Polyglycerols by Ring-Opening Multibranching Polymerization" Macromolecules, 32(13):4240-4246.
Sunder et al. (1999) "Molecular Nanocapsules Based on Amphiphilic Hyperbranched Polyglycerols" Angew. Chem. Int. Ed. Engl. 38(23):3552-3555.
Sunder et al. (2000) "Hyperbranched Polyether Polyols: A Modular Approach to Complex Polymer Architectures" Adv. Mater. 12(3):235-239.
Sunder et al. (2000) "Hyperbranched Polyether-Polyols Based on Polyglycerol: Polarity Design by Block Copolymerization with Propylene Oxide" Macromolecule.s 33(2):309-314.
Sunder et al. (2000) "Synthesis and Thermal Behavior of Esterified Aliphatic Hyperbranched Polyether Polyols" Macromolecules. 33(4):1330-1337.
Thongborisute & Takeuchi (2008) "Evaluation of mucoadhesiveness of polymers by BIACORE method and mucin-particle method" Int. J. Pharm. 354(1-2):204-209.
Tian & Stella (2010) "Degradation of paclitaxel and related compounds in aqueous solutions III: Degradation under acidic pH conditions and overall kine" J. Pharm. Sci. 99(3)1288-1298.
Tsallas et al. (2011) "The uptake of paclitaxel and docetaxel into ex vivo porcine bladder tissue from polymeric micelle formulations" Cancer Chemother Pharmacol. 68(2):431-444.
Tziveleka et al. (2006) "Novel functional hyperbranched polyether polyols as prospective drug delivery systems" Macromol. Biosci. 6(2):161-169.
Wang et al. (2008) "Current Patents of Dendrimers and Hyperbranched Polymers in Membranes" Recent Patents on Chemical Engineering 1(1):41-51.
Ye et al. (2011) "Synthesis and Characterization of Carboxylic Acid Conjugated, Hydrophobically Derivatized, Hyperbranched Polyglycerols as Nanoparticulate Drug Carriers for Cisplatin" Biomacromolecules 12(1):145-155. Epub 2010.
Yeh et al. (2010) "A silicone-based microfluidic chip grafted with carboxyl functionalized hyperbranched polyglycerols for selective protein capture" Microfluid Nanofluid 9:199-209.
Ali et al. (1995) "Novel cytotoxic 3'-(tert-butyl) 3'-dephenyl analogs of paclitaxel and docetaxel." Journal of medicinal chemistry 38(19): 3821-3828.
Bissery et al. (1991) "Experimental antitumor activity of taxotere (RP 56976, NSC 628503), a taxol analogue." Cancer Res, 51(18): 4845-4852.
Bissery et al. (1995) "Docetaxel (Taxotere): a review of preclinical and clinical experience. Part I: Preclinical experience." Anticancer Drugs, 6(3):339-355, 363-368.
Center for Drug Evaluation and Research. Application No. NDA 20-892 Pharmacology Review(s)—Part 1. Division of Oncology Drug Products, HFD-150, Review and Evaluation of Pharmacology and Toxicology Data 1998 [cited Nov. 26, 2014]; Available from: http://www.accessdata.fda.gov/drugsatfda_docs/nda/98/20892_phrmr_P1.pdf.
Center for Drug Evaluation and Research. Application No. NDA 20-892 Pharmacology Review(s)—Part 2. Division of Oncology Drug Products, HFD-150, Review and Evaluation of Pharmacology and Toxicology Data 1998 [cited Nov. 26, 2014]; Available from: http://www.accessdata.fda.gov/drugsatfda_docs/nda/98/20892_phrmr_P2.pdf.
Cozzi et al. (1999) "Toxicology and pharmacokinetics of intravesical gemcitabine: a preclinical study in dogs" Clin. Cancer Res, 5(9): 2629-2637.
Dalton et al. (1999) "Pharmacokinetics of aminolevulinic acid after intravesical administration to dogs." Pharm Res, 16(2): 288-295.
Debruyne et al. (1985) "Intravesical and intradermal BCG-RIVM application: a toxicity study." Prog Clin Biol Res, 185B: 151-159.
Dumontet & Sikic (1999) "Mechanisms of action of and resistance to antitubulin agents: microtubule dynamics, drug transport, and cell death," J Clin Oncol, 17(3): 1061-1070.
Gao et al. (1998) "Bladder tissue uptake of mitomycin C during intravesical therapy is linear with drug concentration in urine." Clin Cancer Res, 3(1): 139-143.
Haldar et al. (1997) "Bcl2 is the guardian of microtubule integrity." Cancer Res, 57 (2):229-233.
Laudano et al. (2010) "Long-term clinical outcomes of a phase I trial of intravesical docetaxel in the management of non-muscle-invasive bladder cancer refractory to standard intravesical therapy." Urology, 75(1):134-137.
Lee et al. (2011) "Development of docetaxel-loaded intravenous formulation, Nanoxel-PM using polymer-based delivery system" J Control Release, 155(2): 262-271.
Malleswara et al. (2010) "Evaluation of the pharmaceutical quality of docetaxel injection using new stability indicating chromatographic methods for assay and impurities." Sci Pharm, 7 (2): 215-231.
Mauroy et al. (1999) "Study of the synergy of microwave hyperthermia/intravesical chemotherapy in the prevention of recurrences of superficial tumors of the bladder" Prog Urol, 9(1): 69-80.
McKiernan et al, (2006) "Phase I trial of intravesical docetaxel in the management of superficial bladder cancer refractory to standard intravesical therapy." J Clin Oncol, 24(19): 3075-3080.
Meijden et al. (1986) "The effects of intravesical and intradermal application of a new B.C.G. on the dog bladder." Urol Res, 14(4): 207-210.
Pusztai (2007) "Markers predicting clinical benefit in breast cancer from microtubule-targeting agents." Annals of Oncology. 18(12): xii15-20.
Wientjes et al. (1991) "A method to study drug concentration-depth profiles in tissues: mitomycin C in dog bladder wall." Pharm Res, 8(2): 168-173.
Wientjes et al. (1991) "Bladder wall penetration of intravesical mitomycin C in dogs." Cancer Res, 51 (16): 4347-4354.
Wientjes et al. (1993) "Penetration of mitomycin C in human bladder." Cancer Res, 53(14): 3314-3320.
Wosnitzer et al. (2011) "Predictive value of microtubule associated proteins tau and stathmin in patients with nonmuscle invasive bladder cancer receiving adjuvant intravesical taxane therapy." J Urol, 186(5):2094-100.
Zaske et al. (2001) "Docetaxel :Solid state characterization by X-ray powder diffraction and thermogravimetry." J. Phys. IV France, 11: Pr10-221-pr10-226.
Mugabe et al. (2012) "Tissue uptake of docetaxel loaded hydrophobically derivatized hyperbranched polyglycerols and their effects on the morphology of the bladder urothelium." Biomaterials, 33(2): 692-703. Epub Oct. 19, 2011.
Mugabe et al. (2013)"Tolerability and Pharmacokinetic Properties of Intravesical Docetaxel Loaded Amine Terminated Hyperbranched Polyglycerol Nanoparticles." SIU Academy, Sep. 9, 2013.
Ooya (2004) "Hydrotropic Dendrimers of Generations 4 and 5: Synthesis, Characterization, and Hydrotropic Solubilization of Paclitaxel." Bioconjugate Chem, 15: 1221-1229.
Ooya (2005) "Self-assembly of cholesterol-hydrotropic dendrimer conjugates into micelle-like structure: Prepartion and hydrotropic solubilisation of paclitaxel." Science and Technology of Advanced Materials, 6: 452-456.
Panyam (2002) "Rapid endo-lysosomal escape of poly(DL-lactide-co-glycolide) nanoparticles: implications for drug and gene delivery." FASEB J., 16: 1217-1226.
Reichert (2011) "Size-dependant cellular uptake of dendritic polyglycerol." 7(6): 820-829. Epub Feb. 18, 2011.
Rosato (2006) "HYTADI-p20: A new paclitaxel-hyaluronic acid hydrosoluble bioconjugate for treatment of superficial bladder cancer." Urologic Oncology: Seminars and Original Investigations. 24: 207-215.
Rossi et al. (2010) "Enhanced cell surface polymer grafting in concentrated and nonreactive aqueous polymer solutions." J Am Chem Soc. 17, 132(10): 3423-3430.

(56) References Cited

OTHER PUBLICATIONS

Rossi et al. (2010) "Red blood cell membrane grafting of multifunctional hyperbranched polyglycerols." Biomaterials. 31(14): 4167-4178. Epub Feb. 20, 2010.
Seiler (2006) "Hyperbranched Polymers: Phase behavior and new applications in the field of chemical engineering." Fluid Phase Equilibria, 241: 155-174.
Shelley (2010) "Intravesical Therapy for Superficial Bladder Cancer: A systematic Review of Randomised Trials and Meta-Analyses." Cancer Treatment Reviews,36: 195-205.
Shen (2008) "Intravesical Treatments of Bladder Cancer: Review." Pharmaceutical Research, 25(7): 1500-1510.
Shenoy (2005) "Poly(Ethylene Oxide)-Modified Poly(β-amino Ester) Nanoparticles as a pH-Sensitive System for Tumor-Targeted Delivery of Hydrophobic Drugs: Part I. In vitro Evaluations." Mol Pharm, 2(5): 357-366.
Smart (2005) "The basics and underlying mechanisms of mucoadhesian." Advanced Drug Delivery Reviews, 57: 1556-1568.
Sogias (2008) "Why is Chitosan Mucoadhesive." Macromolecules, 9(7): 1837-1842.
Song et al (1997) "Bladder Tissue Pharmacokinetics of Intravesical Taxol" Cancer Chemother Pharmacol, 40(4): 285-292.
Sparreboom (2005) "Comparative Preclinical and Clinical Pharmacokinestics of a Cremophor-Free, Nanoparticle Albumin-Bound Paclitaxel (ABI-007) and Paclitaxel Formulated in Cremophor (Taxol)." Clin Cancer Res, 11: 4136-4143.
Sternberg (2013) "ICUD-EAU International Consultation on Bladder Cancer 2012: Chemotherapy for Urothelial Carcinoma—Neoadjuvant and Adjuvant Settings." European Urology, 63: 58-66.
Vicari et al. (2008) "Paciltaxel loading in PLGA nanospheres affected the in vitro drug cell accumulation and antiproliferative activity." BMC Cancer., 8: 212.
Wilms (2010) "Hyperbranched Polyglycerols: From the controlled Synthesis of Biocompatible Polyether Polyols to Multipurpose Applications." Accounts of Chemical Research, 43(1): 129-141.
Wosnitzer et al. (2012) "A Comparison of the Outcomes of Neoadjuvant and Adjuvant Chemotherapy for Clinical T2-T4 a N0-N2 MO Bladder Cancer." Cancer, 2012 118(2): 358-364.
Xiao (2003) "Whole bladder photodynamic therapy for orthotopic superficial bladder cancer in rats: a study of intravenous and intravesical administration of photosensitizers." J Urol., 169: 352-356.
Yan and Muller (1997) "Molecular Parameters of Hyperbranched Polymers Made by Self-condensing Vinyl Polymerization. 2. Degree of Branching," Macromolecules., 30: 7024-7033.
Yeh et al. "Self-assembled monothiol-terminated hyperbranched polyglycerols on a gold surface: a comparative study on the structure, morphology, and protein adsorption characteristics with linear poly(ethylene glycol)s." Langmuir., 24(9): 4907-16. Epub Mar. 25, 2008.
Zapatero (2012) "Long-Term Results of Two Prospective Bladder-sparing Trimodality Approaches for Invasive Bladder Cancer: neoadjuvant Chemotherapy and Concurrent Radio-chemotherapy." Urology., 80: 1056-1062.
Zhang et al. (2008) "Conjugation to hyperbranched polyglycerols improves RGD-mediated inhibition of platelet function in vitro." Bioconjug Chem., 19(6): 1241-7. Epub May 14, 2008.
Zhigaltsev (2010) "Development of a weak-base docetaxel derivatives that can be loaded into lipid nanoparticles." J. Control Release., 144(3): 332-340.
Lu (2004) "Paclitaxel Gelatin Nanoparticles for Intravesical Bladder Cancer Therapy." J Urol., 185(4): 1478-1483.
Kainthan et al. (2007) "In Vitro biological evaluation of high molecular weight hyperbranched polyglycerols," Biomaterials, 28(3): 4581-4590 Epub Aug. 3, 2007.
Abbo et al. (2010) "Phase I clinical trial and pharmacokinetics of intravesical mitomycin C in dogs with localized transitional cell carcinoma of the urinary bladder," J Vet Intern Med, 24(5):1124-30.
Arentsen et al. (2011) "Pharmacokinetics and toxicity of intravesical TMX-101: a preclinical study in pigs," BJU Int, 108(7): 1210-1214.
Barthelmes et al. (2011) "Development of a mucoadhesive nanoparticulate drug delivery system for a targeted drug release in the bladder," Int J Pharm, 416 (1): 339-345.
Chang et al. (2009) "Optimization of epirubicin nanoparticles using experimental design for enhanced intravesical drug delivery," Int J Pharm, 376(1-2): 195-203.
Cho (1992) "Adriamycin absorption after Nd:YAG laser coagulation compared to electrosurgical resection of the bladder wall," J Urol, 147(4):1139-1141.
Dalmose et al. (2000) "Surgically induced urologic models in swine," J Invest Surg, 13(3): 133-145.
Di Stasi et al. (1997) "Electromotive administration of oxybutynin into the human bladder wall," J Urol, 158(1): 228-233.
Di Stasi et al. (1997) "Electromotive delivery of mitomycin C into human bladder wall," Cancer Res, 57(5): 875-880.
Di Stasi et al. (2003) "The stability of lidocaine and epinephrine solutions exposed to electric current and comparative administration rates of the two drugs into pig bladder wall," Urol Res, 31(3): 169-176.
Dumey et al. (2005) "In vivo retroviral mediated gene transfer into bladder urothelium results in preferential transduction of tumoral cells," Eur Urol, 47(2): 257-263.
Gontero et al. (2010) "Pharmacokinetic study to optimize the intravesical administration of gemcitabine," BJU Int, 106(11): 1652-1656.
Hara (1989)"Fundamental studies on intravesical instillation of interferons in the treatment of bladder cancer," Nihon Hinyokika Gakkai Zasshi, 80(2): 158-166.
Hirao et al. (1985) "Fundamental studies on intravesical instillation of cis-diamminedichloroplatinum for treatment of urinary bladder tumors. I: On the effects of intravesical instillation of cis-diamminedichloroplatinum in normal beagle dogs," Hinyokika Kiyo, 31(1): 31-38.
Matsumura et al. (1983) "Intravesical adriamycin chemotherapy in bladder cancer," Cancer Chemother Pharmacol, 11: 69-73.
Mross et al. (1992) "Tissue disposition and plasma concentrations of idarubicin after intravesical therapy in patients with bladder tumors," Cancer Chemother Pharmacol, 29(6): 490-494.
Ohmori et al. (1996) "Experimental studies on intravesical instillation of SM-5887, a novel anthracycline derivative for treatment of bladder carcinoma," Gan to Kagaku Ryoho, 23(5): 601-606.
Song et al. (1997)"Bladder tissue pharmacokinetics and antitumor effect of intravesical 5-fluorouridine," Clin Cancer Res, 3(6): 901-909.
Tsushima (1985) "Fundamental studies on intravesical instillation of 4'-epi-adriamycin for the treatment of bladder cancer," Hinyokika Kiyo, 31(11): 1945-1956.
Van Staveren et al. (2002) "Comparison of normal piglet bladder damage after PDT with oral or intravesical administration of ALA," Lasers Med Sci, 17(4): 238-245.
Wientjes et al. (1996) "M.G., Badalament, R.A., and Au, J.L., Penetration of Intravesical Doxorubicin in Human Bladders," Cancer Chemother Pharmacol, 37(6): 539-546.
Witjes et al. (2003) "Pharmacokinetics of intravesical gemcitabine: a preclinical study in pigs," Eur Urol, 44(5): 615-619.
Ahn & McKiernan (2013) "New Agents for Bacillus Calmette-Guerin-Refactory Bladder Cancer." Urol Clin N Am.: 1-14.
Andrews (2009) "Mucoadhesive polymeric platforms for controlled drug delivery." European journal of pharmaceutics and biopharmaceutics : official journal of Arbeitsgemeinschaft fur Pharmazeutische Verfahrenstechnik e.C., 71(3): 505-518.
Au (2001) "Methods to Improve Efficacy of Intravesical Mitomycin C: Results of a Randomized Phase III Trial" J Natl cancer Inst, 18;93(8):597-604.
Barlow (2013) "Experience with Newer Intravesical Chemotherapy for High-Risk Non-Muscle-Invasive Bladder Cancer" Curr Urol Rep, 14: 65-70.

(56) References Cited

OTHER PUBLICATIONS

Barlow (2013) "Long Term Survival Outcomes with Intravesical Docetaxel for Recurrent Nonmuscle Invasive Bladder Cancer After Previous Bacillus Calmette-Guerin Therapy" The Journal of Urology, 189: 834-839.
Bassi (2011) "Paclitaxel-Hyaluronic Acid for Intravesical Therapy of Bacillus Calmette-Guerin Refactory Carcinoma In-Situ of the Bladder Cancer: Results of a Phase I Study." The Journal of Urology, 85: 445-449.
Bélanger & Marois (2001) "Hemocompatibility, Biocompatibility, Inflammatory and in Vivo Studies of Primary Reference Materials Low-Density Polyethylene and Polydimethylsiloxane: A Review." J.Biomed Mater Res (Appl Biomater) 58(5): 467-477. Epub Jul. 5, 2001.
Burjak et al. (2001) "The study of drug release from microspheres adhered on pig vesical mucosa." Int J Pharmaceutics, 224(1-2):123-130.
Chen et al. (2003) "Effect of Dimethyl Sulfoxide on Bladder Tissue Penetration of Intravesical Paclitaxer" Clinical Cancer Res, 9(1): 363-369.
Elsasser-Beile et al. (2005) "Adjuvant Intravesical Treatment of Superficial Bladder Cancer with a Standardized Mestletoe Extract." The Journal of Urology, 174: 76-79.
Eroglu (2002) "Design and evaluation of a mucoadhesive therapeutics agent delivery system for postoperative chemotherapy in superficial bladder cancer" International Journal of Pharmaceutics, 235: 51-59.
Fefelova (2007) "Mucoadhesive interactions of amphiphilic cationic copolymers based on [2-(methacryloyloxy)ethyl]trimethylammonnium chloride," International Journal of Pharmaceutics. 339, 25-32.
Frey (1999) "Degree of branching in hyperbranched polymers. 3 copolymerization of ABm-monomers with AB and ABn-monomers." Acta Polymerica. 50 (203): 67-76.
Gaison (2006) "Improving Efficacy of Intravesical Chemotherapy." European Urology. 50: 225-234.
Giannantoni (2006) "New Frontiers in Intravesical Therapies and Drug Delivery." European Urology. 50: 1183-1193.
Gong (2007) "In vitro and in vivo degradability and cytocompatibility of poly(L-lactic acid) scaffold fabricated by gelatin particle leaching method." Acta Biomaterialia. 3: 531-540.
Hall (2007) "Chapter 1: The Management of Bladder Cancer: Diagnosis and Treatment Recommendations (Guidelines for the Management of Nonmuscle Invasive Bladder Cancer: (Stages TA, T1 and TIS: Update." The Journal of Urology, 178:2314-2330.
Hasselmann (1998) "Hyperbranched Polymers Prepared via the Core-Dilutions/Slow Addition Techniques: Computer Simulation of Molecular Weight Distribution and Degree of Branching." Macromolecules. 31: 3790-3801.
Haxton & Burt (2009) "Polymeric drug delivery of platinum-based anticancer agents." J Pharm Sci. 98(7): 2299-2316. Epub Nov. 13, 2008.
Hennenfent (2006) "Novel Formulations of Taxanes: a review. Old wine in a new bottle." Annals of Oncology, 17: 735-749.
Highley (1999) "Intravesical Drug Delivery Pharmacokinetic and Clinical Consideration." Clin Pharmacokinet, 3(1): 59-73.
Hölter (1997) "Degree of branching in hyperbranched polymers" Acta Polymer, 48: 30-35.
Hreczuk-Hirst (2001) "Dextrins as potential carriers for drug targeting: tailored rates of dextrin degradation by introduction of pendant groups." International Journal of Pharmaceutics, 230: 57-66.
Kainthan & Brooks (2007) "In vivo biological evaluation of high molecular weight hyperbranched polyglycerols." Biomaterials, 28(32): 4779-4787. Epub Aug. 15, 2007.
Kainthan et al. (2006) "Blood compatibility of novel water soluble hyperbranched polyglycerol-based multivalent cationic polymers and their interaction with DNA" Biomaterials, 27(31): 5377-5390. Epub Jul. 18, 2006.
Kainthan et al. (2006) "Synthesis, Characterization, and Viscoelastic Properties of High Molecular Weight Hyperbranched Polyglycerols." Macromolecules, 31;39(22): 7708-7717.
Kainthan et al. (2006) "Biocompatibility Testing of Branched and Linear Polyglycidol." Biomacromolecules, 7(3): 703-709.
Kala (2014) "Combination of Dendrimer-nanovector-Medicated Small Interfereing RNA Delivery to Target Akt with the Clinical Anticancer Drug Paclitaxel for Effective and Potent Anticancer Activity in Treating Ovarian Cancer." J. Med. Chem., 57(6): 2634-2642.
Kerec (2005) "Permeability of Pig Urinary Bladder Wall: the effect of chitosan and the role of calcium." European of Pharmaceutical sciences, 25: 113-121.
Kerec (2006) "Permeability of Pig Urinary Bladder Wall: Time and Concentration Dependent Effect of Chitosan." Biol. Pharm. Bull., 29(8) 1685-1691.
Kerec et al. (2009) "Enhanced permeability of the urinary bladder wall; the role of polymer charge." Pharmazie, 64(4): 232-237.
Khan et al. (2006) "Water soluble nanoparticles from PEG-based cationic hyperbranched polymer and RNA that protect RNA from enzymatic degradation." Biomacromolecules, 7(5): 1386-1388. Epub Apr. 8, 2006.
Kizhakkedathu et al. (2010) "High molecular weight polyglycerol-based multivalent mannose conjugates." Biomacromolecules, 11(10): 2567-2575.
Knemeyer et al. (1999) "Cremophor reduces paclitaxel penetration into bladder wall during intravesical treatment." Cancer Chemother Pharmacol, 44 (3): 241-248.
Knuchel (1989) "Sensitivities of Monolayers and Spheroids of the Human Bladder Cancer Cell Line MGH-U1 to the Drugs Used for Intravesical Chemotherapy," Cancer Research, 49: 1397-1401.
Koç et al. (2005) "Highly Regioselective Synthesis of Amino-Functionalized Dendritic Polyglycerols by a One-Pot Hydroformylation/Reductive Amination Series." J Org Chem, 70(6): 2021-2025. Epub Feb. 16, 2005.
Kolishetti (2010) "Engineering of self-assembled nanoparticle platform for precisely controlled combination drug therapy." PNAS. 107(42): 17939-17944.
Kumar et al. (2004) "Atom Transfer Radical Polymerization using multidentate amine ligands supported on soluble hyperbranched polyglycidol." Macromol Chem Phys, 205(5): 567-573.
Le Visage (2004) "Efficacy of Paclitaxel Released from Bio-Adhesice Polymer Microspheres on Model Superficial Bladder Cancer" The Journal of Urology, 171: 1324-1329.
Leakakos et al. (2003) "Intravesical administration of doxorubicin to swine bladder using magnetically targeted carriers." Cancer Chemother Pharmacol, 51(6): 445-450.
Lee (2005) "Designing Dendrimers for Biological Applications." Nature Biotechnology, 23(12): 1517-1526.
Lee et al. (2005) "Bioadhesive drug delivery system using glyceryl monooleate for the intravesical administration of paclitaxel" Chemotherapy, 51(6): 311-318.
Liu et al. (2010) "Adsorption of amphiphilic hyperbranched polyglycerol derivatives onto human red blood cells." Biomaterials, 31(12): 3364-73. Epub Feb. 1, 2010.
Lu et al. (2011) "Paclitaxel Gelatin Nanoparticles for Intravesical Bladder Cancer Therapy," J Urol, 185(4): 1478-1483.
Luo (2002) "Cellular Internalization of Poly(ethylene oxide)-b-poly-(ε-caprolactone) Diblock Copolymer Micelles," Bioconjugate Chem, 13: 1259-1265.
McKiernan (2011) "A Phase I Trial of Intravesical Nanoparticle Albumin-Bound Paclitaxel in the Treatment of Bacillus Calmette-Guerin Refactory Nonmuscle Invasive Bladder Cancer." The Journal of Urology, 186: 448-451.
McKiernan (2012) "Updated Results of the Combined Phase I/II Trial of Intravesical Nanoparticle Albumin-bound Paclitaxel in the Treatment of BCG Refractory Non-muscle Invasive Transitional Cell Carcinoma." Bladder Cancer: Superficial II, AUA Annual Meeting, 2012. http://www.aua2012.org/abstracts/printpdf.cfm?ID=1769.
Meng (2006) "Uptake and metabolism of novel biodegradable poly(glycerol-adipate) nanoparticles in DAOY monolayer." Journal of Controlled Release, 116: 314-321.

(56) References Cited

OTHER PUBLICATIONS

Mugabe et al. (2008) "Paclitaxel incorporated in hydrophobically derivatized hyperbranched polyglycerols for intravesical bladder cancer therapy." BJU International, 103(7): 978-986. Epub Oct. 31, 2008.

Mugabe et al. (2012) "Enhanced tissue uptake of docetaxel loaded hydrophobically derivatized hyperbranched polyglycerols and their effects on the morphology of the bladder urothelium." Abstract, 27th Annual Congress of the European Association of Urology, Feb. 24-28.

"SEC Analysis of Polymers with Light Scattering Detection," (2004) G.I.T. Laboratory Journal, 2-5.

Chen (2006) "Synthesis of Multarm Star Poly(glycerol)-block-Poly(2-hydroxyethyl methacrylate)." Biomacromolecules, 7: 919-926.

Dworak et al., (1995) "Cationic polymerization of glycidol. Polymer Structure and polymerization mechanism," Macromol. Chem. Phys., 196:1963-1970.

Kautz et al. (2001) "Control of the Molecular Weight of Hyperbranched Polyglycerols" Macromol. Symp. 163:67-73.

Tokar et al., (1994) "Cationic Polymerization of Glycidol: Coexistence of the Activated Monomer and Active Chain End Mechanism," Macromolecules, 27:320-322.

Zhang et al. (1996) "Development of amphiphilic diblock copolymers as micellar carriers of taxol," International J. Pharmaceutics, 132: 195-206.

\* cited by examiner

DERIVATIZED HYPERBRANCHED POLYGLYCEROLS

CROSS REFERENCE TO RELATED APPLICATIONS

This application is a continuation of U.S. application Ser. No. 13/581,463, filed Jan. 18, 2013, now U.S. Pat. No. 9,186,410, which is a National Stage entry of International Application No. PCT/CA2011/000225, filed Mar. 1, 2011, which claims the benefit of U.S. Provisional Patent Application Ser. No. 61/309,304 entitled "BIOADHESIVE DERIVATIZED HYPERBRANCHED POLYGLYCEROLS" filed on Mar. 1, 2010, the disclosures of each of which are incorporated herein by reference in their entirety.

TECHNICAL FIELD

This invention relates to therapeutics, their uses and methods for the delivery of drugs or other biologically active moieties to biological tissues. In particular, the invention relates to polymers based on derivatized hyperbranched polyglycerols (dHPGs) and methods for treating cancer, infections and inflammatory or autoimmune diseases.

BACKGROUND

Bladder cancer is the second most common genitourinary malignancy. At initial diagnosis, approximately 70% of cases are non-muscle-invasive. Current treatment options for superficial disease include treating bladder cancer topically via intravesicular installation of a chemotherapeutic agent into the bladder with a catheter. However, these treatment options are of limited efficacy. Despite intravesical chemotherapy and/or immunotherapy, up to 80% of patients with non-muscle-invasive bladder cancer develop recurrent tumours, of which 20-30% develop into more aggressive, potentially lethal tumours (Dalbagni, G. (2007) *Nat. Clin. Pract. Urol.* 4: 254-260).

Treatment failure is thought to be due in part to the short dwell-time of drugs active against bladder cancer cells in the bladder. For example, taxanes are generally not used for intravesicular installation due to poor bioavailability of the current formulations in the bladder. Paclitaxel has documented antitumuor activity in systemic bladder cancer therapy as it penetrates bladder tissues at a rate 20 times faster than that of water-soluble drugs such as mitomycin C, allowing for prolonged retention of therapeutic doses even after the instilled solution is removed. However, its intravesical use is hampered by the presence of Cremophor™-EL in the commercial formulation (Taxol™) as it entraps the drug in an aqueous environment and reduces paclitaxel penetration into the bladder wall (Mugabe, C., et al. (2008) *British J. Urology Int.* 102(7): 978-986).

While many active agents are hydrophobic or otherwise water insoluble, they are often needed in water-based or otherwise aqueous environments for effective treatment of numerous indications, including cancer (such as cancers of the bowel, lung, bladder and genitourinary system), infections (such as those of the digestive tract and the airways) and inflammatory or autoimmune diseases (such as irritable bladder, inflammatory bowel disease and chronic and acute inflammation). As such, multiple systems have been developed as delivery vehicles for such agents. One of these systems includes the use of polymeric micelles.

Polymeric micelles are amphiphilic, having a hydrophobic core and a hydrophilic shell, and as such, they can encapsulate hydrophobic molecules in the core due to hydrophobic interactions. The hydrophilic shell keeps the system soluble in water. However, these systems may be unstable in the bladder due to dilution effects or environmental factors.

Hyperbranched polyglycerols ("HPGs") are one of the few hyperbranched polymers that can be synthesized in a controlled manner with pre-determined molecular weights and narrow polydispersity (Kainthan, R. K., et al. (2008) *Biomacromolecules* 9: 886-895). Hydrophobic molecules may be encapsulated in the hydrophobic core of an HPG (WO2006/130978).

SUMMARY

This invention is based in part on the discovery that derivatized hyperbranched polyglycerols ("dHPGs") described herein may be used as agents for the delivery of a drug or other biologically active moiety to the urinary tract (for example, the urethra and bladder), the digestive tract (for example, the mouth, esophagus and colon), the airways (for example, the nose and lungs), the vaginal cavity and cervix and the peritoneal cavity to treat indications such as cancer (for example, bladder, gastric, esophageal, lung, laryngeal, oral, sinus, vaginal or cervical cancers), infection (for example, infections of the digestive tract or the airways), and inflammatory or autoimmune diseases (for example, irritable bladder, inflammatory bowel disease or chronic or acute inflammation) as well as other indications wherein delivery of a drug or other biologically active moiety to a tissue or cell is desired. For example, polymers identified herein may be useful in installation therapy of non-muscle-invasive bladder cancer. Polymers identified herein may show mucoadhesive properties which may be useful in installation therapy of non-muscle-invasive bladder cancer.

The dHPGs herein described may be used as a carrier for a drug or other biologically active moiety and for the preparation of a therapeutic medicament for delivery of such drugs or moieties to target tissues or cells. In particular, the dHPGs herein described may be used as a carrier for a taxane for the treatment of non-muscle-invasive bladder cancer.

The condensed core dHPGs described herein have surprising attributes that are particularly desirable for delivery of a drug to a target tissue. In particular, as shown herein, condensed core dHPGs are less toxic and have greater tolerability properties.

In accordance with an embodiment, there is provided a hyperbranched polyglycerol, the hyperbranched polyglycerol comprising: a core comprising hyperbranched polyglycerol derivatized with $C_1$-$C_{20}$ alkyl chains, wherein the ratio of $C_1$-$C_{20}$ alkyl chains to glycerol units is greater at a centre of the core compared to a periphery of the core; and a shell comprising at least one hydrophilic substituent bound to hydroxyl groups of the core, wherein the hyperbranched polyglycerol comprises from about 1 to about 200 moles of the at least one hydrophilic substituent per mole of the hyperbranched polyglycerol.

In accordance with another embodiment, there is provided a method of delivering a biologically active moiety to a biological tissue, the method comprising: administering a hyperbranched polyglycerol loaded with the biologically active moiety to the biological tissue, wherein the hyperbranched polyglycerol comprises: a core comprising hyperbranched polyglycerol derivatized with $C_1$-$C_{20}$ alkyl chains, wherein the ratio of $C_1$-$C_{20}$ alkyl chains to glycerol units is greater at a centre of the core compared to a periphery of the core; and a shell comprising at least one hydrophilic substituent bound to hydroxyl groups of the core, wherein the hyperbranched polyglycerol comprises from about 1 to about 200 moles of the at least one hydrophilic substituent per mole of the hyperbranched polyglycerol. The method may further comprise incorporating the biologically active moiety into the hyperbranched polyglycerol.

In accordance with a further embodiment, there is provided a use of a hyperbranched polyglycerol for delivering a biologically active moiety to a biological tissue, wherein the hyperbranched polyglycerol comprises: a core comprising hyperbranched polyglycerol derivatized with $C_1$-$C_{20}$ alkyl chains, wherein the ratio of $C_1$-$C_{20}$ alkyl chains to glycerol units is greater at a centre of the core compared to a periphery of the core; and a shell comprising at least one hydrophilic substituent bound to hydroxyl groups of the core, wherein the hyperbranched polyglycerol comprises from about 1 to about 200 moles of the at least one functional group per mole of the hyperbranched polyglycerol.

In accordance with another embodiment, there is provided a use of a hyperbranched polyglycerol for preparing a medicament for delivering a biologically active moiety to a biological tissue, wherein the hyperbranched polyglycerol comprises: a core comprising hyperbranched polyglycerol derivatized with $C_1$-$C_{20}$ alkyl chains, wherein the ratio of $C_1$-$C_{20}$ alkyl chains to glycerol units is greater at a centre of the core compared to a periphery of the core; and a shell comprising at least one hydrophilic substituent bound to hydroxyl groups of the core, wherein the hyperbranched polyglycerol comprises from about 1 to about 200 moles of the at least one functional group per mole of the hyperbranched polyglycerol.

In accordance with a further embodiment, there is provided a pharmaceutical composition comprising a hyperbranched polyglycerol and a biologically active moiety, wherein the hyperbranched polyglycerol comprises: a core comprising hyperbranched polyglycerol derivatized with $C_1$-$C_{20}$ alkyl chains, wherein the ratio of $C_1$-$C_{20}$ alkyl chains to glycerol units is greater at a centre of the core compared to a periphery of the core; and a shell comprising at least one hydrophilic substituent bound to hydroxyl groups of the core, wherein the hyperbranched polyglycerol comprises from about 1 to about 200 moles of the at least one functional group per mole of the hyperbranched polyglycerol.

In accordance with an embodiment, there is provided a hyperbranched polyglycerol, comprising: a core comprising hyperbranched polyglycerol derivatized with $C_1$-$C_{20}$ alkyl chains; and a shell comprising at least one hydrophilic substituent bound to hydroxyl groups of the core, wherein the at least one hydrophilic substituent comprises at least one functional group selected from one or more of the following: —$NH_2$, =$NH_2^+$, —$NH_3^+$, and —$NR_3^+$, wherein each R is independently a $C_1$-$C_6$ alkyl group or one R is independently a $C_1$-$C_6$ alkyl group and two R's together form a $C_3$-$C_{12}$ cyclic alkyl group so that $R_3$ forms a quaternary amine with the nitrogen, and wherein the hyperbranched polyglycerol comprises from about 1 to about 200 moles of the at least one functional group per mole of the hyperbranched polyglycerol.

In accordance with a further embodiment, there is provided a use of a hyperbranched polyglycerol, the hyperbranched polyglycerol comprising: a core comprising hyperbranched polyglycerol; and a shell comprising at least one hydrophilic substituent bound to hydroxyl groups of the core, wherein the at least one hydrophilic substituent comprises at least one functional group selected from one or more of the following: —$NH_2$, =$NH_2^+$, —$NH_3^+$, and —$NR_3^+$, wherein each R is independently a $C_1$-$C_6$ alkyl group or one R is independently a $C_1$-$C_6$ alkyl group and two R's together form a $C_3$-$C_{12}$ cyclic alkyl group so that $R_3$ forms a quaternary amine with the nitrogen, and wherein the hyperbranched polyglycerol comprises from about 1 to about 200 moles of the at least one functional group per mole of the hyperbranched polyglycerol, for use as a pretreatment or co-treatment to increase drug uptake in a tissue. In an embodiment, the core may be further derivatized with $C_1$-$C_{20}$ alkyl chains.

In accordance with another embodiment, there is provided a hyperbranched polyglycerol, comprising: a core comprising hyperbranched polyglycerol; and a shell comprising at least one hydrophilic substituent bound to hydroxyl groups of the core, wherein the at least one hydrophilic substituent comprises at least one functional group selected from one or more of the following: —$NH_2$, =$NH_2^+$, —$NH_3^+$, and —$NR_3^+$, wherein each R is independently a $C_1$-$C_6$ alkyl group or one R is independently a $C_1$-$C_6$ alkyl group and two R's together form a $C_3$-$C_{12}$ cyclic alkyl group so that $R_3$ forms a quaternary amine with the nitrogen, and wherein the hyperbranched polyglycerol comprises from about 1 to about 200 moles of the at least one functional group per mole of the hyperbranched polyglycerol, for use as a pretreatment or co-treatment to increase drug uptake in a tissue. The core may be further derivatized with $C_1$-$C_{20}$ alkyl chains. In an embodiment, increasing drug uptake in a tissue may cause loss of umbrella cells of the tissue. In an embodiment, increasing drug uptake in a tissue may be without causing necrosis and/or inflammation of the tissue.

In accordance with another embodiment, there is provided a hyperbranched polyglycerol, the hyperbranched polyglycerol comprising: a core comprising hyperbranched polyglycerol polymerized from a glycerol epoxide and a $C_1$-$C_{20}$ alkyl epoxide or a $C_1$-$C_{20}$ alkyl glycidyl ether, wherein all or substantially all of the $C_1$-$C_{20}$ alkyl epoxide or $C_1$-$C_{20}$ alkyl glycidyl ether is polymerized before all or substantially all of the glycerol epoxide is polymerized; and a shell comprising at least one hydrophilic substituent covalently bonded to hydroxyl groups of the core, wherein the hyperbranched polyglycerol comprises from about 1 to about 200 moles of the at least one functional group per mole of the hyperbranched polyglycerol. In accordance with a further embodiment, there is provided a method of synthesizing a hyperbranched polyglycerol, the method comprising: polymerizing a glycerol epoxide and a $C_1$-$C_{20}$ alkyl epoxide or a $C_1$-$C_{20}$ alkyl glycidyl ether such that all or substantially all of the $C_1$-$C_{20}$ alkyl epoxide or $C_1$-$C_{20}$ alkyl glycidyl ether is polymerized before all or substantially all of the glycerol epoxide is polymerized to form hyperbranched polyglycerol; and derivatizing hydroxyl groups of the hyperbranched polyglycerol with at least one hydrophilic substituent, wherein the hyperbranched polyglycerol comprises from about 1 to about 200 moles of the at least one functional group per mole of the hyperbranched polyglycerol. The glycerol epoxide may be glycidol. The $C_1$-$C_{20}$ alkyl epoxide may be 1,2-epoxyoctadecane. The $C_1$-$C_{20}$ alkyl glycidyl ether may be $C_8$-$C_{10}$ alkyl glycidyl ether.

In accordance with another embodiment, there is provided a hyperbranched polyglycerol, the hyperbranched polyglycerol comprising: a core comprising hyperbranched polyglycerol derivatized with $C_1$-$C_{20}$ alkyl chains and loaded with docetaxel; and a shell comprising at least one hydrophilic substituent bound to hydroxyl groups of the core, wherein the hyperbranched polyglycerol comprises from about 1 to about 200 moles of the at least one functional group per mole of the hyperbranched polyglycerol.

In accordance with a further embodiment, there is provided a use of a hyperbranched polyglycerol for delivering docetaxel to a biological tissue, wherein the hyperbranched polyglycerol comprises: a core comprising hyperbranched polyglycerol derivatized with $C_1$-$C_{20}$ alkyl chains and loaded with docetaxel; and a shell comprising at least one hydrophilic substituent bound to hydroxyl groups of the core, wherein the hyperbranched polyglycerol comprises from about 1 to about 200 moles of the at least one functional group per mole of the hyperbranched polyglycerol.

The hyperbranched polyglycerol may further include a biologically active moiety. The hyperbranched polyglycerol may be used as a pretreatment or co-treatment for increasing drug uptake of a biologically active moiety. The biologically active moiety may be one or more hydrophobic drugs. The biologically active moiety may be selected from one of more of valrubicin, cisplatin, paclitaxel, docetaxel. The biologically active moiety may be a taxane or an analog thereof. The taxane may be paclitaxel or an analog thereof. The taxane may be docetaxel or an analog thereof. The biologically active moiety may be mitomycin or an analog thereof. Mitomycin may include all mitomycin analogs. Mitomycin and analogs thereof may include, for example, mitomycin A, mitomycin B, mitomycin C, mitomycin D, mitomycin F, mitomycin G, mitomycin H, mitomycin K and analogs thereof. The biologically active moiety may be mitomycin C. The biologically active moiety may be mitomycin F. The biologically active moiety may be valrubicin. The biologically active moiety may be vinblastine. The biologically active moiety may be cisplatin. The biologically active moiety may be methotrexate. The biologically active moiety may be doxorubicin or an analog thereof. The biologically active moiety may be epirubicin. The biologically active moiety may be gemcitabine. The biologically active moiety may be everolimus. The biologically active moiety may be suramin. The biologically active moiety may be a combination of moieties. The combination of moieties may be methotrexate, vinblastine, and doxorubicin (M-VAC). The combination of moieties may be M-VAC and cisplatin.

The hydrophilic substituent may be polyethylene glycol (PEG) (200 to 450 g/ml), or methoxy polyethylene glycol (MPEG) (200 to 450 g/ml), or combinations thereof. The at least one hydrophilic substituent may be MePEG or PEG. The at least one hydrophilic substituent may be MePEG. The at least one hydrophilic substituent may be PEG. The at least one hydrophilic substituent may comprise at least one functional group that is —OH, —COOH, —NHS, —SH, —$NH_2$, —$NH_3^+$, or —$NR_3^+$, wherein each R may independently be a $C_1$-$C_6$ alkyl group or one R may independently be a $C_1$-$C_6$ alkyl group and two R's together may form a $C_3$-$C_{12}$ cyclic alkyl group so that $R_3$ forms a quaternary amine with the nitrogen.

The at least one functional group may be —$NH_2$, —$NH_3^+$, or —$NR_3^+$, wherein each R may independently be a $C_1$-$C_6$ alkyl group or one R may independently be a $C_1$-$C_6$ alkyl group and two R's together may form a $C_3$-$C_{12}$ cyclic alkyl group so that $R_3$ forms a quaternary amine with the nitrogen. The at least one functional group may be —$NH_2$, or —$NH_3^+$. The at least one functional group may be an amine. Alternatively, the at least one functional group may be —$NH_2$.

The hyperbranched polyglycerol may comprise from about 1 to about 200 moles of the at least one hydrophilic substituent per mole of the hyperbranched polyglycerol. The hyperbranched polyglycerol may comprise from about 1 to about 100 moles of the at least one hydrophilic substituent per mole of the hyperbranched polyglycerol. The hyperbranched polyglycerol may comprise from about 1 to about 40 moles of the at least one hydrophilic substituent per mole of the hyperbranched polyglycerol. The hyperbranched polyglycerol may comprise from about 5 to about 40 moles of the at least one hydrophilic substituent per mole of the hyperbranched polyglycerol. The hyperbranched polyglycerol may comprise from about 10 to about 40 moles of the at least one hydrophilic substituent per mole of the hyperbranched polyglycerol. The hyperbranched polyglycerol may comprise from about 10 to about 30 moles of the at least one hydrophilic substituent per mole of the hyperbranched polyglycerol. The hyperbranched polyglycerol may comprise from about 30 to about 40 moles of the at least one hydrophilic substituent per mole of the hyperbranched polyglycerol. The hyperbranched polyglycerol may comprise from about 5 to about 15 moles of the at least one hydrophilic substituent per mole of the hyperbranched polyglycerol. The at least one hydrophilic substituent may bind to about 1% to about 40% of the hydroxyl groups. The at least one hydrophilic substituent may bind to about 5% to about 30% of the hydroxyl groups. The at least one hydrophilic substituent may bind to about 20% of the hydroxyl groups.

The amount of the hydrophilic substituent per mol of the hyperbranched polyglycerol may be determined by measuring the molecular weight of the hyperbranched polyglycerol and measuring the amount of the hydrophilic substituent present in an amount of the hyperbranched polyglycerol. The person of ordinary skill in the art will appreciate that the molecular weight of the hyperbranched polyglycerol may be measured using different methods, for example, gel permeation chromatography. The molecular weight of the hyperbranched polyglycerol may be measured, for example, using gel permeation chromatography with multi-angle laser light scattering detection. The amount of the hydrophilic substituent present in an amount of the hyperbranched polyglycerol may be measured, for example, by a titration method. The titration method may be a forward titration method. The titration method may be a back titration method. For example, where the hydrophilic substituent comprises at least one functional group that may be —$NH_2$, a forward titration method against an acid, such as HCl, may be used to measure the amount of hydrophilic substituent present in an amount of HPG. Where the hydrophilic substituent comprises at least one functional group that may be —$NH_2$, a back titration method using a known amount of an acid, such as HCl, and titrating against a base, such as NaOH, may be used. The amount of the hydrophilic substituent present in an amount of hyperbranched polyglycerol may be measured, for example, by a colorimetric method. The amount of the hydrophilic substituent present in an amount of hyperbranched polyglycerol may be measured, for example, by a fluorescence method. Where the hydrophilic substituent comprises at least one functional group that may be —$NH_2$, a fluorescamine assay may be used. The amount of the hydrophilic substituent present in an amount of hyperbranched polyglycerol may be measured by more than one method and an average value of the amount of the hydrophilic substituent measured by the more than one methods may be used to calculate the mol of hydrophilic substituent per mol of hyperbranched polyglycerol. Where the hydrophilic substituent comprises at least one functional group that may be —$NH_2$, a fluorescamine assay may be the preferred method to determine the amount of the hydrophilic substituent present in an amount of hyperbranched polyglycerol.

The hyperbranched polyglycerol may comprise from about 1 to about 200 moles of the at least one functional group per mole of the hyperbranched polyglycerol. The hyperbranched polyglycerol may comprise from about 1 to about 100 moles of the at least one functional group per mole of the hyperbranched polyglycerol. The hyperbranched polyglycerol may comprise from about 1 to about 40 moles of the at least one functional group per mole of the hyperbranched polyglycerol. The hyperbranched polyglycerol may comprise from about 5 to about 40 moles of the at least one functional group per mole of the hyperbranched polyglycerol. The hyperbranched polyglycerol may comprise from about 10 to about 40 moles of the at least one functional group per mole of the hyperbranched polyglycerol. The hyperbranched polyglycerol may comprise from about 10 to about 30 moles of the at least one functional group per mole of the hyperbranched polyglycerol. The hyperbranched polyglycerol may comprise from about 30 to about 40 moles of the at least one functional group per mole of the hyperbranched polyglycerol. The hyperbranched polyglycerol may comprise from about 5 to about 15 moles of the at least one functional group per mole of the hyperbranched polyglycerol.

The amount of the functional group per mol of the hyperbranched polyglycerol may be determined by measuring the molecular weight of the hyperbranched polyglycerol and measuring the amount of the functional group present in an amount of the hyperbranched polyglycerol. The person of ordinary skill in the art will appreciate that the molecular weight of the hyperbranched polyglycerol may be measured using different methods, for example, gel permeation chromatography. The molecular weight of the hyperbranched polyglycerol may be measured, for example, using gel permeation chromatography with multi-angle laser light scattering detection. The amount of the functional group present in an amount of the hyperbranched polyglycerol may be measured, for example, by a titration method. The titration method may be a forward titration method. The titration method may be a back titration method. For example, where the at least one functional group may be —$NH_2$, a forward titration method against an acid, such as HCl, may be used to measure the amount of —$NH_2$ per present in an amount of HPG. Where the at least one functional group may be —$NH_2$, a back titration method using a known amount of an acid, such as HCl, and titrating against a base, such as NaOH, may be used. The amount of the functional group present in an amount of hyperbranched polyglycerol may be measured, for example, by a colorimetric method. The amount of the functional group present in an amount of hyperbranched polyglycerol may be measured, for example, by a fluorescence method. Where the at least one functional group may be —$NH_2$, a fluorescamine assay may be used. The amount of the functional group present in an amount of hyperbranched polyglycerol may be measured by more than one method and an average value of the amount of the functional group measured by the more than one methods may be used to calculate the mol of functional group per mol of hyperbranched polyglycerol. Where the at least one functional group may be —$NH_2$, a fluorescamine assay may be the preferred method to determine the amount of the functional group present in an amount of hyperbranched polyglycerol.

The $C_1$-$C_{20}$ alkyl chains may be $C_5$-$C_{20}$ alkyl chains. The $C_1$-$C_{20}$ alkyl chains may be $C_8$-$C_{18}$ alkyl chains. The $C_1$-$C_{20}$ alkyl chains may be $C_8$-$C_{10}$ alkyl chains.

A portion of the at least one hydrophilic substituent may be located in the core.

The biological tissue may be a mucosal membrane. The biological tissue may be a cell. The biological tissue may be the urothelial surface of a bladder.

The dHPGs as described herein may be described through a common nomenclature which identifies the basic hyperbranched structure, the core attributes, and the surface attributes as follows:

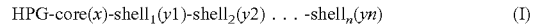

$$\text{HPG-core}(x)\text{-shell}_1(y1)\text{-shell}_2(y2) \ldots \text{-shell}_n(yn) \qquad (I)$$

which designates a polymer composed of hyperbranched polyglycerol, comprising a core derivatized a substituent selected from hydrophobic groups such as $C_8$, $C_{10}$, $C_{12}$ or $C_{18}$ alkyl groups that are either linear or branched or contain aryl substituents, wherein the amount of the core substituent is x, expressed in number of moles or as a percentage. The polymer also has n substituents on the shell, such as PEG or MePEG, or substituents having carboxyl groups (COOH), hydroxyl groups, amines ($NR_2$), N-hydroxysuccinimides (NHS), charged amines ($NR_3^+$), thiols (SH) etc., as described herein. Each shell substituent may be designated as being present in a certain amount y1, y2 or yn and can be expressed in number of moles or as a percentage. In some notations, general classes can be designated in the same manner, but without explicitly identifying the amounts of each. In addition, when the shell substituent is PEG or MePEG, it may be further defined by the chain length of this polymeric component, for example MePEG350, PEG200, etc. For the general class however, the molecular weight may be omitted.

For example, HPG-$C_{8/10}$-MePEG or HPG-$C_{8/10}$—$NH_2$ each designate the core (x) as $C_{8/10}$. The term "HPG-$C_{8/10}$-MePEG", or the like, anywhere herein may be used interchangeably with the term "HPG-C10-MePEG". In some circumstances the core(x) is not identified and may be assumed to be $C_{8/10}$. Nevertheless, other alkyls having $C_1$-$C_{20}$ may be used. In accordance with a further embodiment, there is provided a use of a dHPG described herein for drug delivery to a target tissue. In accordance with a further embodiment, there is provided a use of a dHPG described herein in the preparation of a medicament for drug delivery to a target tissue. In accordance with a further embodiment, there is provided a use of a dHPG described herein as a pre-treatment or co-treatment for increasing drug uptake in a tissue. In accordance with a further embodiment, there is provided a use of a dHPG described herein for the treatment of non-muscle-invasive bladder cancer. In accordance with a further embodiment, there is provided a use of a dHPG described herein as a pre-treatment or co-treatment for increasing drug uptake in a tissue of a drug for the treatment of non-muscle-invasive bladder cancer. In accordance with a further embodiment, there is provided a use of a dHPG described herein in the preparation of a medicament for the treatment of non-muscle-invasive bladder cancer. The treatment of the non-muscle-invasive bladder cancer may be in a mammal. The mammal may be human. In accordance with another embodiment, there is provided a pharmaceutical composition comprising a dHPG as set out herein and a pharmaceutically acceptable excipient. In accordance with a further embodiment, there is provided one or more of the dHPGs described herein for drug delivery to a target tissue. In accordance with a further embodiment, there is provided a method for preparing a dHPG described herein.

The polymers described herein are meant to include all racemic mixtures and all individual structural isomers or variants, in particular as defined by the branch patterns within the HPG structure, or in terms of the physical attachment of the surface substituents to the HPG.

DETAILED DESCRIPTION

Figure 1:
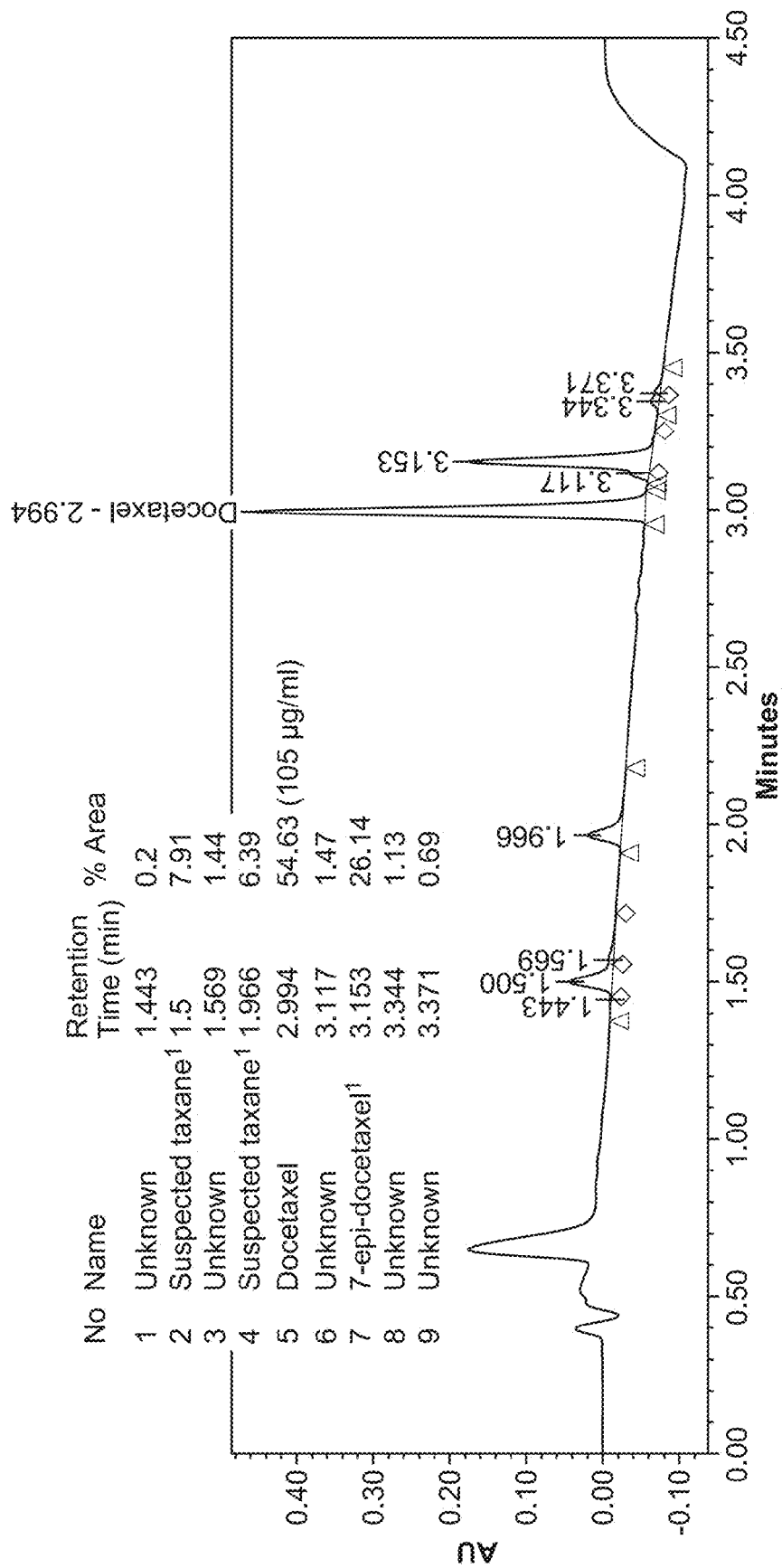
FIG. 1 shows a sample UPLC chromatograph of docetaxel (DTX).

Novel polymers described herein include those shown in Formula I, which all appear to be related to HPG. Synthesis of HPG has been previously described, including the production of amphiphilic copolymers and amphiphilic block copolymers, including derivatization with various functional groups and/or the production of copolymers and block copolymers (such as the addition of alkyl groups through ester linkages and the addition of polyalkylene glycol groups). Publications describing preparation of HPG include: U.S. Pat. No. 5,112,876; U.S. Pat. No. 6,469,218; U.S. Pat. No. 6,765,082; U.S. Pat. No. 6,822,068; WO 2000/77070; Sunder, A. et al. (1999) Macromolecules 32:4240-46, (2000) Macromolecules 33:309-14, (2000) Macromolecules 33:1330-37, and (2000) Adv. Mater 12:235-239; Knischaka, R. et al., (2000) Macromolecules 33:315-20; Haag, R., et al. (2000) Macromolecules 33:8158-66, and (2002) J. Comb. Chem. 4:112-19; Kautz, H., et al. (2001) Macromol. Symp. 163:67-73; Karger-Kocsis, J., et al. (2004) Polymer, 45:1185-95; Gao, C. & Yan, D. (2004) Prog. Polym. Sci. 29:183-275; and Tziveleka, L. et al., (2006) Macromol. Biosci. 6:161-169). Sunder, A. et al., (1999) Angew. Chem. Int. Ed. 38:3552-55 contains a description of the preparation of amphiphilic modified HPG, as well as derivatization of such polymers, including derivatization with various substituents and functional groups.

The dHPGs described herein may include $C_1$-$C_{30}$ alkyl chains, or other similar alkyl chains. However, the dHPGs described herein may also include $C_1$-$C_{20}$ alkyl chains, or other similar alkyl chains The term "alkyl" is used as it is normally understood to a person of skill in the art and often refers to monovalent saturated aliphatic hydrocarbyl groups having from one to 20 carbon atoms, unless otherwise defined. The hydrocarbon may be either straight-chained or branched and may contain cycloaliphatic or aryl substituents. Alkyl chains may be selected from one or more of $C_1$-$C_{20}$ alkyl chains. Alternatively, the alkyl chains may be selected from one or more of $C_2$-$C_{19}$ or $C_3$-$C_{18}$ or $C_4$-$C_{17}$ alkyl chains. Alternatively, the alkyl chains may be selected from one or more of $C_5$-$C_{16}$ or $C_6$-$C_{15}$ or $C_7$-$C_{14}$ alkyl chains. Alternatively, the alkyl chains may be selected from one or more of $C_8$-$C_{13}$ or $C_9$-$C_{12}$ or $C_{10}$-$C_{15}$ alkyl chains. Alternatively, the alkyl chains may be selected from one or more of $C_5$-$C_{15}$ or $C_5$-$C_{10}$ or $C_5$-$C_{20}$ alkyl chains. The alkyl chain or chains selected for the core may depend on the intended use for the dHPG. For example, a $C_{18}$ alkyl did not work as well as a $C_{8/10}$ alkyl for loading paclitaxel.

The HPGs as described herein may include HPGs derivatized with substituents having functional groups such that the derivatized HPGs ("dHPGs") are mucoadhesive and more generally bioadhesive. In the most general meaning of the term, the dHPGs will form a bond or interact with a biological tissue, which could be a cell or an extracellular material. The bond or interaction may be of any type, including van der Waals interactions, hydrogen bonds, electrostatic interactions, ionic bonds or covalent bonds.

The term "mucoadhesion" or "mucoadhesive" is used as it is normally understood to a person of skill in the art and often refers to an adhesive phenomenon occurring between polymeric materials and the biological tissue which can include cell surfaces, mucus on cell surfaces or a mucus-gel layer covering mucosal membranes. As mucin is present at the urothelial surface of the bladder, dHPGs containing mucoadhesive functional groups may be used for targeted drug delivery to the surface of the bladder, as well as to other mucosal membranes.

Generally, the dHPGs described herein have a "core", which includes and an initiator (for example, trimethyloyl propane (TMP)) and hyperbranched polyglycerol. In an embodiment, the hyperbranched polyglycerol core may be derivatized with $C_1$-$C_{20}$ alkyl chains. In an embodiment, the "core" may be enclosed in a "shell", wherein the shell comprising at least one hydrophilic substituent bound to hydroxyl groups of the core, and wherein the hyperbranched polyglycerol comprises from about 1 to about 200 moles of the at least one hydrophilic substituent per mole of the hyperbranched polyglycerol.

"Initiator" as used herein is defined as small molecule comprising an alkyl component and more than one, but preferably more than two hydroxyl groups. However, the initiator may have three or four or more hydroxyl groups. An example of an initiator is trimethyloyl propane (TMP).

"Condensed core" as used herein is defined as a core wherein the ratio of $C_1$-$C_{20}$ alkyl chains to glycerol units is greater at a centre of the core compared to a periphery of the core. For example, a $C_{10}$ alkyl chain, may be incorporated into the structure such that it is not evenly distributed relative to the glycerol throughout the entire hyperbranched structure, but rather it is distributed such that it is more concentrated in the centre of the hyperbranched core structure (for example, adjacent the initiator) than near its periphery immediately adjacent to the shell substituents. The degree to which the core architecture is "condensed" may be controlled by the addition of reagents. The term "centre" may be defined as being the precise centre having a zero volume point. Alternatively, a dHPG may have a radius "r" where the alkyl to glycerol ratio is greater in a central volume having a radius "rc", where rc<r, than the alkyl to glycerol overall ratio in the dHPG as a whole.

For a "regular" or "normal" core, a glycerol epoxide (the hyperbranching component monomer) and an alkyl epoxide (which imparts the hydrophobic nature to the core) may be added at a constant ratio throughout the reaction. For a condensed core, the alkyl epoxide is added in higher proportion at the earliest stage of the reaction, and is reduced to a lower proportion (as low as zero) at the later stages of the reaction. This reduction may occur continuously or occur in discrete steps, there being a minimum of two discrete steps.

The core architecture can be defined in terms of the rate of addition of components. For example, a condensed core polymer can be synthesized in multiple steps, with each step having a defined ratio of core monomers, one being a glycerol epoxide and the other being a hydrophobic alkyl epoxide. A condensed core molecule can be made by having a higher ratio of alkyl epoxides added in earlier step(s) compared to the ratio of the components added in the later or last step(s). Alternatively, the ratio can be altered over a time course, such that for a first (or earlier) period of time during the reaction a higher ratio of alkyl epoxide to glycerol epoxide is added than is added over later periods of time. In this approach, the ratio can be constantly changed as a gradient throughout the reaction.

The remaining hydroxyl groups of the polymer may be "derivatized" with other hydrophilic substituents such as MePEG or PEG to form a hydrophilic shell, including substituents having hydroxyl, carboxyl, amine (including primary, secondary and tertiary amines) NHS, ether, thiol, halo, thioether, ester, thioester, amide, succinimides and other similar functional groups. During shell formation, it may be possible for a portion of the shell substituents to react with hydroxyl groups located towards the centre of the polymer. Even if such reactions occur, the core maintains its hydrophobic character.

As used herein, the term "amphiphilic", or "amphiphilic polymer", is used as it is normally understood to a person of skill in the art and often refers to the presence of both a hydrophobic and hydrophilic moiety in a single molecule. Hydrophobic refers to any substance or portion thereof which is more soluble in a non-polar solvent than in a polar solvent. Hydrophobicity can be conferred by the inclusion of apolar groups in a molecule, including, but not limited to, long chain saturated and unsaturated aliphatic hydrocarbon groups and such groups substituted by one or more aromatic, cycloaliphatic or heterocyclic group(s). Hydrophilic refers to any substance or portion thereof which is more soluble in a polar solvent than in a non-polar solvent. Hydrophilic characteristics derive from the presence of polar or charged groups such as carbohydrates, phosphate, carboxylic, sulfato, amino, sulfhydryl, nitro, hydroxyl and other similar groups. The hydrophilic portion may comprise MePEG, amine, carboxylic acid or NHS.

The term "polyethylene glycol", or "PEG", is used as it is normally understood to a person of skill in the art and often refers to such compounds having a molecular weight between about 200 to about 20,000, depending on the number of ethylene oxide units in the polymer chain. Preferred molecular weights are from about 200 to about 400, about 200 to about 1000 and about 200 to about 2000 although molecular weights of about 2000 to about 8000 may also be used.

The term "methoxypoly(ethylene oxide)", or "MePEG", is used as it is normally understood to a person of skill in the art and often refers to such compounds having a molecular weight between about 350 to about 10,000, depending on the number of ethylene oxide units in the polymer chain. Preferred molecular weights are from about 350 to about 550, about 350 to about 750 and about 350 to about 2000 although molecular weights of about 2000 to about 5000 may also be used.

The phrase "local or targeted delivery" is used as it is normally understood to a person of skill in the art and often refers to delivery of a compound directly to a target site within an organism.

In some embodiments, the dHPGs as described herein may be used for local or targeted treatment of an indication of the urinary tract (for example, the urethra and bladder), the digestive tract (for example, the mouth, esophagus and colon), the airways (for example, the nose and lungs), the vaginal cavity and cervix and the peritoneal cavity to treat indications such as cancer (for example, bladder, gastric, esophageal, lung, laryngeal, oral, sinus, vaginal or cervical cancers), infection (for example, infections of the digestive tract or the airways), and inflammatory or autoimmune diseases (for example, irritable bladder, inflammatory bowel disease or chronic or acute inflammation) as well as other indications wherein delivery of a drug or other biologically active moiety to a tissue or cell is desired. For example, the dHPGs as described herein may be used for local or targeted treatment of non-muscle-invasive bladder cancer. In some embodiments, the polymers as described herein may be used in the preparation of a medicament or a composition for local or targeted treatment of one or more of the indications listed herein (for example, non-muscle-invasive bladder cancer). Some aspects of this invention make use of compositions comprising a dHPG described herein and a pharmaceutically acceptable excipient or carrier. Methods of treating one or more of the indications listed herein (for example, non-muscle-invasive bladder cancer) are also provided. Such methods may include administering a dHPG as described herein or a composition of a dHPG as described herein, or an effective amount of a dHPG as described herein or composition of a dHPG as described herein to a subject in need thereof, wherein the dHPG incorporates a biologically active agent.

In some embodiments, the dHPGs as described herein may be used as pre-treatment or co-treatment for increasing drug uptake in a tissue. In some embodiments, the dHPGs as described herein may be used as pre-treatment or co-treatment for increasing drug uptake of a drug for local or targeted treatment of an indication of the urinary tract (for example, the urethra and bladder), the digestive tract (for example, the mouth, esophagus and colon), the airways (for example, the nose and lungs), the vaginal cavity and cervix and the peritoneal cavity to treat indications such as cancer (for example, bladder, gastric, esophageal, lung, laryngeal, oral, sinus, vaginal or cervical cancers), infection (for example, infections of the digestive tract or the airways), and inflammatory or autoimmune diseases (for example, irritable bladder, inflammatory bowel disease or chronic or acute inflammation) as well as other indications wherein delivery of a drug or other biologically active moiety to a tissue or cell is desired. For example, the dHPGs as described herein may be used as pre-treatment or co-treatment to increase drug uptake of a drug for local or targeted treatment of non-muscle-invasive bladder cancer. In some embodiments, the dHPGs as described herein may be used as pre-treatment for increasing drug uptake in a tissue. In some embodiments, the dHPGs as described herein may be used as co-treatment for increasing drug uptake in a tissue. In an embodiment, use of the dHPGs as co-treatment may include where the drug or biologically active moiety is not loaded in the dHPG during treatment with the drug or biologically active moiety. In an embodiment, use of the dHPGs as co-treatment may include where a portion of or all of the drug or biologically active moiety is loaded in the dHPG during treatment with the drug or biologically active moiety. In some embodiments, the dHPGs as described herein may be used as pre-treatment and co-treatment for increasing drug uptake in a tissue. In some embodiments, the dHPGs as described herein may be used as pre-treatment or co-treatment for increasing drug uptake in a tissue as compared to drug uptake in the tissue in the absence of pre-treatment or co-treatment. In some embodiments, the dHPGs as described herein may be used as pre-treatment or co-treatment for increasing drug uptake in a tissue without causing necrosis and/or inflammation of the tissue. In some embodiments, increasing drug uptake in a tissue may include causing loss of umbrella cells. In some embodiments, increasing drug uptake in a tissue may include causing loss of umbrella cells without causing necrosis and/or inflammation of the tissue. In some embodiments, the umbrella cells may be umbrella cells of the urothelial surface of the bladder. The expression "increasing drug uptake" is used as it is normally understood to a person of skill in the art and often refers to increasing concentration or accumulation of a drug in a cell or tissue.

In some embodiments, increase in drug uptake may be measured in terms of increase in Cavg of drug uptake with use of dHPGs as pre-treatment or co-treatment as compared to Cavg of drug uptake in the absence of pre-treatment or co-treatment. The person of ordinary skill in the art will appreciate that Cavg may be measured at different ranges or points of tissue depth. For example, Cavg may be measured for 0>3350, 0>1500, 200>3350, or 200>1500 μm ranges of tissue depth. In an embodiment, Cavg of drug uptake with the use of dHPGs as pre-treatment or co-treatment may be increased by a factor of 1.3 to 4.0, 1.8 to 2.8, 1.3 to 2.4, 2.0 to 2.6, 1.5, 1.8, 2, 2.2, 2.4, 2.6, 2.8, 3.0, 3.2, 3.4, 3.6, 3.8, or 4.0 fold as compared to Cavg of drug uptake in the absence of pre-treatment or co-treatment. In some embodiments, increase in drug uptake may be measured in terms of increase in Cmax of drug uptake with use of dHPGs as pre-treatment or co-treatment as compared to Cmax of drug uptake in the absence of pre-treatment or co-treatment. In an embodiment, Cmax of drug uptake with the use of dHPGs as pre-treatment or co-treatment may be increased by a factor of 1.3 to 4.0, 1.8 to 2.8, 1.3 to 2.4, 2.0 to 2.6, 1.5, 1.8, 2, 2.2, 2.4, 2.6, 2.8, 3.0, 3.2, 3.4, 3.6, 3.8, or 4.0 fold as compared to Cmax of drug uptake in the absence of pre-treatment or co-treatment. In some embodiments, increase in drug uptake may be measured in terms of increase in AUC(x-y) of drug uptake with use of dHPGs as pre-treatment or co-treatment as compared to AUC(x-y) of drug uptake in the absence of pre-treatment or co-treatment. The person of ordinary skill in the art will appreciate that AUC(x-y) may be measured at different ranges or points of tissue depth. For example, AUC(x-y) may be measured for 0>infinity, 0>3350, 0>1500, 200>infinity, 200>3350, or 200>1500 μm ranges of tissue depth. In an embodiment, AUC(x-y) of drug uptake with the use of dHPGs as pre-treatment or co-treatment may be increased by a factor of 1.3 to 4.0, 1.8 to 2.8, 1.3 to 2.4, 2.0 to 2.6, 1.5, 1.8, 2, 2.2, 2.4, 2.6, 2.8, 3.0, 3.2, 3.4, 3.6, 3.8, or 4.0 fold as compared to AUC(x-y) of drug uptake in the absence of pre-treatment or co-treatment. The person of ordinary skill in the art will appreciate that there are alternative methods for measuring increase in drug uptake, for example, a permeability enhancement ratio, R, calculated as a quotient of permeabilities in the presence and absence of pre-treatment or co-treatment, as reported in Grabnar et al. (*International Journal of Pharmaceutics* 256 (2003) 167-173) may be used.

In some embodiments, the dHPGs as described herein may be in the solvent addition form. The dHPGs may be associated with a non-stoichiometric amount of a solvent, water and/or buffers, typically expressed as weight or volume percent. The solvent may be, for example, and without limitation, a pharmaceutically acceptable solvent or other biocompatible solvent including ethanol, DMSO, propylene glycol, glycerol, PEG200, PEG300, Transcutol or Solutol.

The embodiments the dHPGs as described herein include all possible stereochemical alternatives, including those illustrated or described herein.

In some embodiments, dHPGs as described herein include isomers such as geometrical isomers having different branch patterns. The dHPGs synthesized by methods disclosed herein are random branching HPGs and will contain glycerol monomers that are fully reacted, e.g. linked in three directions, or partially reacted, being linked to another monomer in one or two directions. The presence of each branching architecture may be confirmed by analytical techniques (for example, 2D NMR HSQC experiments).

Compositions and dHPGs according to some embodiments described herein may be administered in any of a variety of known routes. The dHPGs could be administered as an intravesical dosing solution or in other compositions created to function as a rinse (including an oral rinse, an intraperitoneal irrigation solution or an irrigation for nasal or vaginal cavities), an eyedrop, an oral solution to be swallowed, an aerosol, or a solution for inhalation as a spray, or as a semi-solid to be inserted into close proximity to a biological tissue such as a mucosal surface.

It is understood that it could be potentially beneficial to restrict delivery of the dHPGs described herein incorporating a drug or other biologically active agent to the target tissue or cell to which drug delivery is desired. For example, it is contemplated that the selective delivery of dHPGs as described herein incorporating a biologically active agent to the urothelial surface of the bladder in a subject having or suspected of having non-muscle-invasive bladder cancer may provide therapeutic effect without producing significant side effects in other tissues of the body. An example of a method that may be suitable for the administration of a dHPG as described herein incorporating a taxane is intravesical installation. Intravesical installation is also an example of a method that may be suitable for administration of a dHPG as described herein for use as a pre-treatment or co-treatment for increasing drug uptake in a tissue. Intravesical installation is a means of drug delivery whereby a solution is inserted into a vesical such as the bladder. In delivery to the bladder, the solution is typically administered by means of a catheter inserted through the urethra into the bladder. The solution is instilled and typically retained in the bladder for a period of time such as about 1 or about 2 hours. A typical volume of installation is in the range of about 10 to about 50 mL. After the dwell time, the volume of solution, and any accumulated urine which has diluted the solution would be evacuated to end the procedure. The dwell time represents the time of maximum drug exposure during intravesical therapy, as the majority of the drug is removed during the evacuation step. Other examples of compositions or methods to facilitate localized tissue delivery would be apparent to one of skill in the art. For example, the dHPGs as described herein may be used could be in pharmaceutical compositions wherein the dHPG contains a taxane or other hydrophobic drug in the core of the dHPG along with a second drug, which may also be formulated into the HPG, or the second drug may be combined in solution with the dHPG for delivery. Furthermore, the dHPGs may be combined with a targeting agent (for example, an antibody to epidermal growth factor receptor, which is overexpressed in bladder tumuors, Herceptin, or VEGF).

Suitable pharmaceutical compositions may be formulated by means known in the art and their mode of administration and dose determined by the skilled practitioner. For intravesical installation, a dHPG incorporating a biologically active agent may be dissolved in an installation vehicle such as water, a co-solvent system containing water, an isotonic aqueous solution such as normal saline or dextrose 5% in water, or in a buffered system to control pH at a favorable level, such as about pH 6-8, or another suitable range, e.g. about pH 4-6 or above pH 8. The pH may be controlled at a specific range to provide benefit in optimizing drug release kinetics, drug stability, maximal mucoadhesion, maximum solubility or a combination thereof. Other pharmaceutically acceptable vehicles used for administration of a water-soluble drug delivery systems are also contemplated. Many techniques known to one of skill in the art are described in *Remington: the Science & Practice of Pharmacy by Alfonso Gennaro*, 20$^{th}$ ed., Lippencott Williams & Wilkins, (2000).

An "effective amount" of a pharmaceutical composition as used herein includes a therapeutically effective amount or a prophylactically effective amount. A "therapeutically effective amount" refers to an amount effective, at dosages and for periods of time necessary, to achieve the desired therapeutic result, such as decreased cancer cell proliferation, increased life span or increased life expectancy. A therapeutically effective amount of a dHPG incorporating a biologically active agent may vary according to factors such as the disease state, age, sex, and weight of the subject, and the ability of the biologically active agent to elicit a desired response in the subject. Dosage regimens may be adjusted to provide the optimum therapeutic response. A therapeutically effective amount is also one in which any toxic or detrimental effects of the formulation are outweighed by the therapeutically beneficial effects. A "prophylactically effective amount" refers to an amount effective, at dosages and for periods of time necessary, to achieve the desired prophylactic result, such as the prevention or the prevention of the progression of an indication. Typically, a prophylactic dose is used in subjects prior to or at an earlier stage of disease.

It is to be noted that dosage values may vary with the severity of the condition to be alleviated. For any particular subject, specific dosage regimens may be adjusted over time according to the individual need and the professional judgment of the person administering or supervising the administration of the compositions. The amount of composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate compositions in dosage unit form for ease of administration and uniformity of dosage.

In some embodiments, dHPGs as described herein may be used, for example, and without limitation, in combination with other treatment methods. For example, dHPGs as described herein incorporating a biologically active agent may be used as neoadjuvant (prior), adjunctive (during), and/or adjuvant (after) therapy in combination with other therapies known to one of ordinary skill in the art.

In general, dHPGs as described herein may be used to reduce toxicity. Toxicity of the dHPGs described herein may be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances, however, such as in severe disease conditions, it may be necessary to administer substantial excesses of the compositions. Some dHPGs of this invention may be toxic at some concentrations. Titration studies may be used to determine toxic and non-toxic concentrations. Toxicity may be evaluated by examining a particular dHPG's or composition's specificity across cell lines. Animal studies may also be used to provide an indication if the polymer has any effects on other tissues.

The dHPGs as described herein may be administered to a subject. As used herein, a "subject" may be a human, non-human primate, rat, mouse, cow, horse, pig, sheep, goat, dog, cat, etc. The subject may be suspected of having or at risk for having cancer or other disease associated with a tissue having a mucosal surface. Such an indication may be of the urinary tract (for example, the urethra and bladder), the digestive tract (for example, the mouth, esophagus and colon), the airways (for example, the nose and lungs), the vaginal cavity and cervix and the peritoneal cavity. A cancer (for example, bladder, gastric, esophageal, lung, laryngeal, oral, sinus, vaginal or cervical cancers), an infection (for example, infections of the digestive tract or the airways), or an inflammatory or autoimmune diseases (for example, irritable bladder, inflammatory bowel disease or chronic or acute inflammation) as well as other indications may be desired targets of the dHPGs described herein for the delivery of a drug or other biologically active moiety. Diagnostic methods for cancers, infections, and inflammatory or autoimmune diseases are known to those of ordinary skill in the art.

For example, the dHPGs described herein may be used for treatment of non-muscle-invasive bladder cancer. The dHPGs described herein may be used for preparation of a medicament for treatment of non-muscle-invasive bladder cancer. dHPGs described herein may be used in a method for treatment of non-muscle-invasive bladder cancer. The method may comprise administering to a subject in need thereof an effective amount of a dHPG described herein incorporating a biologically active agent (for example, a taxane). For example, the dHPGs described herein may be used as a pre-treatment or co-treatment to increase drug uptake of a drug for treatment of non-muscle-invasive bladder cancer.

Methods of preparing or synthesizing dHPGs described herein will be understood by a person of skill in the art having reference to known chemical synthesis principles. For example, WO2006/130978 describes suitable synthetic procedures that may be considered and suitably adapted for preparing polymers described herein.

A general methodology for chemical preparation of a dHPG is described in the following non-limiting exemplary scheme:

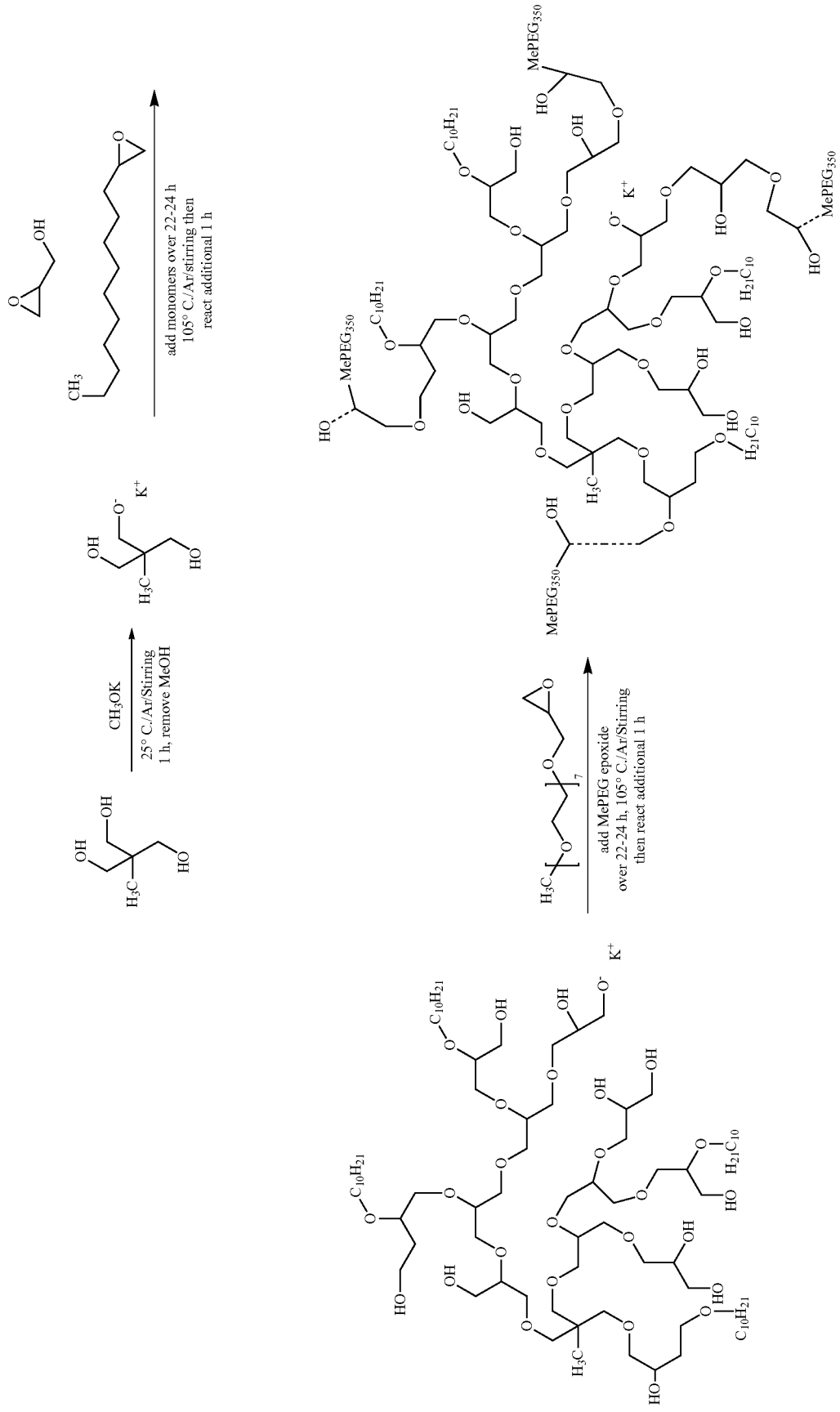

Step 2, addition of monomers, is further defined by the rate of addition of the monomers over the 22-24 hour period. For condensed core polymers, the rate of addition of the alkyl epoxide is faster at earlier stages of the reaction period and the rate of addition of the glycerol epoxide may be slower at earlier stages. However, adjusting the rate of addition is not required as long as the ratio of the components favors addition of the alkyl component in the earlier stages of the reaction relative to the later stages.

Various alternative embodiments and examples are described herein. These embodiments and examples are illustrative and should not be construed as limiting the scope of the invention.

EXAMPLES

Example 1

Synthesis and Characterization of Derivatized HPGs

All chemicals were purchased from Sigma-Aldrich Canada Ltd. (Oakville, Canada) and used without further purification. All solvents were HPLC grade from Fisher Scientific (Ottawa, Canada) and used without further purification.

Polymerizations were carried out in a three-neck round-bottom flask equipped with a mechanical stirrer. The second neck was connected to a dual manifold Schlenk line, and the third was closed with a rubber septum through which reagents were added. A typical polymerization reaction procedure for HPG-$C_{8/10}$-MePEG is as follows. The initiator trimethyloyl propane (TMP) is added to the flask under argon atmosphere followed by potassium methylate solution in methanol (20 wt %). The mixture is stirred using a magnetic stir bar for 15 minutes, after which excess methanol is removed in a vacuum. The flask is kept in an oil bath at 95° C., and glycidol is added dropwise over a period of 12 hours using a syringe pump. After completion of the monomer addition, the mixture is stirred for an additional 5 hours. Octyl/decyl glycidyl ether is then added and the mixture stirred for 24 hours to form HPG-$C_{8/10}$. To this mixture, MePEG350 is added dropwise over a period of 12 hours and then stirred for an additional 5 hours. MePEG is preferred over PEG because the methyl group of MePEG protects one end of the monomer such that the monomer does not become bivalent, which could result in cross-linking between the dHPG molecules. Other protecting groups are also contemplated, including those that can be removed after the synthesis. In this fashion the HPG may be prepared with PEG chains on the surface that may be further modified by the addition of other chemical groups or biomolecules, including peptides, glycopeptides, proteins and the like. This procedure may be modified to synthesis different HPG's, for example, 1,2-epoxyoctadecane may be added to the mixture after addition of glycidol to form HPG-$C_{18}$.

The product is then dissolved in methanol and neutralized by passing it three times through a cation exchange column (Amberlite™ IRC-150). The unreacted octyl/decyl glycidyl ether is removed by extraction with hexane. Methanol is removed and the polymer is dialysed for three days against water using cellulose acetate dialysis tubing (MWCO: 1000 g/mol, Spectrum Laboratories Inc.), with three water changes per day. The dry polymer is then obtained by freeze-drying and heat drying.

This procedure can be modified in order to synthesize condensed core dHPGs in which the alkyl chains are concentrated toward the center of the polymer, instead of the regular core dHPG wherein the alkyl chains are positioned randomly throughout the polymer. The core of the polymer is modified by adding the glycerol epoxide and alkyl monomers to the reaction mixture at different rates and/or in different proportions. In order to form a condensed core dHPG, all of the alkyl monomer is added before the glycerol epoxide addition is complete so that the outer portion of the hyperbranched structure does not contain any alkyl component. Instead, the alkyl component is located towards the core of the HPG.

HPG-$C_{8/10}$—COOH was synthesized by first preparing HPG-$C_{8/10}$ as described above. Scheme II shows the reaction for the addition of carboxylic acid functional groups to HPG-$C_{8/10}$:

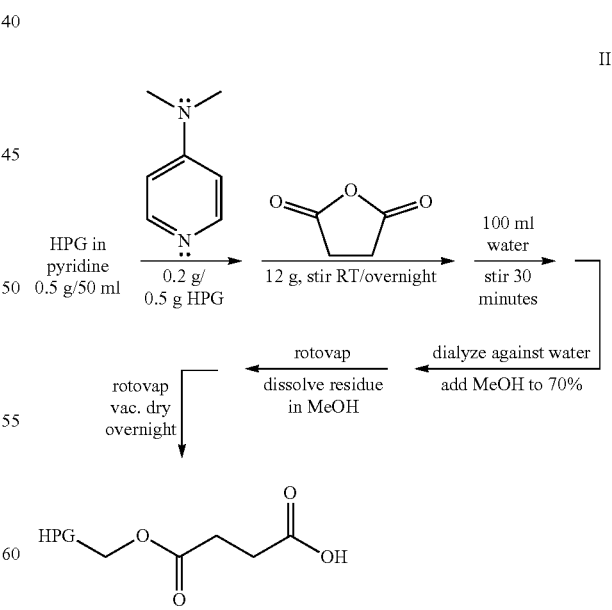

II

Pyridine (50 mL) was added to HPG-$C_{8/10}$ (0.5 g) and stirred rapidly to dissolve the polymer. Dimethylaminopyridine (0.2 g, 0.0016 moles) was added followed by the slow addition of succinic anhydride (12 g, 0.12 moles). The reaction was stirred overnight at room temperature (approximately 22° C.). Water was added (100 mL) and the mixture stirred for 30 minutes. Solvents were removed by rotary evaporation with the periodic addition of water to enable better evaporation of pyridine by azeotropic distillation. The residue was dissolved in methanol and dialyzed against distilled water for 16 hours using a Spectra/PorDialysis membrane (MWCO: 3500 g/mol). The dialysis medium was changed four times, each time with a greater methanol concentration. The final composition of the dialysis medium was 70% methanol in distilled water. The solvent was removed by rotary evaporation and the polymer dried in a vacuum oven overnight.

Scheme III shows the first reaction scheme attempted for the addition of succinimidyl carbonate to HPG-$C_{8/10}$. Briefly, HPG-$C_{8/10}$ was dried under vacuum at 110° C. and then cooled to room temperature. Acetonitrile and DCM were added to dissolve the polymer. N,N'-disuccinimidyl carbonate (DSC) was then added to the flask. The flask was evacuated and then purged with argon and the reaction was allowed to proceed overnight at room temperature after adding pyridine. After the reaction, most of acetonitrile was removed by rotary evaporation. Methyl tert-butyl ether (MTBE) was added to precipitate the polymer. The supernatant was decanted and DCM was added to dissolve the polymer. The material was filtered through a 10-15 μm Buchner funnel to obtain a clear solution, which was rotovapped to remove the DCM. MTBE was added to precipitate the polymer. The final HPG-$C_{8/10}$—NHS product was dried under vacuum at room temperature.

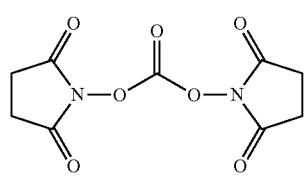

N,N'-Disuccinimidyl Carbonate (DSC)

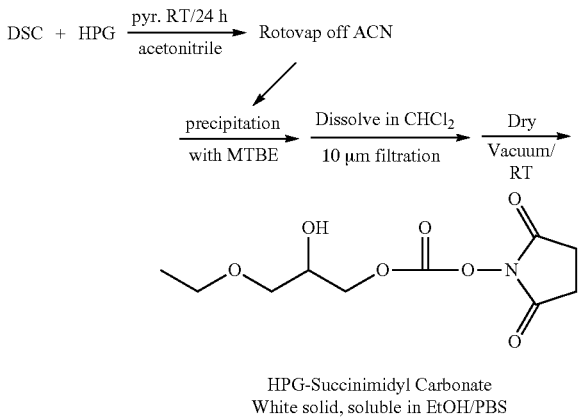

HPG-Succinimidyl Carbonate
White solid, soluble in EtOH/PBS

A second synthetic route was attempted after it was shown that the first attempt produced HPG-$C_{8/10}$—NHS that was highly reactive, to the extent that it was unstable even when stored at −20° C., resulting in cross-linking of the matrix. Scheme IV shows the second reaction scheme attempted for the production of HPG-$C_{8/10}$—NHS. The synthesis involves producing HPG-$C_{8/10}$—COOH as described above as an intermediate, then reacting it further with NHS to produce HPG-$C_{8/10}$—COOH—NHS.

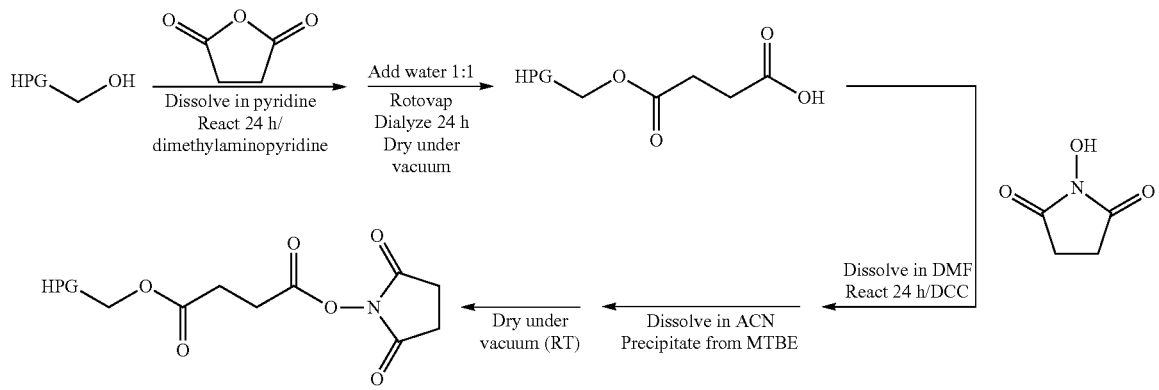

HPG-$C_{8/10}$ and succinic anhydride are dissolved in pyridine and reacted for 24 h at room temperature with dimethylaminopyridine (DMAP) as a catalyst. The reaction was terminated by the addition of an equal volume of water and the pyridine was removed by rotovapping the solution. The aqueous solution of HPG-$C_{8/10}$—COOH was dialyzed for 72 h (MWCO: 3500 g/mol) to remove residual solvent, and freeze dried. The HPG-$C_{8/10}$—COOH was further reacted with N-hydroxy succinamide (NHS) for 24 hours at room temperature in dimethyl formamide (DMF) with N,N'-dicyclohexylcarbodiimide (DCC) as the catalyst. At the end of the reaction, DMF was removed through rotary evaporation. The product was isolated as described above. It was precipitated with MTBE, filtered in acetonitrile, rotovapped and precipitated with MTBE prior to drying.

HPG-$C_{8/10}$-MePEG-$NH_2$ batches with various amine densities were produced using the procedure below, summarized in Scheme V. Various stoichiometries of reagents were used for each batch, described in Table 1.

V

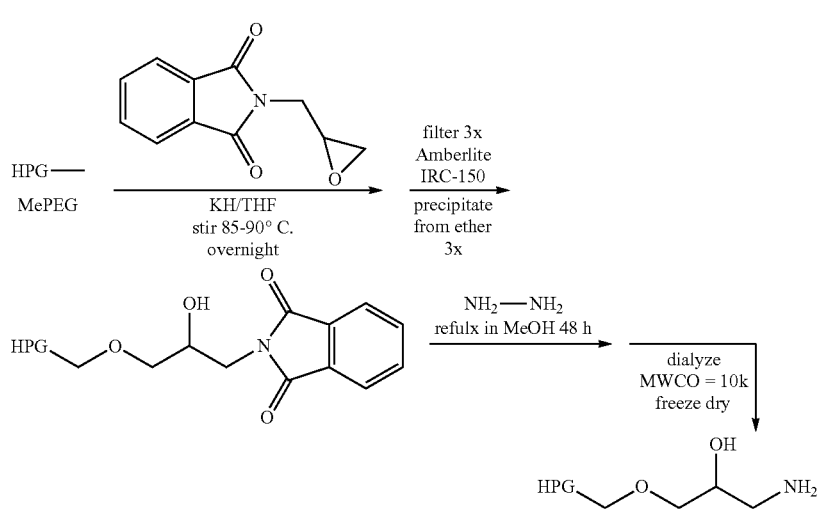

HPG-C$_{8/10}$-MePEG (4 g) was dissolved in 15 ml anhydrous 1,4-dioxane. Potassium hydride (0.45 g) was rinsed with hexanes three times and dried under vacuum. The polymer solution was combined with the KH and stirred at room temperature until a clear solution was formed, approximately 20% of the OH groups on HPG-C$_{8/10}$-MePEG were deprotonated. N-(2,3-epoxypropyl)phthalimide) (EPP) (1.184 g) was dried by dissolution in dichloromethane with stirring overnight over Na$_2$SO$_4$ or MgSO$_4$. The solution was filtered and dried under vacuum to remove the dichloromethane. The dried EPP was dissolved in anhydrous 1,4-dioxane and added to the polymer with stirring overnight at about 85-90° C. The product was neutralized by passing it three times through a cation exchange resin column (Amberlite IRC-150) and then precipitated three times from ether to remove unreacted EPP. By NMR, 15.5% of the phthalimide groups were attached to the HPG-C$_{8/10}$-MePEG. Cleavage of the phthalimide function was achieved by hydrazinolysis (refluxing with hydrazine monohydrate). Excess hydrazine monohydrate solution (2 mL) was added to the solution of the polymer in methanol and the mixture was refluxed for 48 h. After refluxing, the methanol was evaporated, the polymer was dialysed against water using a MWCO: 10000 g/mol membrane for 48 h and freeze dried.

TABLE 1

Stoichiometry of reagents used to produce HPG-C$_{8/10}$—MePEG-NH$_2$

| Target NH$_2$ substitution % | HPG-NH$_2$ information Mass of reagents (g) | | |
|---|---|---|---|
| | HPG-C$_{8/10}$—MePEG | KH | EPP |
| 5% | 2 | 0.1 | 0.2 |
| 15% | 4 | 0.45 | 1.184 |
| 20% | 4 | 0.6 | 1.575 |

The obtained polymers have been characterized by NMR, FTIR, DSC and TGA. NMR is particularly useful in confirming the branched structure and the presence of surface groups added to the shell of the polymer. For some surface chemistries, FTIR analysis is also useful to confirm the consumption of hydroxyl groups and their replacement with other groups, wherein the chemistry of those groups provides a distinct IR spectrum from the rest of the HPG structure, for example, the addition of C═O bonds. For example, FTIR may be used to confirm the addition of —COOH groups to the surface or the addition of groups through an ester linkage.

Example 2

Encapsulation of Paclitaxel or Docetaxel into the dHPGs

Paclitaxel or docetaxel together with a dHPG may be dissolved in a small amount of acetonitrile and dried in an oven at 60° C. for one hour, then flashed with a nitrogen stream to eliminate traces of the organic solvent. The resulting dHPG/paclitaxel or dHPG/docetaxel matrix may be hydrated with 10 mM phosphate buffered saline (pH 7.4), vortexed for two minutes and incubated in an oven at 60° C. for one hour. The resulting solution is generally clear. In those cases where a white precipitation was observed, the solution may be centrifuged (18 000 g for ten minutes) and the supernatant may be transferred to a new vessel and kept in a cool place until use.

Example 3

Stability of Docetaxel and Paclitaxel in dHPGs

The stability of docetaxel ("DTX") incorporated into dHPGs is characterized in terms of the degradation of DTX to inactive breakdown products, and its interconversion to its bioactive epimer ("7-epi-DTX"). Formation of the epimer for paclitaxel and docetaxel is known to occur as an equilibrium whereas degradation to inactive breakdown products is irreversible. Stability as described in various dHPGs has been analyzed using ultra performance liquid chromatography (UPLC). A Waters Acquity UPLC BEH C$_{18}$ column (2.1×50 mm, 1.7 μm) was used for separation of major degradation peaks. The injection volume was 3 μL. The mobile phase was a 10 mM solution of ammonium acetate that was prepared by weighing 0.385 g of the salt and dissolving it into 500 mL of HPLC grade water. The pH was adjusted to pH 4.0 using acetic acid. Stock solutions of DTX (2 mg/mL) were prepared in methanol and stored in a −20°

C. freezer. A set of standards containing DTX were prepared in 50/50 methanol/water over a range of 0.5-100 μg/mL. Limit of detection (LOD) and limit of quantitation (LOQ) were both 1 μg/mL. The calibration curve from 1-100 μg/mL was linear with $R^2$ of 0.9998 for DTX. A 1/x weighting was applied. Method accuracy and precision were verified at LOQ (1 μg/mL) and mid-range (10 μg/mL). Five replicate injections were made in each case. Table 2 summarizes the accuracy and precision obtained for DTX at these concentrations.

TABLE 2

Accuracy and precision obtained for detection of DTX by UPLC

| Sample # | Analyte Name | Theoretical Conc. (μg/mL) | Average Conc. (μg/mL) | Accuracy | % RSD n = 5 |
|---|---|---|---|---|---|
| 1 | DTX | 1.00 | 1.12 | 112% | 8% |
| 2 | DTX | 10.0 | 9.90 | 99% | 0% |

Forced degradation of DTX was performed to generate samples for evaluation of method specificity. Degradation of DTX was achieved by preparing a solution containing 300 μL of methanol, 150 μL of 5% ammonium hydroxide, and 50 μL of a stock DTX prodrug which degrades to DTX within minutes at alkaline pH. DTX prodrug conversion to DTX and DTX degradation were monitored for over two hours. After 2.2 hours on-tray (room temperature), effectively all prodrug degraded to DTX and other components. The degraded sample was analyzed using the method described above to ascertain resolution of DTX prodrug, DTX, and related degradants.

Figure 2:
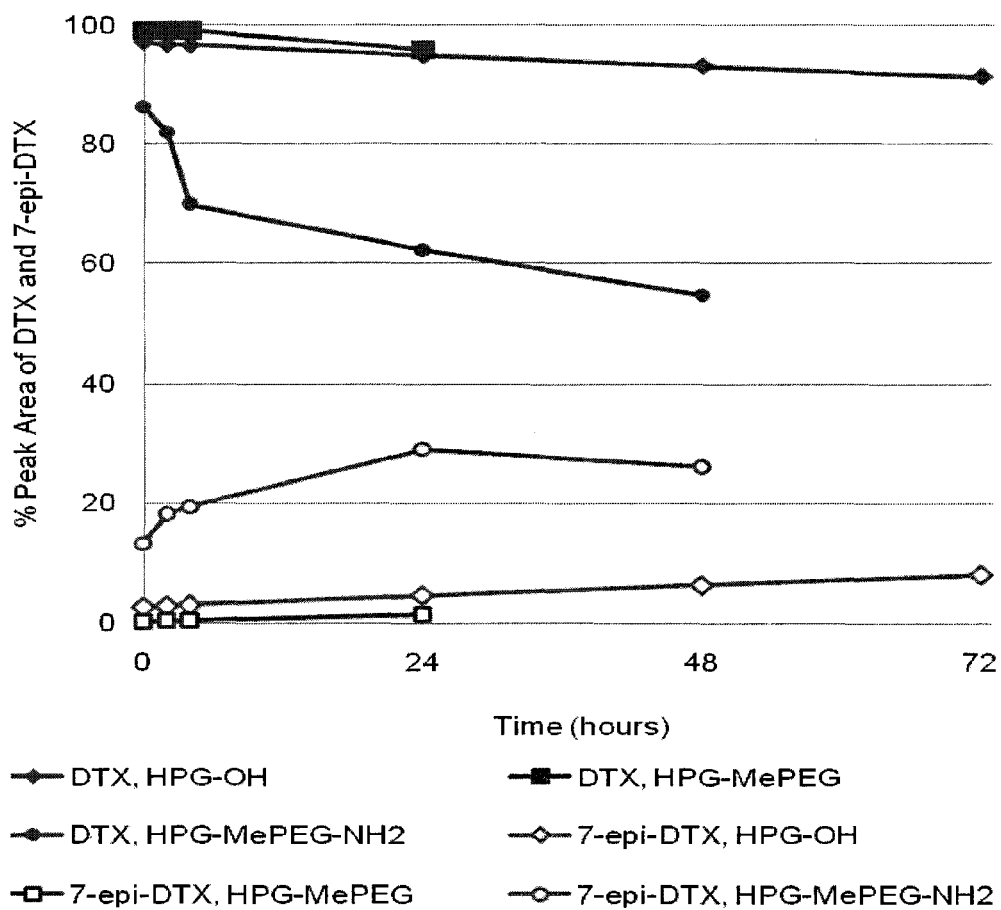
FIG. 2 shows the peak area of eluents of DTX and its epimer (7-epi-DTX) as a function of time to determine the stability of dHPGs as described herein incorporating DTX.

Using the above UPLC method, DTX is the eluent at 2.99 minutes and 7-epi-DTX is the eluent at 3.15 minutes. A sample chromatograph is shown in FIG. 1. The peaks between 1.4 and 2.0 minutes are products of the degradation of DTX and 7-epi-DTX. The peak area of DTX and 7-epi-DTX was calculated as a function of time and then used to determine the percentage of DTX or epi-DTX remaining in the dHPG. The results are shown in FIG. 2. As can be seen from FIG. 2, those formulations comprising DTX were stable when the HPG polymer was HPG-$C_{8/10}$ and HPG-$C_{8/10}$-MePEG which retained over 90% of the incorporated DTX as DTX and 7-epi-DTX over a period of 72 hours in PBS buffered to pH 7.3. The remaining amount of drug had degraded to inactive components and each of these which contributed more than 2% of the total samples were identified by mass spectrometry MRM experiments. These experiments were conducted to identify the ion fragments associated with DTX's known degradation products.

Figure 3A:
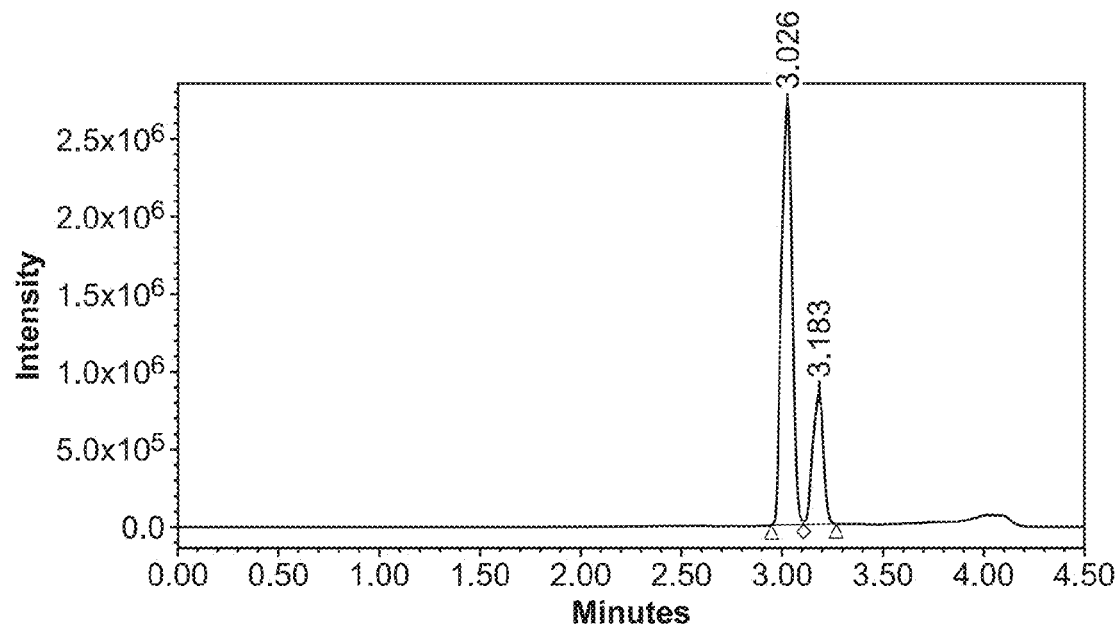
FIG. 3A shows a single ion recording (SIR) of DTX and 7-epi-DTX ion ($+H^+$) m/z 808.5 in HPG-$C_{8/10}$ incorporating DTX.
Figure 3B:
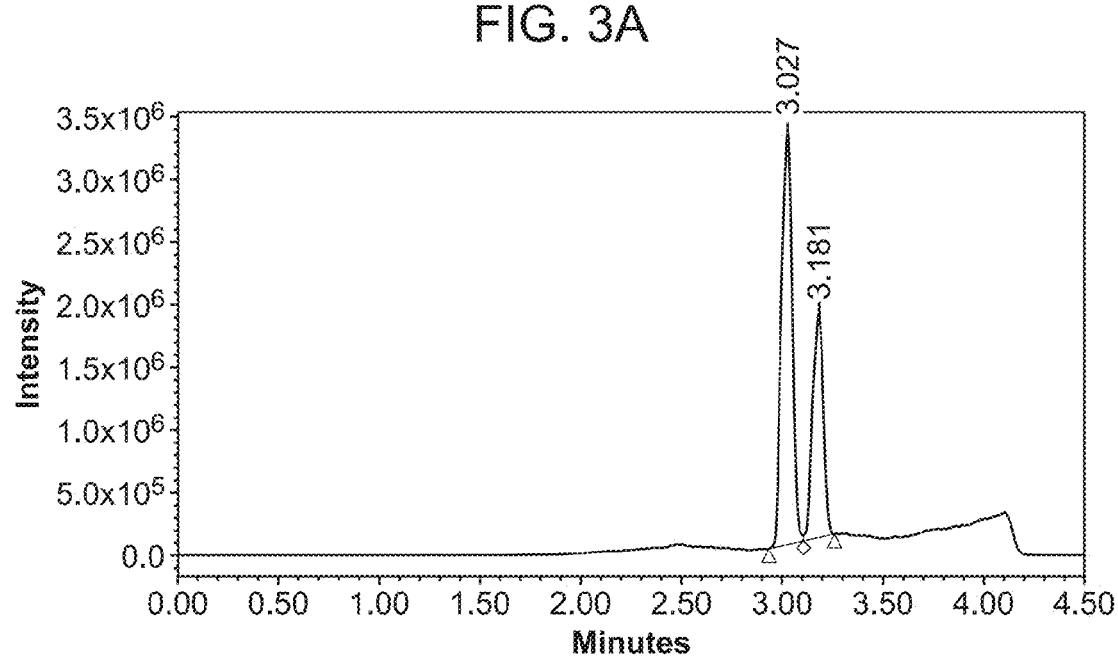
FIG. 3B shows a SIR of DTX and 7-epi-DTX ion ($+H^+$) m/z 808.5 in HPG-$C_{8/10}$-MePEG-$NH_2$ incorporating DTX.
Figure 4:
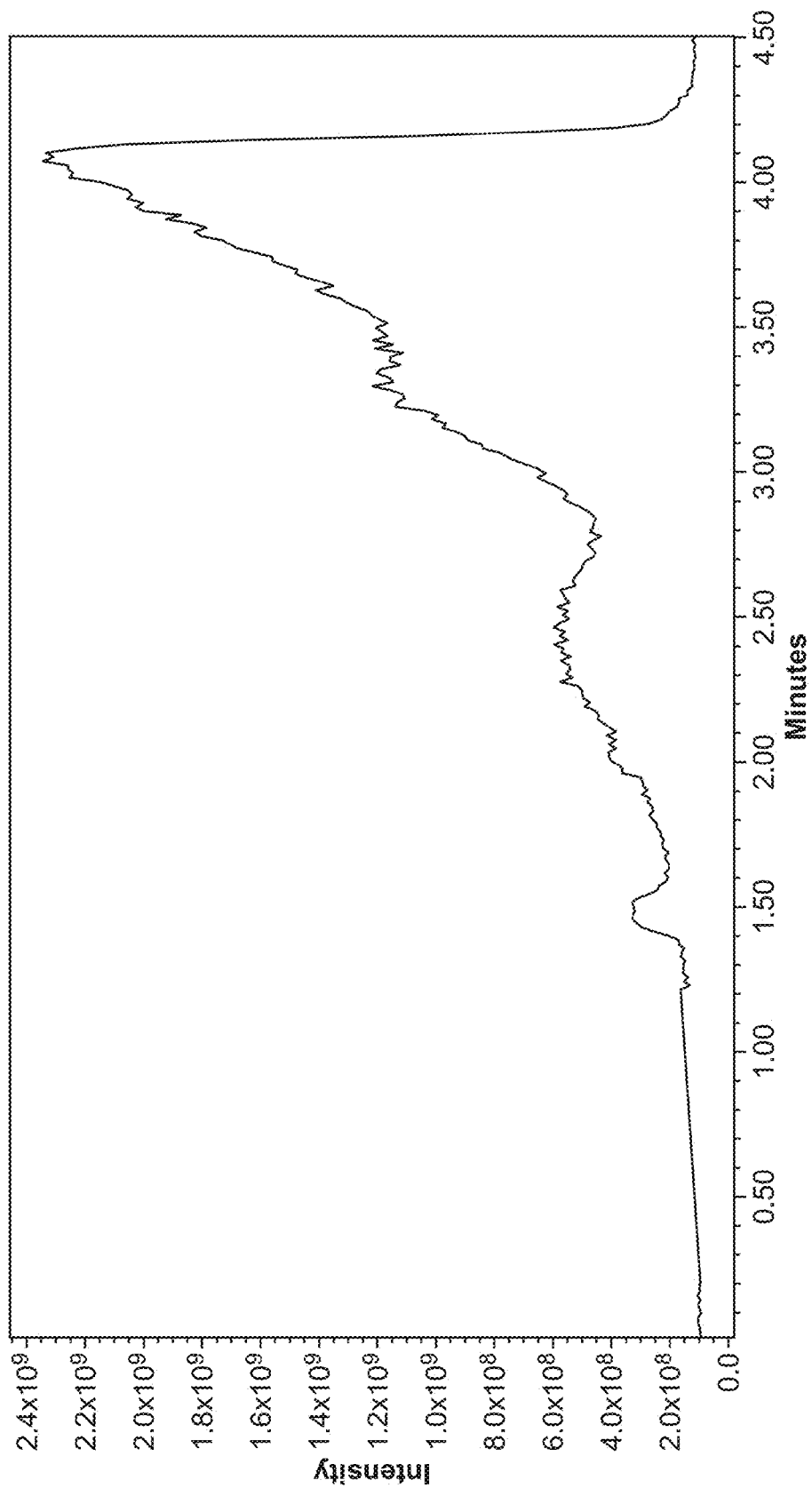
FIG. 4 shows the total ion current (TIC) for HPG-$C_{8/10}$-MePEG-$NH_2$ incorporating DTX.
Figure 5:
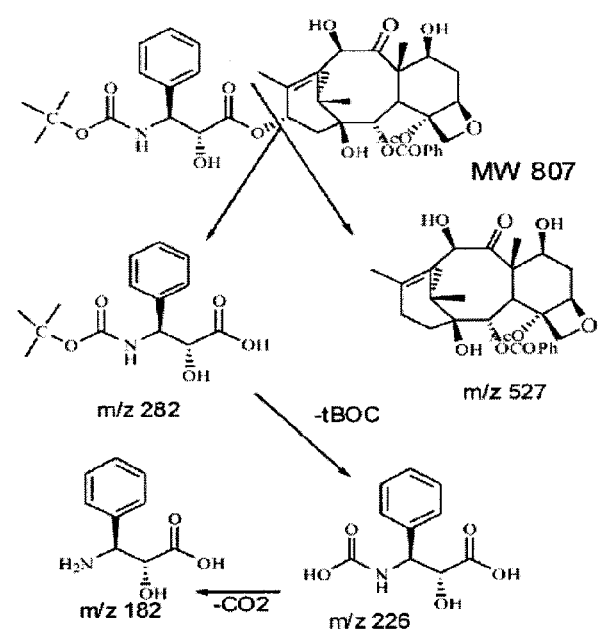
FIG. 5 shows a prior art fragmentation pattern proposed for DTX.

A single ion recording (SIR) of DTX and 7-epi-DTX ion (+$H^+$) m/z 808.5 in the HPG-$C_{8/10}$ and HPG-$C_{8/10}$-MePEG-$NH_2$ formulations are compared in FIGS. 3A and 3B, respectively. Both chromatograms show the presence of the 7-epi degradant, although it is present in greater proportion in the HPG-MePEG-$NH_2$ sample. For FIGS. 3A and 3B the tallest peaks are DTX and the lower peaks are 7-epi-DTX. Although the total ion chromatogram shows a very high signal overall due to the polymeric constituents (FIG. 4) in the formulation, additional masses known to match DTX degradant fragments (Kumar et al 2007 Isolation and characterization of degradation impurities in docetaxel drug substance and its formulation, Kumar et al., Journal of Pharmaceutical and Biomedical Analysis 12 Mar. 2007 43(4):1228-1235) were identified coinciding with the largest degradant peaks (FIG. 5). M/z of 226 and 282 were observed at 1.5 minutes, which may correspond to fragments from the DTX side chain. However, m/z of 583 was present, which corresponds to 10-deacetyl baccatin III+$K^+$, indicating the taxane contains both the core and the sidechain. M/z of 320 and 562 were also observed. The peak at 2 minutes had m/z=581 and 583, which may correspond to 10-oxo-10-deacetylbaccatin III+$K^+$ and 10-deacetyl baccatin III+$K^+$, respectively. This peak position is also in the region of the chromatogram where baccatin degradants are expected to be observed.

Figure 6:
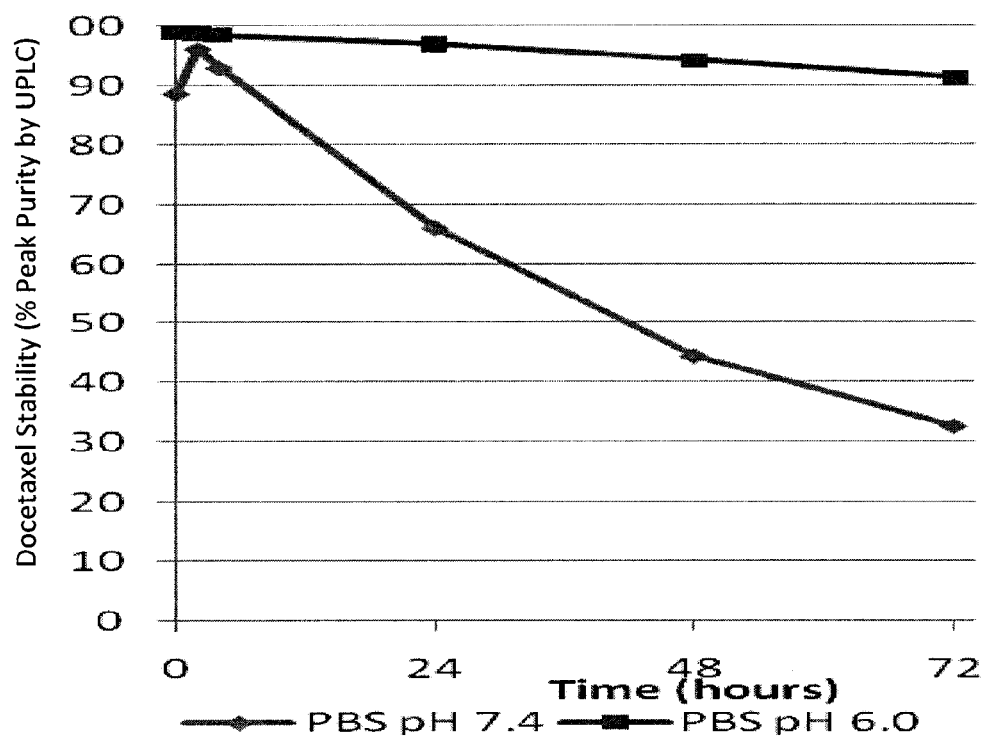
FIG. 6 shows the peak area of eluents of DTX (and 7-epi-DTX) as a function of time for HPG-$C_{8/10}$-MePEG-$NH_2$ incorporating DTX at pH 7.4 and at pH 6.0.

Stability of some of the formulations may be further increased by adjusting the pH of the formulations. For example, a composition comprising HPG-$C_{8/10}$-MePEG-$NH_2$ incorporating DTX dissolved in an aqueous medium with buffer salts in a ratio in order to obtain a pH of 5.5-6.5 is more stable than the same composition excluding the buffer salts, or a composition with altered buffer salt composition, e.g. a PBS buffer yielding a pH of 7.4 (FIG. 6). Appropriate buffer salts include phosphate buffering salts. Alternatively, the pH of the composition could be lowered by adding an acid such as HCl to the composition. Furthermore, the degradation of DTX is slowed significantly by altering the pH of the composition.

Example 4

In Vitro Biocompatibility of dHPGs

Figure 7A:
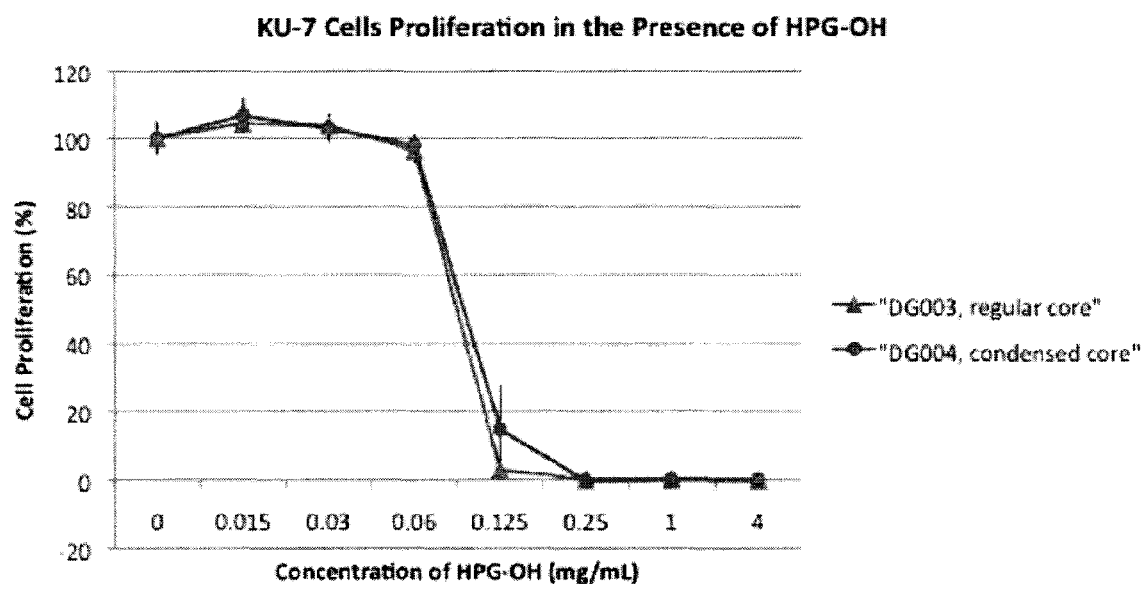
FIG. 7A shows percent KU7 cell proliferation as a function of concentration of HPG-$C_{8/10}$ for a normal core (NC) formulation and a condensed core (CC) formulation.
Figure 7B:
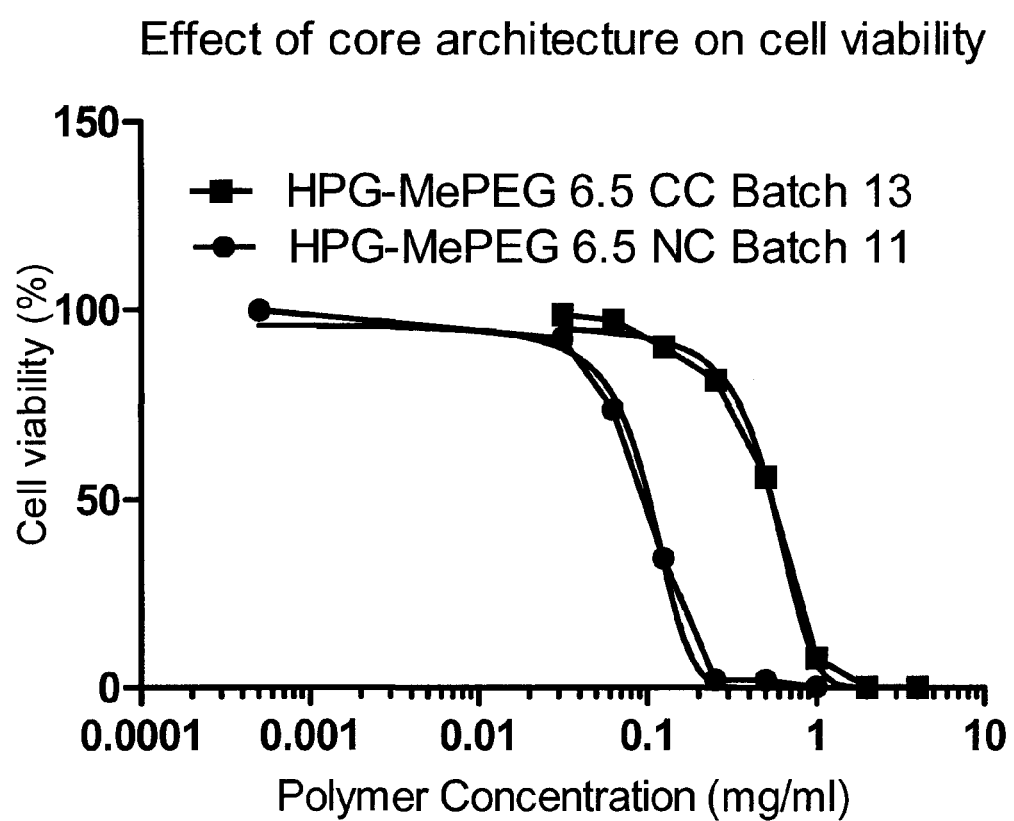
FIG. 7B shows percent KU7 cell proliferation as a function of concentration of HPG-$C_{8/10}$-MePEG for a normal core (NC) formulation and a condensed core (CC) formulation.

The toxicity of the dHPGs was measured by determining whether different dHPG formulations could kill KU7 cancer cells. These experiments were conducted using dHPGs that did not incorporate any drug or biologically active moiety. The results are shown in FIGS. 7A and 7B. FIG. 7A shows the percent KU7 cell proliferation as a function of concentration of HPG-$C_{8/10}$, for both a regular core formulation and a condensed core formulation. Changing the core architecture did not affect the stability of HPG-$C_{8/10}$ significantly. FIG. 7B shows the viability of KU-7 cells as a function of concentration of HPG-$C_{8/10}$-MePEG, for both regular core formulations and condensed core formulations. Polymers with a condensed core show a 10 times higher IC50 for cell viability as compared to a regular core polymer. The dHPGs having a condensed core are better tolerated by cells than dHPGs having a regular core. Both formulations contained 6.5 mol of MePEG per mol of HPG. The condensed core formulations were less cytotoxic to the KU-7 cells than the regular core formulations. Table 3 shows the volume ratios of monomers used to prepare the formulations shown in FIGS. 7A and 7B.

TABLE 3

Volume Ratios of monomers used to prepared formulations shown in FIGS. 7A and 7B

| Formulation | Reaction Step | Volume Glycidol (mL/% v/v) | Volume Octyl/decyl glycidyl ether (mL/% v/v) |
|---|---|---|---|
| regular core | 1 | 13/59% | 9/41% |
| condensed core | 1 | 9/50% | 9/50% |
| regular core | 1 | 13/59% | 9/41% |
| condensed core | 1 | 9/50% | 9/50% |
|  | 2 | 4/100% | 0/0% |
| condensed core | 1 | 9/50% | 9/50% |
|  | 2 | 8/100% | 0/0% |
| regular core | 1 | 13/59% | 9/41% |

Figure 8:
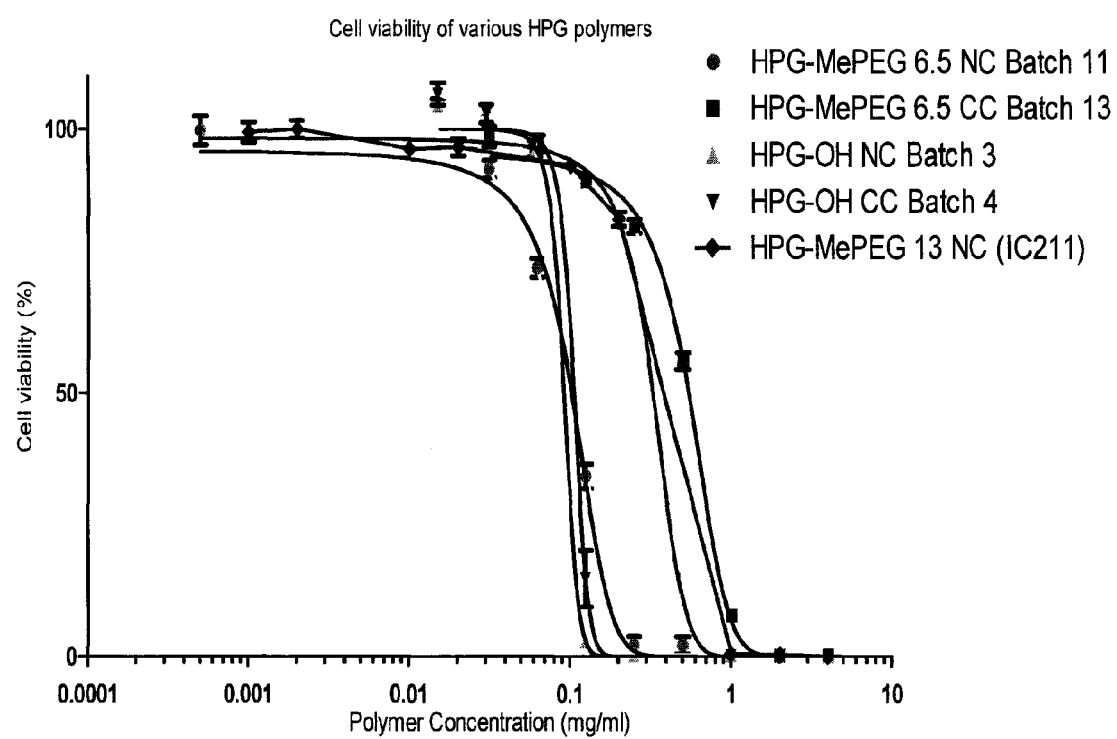
FIG. 8 shows percent KU7 cell proliferation as a function of polymer concentration to determine biocompatibility of various dHPGs.

FIG. 8 shows that HPG-$C_{8/10}$ polymers, without a MePEG outer shell are among the least tolerated, and that without the MePEG shell, altering the core from the regular to the condensed core architecture has no benefit in terms of improved cell viability. HPG-OH signifies that it is a HPG without MePEG on the surface. However, when MePEG is added the benefit becomes noticeable. The HPG-$C_{8/10}$-MePEG$_{6.5}$ formula (with 6.5 mol MePEG per HPG) shows tolerability comparable to the HPG-$C_{8/10}$ when the normal core versions are compared, but when the condensed core architecture is used, the tolerability of the HPG-$C_{8/10}$-MePEG$_{6.5}$ improves to the level of the regular core HPG-$C_{8/10}$-MePEG13, which has double the amount of MePEG in the shell. Previously disclosed HPG-MEPEG polymers (Mugabe C. et al. 2008 BJUI 103:978-986) also had higher MEPEG amount, although they were not quantified, they are estimated at >15 mol % and were being well tolerated.

Example 5

In Vitro Cell Uptake Assay Showing that dHPGs are Carried into Cells

The uptake of fluorescien-labeled HPG-$C_{8/10}$—COOH—NHS and HPG-$C_{8/10}$—COOH into KU7 cells was examined. The dHPG was dissolved in FBS-free media at 1 mg/mL. Into each plate of a 12-well plate, 250 µL of dHPG was exposed to cells on coverslips. The plate was washed twice with PBS followed by a 10 minute fix with 3.7% formaldehyde in PBS. Again the plate was washed twice with PBS. The coverslips were mounted using Prolong Gold™ with DAPI.

A Z-stack of HPG-$C_{8/10}$—COOH was also viewed in order to confirm that the polymer was actually taken up into the KU-7 cell and did not merely remain on the surface of the cell. As fluorescence was observed at all angles viewed, it was found that the dHPGs were inside the cell. These results show that the dHPGs are taken up into the cells and do not cause any untoward effects inside the cell. In vitro data shows that when HPGs are exposed to cells, the HPG-$C_{8/10}$—COOH—NHS and HPG-$C_{8/10}$—COOH are both taken up by one hour. In the body however, the contact is not as complete as the in vitro scenario and prolonged exposure to facilitate this uptake is required.

Example 6

Loading of Taxanes into Condensed Core and Regular Core dHPGs

The maximum drug loading of condensed and regular core HPG-$C_{8/10}$-MePEG was investigated. DTX and PTX were loaded into HPG-$C_{8/10}$-MePEG to target drug concentrations of 0.5, 1.0, 2.0 and 3.0 mg/mL. Solutions of 100 mg/mL of polymer in THF were prepared and DTX or PTX were added. The THF was dried under a $N_2$ stream for about two hours and then dried in a hood oven overnight. The HPG-$C_{8/10}$-MePEG/PTX and HPG-$C_{8/10}$-MePEG/DTX matrices were hydrated with PBS buffer (pH 7.4). The resulting solutions were spun down at 14000 rpm for about 15 minutes. The supernatant liquids were tested by HPLC to obtain the concentrations of drug encapsulated in the HPG-$C_{8/10}$-MePEG. The results are shown in Table 4.

TABLE 4

Theoretical and actual loading of DTX and PTX into condensed core ("CC") and regular core ("RC") HPG-$C_{8/10}$-MePEG

| Target Loading (mg/mL) | Actual Loading of DTX into CC HPG-$C_{8/10}$-MePEG (mg/mL) | Actual Loading of PTX into CC HPG-$C_{8/10}$-MePEG (mg/mL) | Actual Loading of DTX into RC HPG-$C_{8/10}$-MePEG (mg/mL) | Actual Loading of PTX RC HPG-$C_{8/10}$-MePEG (mg/mL) |
|---|---|---|---|---|
| 0.5 | 0.47 | 0.37 | 0.47 | 0.45 |
| 1.0 | 0.92 | 0.67 | 0.88 | 0.67 |
| 2.0 | 1.40 | 0.80 | 1.80 | 0.70 |
| 3.0 | 2.30 | 0.29 | 2.30 | 0.50 |

It was found that loading was superior for DTX than for PTX.

Example 7

Synthesis and Characterization of HPG-$C_{8/10}$ and HPG-$C_{8/10}$-MePEG

Polymerization of octyl/decyl glycidyl ether (O/DGE, $C_{8/10}$) core modified HPGs was carried out in a single pot synthetic procedure based on ring-opening polymerization of epoxides according to reported protocols (Kainthan, R. K., Mugabe, C., Burt, H. M., Brooks, D. E., 2008. *Biomacromolecules* 9, 886-895).

All chemicals were purchased from Sigma-Aldrich (Oakville, ON) and all solvents were HPLC grade from Fisher Scientific (Ottawa, ON). α-epoxy, ω-methoxy polyethylene glycol 350 (MePEG 350 epoxide) was synthesized from a reaction of MePEG 350, sodium hydroxide, and epichlorohydrin. Octyl/decyl glycidyl ether, potassium methylate and trimethyloyl propane (TMP) were obtained from Sigma-Aldrich and used without further purification.

120 mg of the initiator (TMP) was mixed with 1.5 ml of potassium methylate solution in methanol (25%, w/v) and added to a three-neck round-bottom flask under argon atmosphere. The mixture was stirred at 105° C. for 1 h, after which excess methanol was removed under vacuum, then, 13 ml of glycidol and 9 ml of O/DGE mixture was injected using a syringe pump at a rate of 1.4 ml/h to the initiator. The stirring rate was fixed at 68 rpm using a digital overhead stirring system (BDC2002). After completion of monomer addition the mixture was stirred for an additional 6 h. Purified polymers were obtained by extraction with hexane to remove unreacted octyl/decyl glycidyl ether. The product was then dissolved in methanol and neutralized by passing three times through a cation exchange column (Amberlite IRC-150, Rohmand Haas Co., Philadelphia, Pa.). Methanol was removed under vacuum and an aqueous solution of the polymer was then dialysed for three days against water using cellulose acetate dialysis tubing (MWCO 10,000 g/mol, Spectrum Laboratories), with three water changes per day.

$^1$H NMR (400 MHz, D$_6$-DMSO) δ$_H$: 0.75-0.82 (—CH$_3$, TMP); 0.82-0.91 (—CH$_3$-alkyl on O/DGE); 1.16-1.53 (—CH$_2$—, alkyl on O/DGE); 2.46 (solvent, D$_6$-DMSO); 3.16-3.80 (—CH and —CH$_2$—, from HPG core); 4.8 (—OH).

HPG-C$_{8/10}$-MePEG containing different amounts of MePEG were prepared and designated HPG-C$_{8/10}$-MePEG$_{6.5}$ and HPG-C$_{8/10}$-MePEG$_{13}$ to indicate the amount of MePEG added to the feed (6.5 and 13 mol of MePEG per mole of HPG, respectively). The synthesis was carried out in a similar fashion as the HPG-C$_{8/10}$ reaction except that different amounts of MePEG 350 epoxide were added to the reaction mixture in the final step of the synthesis. The reaction scheme for the one-pot synthesis of alkyl (R) derivatized HPG-C$_{8/10}$-MePEG is summarized in Scheme VI.

After all of the mixture of glycidol and O/DGE was injected, the reaction was continued to about 6 h. Then 0.1 ml of potassium hydride (KH) was added to the flask. The mixture was stirred for 1 h, after which 10 ml or 20 ml of MePEG 350 epoxide was added as a terminal step in the "one pot" synthesis using a syringe pump at a rate of 1.4 ml/h. The amount of MePEG 350 was added according to the targeting density on HPGs (i.e. 10 ml of MePEG350 is for the targeting of 6.5 mol of MePEG on per mole of HPG). The stirring rate was then increased to 90 rpm and the reaction was continually carried out at 105° C. for overnight. Any traces of unreacted octyl/decyl glycidyl ether were removed by extraction with hexane. The product was dissolved in methanol and neutralized by passing it three times through a cation exchange column (Amberlite IRC-150, Rohm and

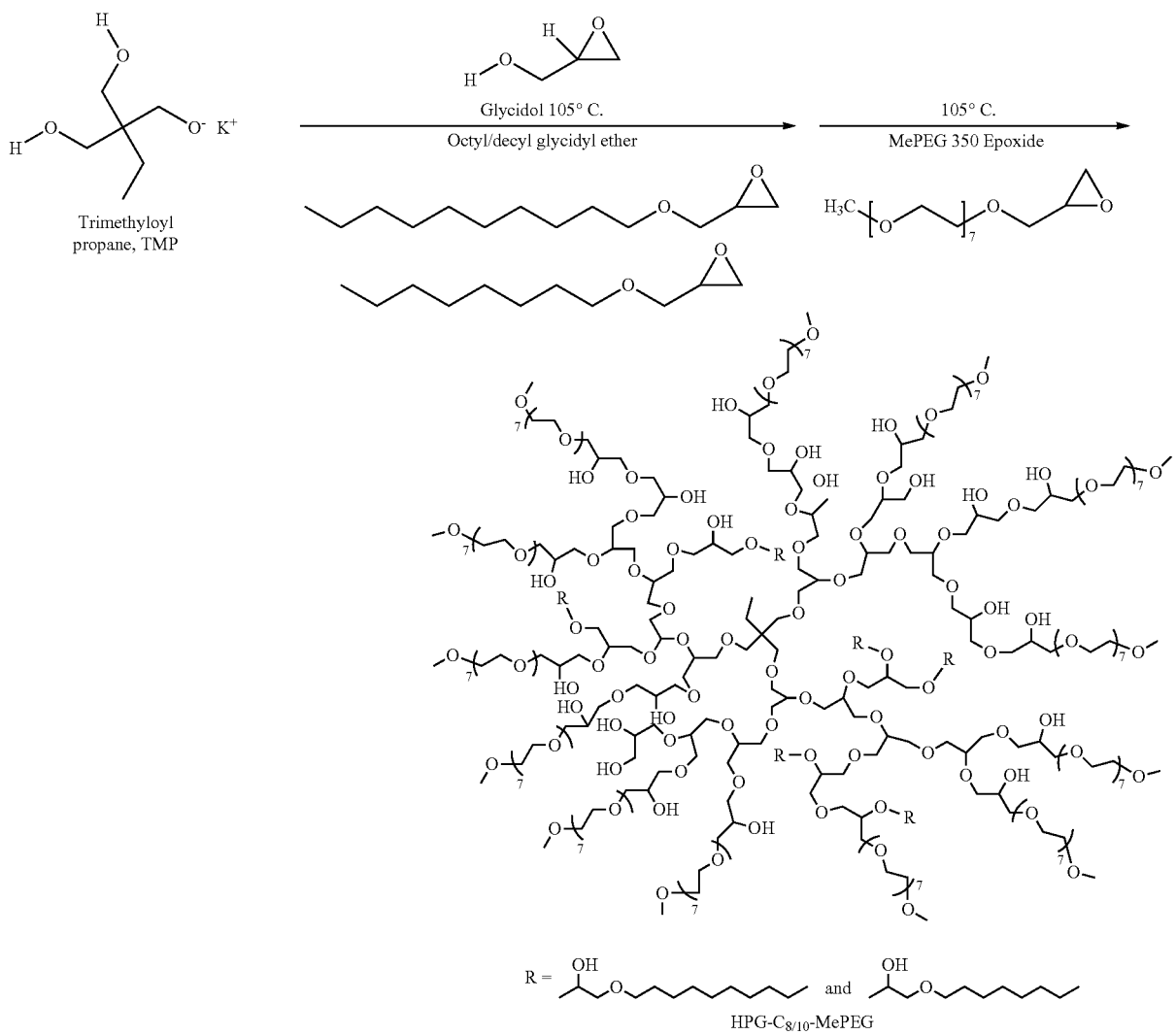

120 mg of the initiator (TMP) was mixed with 1.5 ml of potassium methylate solution in methanol (25%, w/v) and added to a three-neck round-bottom flask under argon atmosphere. The mixture was stirred at 105° C. for 1 h, after which excess methanol was removed under vacuum, then, 13 ml of glycidol and 9 ml of O/DGE mixture was injected using a syringe pump at a rate of 1.4 ml/h to the initiator.

Haas Co., Philadelphia, Pa.). Methanol was removed under vacuum and an aqueous solution of the polymer was then dialysed for three days against water using cellulose acetate dialysis tubing (MWCO 10,000 g/mol, Spectrum Laboratories), with three water changes per day to remove unreacted MePEG epoxides. Dry polymer was then obtained by freeze-drying.

$^1$H NMR (400 MHz, D$_6$-DMSO) $\delta_H$: 0.75-0.82 (—CH$_3$, TMP); 0.82-0.92 (—CH$_3$-alkyl on O/DGE); 1.15-1.55 (—CH$_2$—, alkyl on O/DGE); 2.50 (solvent, D$_6$-DMSO); 3.15-3.80 (—CH and —CH$_2$—, from HPG core); 3.23 (—OCH$_3$— from MePEG); 3.32 (residual water); 4.8 (—OH).

HPG-C$_{8/10}$ (HPG without MePEG chains) was prepared by anionic ring opening multibranching polymerization of glycidol from partially deprotonated trimethylol propane (TMP) using potassium methylate. HPG-C$_{8/10}$ has numerous terminal hydroxyl end groups, the number per molecule being roughly equal to the degree of polymerization. The HPG-C$_{8/10}$ core was derivatized with C$_{8/10}$ alkyl chains to create a hydrophobic core, to allow for loading of drug, for example, taxanes. MePEG chains were linked to hydroxyl groups on HPGs. Since MePEG 350 epoxide was added to the polymerization reaction after reaction of the other components, a hydrophilic shell is formed to increase the aqueous solubility of the HPGs.

Figure 9:
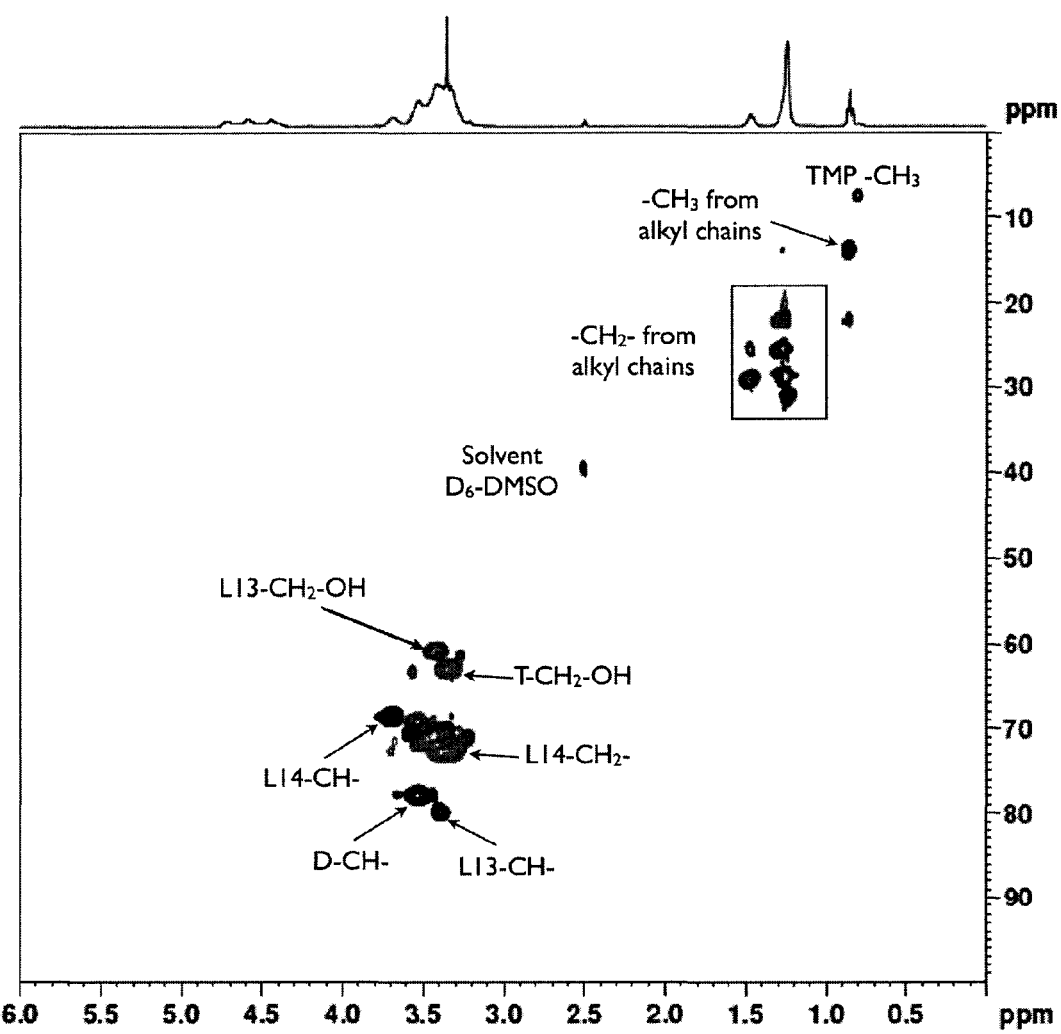
FIG. 9 shows 400 MHz proton (top) and HSQC spectra of HPG-$C_{8/10}$ in $D_6$-DMSO. D, $L_{13}$, and $L_{14}$ represent dendritic, linear 1-3, and linear 1-4 units, respectively.
Figure 10:
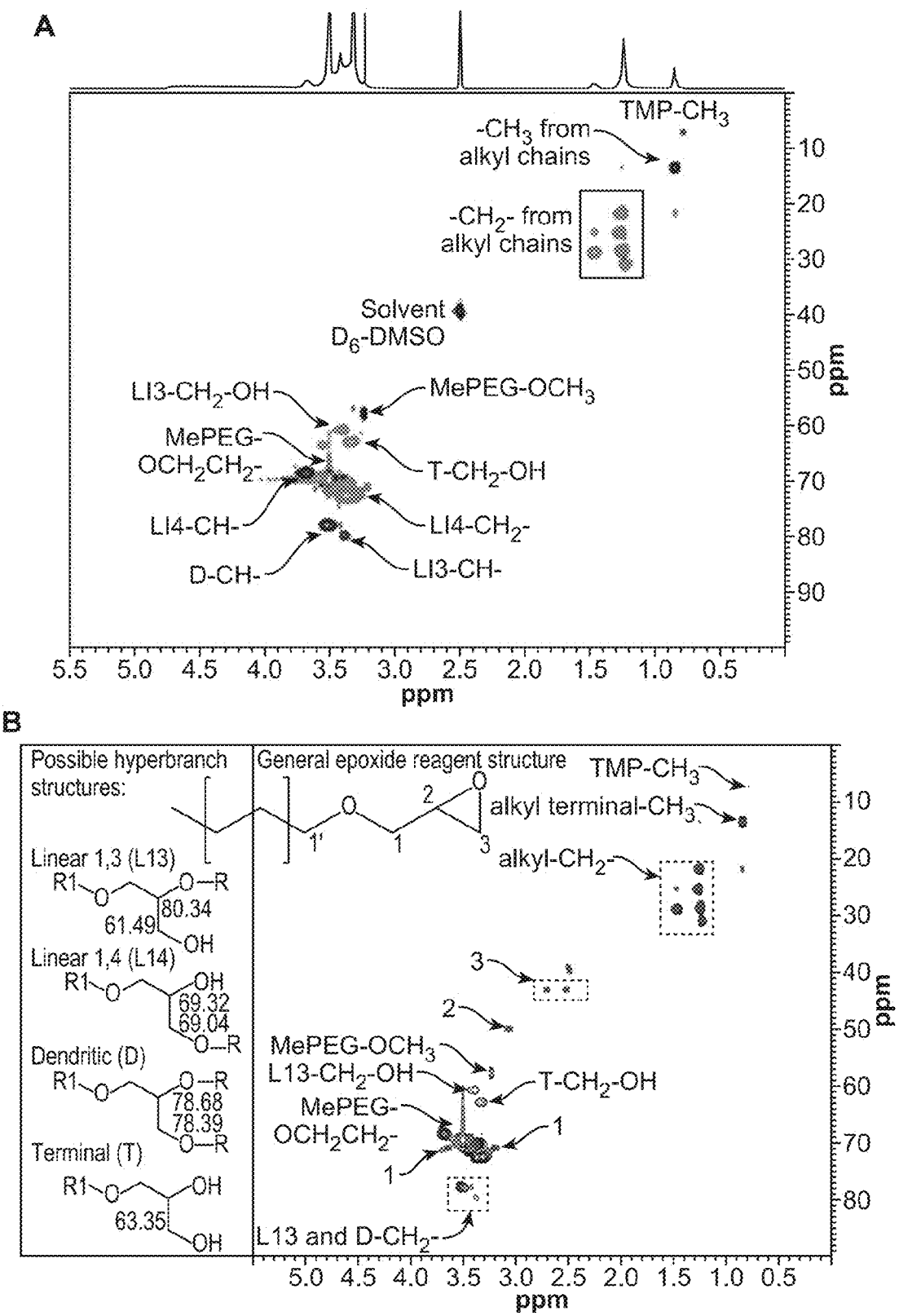
FIG. 10 shows (A) 400 MHz HSQC proton (top) and HSQC spectra of HPG-$C_{8/10}$-MePEG$_{6.5}$ and (B) superimposed 400 MHz HSQC spectra of MePEG 350 epoxide, O/DGE, and HPG-$C_{8/10}$-MePEG$_{13}$ polymer.

NMR experiments were conducted to characterize the structure of the HPG polymers. The fractions of MePEG and alkyl chains on HPGs were estimated from heteronuclear single quantum coherence (HSQC) NMR experiments recorded on a Bruker Avance 400 MHz NMR spectrometer using deuterated solvents (Cambridge Isotope Laboratories, 99.8% D). Chemical shifts were referenced to the residual solvent peak. HSQC spectra were analyzed using Sparky (T. D. Goddard and D. G. Kneller, Sparky 3, University of California, San Francisco). FIGS. 9 and 10 show representative proton and 2D HSQC spectra of HPG-C$_{8/10}$ and HPG-C$_{8/10}$-MePEG polymers. All the peaks were assigned to the structural components of the HPGs, using the raw material spectra as the starting reference (FIG. 10B). The proton NMR spectra were similar to those reported (Kainthan, R. K., Janzen, J., Kizhakkedathu, J. N., Devine, D. V., Brooks, D. E., 2008. *Biomaterials* 29, 1693-1704; Kainthan, R. K., Mugabe, C., Burt, H. M., Brooks, D. E., 2008. *Biomacromolecules* 9, 886-895). HSQC NMR data confirmed the structure of HPGs as hyperbranched polymers with the branching architectures evident in the spectra (FIGS. 9 and 10). The fractions of each of the substituents were calculated from the volume integrals in HSQC experiments. By comparing the integrals of the MePEG methoxy-group and the O/DGE methyl group to the integral of the TMP CH$_3$ group, the fractions of O/DGE and MePEG (mol/mol) were calculated for each HPG polymer. The HSQC data showed the absence of unreacted epoxide monomers (FIG. 10), which indicates the absence of contamination of the polymer by unreacted monomers.

Molecular weights and polydispersities of the dHPG polymers were determined by gel permeation chromatography with multi-angle laser light scattering detection (GPC-MALLS). Molecular weights were around 80,000 g/mol (Table 5).

The physicochemical characteristics of dHPGs are summarized in Table 5.

TABLE 5

The physical characteristics of HPG-C$_{8/10}$-OH and HPG-C$_{8/10}$-MePEG loaded with PTX and DTX

| HPGs | Structure by NMR (mol/mol HPG) | | Molecular weight & Polydispersity | | Thermal properties | | | |
|---|---|---|---|---|---|---|---|---|
| | MePEG | O/DGE | M$_w$ × 10$^4$ | M$_w$/M$_n$ | Tg (° C.)[1] | Td (° C.)[2] | Tg (PTX)[3] | Tg (DTX)[3] |
| HPG-C$_{8/10}$ | — | 4.7 | ND | ND | −37.5 | 338 | — | — |
| HPG-C$_{8/10}$-MePEG$_{6.5}$ | 4.0 | 4.7 | 7.6 | 1.01 | −45.2 | 341 | −68.8 | −68.3 |
| HPG-C$_{8/10}$-MePEG$_{13}$ | 4.6 | 4.7 | 8.3 | 1.22 | −55.4 | 344 | −54.9 | −58.4 |

[1]Tg, glass transition taken at midpoint of transition
[2]Td, degradation temperature taken at maximum weight loss
[3]PTX and DTX were loaded at the maximum loading capacity of HPG-C$_{8/10}$-MePEG
M$_w$, weight average molecular weight determined by gel permeation chromatography connected to MALLS detector (GPC-MALLS)
M$_w$/M$_n$ polydispersity
ND, not determined Example 8

Effect of Purification Processes on Thermal Properties of dHPGs and on Physical and Chemical Stabilities of dHPGs Loaded PTX and DTX The effect of purification processes on the thermal and degradation properties of dHPGs was evaluated by differential scanning calorimetry (DSC) and thermogravimetric analysis (TGA). Purified dHPGs are referred to polymers that have been through various purification steps, for example, extraction with hexane to remove unreacted C$_{8/10}$ alkyl chains followed by neutralization through a cation exchange column and then dialysis.

Thermal analysis was conducted using a TA Instruments DSC Q100 and a TGA Q50. DSC runs were obtained by cycling weighed samples in hermetic sealed aluminum pans through a "heat-cool-heat" cycle at 10° C./min over the temperature range of −90 to 85° C. TGA runs were conducted at a constant ramping temperature program (20.0° C./min to 500° C.) with a gas flow of 40 ml/min (nitrogen). The real-time weight percentage and TGA chamber temperature were recorded. Analysis of the data was performed using TA Universal Analysis 2000 software (Version 4.2E, TA Instruments) to find the onset points. The amount of water content in dHPGs was determined by titration using Mettler Toledo DL39 Karl Fisher Coulometer equipped with AB104-S balance. Known amount of dHPGs were dissolved in anhydrous methanol and titrated with HYDRANAL®-Coulomat reagent (Sigma). The final results were obtained by subtracting the background reading from anhydrous methanol.

HPG-C$_{8/10}$ and HPG-C$_{8/10}$-MePEG exhibited glass transitions at temperatures decreasing from −38 to −55° C. as the MePEG content increased from 0 (HPG-C$_{8/10}$) to 4.6 mol MePEG/HPG (Table 5). The purification process was observed to have no effect on Tg values of dHPGs and no significant effects were observed on thermal stability. Both purified and unpurified dHPGs were stable up to a temperature of 300° C. with no indication of thermal decomposition (Table 6).

The effect of purification processes on physical and chemical stabilities of PTX and DTX loaded HPG-$C_{8/10}$-MePEG was also evaluated. Both PTX and DTX were loaded into purified or unpurified HPG-$C_{8/10}$-MePEG and the physical stabilities were evaluated by observing the onset of drug precipitation from PBS (pH 7.4). Chemical stabilities were assessed by LC/MS/MS to determine the amounts of PTX and DTX and their degradation products.

Figure 11:
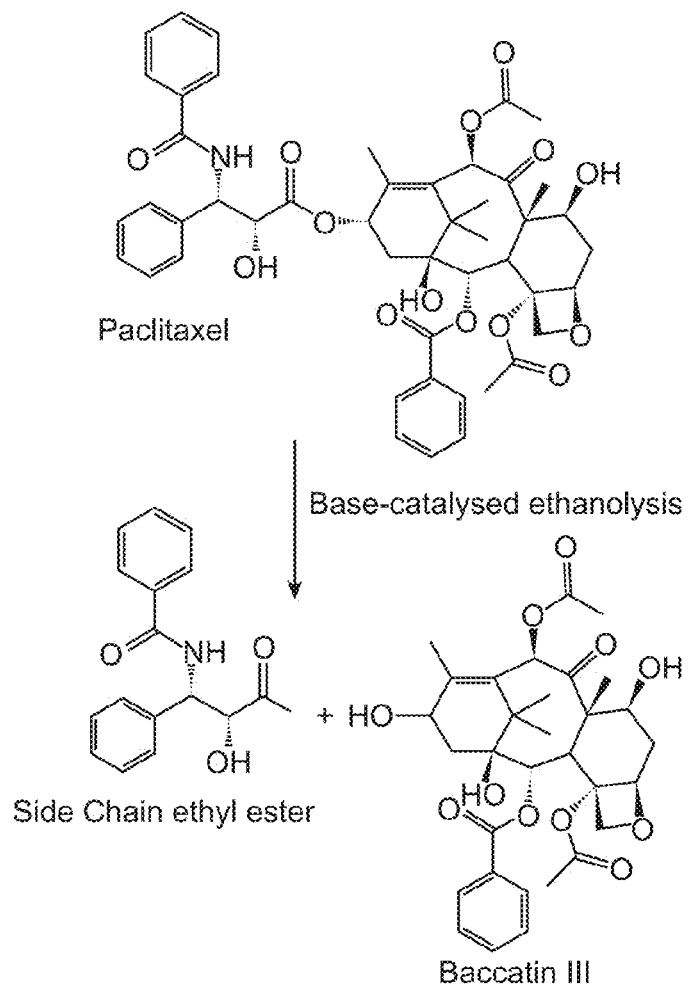
FIG. 11 shows (A) base-catalyzed ethanolysis of PTX ester linkage to generate Baccatin III and its side chain ethyl ester (N-benzoyl-3-phenylisoserine ethyl ester) and (B) representative chromatograms illustrating the identification of degradants of PTX by a UPLC-MS/MS assay in a formulation prepared using unpurified HPG-$C_{8/10}$-MePEG.
Figure 11:
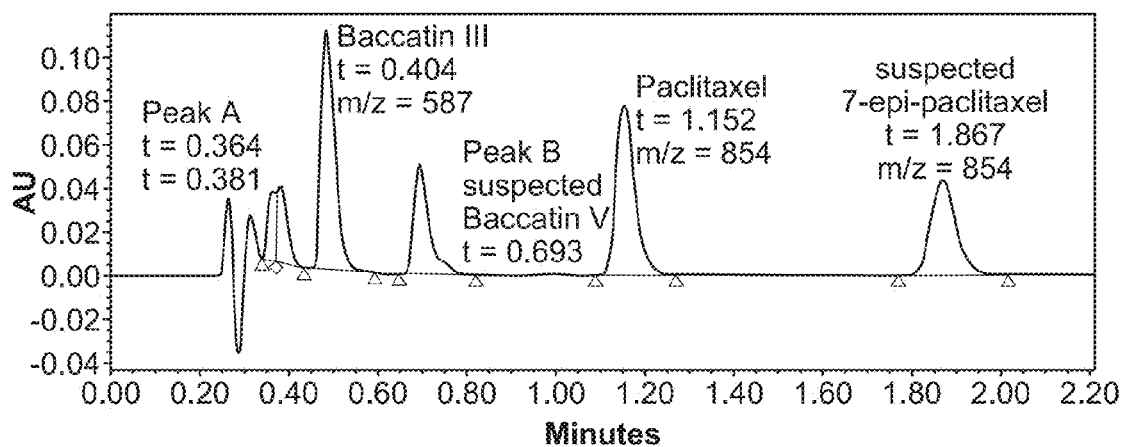
Figure 12:
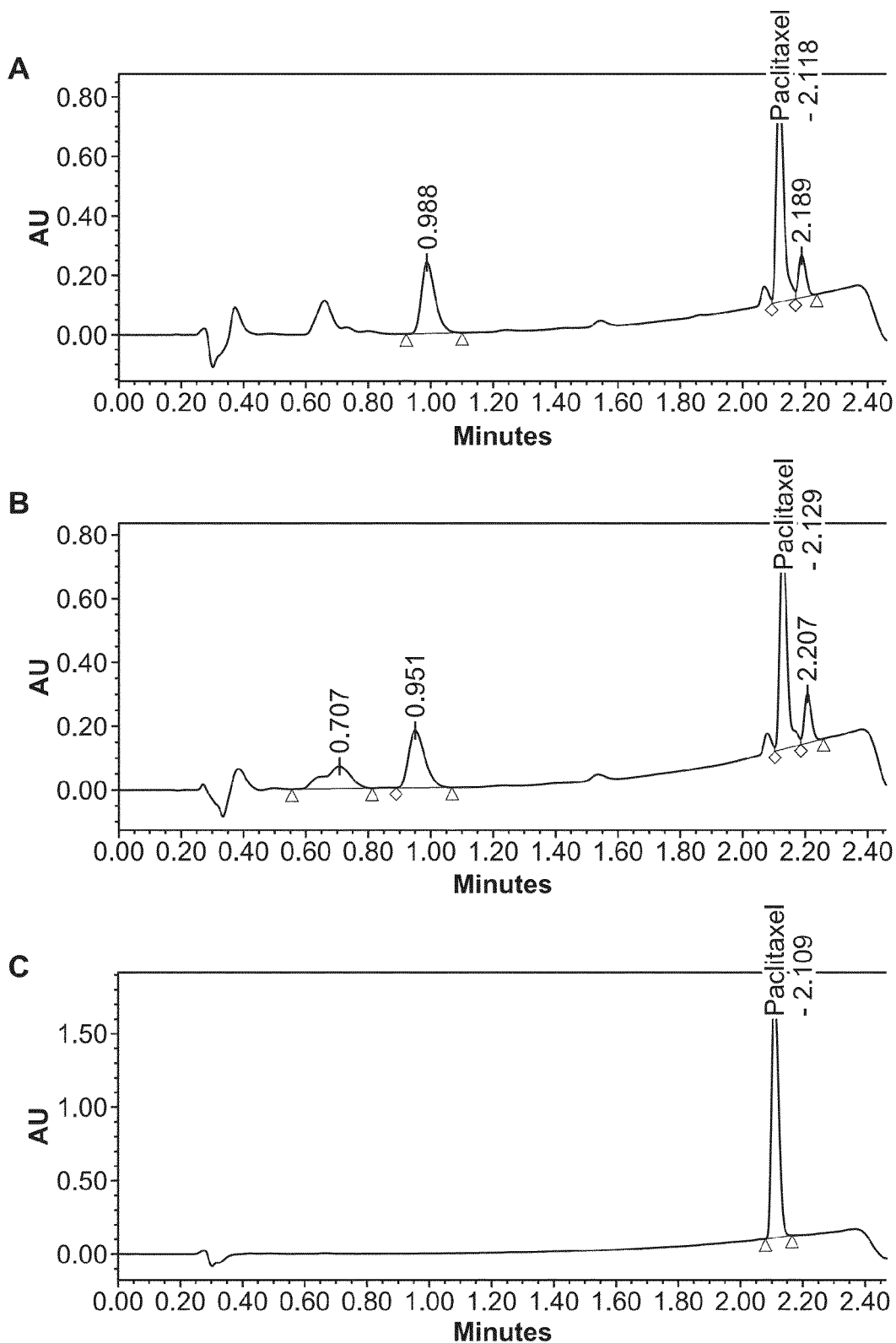
FIG. 12 shows representative chromatograms illustrating the effect of purification of HPG-$C_{8/10}$-MePEG$_{13}$ on the chemical stability of PTX (retention time of 2.1 min) measured by UPLC UV analysis. (A) Chromatogram of PTX formulated into unpurified HPG freshly constituted in PBS (pH 7.4), (B) a chromatogram of the same formulation in (A), aged 48 h, and (C) a chromatogram of PTX formulated into purified HPG, freshly constituted in PBS (pH 7.4).

The purification processes affected the physical and chemical stabilities of PTX and DTX loaded dHPGs. Maximum achievable PTX and DTX loadings were greater for unpurified polymers and these formulations were found to be physically more stable than formulations made with purified HPGs (Table 6). Samples prepared with unpurified polymer did not precipitate for several days (>3 d), with taxane loading as high as 5% (w/w) whereas those prepared with purified polymer and 5% (w/w) taxane loading precipitated within a few hours, or immediately upon constitution in PBS (Table 6). However, it was observed that PTX and DTX were chemically unstable in unpurified dHPGs and large fractions of the taxanes were degraded during the preparation of the formulations. About 75-80% of PTX was degraded immediately following loading in unpurified HPG-$C_{8/10}$-MePEG regardless of whether it was dry (bulk) matrix or after it was reconstituted in PBS (pH 7.4) (Table 6). However, once in buffer no further PTX degradation occurred, whereas PTX in the dry matrix continued to degrade over 24 h. FIG. 11B shows a chromatogram from a formulation of PTX in unpurified HPG-$C_{8/10}$-MePEG, with a peak corresponding to PTX and other peaks resulting from the formation of several degradation products. The chromatogram was obtained from a formulation dissolved in acetonitrile immediately after solvent drying (e.g. in the bulk state, prior to constitution in PBS). Two major degradants were identified by LC/MS/MS, having m/z values of 587 and 854, respectively. Based on these masses and the relative retention times of these peaks, their identities are assumed to be baccatin III (m/z 587, FIG. 11A) and 7-epi-taxol (m/z 854), respectively. Other degradation products (peak A & B, FIG. 11B) were also observed in unpurified formulations. Based on their relative retention times, peak areas, and the known degradation mechanisms of taxanes, peak B (FIG. 11B) is believed to be baccatin V, which is the 7-epi-baccatin III, while peak A is believed to be 10-deacetylbaccatin III. Taxanes loaded in purified polymers however, exhibited different behavior. PTX was found to be chemically stable both in bulk and in solution for several days and no major degradants were observed during the preparation of the formulations (Table 6 and FIG. 12C). It was observed that PTX and DTX in unpurified HPGs are quickly degraded and this is believed to be due to the presence of basic impurities in the unpurified polymers. The most likely basic impurities came from the excess of potassium methylate and potassium hydride added during the synthesis of HPGs. Both potassium methylate and hydride are strong bases and in combination with the residual moisture in the polymer would create an environment favorable for both epimerization at the C7 position and ester cleavage of PTX to produce baccatin III (or 10-deacetyl baccatin III for DTX) (FIG. 11A). The measurement of the pH of dHPG polymers in distilled water showed that unpurified polymers had a basic pH while purified polymers had an acidic pH (due to the treatment with Amberlite IRC-150, a cation exchange resin), a more stable environment for taxanes. It has been reported that the maximum stability of taxanes is in the pH range of 3-5 (Dordunoo, S. K., Burt, H. M., 1996. *Int. J. Pharm.* 133, 191-201; Tian, J., Stella, V. J., 2010. *J. Pharm. Sci.* 99, 1288-1298). The purified polymers were within this pH range (Table 6), hence the improved chemical stability of the loaded taxanes. The apparent higher drug loadings and greater physical stability of taxanes loaded in unpurified dHPG polymers may be explained by the fact that the majority of the loaded drugs were degraded to smaller and more hydrophilic molecules (baccatin III and baccatin V) than the parent taxanes, suggesting that these degraded molecules were more effectively loaded into dHPGs.

TABLE 6

Effects of polymer purification on polymer properties, and on the physical and chemical stability of taxane loaded formulations made with purified and unpurified HPG-$C_{8/10}$—MePEG$_{13}$

| Polymer properties | Unpurified HPG-$C_{8/10}$—MePEG$_{13}$ | | Purified HPG-$C_{8/10}$—MePEG$_{13}$ | |
|---|---|---|---|---|
| Tg | −55.8° C. | | −55.4° C. | |
| Td | 310° C. | | 344° C. | |
| Water content (% w/w) | 0.326 ± 0.001 | | 2.051 ± 0.001 | |
| pH (10% aqueous solution) | 8.5-9 | | 4.4-4.7 | |
| Physical stability (time to precipitation) with increasing taxane loading (% w/w) [1] | PTX (h) | DTX (h) | PTX (h) | DTX (h) |
| 1.0 | >72 | >72 | >12 | >72 |
| 2.0 | >72 | >72 | 1 | >48 |
| 3.0 | >72 | >72 | 0 | 24 |
| 5.0 | >72 | >72 | 0 | 1 |
| Chemical stability of PTX in "bulk" [2] formulation (% remaining) (t = 0) | 26.2 | | 99.8 | |
| Chemical stability of PTX (% remaining) (t = 24 h) | Unpurified | | Purified | |
| In "bulk" matrix | 15.6 | | 99.4 | |
| In PBS pH 7.4 constituted formulation | 25.8 | | 98.4 | |

[1] PTX and DTX loading (%, w/w) in HPG-$C_{8/10}$—MePEG$_{13}$, also constituted to an equivalent aqueous concentration (mg/ml)
[2] "Bulk" matrix signifies the taxane loaded HPG-$C_{8/10}$—MePEG$_{13}$ polymer prepared by solvent evaporation prior to constitution with PBS buffer. t = 0 for the bulk matrix is immediately after its final preparation step, drying to remove solvent.

Example 9

Effect of MePEG Derivatization on Thermal Properties, Surface Charge and Particle Size of dHPGs Particle size and zeta potential analysis was conducted using a Malvern NanoZS Particle Size analyzer using DTS0012 disposable sizing cuvettes for each analysis. Polymer solutions at a concentration of 15 mg/ml were prepared in 1 mM NaCl and filtered with 0.22 μm syringe filter (PALL Acrodisc 13 mm with nylon membrane). Sample acquisition parameters were: angle was 173° back-scatter with automatic attenuation; number of runs 11 (10 s/run); dispersant was water at 25° C. (viscosity 0.8872 cP and RI 1.330); Mark-Houwink parameter A=0.428 and K=7.67e-05 $cm^2$/s. dHPGs were assumed to have a similar refractive index as polyethylene glycol (PEG) with a RI=1.460 and absorption 0.01. The final data represented the average of all the runs.

dHPG particles sizes were consistently less than 10 nm in diameter with the loading of PTX and DTX having no effect on the size of HPG-MePEG (data not shown). Drug loaded HPGs form extremely small nanoparticles of less than 10 nm.

The presence of MePEG chains on the surface of HPGs had no significant effect on the overall surface charge on these nanoparticles as measured by the zeta potentials as follows: HPG-$C_{8/10}$=–1.29±0.97 mV; HPG-$C_{8/10}$-MePEG$_{6.5}$=–0.92±1.68 mV; HPG-$C_{8/10}$-MePEG$_{13}$= 0.18±0.16 mV.

Effects on the glass transition temperature with increasing MePEG density were observed. The Tg decreased from –37.5° C. for the HPG-$C_{8/10}$ polymer to –45.2 and –55.4° C. for the HPG-$C_{8/10}$-MePEG$_{6.5}$ and HPG-$C_{8/10}$-MePEG$_{13}$, respectively (Table 5). Loading with PTX or DTX also decreased the Tg (Table 5).

Example 10

Loading, Quantification, and Stability of PTX and DTX in dHPGs and Release of PTX and DTX from dHPGs PTX or DTX and dHPGs were dissolved in 1 ml acetonitrile solution in 4 ml vials and dried in an oven at 60° C. for 1 h and flashed with nitrogen to eliminate traces of the organic solvent. The resulting dHPG/taxane matrix was hydrated with 1 ml of 50° C. warm 10 mM phosphate buffered saline (PBS, pH 7.4) and vortexed for 2 min. The resulting solutions were generally clear but in cases where white particles were observed, the solutions were centrifuged (18,000×g for 10 min) and supernatants were transferred to new vials.

The amount of PTX and DTX incorporated into HPGs was determined by reversed phase HPLC as previously described (Jackson, J. K., Smith, J., Letchford, K., Babiuk, K. A., Machan, L., Signore, P., Hunter, W. L., Wang, K., Burt, H. M., 2004. Int. J. Pharma. 283, 97-109). 100 µl of dHPG/PTX or DTX solution was dissolved with 900 µl of acetonitrile/water (60:40, v/v) and transferred into HPLC vials (Canadian Life Science, Peterborough, ON). Drug content analysis was performed using a symmetry C18 column (Waters Nova-Pak, Milford, Mass.) with a mobile phase containing a mixture of acetonitrile, water, and methanol (58:37:5, v/v/v) at a flow rate of 1 ml/min. Sample injection volumes were 20 µl and detection was performed using UV detection at a wavelength of 232 nm. HPG-$C_{8/10}$ had a limited aqueous solubility resulting in low drug loading of taxanes (data not shown). The presence of alkyl ($C_{8/10}$) chains in dHPGs is important for loading of hydrophobic drugs, however it also significantly reduces their water solubility. To increase the water solubility of HPGs, MePEG 350 chains were added in the terminal phase of the reaction during the synthesis these molecules. A relatively small increase in the amount of MePEG in the dHPGs resulted in increased drug loading of HPG-$C_{8/10}$-MePEG$_{13}$ for both PTX and DTX. DTX loading in HPGs was higher than for PTX. dHPGs loaded with DTX showed greater physical stability than PTX formulations. Maximum loading of DTX (5%, w/w) was greater than for PTX in HPG-$C_{8/10}$-MePEG$_{13}$ (2%, w/w).

The physical and chemical stability of taxane loaded dHPGs were evaluated. The physical stability was evaluated by visual observation of clarity of the formulations, where precipitation in less than 24 h was considered a physically unstable formulation. Samples were observed immediately upon rehydration in PBS (t=0), or after 1, 3, 6, 24, 48 and 72 h at room temperature. Chemical stability of PTX and DTX were monitored by the HPLC method as described above. Degradation products were identified by mass spectrometry analysis using Waters TQD mass spectrometer. The system was operated at an electrospray ion source block temperature of 150° C., a desolvation temperature of 350° C., a cone voltage of 45 kV, a capillary voltage of 0.70 kV, extractor voltage of 3 kV, RF voltage of 0.1 kV, a cone gas flow at 25 l/h, a desolvation gas flow at 600 l/h and a collision gas flow at 0.2 ml/min. The molecules undergo electron spray ionization in the positive ion mode.

PTX and DTX release from dHPGs were determined by a dialysis method. 100 mg of dHPGs (HPG-$C_{8/10}$-MePEG$_{6.5}$ or HPG-$C_{8/10}$-MePEG$_{13}$) were weighed and mixed with 1 mg of PTX or DTX in 1 ml acetonitrile solution, spiked with 15 uCi $^3$H-DTX or $^3$H-PTX (15 ul) and dried under nitrogen stream to remove the solvent. Radioactive drugs ($^3$H-DTX or $^3$H-PTX) were obtained from Moravek Biochemicals and Radiochemicals (Brea, Calif.). The dHPGs/taxane matrix was hydrated with 2 ml of PBS and transferred into dialysis bags and dialysed against 500 ml of artificial urine (pH 4.5 or 6.5) with shaking at 100 rpm. Dialysis membrane tubing was purchased from Spectrum Laboratories (Rancho Dominguez, Calif.). Artificial urine was prepared according to the method of Brooks et al. (Brooks, T., Keevil, C. W., 1997. Lett. Appl. Microbiol. 24, 203-206), without the addition of peptone or yeast extract. The pH of the solution was adjusted to pH 4.5 and or 6.5 using 0.1M HCl. At different time points, the volumes of the dialysis bags were measured and a 10 µl sample was taken for measurement of the remaining radioactivity in the dialysis bags and the entire external release media was exchanged with fresh media to maintain sink conditions. The concentration of $^3$H-DTX or $^3$H-PTX remaining in the dialysis bag at each time point was determined by beta scintillation counting (Beckman Coulter Canada, Mississagua, ON). The cumulative percent drug released was calculated by subtracting the amount of drug remaining at each time point from the initial amount of drug at the beginning of the experiment. The data were expressed as cumulative percentage drug released as a function of time. Data represent the mean (SD) of three independent experiments.

Figure 13:
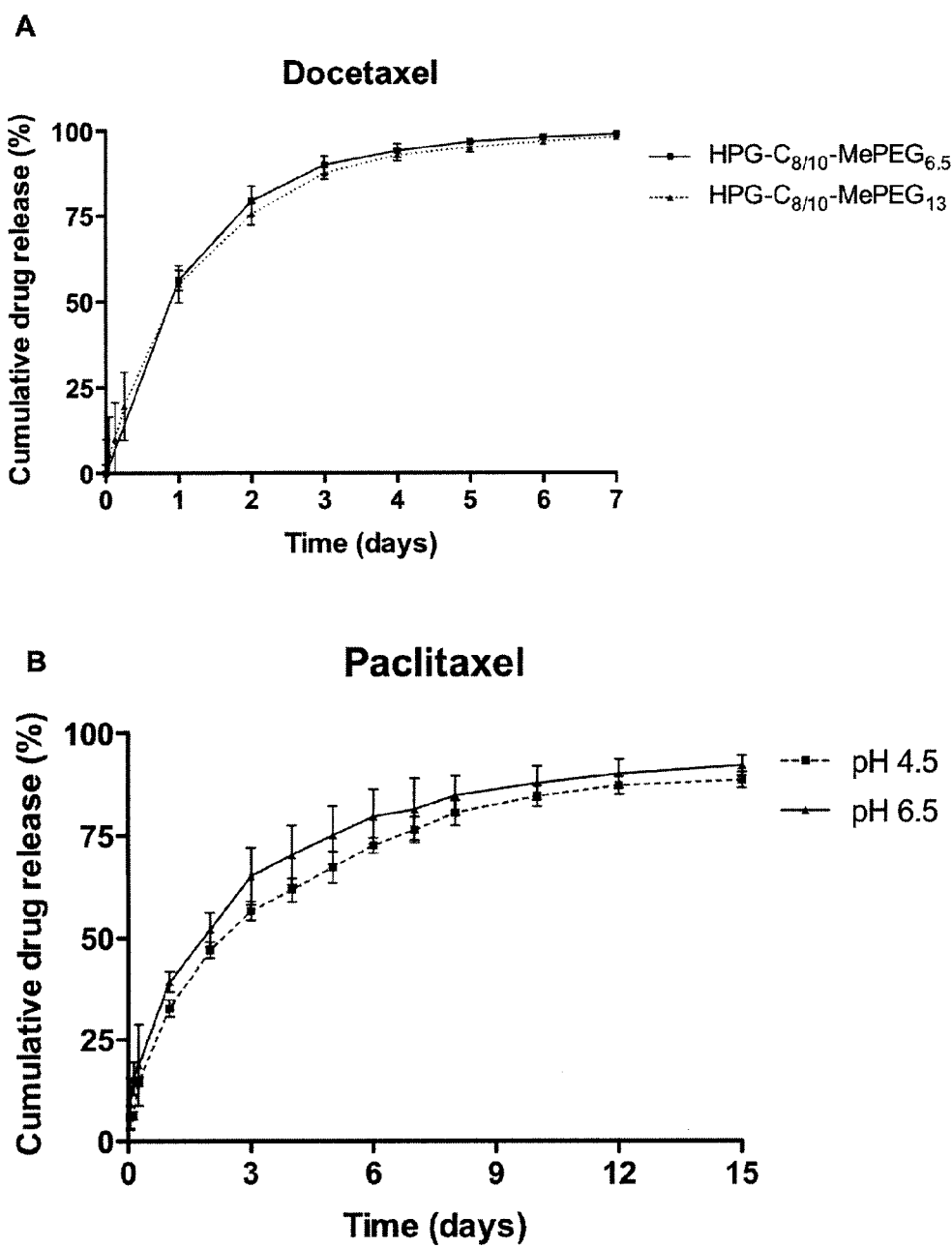
FIG. 13 shows PTX and DTX release from HPG-$C_{8/10}$-MePEG in artificial urine at 37° C. (A) Cumulative DTX release from HPG-$C_{8/10}$-MePEG (6 and 13 mol). (B) Cumulative PTX release from HPG-$C_{8/10}$-MePEG in artificial urine (pH 4.6 and 6.5).

The pH of urine is usually acidic but is known to vary over a wide range (pH 4.5-8), therefore the effect of pH on the release profiles PTX and DTX loaded in HPG-$C_{8/10}$-MePEG was evaluated. The release profiles of taxanes from HPGs were characterized by a continuous controlled release and little or no burst phase of release followed by a slower sustained-release phase. DTX was released more rapidly than PTX (75% vs 50% drug release after 2 days) from HPG-$C_{8/10}$-MePEG and almost all DTX released in 6-7 days, compared to 12-14 days for PTX. This was believed to be due to the greater hydrophilicity of DTX whereas more hydrophobic PTX may have greater compatibility and interactions with the alkyl chains ($C_8/C_{10}$) of the HPG core leading to a slower drug release rate. Increases in the density of MePEG on HPGs were observed to have no effect on drug release (FIG. 13A). Changes in the pH of the release medium (pH 4.5-6.5) were observed to have no effect on drug release from HPG-$C_{8/10}$-MePEG nanoparticles (FIG. 13B). Evaluation of release profiles of PTX and DTX from the HPG nanoparticles using various kinetic models (including first order, higuchi, and korsmeyer model) indicated that both the first order and the higuchi kinetics provided the best fit with $r^2$=0.98-0.99 (data not shown). There was no statistical difference between the formulations in terms of rate of drug release (data not shown).

Example 11

Rhodamine Labeling of HPG-$C_{8/10}$-MePEG$_{13}$ and Cellular Uptake of Rhodamine-Labeled HPG-$C_{8/10}$-MePEG$_{13}$ HPG-$C_{8/10}$-MePEG$_{13}$ was covalently labeled with tetramethylrhodamine-5-carbonyl azide (TMRCA) according to the method of Huang et al. with slight modifications (Huang, S. N., Phelps, M. A., Swaan, P. W., 2003. *J. Pharmacol. Exp. Ther.* 306, 681-687). 500 mg of HPG-$C_{8/10}$-MePEG$_{13}$ was dissolved in 5 ml of anhydrous 1,4-dioxane. An appropriate amount of TMRCA was dissolved in anhydrous 1,4-dioxane to give a final concentration of 1 mg/ml. An aliquot of 675 µl of this fluorescent probe, which corresponds to approximately 20 mol % of HPG, was added to the HPG-$C_{8710}$-MePEG$_{13}$ solution and heated at 80° C. in oil bath under nitrogen stream with stirring for 5 h. The solution was dialysed against DMF (MWCO 12,000-14,000) until the dialysate was colourless and then dialysed against distilled water for 24 h. The fluorescent-labeled polymer (HPG-$C_{8/10}$-MePEG$_{13}$-TMRCA) was freeze-dried and stored at −80° C. in amber vials.

KU7 cells were allowed to grow on several microscope 1 cm×1 cm cover slips on the bottom of a 10 cm Petri dish until a confluence of ~75% was reached which corresponds to a cell number of approximately $7\times10^4$ cells. These cell-containing cover slips were washed with warmed PBS three times and then placed on parafilm-lined petri dishes with the cell side up. 250 µl of HPG-$C_{8/10}$-MePEG$_{13}$-TMRCA solution (1 mg/ml dissolved in Dulbecco's Modified Eagle Medium (DMEM)) were added to the cover slips. Cells were incubated with HPG-$C_{8/10}$ MePEG$_{13}$-TMRCA for 1, 4, 8, and 24 h. For controls, the KU7 cells were incubated in DMEM without any supplementation. The cover slips were then washed four times vigorously with PBS buffer, excess PBS gently blotted and 250 µl of 3.7% paraformaldehyde added to fix the cells for 10 min. Cover slips were washed an additional three times with PBS and submerged in water. After blotting excess liquid, the cells were stained with Prolong® Gold antifade reagent with DAPI (Molecular Probes, Invitrogen) and the slips mounted cell side down on microscope glass slides. The edges of the cover slips were sealed by clear nail varnish to avoid drying. The samples were incubated in the dark overnight to ensure the proper staining of the cells. Samples were observed under an Olympus FV-1000 inverted confocal microscope equipped with DAPI ($\lambda_{ex}$ 340-380 nm; $\lambda_{em}$ 435-485 nm; dichroic splitter, 400 nm) and rhodamine ($\lambda_{ex}$ 530-560 nm; $\lambda_{em}$ 590-650 nm; dichroic splitter, 570 nm) filters. Direct contrast (DIC) was also performed to visualize cell membranes and was activated with a 405 nm laser. In order to clearly show that the labeled polymer was inside the cell, images were analyzed by fluorescence and DIC.

Figure 14:
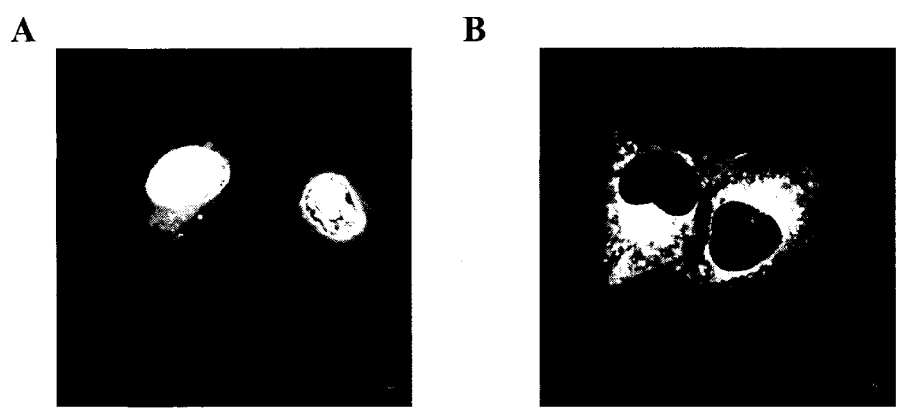
FIG. 14 shows confocal fluorescence imaging of KU7 cells illustrating complete uptake of HPG-$C_{8/10}$-MePEG$_{13}$-TMRCA nanoparticles after a 1 h exposure. (A) Untreated KU7 cells with a DAPI stain allowing visualization of the nuclei in blue (shown as white in image). (B) KU7 cells that have been incubated for 1 h with HPG-$C_{8/10}$-MePEG$_{13}$-TMRCA nanoparticles.

Cellular uptake of rhodamine-labeled HPG-$C_{8/10}$-MePEG$_{13}$ (HPG-$C_{8/10}$-MePEG$_{13}$-TMRCA) was visualized by confocal microscopy of KU7 cells. After one hour of incubation there was evidence of the uptake of HPG-$C_{8/10}$-MePEG$_{13}$-TMRCA into KU7 cells. Representative images of the uptake of HPG-$C_{8/10}$-MePEG$_{13}$-TMRCA at 1 h are shown in FIG. 14. Panel A shows untreated KU7 cells with a DAPI stain, which allows visualization of the nuclei in blue (shown as white in image). The image is an overlay of a direct contrast signal (which shows the contour of the cell) and the fluorescence signals, which shows the nucleus (white), and the absence of any other fluorescence. Panel B shows KU7 cells that have been incubated for 1 h with HPG-$C_{8/10}$-MePEG$_{13}$-TMRCA nanoparticles. The presence of HPG-$C_{8/10}$-MePEG$_{13}$-TMRCA in the cytoplasm is shown by the red fluorescence of the polymer around the nucleus (stained blue with DAPI) (red fluorescence shown as white portion in image. Red fluorescence surrounds nucleus shown as dark portion in image). The z-stack of the same cell population from panel B (z-stack image not shown), demonstrated that the red fluorescent nanoparticles are present throughout the cytoplasm, rather than being only adhered to or present in cell membrane. These nanoparticles appeared to be distributed uniformly in the cytoplasm, although some punctuate structures were observed indicating that HPG-$C_{8/10}$-MePEG$_{13}$-TMRCA nanoparticles were packaged into small vesicles for cellular trafficking. There was no fluorescence from the polymer detected in the nuclear compartment of the KU7 cells. HPG-$C_{8/10}$-MePEG$_{13}$-TMRCA nanoparticles have no effect on the viability and prevalence of the KU7 cells when compared to the control cells at all time points, indicating that these nanoparticles were highly biocompatible with this cell line. HPG-$C_{8/10}$-MePEG$_{13}$-TMRCA nanoparticles were taken up into KU7 cells by 1 h of incubation and there were no differences in the images obtained at 1, 4, 8 or 24 h time points.

Example 12

In Vitro Cytotoxicity Studies of HPG-$C_{8/10}$-MePEG

HPG-$C_{8/10}$-MePEG was prepared according to reported protocols (Kainthan R K, Mugabe C, Burt H M, Brooks D E. *Biomacromolecules*, 9(3), 886-895 (2008)) as described above. $^1$H NMR (400 MHz, $D_6$-DMSO) δH: 0.75-0.82 (—$CH_3$, TMP); 0.82-0.92 (—$CH_3$-alkyl on O/DGE); 1.15-1.55 (—$CH_2$—, alkyl on O/DGE); 2.50 (solvent, $D_6$-DMSO); 3.15-3.80 (—CH and —$CH_2$—, from HPG core); 3.23 (—$OCH_3$— from MePEG), 3.32 (residual water); 4.8 (—OH).

The fractions of MePEG and alkyl chains on HPGs were estimated from heteronuclear single quantum coherence (HSQC) NMR experiments. Chemical shifts were referenced to the residual solvent peak. Molecular weights and polydispersities of the polymers were determined by gel permeation chromatography with multi-angle laser light scattering detection (GPC-MALLS): molecular weight=83,000 g/mol with a polydispersity of 1.22 (data not shown).

Particle size analysis was conducted using a Malvern NanoZS Particle Size analyzer. Drug loaded HPG-$C_{8/10}$-MePEG formed nanoparticles of less than 10 nm (7.5±3.4 to 7.8±2.7 nm, data not shown).

PTX or DTX loaded dHPGs were prepared by dissolving PTX (1 mg) or DTX (0.5 mg) and HPG-$C_{8/10}$-MePEG (100 mg) in 1 ml acetonitrile solution in 4 ml vials and dried in an oven at 60° C. for 1 h and flashed with nitrogen stream to eliminate traces of the organic solvent. Paclitaxel (PTX) powder was obtained from Polymed Therapeutics, Inc. (Houston, Tex.). Docetaxel (DTX) powder was obtained from Natural Pharmaceuticals Inc. (Beverly, Mass.). The resulting HPG-$C_{8/10}$-MePEG/taxane matrix was hydrated with 1 ml of 10 mM phosphate buffered saline (PBS, pH 6) and vortexed for 2 min. The amount of PTX and DTX incorporated in HPG-$C_{8/10}$-MePEG were determined by reversed phase HPLC. PTX and DTX can be loaded with high drug loadings (maximum loading of 2 and 5% w/w, respectively) by the solvent evaporation method.

Cytotoxic effects of commercial formulations, Taxol® and Taxotere® and PTX and/or DTX loaded HPG-$C_{8/10}$-MePEG formulations against the KU7-luc cell line, and both lowgrade (RT4, MGHU3) and high-grade (UMUC3) human urothelial carcinoma cell lines were evaluated. Taxol® was from Bristol-Myers-Squibb (Princeton, N.J.). Taxotere® was purchased from Sanofi-Aventis Canada Inc. (Laval, Quebec). The human bladder cancer cell lines RT4 and UMUC3 were purchased from the American Type Culture Collection. Cells were maintained in McCoy's medium (Invitrogen, Burlington, ON) containing 10% heat-inactivated fetal bovine serum and kept at 37° C. in a humidified 5% $CO_2$ atmosphere. MGHU3 cells were obtained as a generous gift from Dr. Y. Fradet (L'Hotel-Dieu de Quebec, Quebec, Canada) and maintained in MEM supplemented with 10% fetal bovine serum and 2 mM L-glutamine (Invitrogen). KU7 was kindly provided by Dr. C. Dinney (MD Anderson Cancer Center, Houston, Tex., USA) and maintained in DMEM containing 5% fetal bovine serum. For visualization purposes, KU7 cells were infected with a lentivirus containing the firefly luciferase gene by Dr. Graig Logsdon (M.D. Anderson Cancer Center, Houston, Tex., USA), and these subclones were named KU7-luc as previously reported (Hadaschik B A, Black P C, Sea J C et al. *BJU Int,* 100(6), 1377-1384 (2007)). Cells were plated at 5,000 cells/well in 96-well plates in a 100 µl volume of McCoy's Medium supplemented with 10% FBS and allowed to equilibrate for 24 h before freshly prepared solutions of Taxol®; Taxotere®; PTX loaded HPG-$C_{8/10}$-MePEG; or DTX loaded HPG-$C_{8/10}$-MePEG were added. Cells were exposed to the drug formulations for 2 h, to simulate the current clinical standard for installation therapy, and cell viability was determined after 72 h using the CellTiter96 AQueous Non-Radioactive Cell Proliferation (MTS) assay (Promega, Madison, Wis.) as reported previously (Hadaschik B A, ter Borg M G, Jackson J et al. *BJU Int,* 101(11), 1347-1355 (2008)). Each experiment was repeated three times and MTS values fell within a linear absorbance range for all cell lines.

Figure 15:
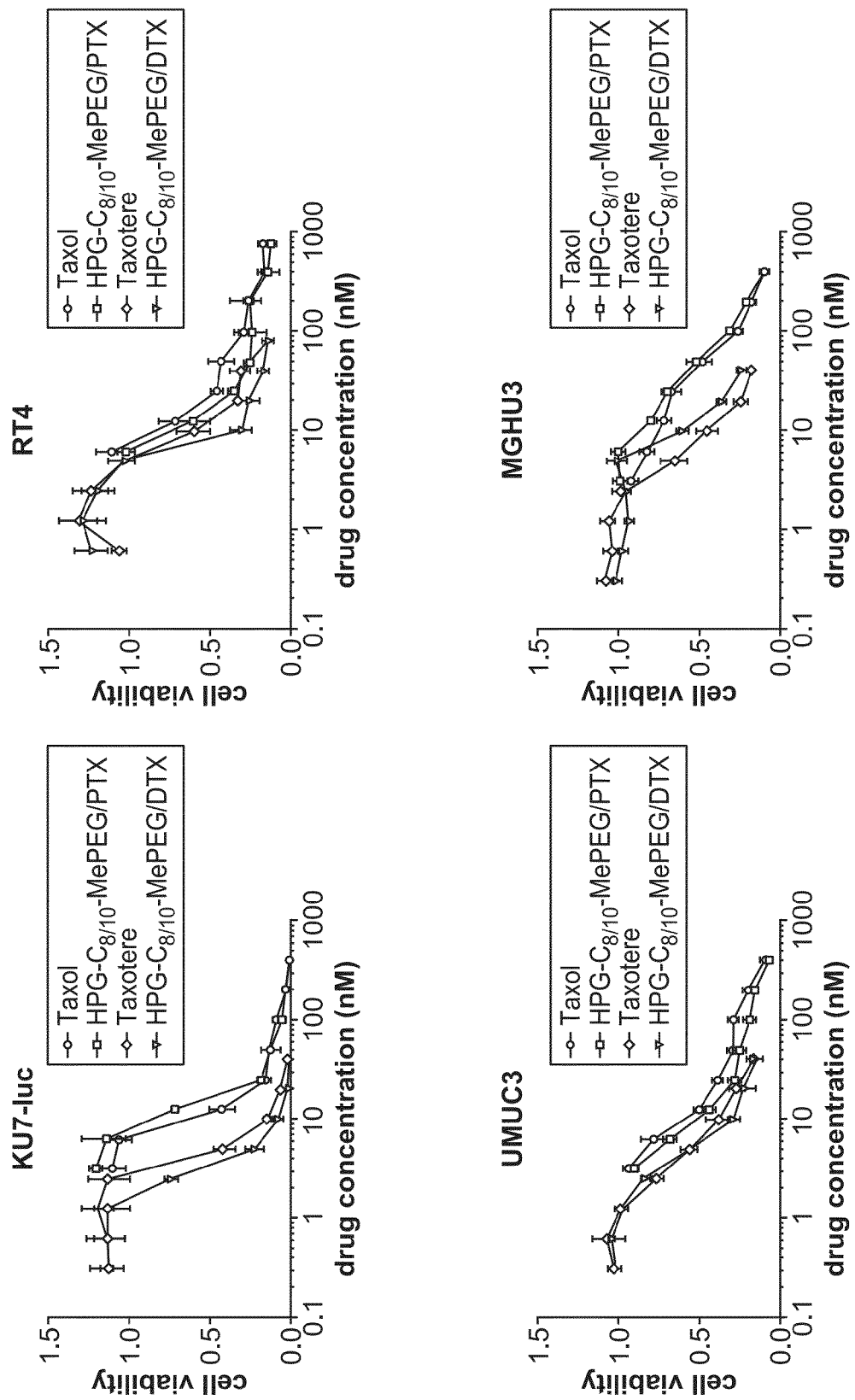
FIG. 15 shows in vitro cytotoxicity effects of commercial formulations, Taxol® and Taxotere® and PTX and/or DTX loaded HPG-$C_{8/10}$-MePEG nanoparticles against KU7-luc cell line, and both low-grade (RT4, MGHU3) and high-grade (UMUC3) human urothelial carcinoma cell lines.

All formulations resulted in concentration-dependent inhibition of the proliferation of all cell lines tested (FIG. 15). DTX formulations were more cytotoxic than PTX formulations although there were no significant differences between groups (P>0.05, one-way ANOVA). The $IC_{50}$ of Taxotere® was about two- to five-fold lower than that of Taxol®. PTX and DTX loaded HPG-$C_{8/10}$-MePEG nanoparticles were found to be as cytotoxic as the commercial formulations of Taxol® and Taxotere®, respectively (FIG. 15). Control HPG-$C_{8/10}$-MePEG nanoparticles (no drug) showed no cytotoxicity across the concentration range of 15-1,500 nM (data not shown), while Cremophor-EL® and Tween 80 have been shown to be toxic to cells even at low concentrations (Iwase K, Oyama Y, Tatsuishi T et al. *Toxicol Lett,* 154(1-2), 143-148 (2004); Henni-Silhadi W, Deyme M, Boissonnade M M et al. *Pharm Res,* 24(12), 2317-2326 (2007)).

Example 13

Figure 16:
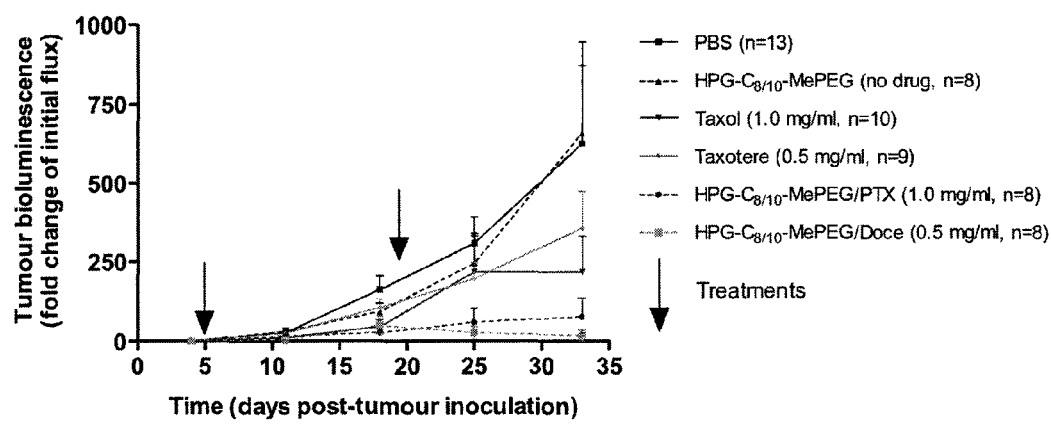
FIG. 16 shows treatment effects of intravesical taxane formulations on orthotopic bladder cancer xenografts. Vehicle controls (PBS & empty HPG-$C_{8/10}$-MePEG), Taxol® (1 mg/ml, Bristol-Myers-Squibb), Taxotere® (0.5 mg/ml, Sanofi-Aventis), or paclitaxel (PTX, 1 mg/ml) and docetaxel (DTX, 0.5 mg/ml) loaded into HPG-$C_{8/10}$-MePEG.
Figure 17:
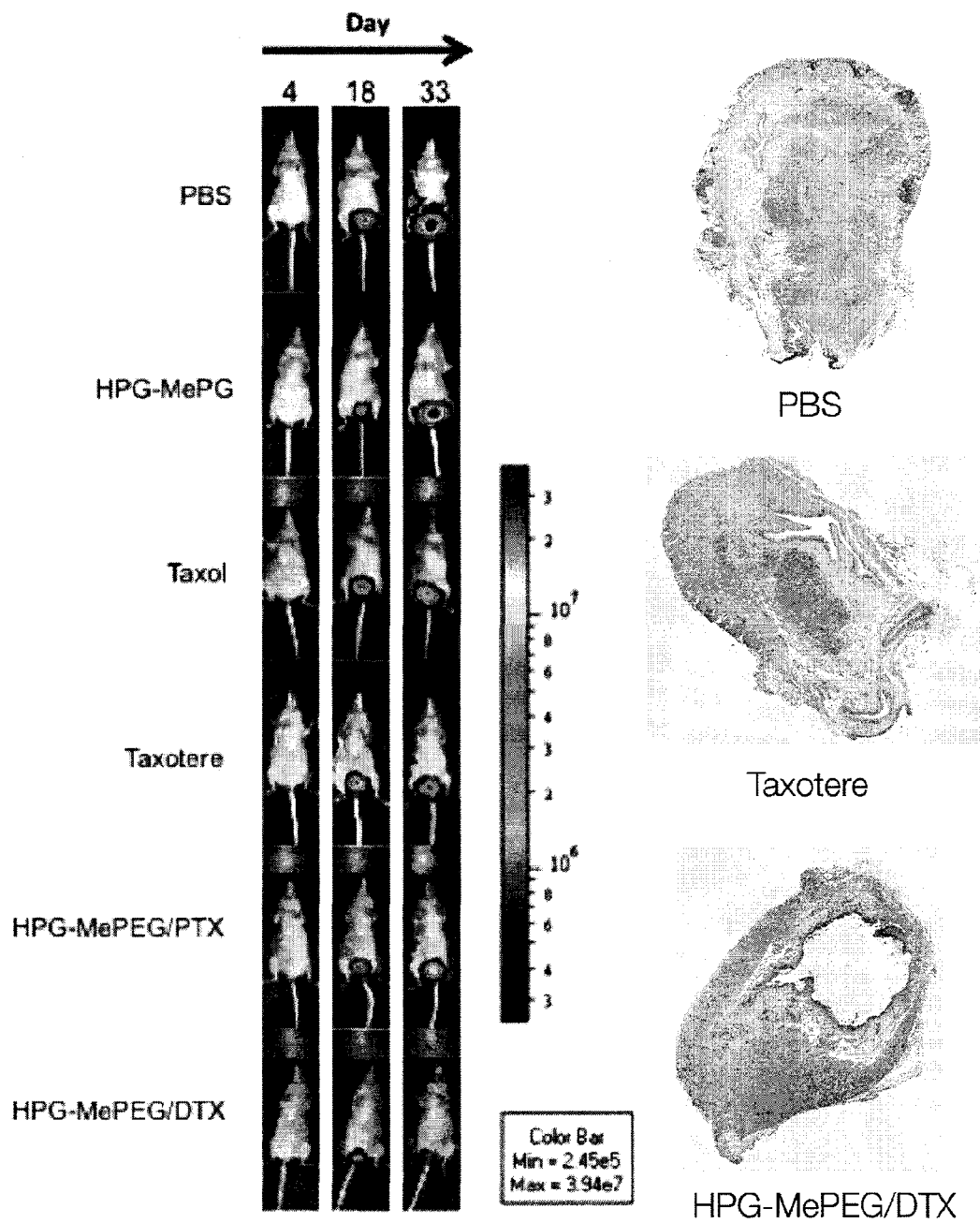
FIG. 17 shows representative sequences of bioluminescence images of mice from different treatment groups taken on the day of randomization and at days 18 and 33. Right, representative bladder cross-sections of the same mice in PBS control, Taxotere®, and DTX loaded HPG-$C_{8/10}$-MePEG treatment groups.
Figure 18:
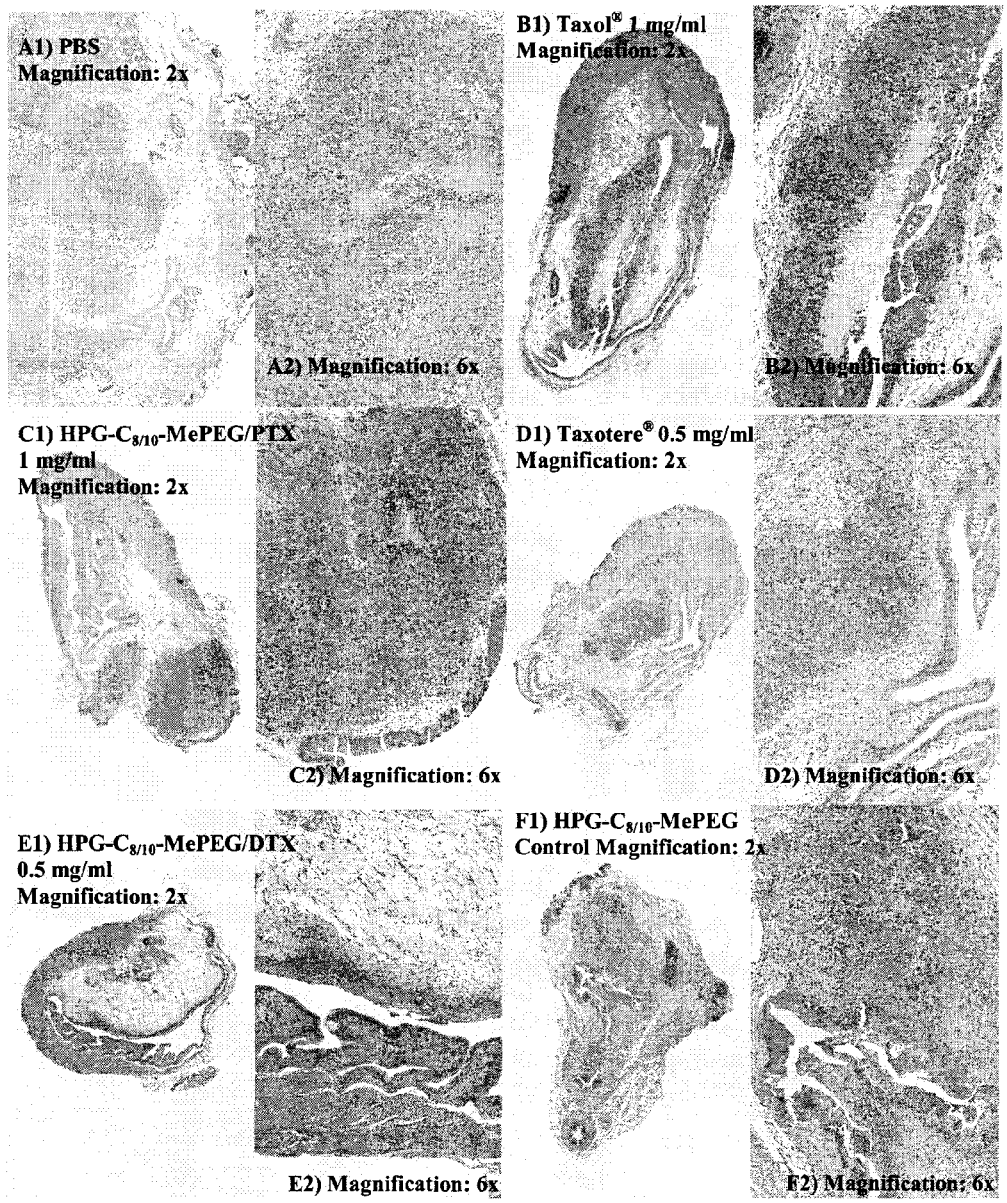
FIG. 18 shows representative histological sections of bladders harvested at the end, from mice receiving various treatments: A) PBS, B) Taxol® (1 mg/ml), C) HPG-$C_{8/10}$-MePEG/PTX (1 mg/ml), D) Taxotere® (0.5 mg/ml), E) HPG-$C_{8/10}$-MePEG/DTX (0.5 mg/ml), F) HPG-$C_{8/10}$-MePEG (no drug).

Efficacy of Intravesical PTX and DTX Formulations in Orthotopic Model Bladder Cancer In vivo studies were done in a total of 60 nude mice to evaluate the efficacy of intravesical Taxol® (1 mg/ml, Bristol-Myers-Squibb); Taxotere® (0.5 mg/ml, Sanofi-Aventis); PTX (1 mg/ml) loaded HPG-$C_{8/10}$-MePEG; and DTX (0.5 mg/ml) loaded HPG-$C_{8/10}$-MePEG in a mouse xenograft model of bladder cancer. This orthotopic mouse model has been reported (Mugabe C, Hadaschik B A, Kainthan R K et al. *BJU Int,* 103(7), 978-986 (2009); Hadaschik B A, Black P C, Sea J C et al. *BJU Int,* 100(6), 1377-1384 (2007); Hadaschik B A, ter Borg M G, Jackson J et al. *BJU Int,* 101(11), 1347-1355 (2008)). Animal studies were carried out in accordance with the Canadian Council on Animal Care. Eleven week old female nude mice (Harlan, Indianapolis, Ind.) were anaesthetized with isoflurane. A superficial 6-0 polypropylene purse-string suture was placed around the urethral meatus before a lubricated 24 G Jelco angiocatheter (Medex Medical Ltd., Lancashire, UK) was passed through the urethra into the bladder. After a single irrigation of the bladder with PBS, two million KU7-luc cells were instilled as a single cell suspension in 50 µl and the purse-string suture was tied down for 2.5 h. To quantify in vivo tumour burden, animals were imaged in supine position 15 min after intraperitoneal injection of 150 mg/kg luciferin on days 4, 11, 18, 25, and 33 with an IVIS200 Imaging System (Xenogen/Caliper Life Sciences, Hopkinton, Mass.). Data were acquired and analyzed using Living Image software (Xenogen). On day five post-tumour inoculation, mice were randomized to receive a 50 µl intravesical treatment with PBS (control); HPG-$C_{8/10}$-MePEG (no drug); Taxol® (1 mg/ml); PTX (1 mg/ml) loaded HPG-$C_{8/10}$-MePEG; Taxotere® (0.5 mg/ml); DTX (0.5 mg/ml) loaded HPG-$C_{8/10}$-MePEG. Intravesical therapy was given on day 5 and 19 post-tumour inoculation. Levels of bioluminescence were equivalent among the groups; however, as tumours varied between individual mice, for statistical analyses, tumour bioluminescence after treatment was normalized against the initial flux on day four in each mouse. Necropsy was performed on day 33 after tumour inoculation. The whole bladders were removed, fixed in 10% buffered formalin and embedded in paraffin. 5 µm sections were prepared and stained with H&E using standard techniques. All slides were reviewed and scanned on a BLISS microscope imaging workstation (Bacus Laboratories Inc., Lombard, Ill.). After intravesical inoculation of KU7-luc cancer cells, all mice developed bladder tumours. However, two mice did not recover from anaesthesia and died on the same day of tumour inoculation. One mouse in the Taxotere® arm was found dead on the last day of imaging (day 33 post-tumour inoculation) this mouse had the largest tumour in the group on the previous measurements. Another mouse in DTX loaded HPG-$C_{8/10}$-MePEG was euthanized due to irreversible weight loss (15% weigh loss). For statistical analysis, these mice were excluded from the study. Overall, intravesical PTX and DTX, either the commercial Taxol® and Taxotere®, or the HPG-$C_{8/10}$-MePEG formulations were well tolerated by mice and no major toxicities or weight losses were observed. Intravesical therapy was given on day 5 and 19 post-tumour inoculation. Compared with control mice (PBS & empty HPG-$C_{8/10}$-MePEG), PTX and DTX loaded HPG-$C_{8/10}$-MePEG significantly inhibited tumour growth (P<0.001, 2-way ANOVA, Bonferroni post-tests) (FIG. 16). Unlike Taxotere®, Taxol® (1 mg/ml) significantly decreased the tumour growth (P<0.01, 2-way ANOVA, Bonferroni post-tests) when compared to the control groups (PBS & empty HPG-$C_{8/10}$-MePEG). However, no significant difference was observed between Taxotere® and Taxol® treatment arms. Intravesical installation doses of PTX (1 mg/ml) and DTX (0.5 mg/ml) were chosen based on a previous report with PTX (Mugabe C, Hadaschik B A, Kainthan R K et al. *BJU Int,* 103(7), 978-986 (2009)) and the in vitro cytotoxicity data demonstrating DTX to be more potent than PTX (FIG. 15). At the end of the study, tumour growth in both PTX and DTX loaded HPG-$C_{8/10}$-MePEG nanoparticles was inhibited by 87 and 97%, respectively, compared to the PBS control group. Taxotere® and Taxol® exhibited a 43 and 65% tumour growth inhibition, respectively. Representative bioluminescence images of mice over time in each treatment group are shown in FIG. 17. Histological examination of bladder tissues show that KU7-luc tumours exhibited an aggressive growth pattern and frequent multifocality, but after 33 days post-tumour inoculation, most of the tumours in the treatment arms were generally confined to the lamina propria and correlated with high-grade pT1 stage disease (FIG. 18).

It is speculated that the low nanometer size range of HPGs may permit penetration between mucin chains and contact the umbrella cells of the urothelium leading to enhanced endocytosis of these nanoparticles into the bladder wall including tumour tissues. It is also possible that the surface MePEG chains on the HPGs might interact with mucin glyoproteins through chain entanglement resulting in entrapment of these nanoparticles in the mucin layers leading to prolonged residence time of the drug loaded nanoparticles in the bladder. Table 7 shows that PTX and DTX loaded HPG-$C_{8/10}$-MePEG nanoparticles exhibited a 2-3-fold higher bladder tissue accumulation than the commercial formulations of Taxol® or Taxotere®.

Example 14

Pharmacokinetics

To evaluate the pharmacokinetic properties of intravesical PTX and DTX formulations, mice were instilled with either Taxol® (1 mg/ml, n=3); Taxotere® (0.5 mg/ml, n=4); PTX loaded HPG-$C_{8/10}$-MePEG (1 mg/ml, n=4); and/or DTX loaded HPG-$C_{8/10}$-MePEG (0.5 mg/ml, n=4). Tail blood samples were taken at 0, 30, and 60 min post intravesical installation. During this period mice were still anaesthetized with isoflurane. After 2 h, all mice were killed using $CO_2$ asphyxiation and additional blood was removed by cardiac puncture. Blood samples were centrifuged in micro-haematocrit tubes (Fisher Scientific, Pittsburgh, Pa.) or serum-separator tubes (Becton Dicknson) and the serum was snap-frozen in liquid nitrogen. Urine and bladder of each mouse were also harvested and before freezing, the bladders were cut open to expose the lumen and were vigorously washed in five sequential 10 ml PBS washes. All samples were stored at −80° C. The UPLC-MS/MS system used for analysis consisted of an integrated Waters Acquity UPLC separation system coupled to a mass spectometry analysis using Waters TQD mass spectrometer. The system was operated at an electrospray ion source block temperature of 150° C., a desolvation temperature of 350° C., a cone voltage of 14 V, a capillary voltage of 0.70 kV, extractor voltage of 3 kV, RF voltage of 0.1 kV, a cone gas flow at 25 l/h, a desolvation gas flow at 600 l/h and a collision gas flow at 0.2 ml/min. The molecules undergo electron spray ionization in the positive ion mode. DTX was extracted from the mouse serum by solvent/solvent extraction method. 50 µl aliquots of the mouse plasma and standards were mixed with 150 µl of 0.1% formic acid in acetonitrile in a 96-well plate and vortexed for 1 min at room temperature. The samples were centrifuged at 5,500 rpm (Allegra™ 25 R centrifuge, Beckman-Coulter) for 10 min at 4° C. Then 100 µl of the supernatant was mixed with 50 µl of distilled water, mixed and vortexed for 30 s. Bladder tissues were weighed and homogenized in 0.1% formic acid/methanol using zirconia beads (Biospec Products) and mini-bead beater equipped with microvial holder (Biospec Products) for 60 s. The samples were centrifuged at 14,000 rpm (Allegra™ 25 R centrifuge, Beckman-Coulter) for 2 min at 4° C. 150 µl of 0.1% trifluoroacetic acid in methanol was added to the samples, mixed and vortexed at 14,000 rpm (Allegra™ 25 R centrifuge, Beckman-Coulter) for 15 min at 4° C. All sample analyses were performed using UPLC-MS/MS. The limit of quantification for DTX was 10 ng/ml with a recovery of 97% from spiked control samples.

Several serum samples had non-quantifiable or no detectable levels. In general, serum levels of both PTX and DTX were low (5-20 ng/ml) following intravesical instillation. There were no significant differences (P>0.05) in serum levels between different groups and/or at different time points (Table 7). However, bladder tissue levels were about 100-500-fold higher than the serum levels. PTX and DTX loaded HPG-$C_{8/10}$-MePEG nanoparticles exhibited a 2-3-fold higher bladder tissue accumulation than the commercial formulations, although, the differences were not statistically significant (P>0.05, 1-way ANOVA, Bonferroni's multiple comparison test). The final drug concentrations in the urine were about 3-5-fold lower than the initial dosing solutions. This was due to the urine dilution during the 2 h period of intravesical instillation. However, there was no significant difference (P>0.05, 1-way ANOVA) in the final urine concentrations of PTX and DTX between different treatment groups. In general, serum levels of both PTX and DTX were low (5-20 ng/ml) following intravesical instillation. There were no significant differences (P>0.05) in serum levels between different groups and/or at different time points (Table 7).

TABLE 7

Pharmacokinetics of intravesical PTX and DTX formulations in orthotopic xenografts

| Taxane formulations | $C_{urine}$[1] | $C_{bladder}$[2] | $C_{serum}$[3] (ng/ml) | |
|---|---|---|---|---|
| (No. of mice) | (µg/ml) | (µg/g) | 1 h | 2 h |
| Taxol ® (3) | 303.2 ± 101.7 | 2.93 ± 0.69 | 8.11 | 5.49 |
| Taxotere ® (4) | 134.3 ± 79.2 | 1.22 ± 0.88 | 13.97 ± 4.8 | 16.02 |
| PTX/HPG-$C_{8/10}$-MePEG (4) | 188.4 ± 38.6 | 7.38 ± 4.16 | 16.02 | 19.36 ± 14.10 |
| DTX/HPG-$C_{8/10}$-MePEG (4) | 180.4 ± 60.5 | 3.60 ± 1.07 | 9.47 | 13.74 ± 3.0 |

[1] Final concentration in mouse urine after 2 h of intravesical instillation measured by HPLC
[2] Concentration of PTX or DTX in mouse bladder tissue following a 2 h intravesical instillation measured by LC/MS/MS
[3] Concentration of PTX or DTX in mouse serum taken at 1 and 2 h post-intravesical instillation measured by LC/MS/MS
Data shown are the mean ± SD

Example 15

Synthesis of HPG-$C_{8/10}$-MePEG and HPG-$C_{8/10}$-MePEG-$NH_2$

HPG-$C_{8/10}$-MePEG was prepared according to the protocol described in Example 7. $^1$H NMR (400 MHz, $D_6$-DMSO) δH: 0.75-0.82 (—$CH_3$, TMP); 0.82-0.92 (—$CH_3$-alkyl on O/DGE); 1.15-1.55 (—$CH_2$—, alkyl on O/DGE); 2.50 (solvent, $D_6$-DMSO); 3.15-3.80 (—CH and —$CH_2$—, from HPG core); 3.23 (—$OCH_3$— from MePEG), 3.32 (residual water); 4.8 (—OH). HPG-$C_{8/10}$-MePEG-$NH_2$ with various target amounts of amine substitution were synthesized using the procedure below. The amounts of reagents used are summarized in Table 8. Target amine substitutions represent the target number of moles of $NH_2$ per mole of HPG and are denoted by HPG-$C_{8/10}$-MePEG-$NH_{2(x)}$, where x is 61, 121, and 161 moles of $NH_2$ per mole of HPG. HPG-$C_{8/10}$-MePEG was dissolved in 15 ml of anhydrous 1,4-dioxane. Potassium hydride (KH) was rinsed with anhydrous hexane three times to remove the mineral oil and dried under vacuum. The polymer solution was combined with KH and stirred at room temperature until a clear solution was formed. N-(2,3-epoxypropyl)-phthalimide) (EPP) (Sigma-Aldrich) was dried by dissolution in dichloromethane with stirring overnight over $Na_2SO_4$ or $MgSO_4$. The solution was filtered and dried under vacuum to remove the dichloromethane. The dried EPP was dissolved in anhydrous 1,4-dioxane and added to the polymer with stirring overnight at 85-90° C. The product was neutralized by passing it three times through a cation exchange resin column (Amberlite IRC-150) and then precipitated three times from ether to remove unreacted EPP. Cleavage of the phthalimide function was achieved by hydrazinolysis with hydrazine monohydrate. Excess hydrazine monohydrate solution (2 ml) was added to the solution of the polymer in methanol and the mixture was refluxed for 72 h. After refluxing, the methanol was evaporated, the polymer was dialysed against water using a 10,000 MWCO membrane for 48 h and freeze dried. $^1$H NMR (400 MHz, $D_6$-DMSO) δH: 0.75-0.82 (—$CH_3$, TMP); 0.82-0.92 (—$CH_3$-alkyl on O/DGE); 1.15-1.55 (—$CH_2$—, alkyl on O/DGE); 2.50 (solvent, $D_6$-DMSO); 2.60-2.80 (—$CH_2$—$NH_2$) 3.15-3.80 (—CH and —$CH_2$—, from HPG core); 3.23 (—$OCH_3$— from MePEG). Reaction scheme for the surface modification of some of the hydroxyl groups (10-20%) on HPG-$C_{8/10}$-MePEG polymer with N-(2,3-epoxypropyl)-phthalimide) (EPP) followed by cleavage of the phthalimide functional groups by hydrazinolysis to produce HPG-$C_{8/10}$-MePEG-$NH_2$ is summarized in Scheme VII (R, represent the hydrophobic core based on mixture of alkyl ($C_8/C_{10}$) chains. ( )7, represent the hydrophilic shell based on MePEG 350).

Scheme VII
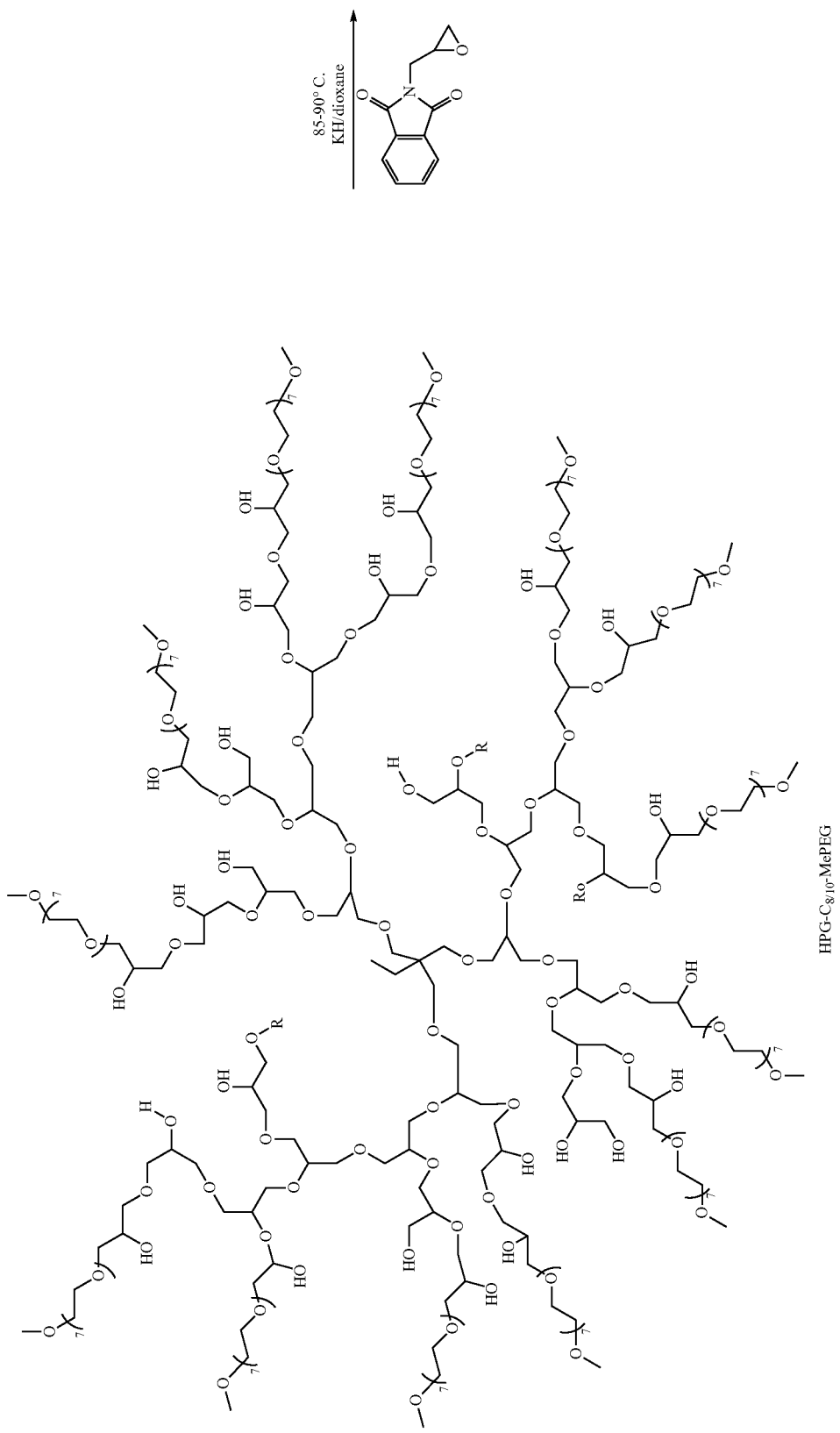
HPG-C$_{8/10}$-MePEG

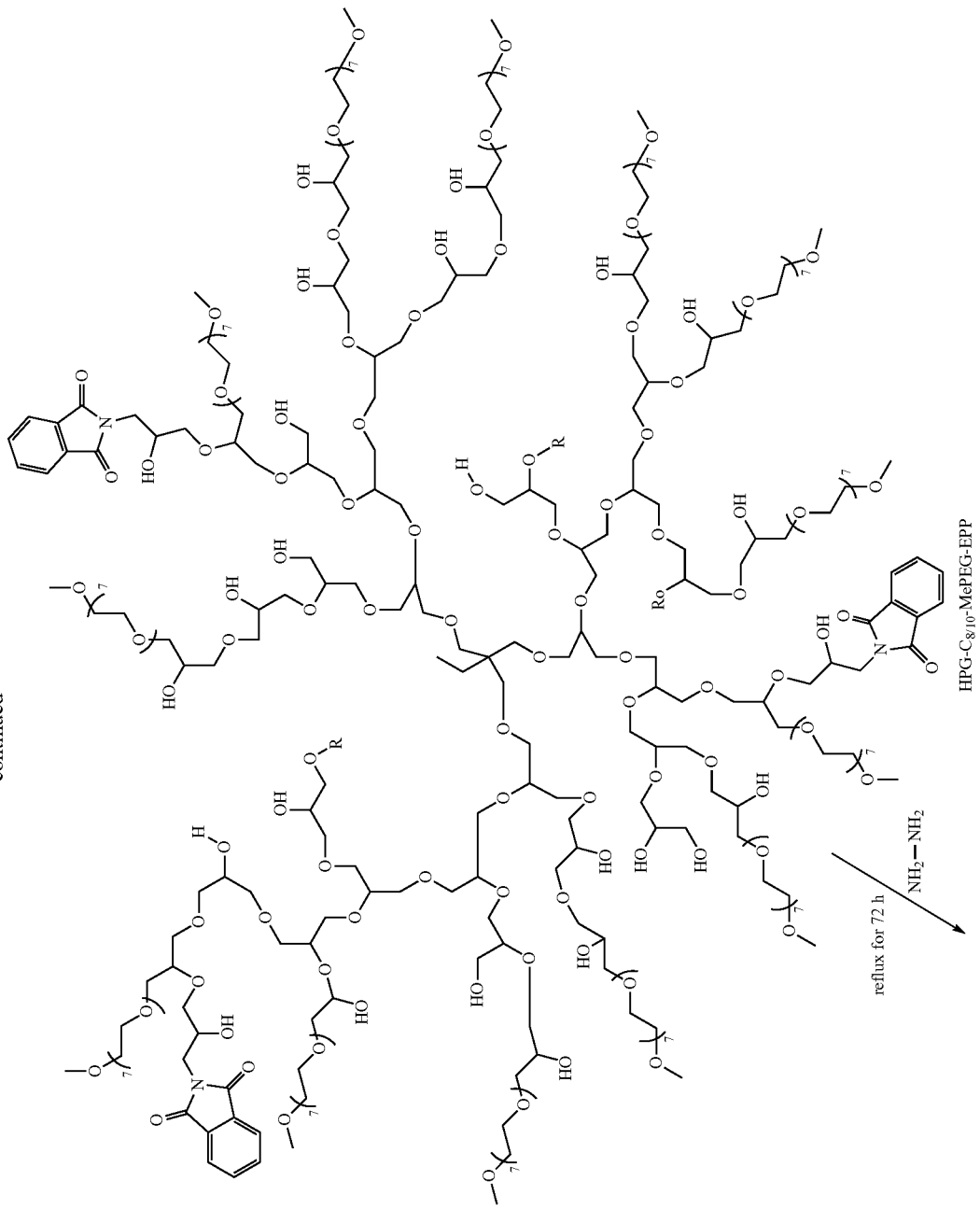

-continued
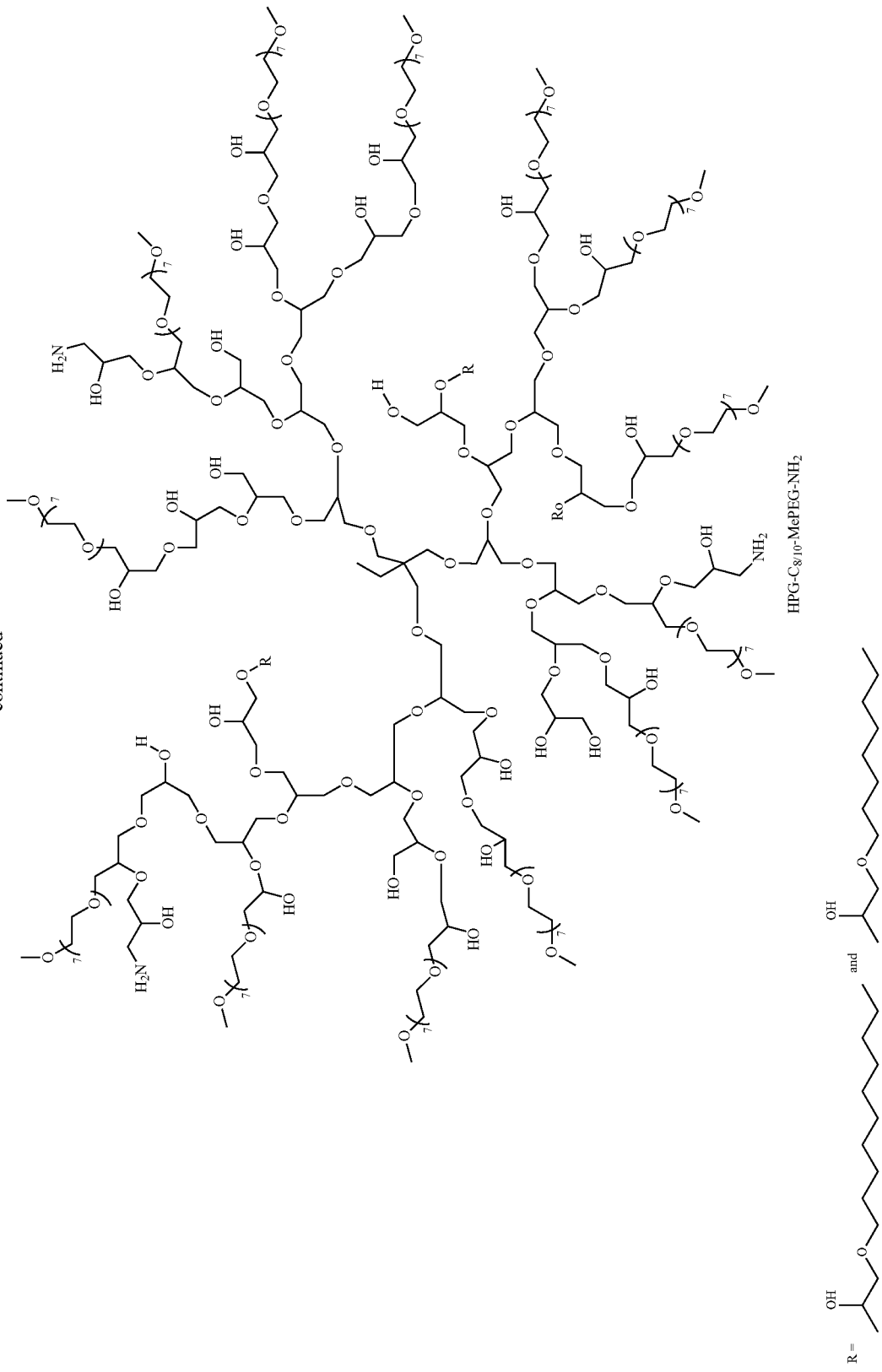

HPG-$C_{8/10}$-MePEG-$NH_{2(121)}$ was selected for drug loading and further evaluation in animal studies.

NMR and GPC

The fractions of MePEG and alkyl chains on HPGs were estimated from heteronuclear single quantum coherence (HSQC) NMR experiments recorded on a Bruker Avance 400 MHz (magnetic field strength 9.4 T) NMR spectrometer using deuterated solvents (Cambridge Isotope Laboratories, 99.8% D). Molecular weights and polydispersities of the polymers were determined by gel permeation chromatography with multi-angle laser light scattering detection (GPC-MALLS).

Figure 19:
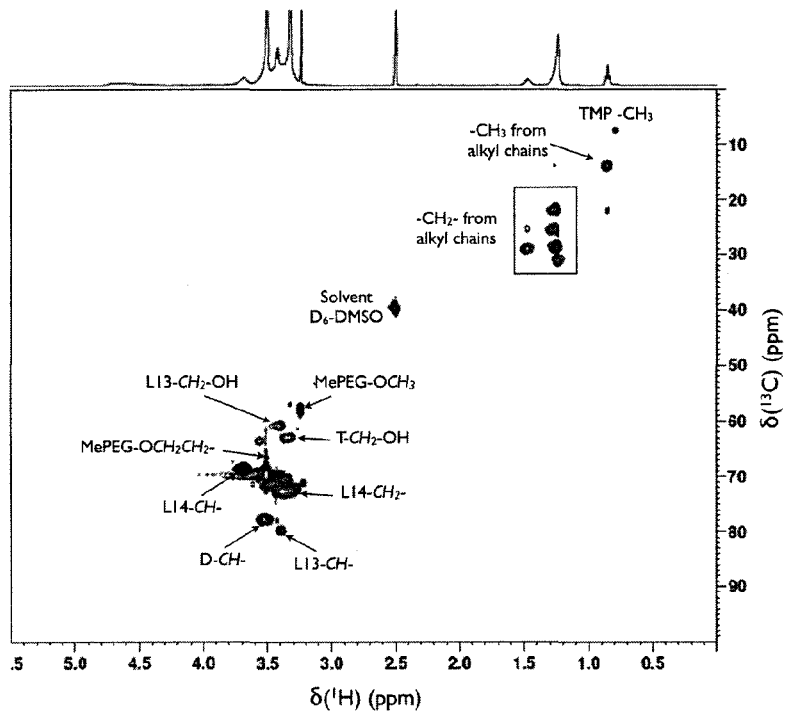
FIG. 19 shows (A) one-dimensional proton spectrum (top trace) and HSQC spectrum of HPG-$C_{8/10}$-MePEG and (B) one-dimensional proton spectrum (top trace) and HSQC spectrum of HPG-$C_{8/10}$-MePEG-$NH_{2(121)}$ acquired at a magnetic field strength of 9.4 T.
Figure 19:
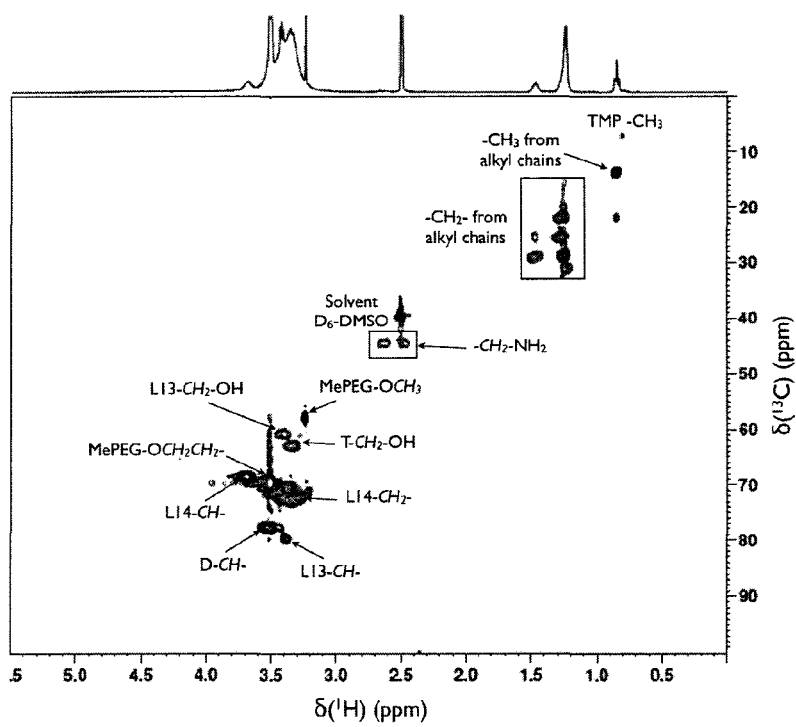

FIG. 19A shows a representative 2D HSQC spectrum of HPG-$C_{8/10}$-MePEG. The surface modification of HPG-$C_{8/10}$-MePEG with N-(2,3-epoxypropyl)-phthalimide) was confirmed by 2D HSQC experiments in which the aromatic phthalimide CH groups were identified ($^1$H chemical shifts 7.2-7.8 ppm & $^{13}$C chemical shifts 125-135 ppm). The success of cleaving the phthalimide groups by hydrazinolysis to generate free amine groups was monitored by both 1D NMR and 2D HSQC experiments. FIG. 19B shows a representative 2D HSQC spectrum of HPG-$C_{8/10}$-MePEG-$NH_{2(121)}$, which shows the success of cleavage of the phthalimide protecting group to generate primary amine groups (2.60-2.80 ppm & $^{13}$C chemical shifts 45 ppm, FIG. 19B). HSQC NMR data confirmed the structure of dHPGs as hyperbranched polymers with branching architectures evident in the spectra (FIG. 19). The mole fraction of $C_{8/10}$ alkyl chains and MePEG on dHPGs can be calculated from the signal integrals in HSQC experiments. By comparing the integrals of MePEG methoxy-group and the octyl/decyl glycidyl ether (O/DGE) methyl group to the integral of the TMP $CH_3$ group, the fractions of MePEG, and O/DGE (mol/mol) were calculated for each dHPG polymer (Table 10).

Conductometric Titrations and Fluorescamine Assay

The mole fractions of amine groups derivatized on HPG-$C_{8/10}$-MePEG polymers were measured by conductometric titration using HCl and NaOH. Conductometric titrations were done on YSI model 35 conductance meter and 3403 cell with platinum electrode at 25° C. A syringe pump (Harvard Instruments) was used to inject a diluted NaOH solution at a constant flow rate of 0.0102 ml/min. For a typical titration, approximately 10 mg of HPG-$C_{8/10}$-MePEG-$NH_2$ was dissolved in distilled water and titrated first with 0.05 N HCl followed by back titration with 0.05 N NaOH. Conductance of the solution was measured at every 30 s. Potassium hydrogen phthalate solution (0.05 N) was used for standardizing sodium hydroxide solution. Based on conductometric titration and molecular weight measurements, the number of moles of amine groups per HPG molecule was calculated and the values obtained were in the range of 50-119 mol/mol which were consistent with the targeted mole ratios of $NH_2$ per mol of HPG-$C_{8/10}$-MePEG-$NH_2$ (Table 8 & 10).

TABLE 8

Stoichiometry of reagents used for the synthesis of HPG-$C_{8/10}$—MePEG-$NH_2$

| HPG-$C_{8/10}$—MePEG-$NH_2$ | Mass of reagents (g) | | | | |
| --- | --- | --- | --- | --- | --- |
| Target $NH_2$ substitution (moles of $NH_2$/mole of HPG) | HPG-$C_{8/10}$—MePEG | KH | EPP | | Target $NH_2$ (mol/mol HPG) |
| HPG-$C_{8/10}$—MePEG-$NH_{2\,(61)}$ | 4 | 0.2 | 0.6 | | 61 |
| HPG-$C_{8/10}$—MePEG-$NH_{2\,(121)}$ | 4 | 0.45 | 1.184 | | 121 |
| HPG-$C_{8/10}$—MePEG-$NH_{2\,(161)}$ | 4 | 0.6 | 1.575 | | 161 |

KH, potassium hydride; EPP, N-(2,3-epoxypropyl)-phthalimide).
Molecular weight properties of HPG-$C_{8/10}$—MePEG, Mw = 83,000 and Mw/Mn = 1.22

The number of moles of amine groups per HPG molecule may also be calculated using fluorescence and molecular weight measurements. For example, a fluorescamine assay for $NH_2$ may be used (Table 9). HPG-$NH_2$ samples were prepared by measuring >5 mg of HPG-$NH_2$ into a 2 mL LC/MS glass vial and adding an appropriate amount of deionized $H_2O$ to make a concentrated stock, then sonicating the mixture until the HPG-$NH_2$ was dissolved. The stock solution was diluted to 1 mg/mL with deionized $H_2O$ per mg of HPG-$NH_2$ Phenylalanine standard was prepared by measuring approximately 1 mg of phenylalanine into a aluminum micro weighing dish and transferring to a 20 mL glass vial, then adding 5 mL of deionized $H_2O$ per mg of phenylalanine, and sonicating the mixture until the phenylalanine was dissolved (0.2 mg/mL phenylalanine stock). 60 μL of 0.2 mg/mL phenylalanine stock was transferred into a glass LC/MS vial. 90 μL of deionized $H_2O$ was added, and vortexed to mix the solution (80 ng/mL phenylalanine working standard).

40 μL of 1 mg/mL HPG-$NH_2$ stock was transferred into a 96-well plate, 10 μL of deionized $H_2O$ was added (or 50 μL, 40 μL, 30 μL, 20 μL, 10 μL, or 0 μL of 80 ng/mL phenylalanine working standard was added and topped up with deionized $H_2O$ to 50 μL if necessary); and the sample was pipetted to mix. 12.5 μL of sodium borate buffer was added to the well and pipetted to mix. The pipette tip was rinsed with 0.03% fluorescamine solution twice to coat the tip and prevent dripping. 12.5 μL of 0.03% fluorescamine solution was added to sample well. The sample was pipetted to mix and then put on a plate shaker, covered, and shaken for 1 min. 175 μL of deionized $H_2O$ was added to react excess fluorescamine and pipetted to mix, and briefly placed on the plate shaker. The sample was analyzed by a fluorescence plate reader set at an excitation wavelength of 390 nm, an emission wavelength of 475 nm, and a 5 nm bandwidth for both excitation and emission wavelengths.

TABLE 9

Mols of amine per mols of HPG measured by fluorescamine assay

| HPG-MePEG-$NH_2$ Sample # | HPG (g) | EPP-A or EPP-S (mg) | $KH^c$ or $NaH^d$ (mg) | Amine (mol/HPG mol) |
| --- | --- | --- | --- | --- |
| 1 | 16 | 4720$^a$ | 540$^c$ | 10.25 |
| 2 | 2 | 620$^a$ | 68$^c$ | 9.72 |
| 3 | 2 | 600$^a$ | 220$^c$ | 11.24 |
| 4 | 2 | 636$^a$ | 560$^c$ | 7.38 |
| 5 | 2 | 631$^a$ | 560$^d$ | 10.42 |
| 6 | 2 | 604$^b$ | 250$^c$ | 13.63 |

TABLE 9-continued

Mols of amine per mols of HPG measured by fluorescamine assay

| HPG-MePEG-NH$_2$ Sample # | HPG (g) | EPP-A or EPP-S (mg) | KH[c] or NaH[d] (mg) | Amine (mol/HPG mol) |
|---|---|---|---|---|
| 7 | 2 | 1200[b] | 504[c] | 37 |
| 8 | 1 | 300[b] | 30[c] | 37.56 |

[a]EPP-A (EPP from Atlantic) Purity: 78% by UPLC and 69% by NMR.
[b]EPP-S (EPP from Sigma-Aldrich) Purity: 91% by UPLC and 95% by NMR.

Thermal Analysis

DSC and TGA were used to evaluate the thermal and degradation properties of the dHPGs. Thermal analysis was conducted using a TA Instruments DSC Q100 and a TGA Q50. DSC runs were obtained by cycling weighed samples in hermetic sealed aluminum pans through a "heat-cool-heat" cycle at 10° C./min over the temperature range of −90 to 85° C. TGA runs were conducted primarily in a "stepwise isothermal" mode where each phase of weight loss in the degradation process was observed under isothermal conditions and the HPGs were heated through to near 100% weight loss at 500° C. Table 10 shows the thermal events of HPG-C$_{8/10}$-MePEG and HPG-C$_{8/10}$-MePEG-NH$_2$ samples. HPG-C$_{8/10}$-MePEG and HPG-C$_{8/10}$-MePEG-NH$_2$ samples showed similar DSC/TGA profiles. HPGs exhibited a glass transition temperature between −45 to −58° C. The presence of amine groups produced a small increase in the Tg of HPGs. The major degradation event was observed at temperatures above 300° C., which shows good thermal stability properties of HPGs. Approximately 3-5% weight loss occurred at temperatures below 100° C. probably due to some residual solvents or water in HPGs. A good thermal stability of HPGs is desirable for pharmaceutical applications to allow for the potential use of heat sterilization methods.

Particle Sizing and Zeta Potential

Particle size and zeta potential analysis were conducted using a Malvern NanoZS Particle Size analyzer using DTS0012 disposable sizing cuvettes for each analysis. Samples were filtered with 0.2 μm in-line syringe filter (PALL Acrodisc 13 mm with nylon membrane). Sample acquisition parameters were: angle at 173° back-scatter with automatic attenuation; number of runs 11 (10 seconds/run); dispersant was water at 25° C. (viscosity 0.8872 cP and RI 1.330); Mark-Houwink parameter A=0.428 and K=7.67e$^{-05}$ (cm$^2$/s). HPGs were assumed to have a similar refractive index as polyethylene glycol (PEG) with a RI=1.460 and absorption 0.01. The final data represented the average of all the runs. HPGs are small nanoparticles with hydrodynamic radii <10 nm. HPGs form extremely small nanoparticles of less than 10 nm. Table 10 shows the particle sizes and zeta potential characteristics of HPGs. The surface derivatization of HPG-C$_{8/10}$-MePEG with amine groups had no effect on their particle size, however, a significant effect on zeta potential was observed. The zeta potential of amine terminated HPG polymers was highly positive at low pH and changed to slight negative values in basic conditions. This pH titratable change in surface charge arises from protonation/deprotonation of the amine groups. At physiological pH of 7.4 some of the amine groups on HPGs are ionized, and therefore, positive zeta potentials were expected (Table 10). However, at pH values greater than 8 essentially all the amine groups are uncharged so the slight negative charge observed at pH 11 was probably due to the electronegative hydroxyl groups present on these HPGs. Drug loading of HPGs had no significant effect on their particle sizes and the HPGs remained well dispersed as unimolecular micelles in solution. DTX loaded HPGs nanoparticles were physically stable, no drug precipitation or aggregation observed during one week storage at room temperature.

TABLE 10

Physicochemical characteristics of HPGs derivatized with C$_{8/10}$ alkyl chains and modified with MePEG and amine groups

| Polymers | Structure by NMR (mol/mol HPG) | | Titration NH$_2$ | DSC/TGA | | Zeta potential (mV) | Particle size (nm) |
|---|---|---|---|---|---|---|---|
| HPGs | MePEG | O/DGE | (mol/mol) | Tg (° C.)[1] | Td (° C.)[2] | | |
| HPG—C$_{8/10}$—MePEG | 4.3 | 4.7 | — | −58.9 | 344 | −1.5 | 7.5 ± 1.0 |
| HPG—C$_{8/10}$—MePEG—NH$_{2\ (61)}$ | 3.5 | 2.9 | 50 | −46 | 325 | 11 | 7.7 ± 2.9 |
| HPG—C$_{8/10}$—MePEG—NH$_{2(121)}$* | 8.1 | 6.3 | 104 | −45.5 | 327 | 11.9 | 9.6 ± 4.5 |
| HPG—C$_{8/10}$—MePEG—NH$_{2\ (161)}$ | 7.9 | 6.3 | 119 | −46.4 | 320 | 13 | 8.1 ± 2.8 |

*This batch was selected for drug loading and in vivo studies;
[1]Tg, glass transition taken at midpoint of transition;
[2]Td, degradation temperature taken at maximum weight loss Example 16

Evaluation of Mucoadhesive Properties

Figure 20:
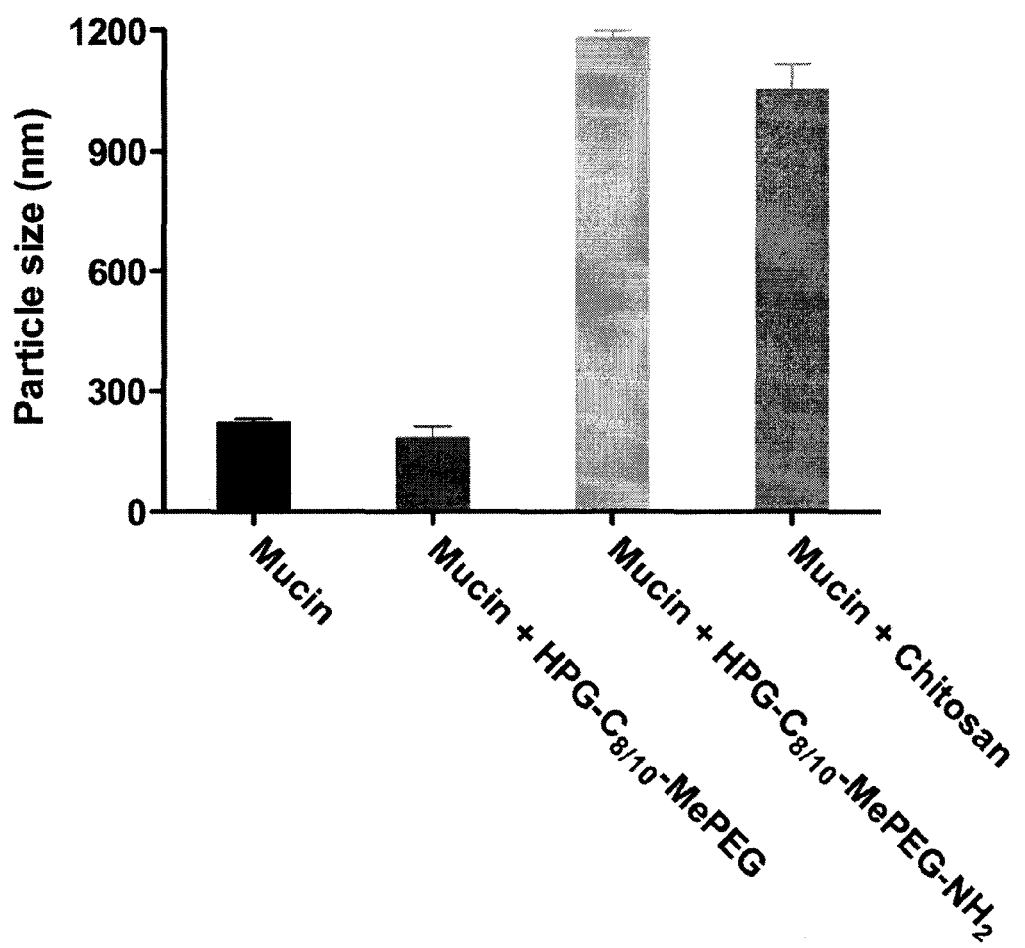
FIG. 20 shows mucoadhesive properties of HPGs as assessed by a mucin-particle method.

To evaluate the mucoadhesive properties of HPGs, the mucin-particle method developed by Thongborisute and Takeuchi was used (Thongborisute, J.; Takeuchi, H. Int. J Pharm. 2008, 354, 204-209). This method is based on changes in particle size due to aggregation of submicron-sized mucin as a result of interaction between adhesive polymer and mucin. Submicron-sized mucin solution was mixed with equal volumes of HPGs (10% w/v) in 100 mM acetate buffer, vortexed and incubated at 37° C. for 30 min. Changes in particle size were monitored by light scattering measurements using 3000 HS Zetasizer (Malvern Instruments, San Bernardino, Calif.). Each test was performed in triplicate and chitosan solution (1% w/v) was used as a positive control. The particle size of the mucin increased significantly after incubation with either chitosan (1% w/v) or HPG-C$_{8/10}$-MePEG-NH$_{2(121)}$ (10% w/v) solutions (FIG. 20). HPG-C$_{8/10}$-MePEG (10% w/v) had no effect on the size of mucin particles. The increased particle size of the sub-micron-sized mucin was due to aggregated particles of mucin and HPG-C$_{8/10}$-MePEG-NH$_2$ nanoparticles and was attributed to mucoadhesive forces between mucin and the amine substituted HPGs. Chitosan, a widely known mucoadhesive polymer was used as a positive control. However, due to its high molecular weight and low solubility in aqueous solution, a diluted solution of chitosan was used (1% w/v). Even this diluted solution exhibited significant changes in particle size of the mucin after co-incubation. The mucoadhesiveness of both chitosan and HPG-$C_{8/10}$-MePEG-$NH_2$ is believed to be due to electrostatic interactions between positively charge amine groups and negatively charged mucin particles but also other contribution such as hydrogen bonding, hydrophobic effects and chain entanglement might have an effect. However, the lack of mucoadhesiveness of HPG-$C_{8/10}$-MePEG suggests that electrostatic attraction appears to be a major contribution to the mucoadhesive properties of HPG-$C_{8/10}$-MePEG-$NH_2$.

Example 17

Cell Proliferation/Binding and Uptake Studies

Cell Proliferation

KU7-luc cells were plated at 5,000 cells/well in 96-well plates in a 100 µl volume of McCoy's Medium supplemented with 10% FBS and allowed to equilibrate for 24 h before freshly prepared solutions of HPG-$C_{8/10}$-MePEG and/or HPG-$C_{8/10}$-MePEG-$NH_2$ (dissolved in PBS, pH 7.4, 0-150 µg/ml) were added. Cells were exposed to the HPG solutions for 2 h and cell viability was determined after 72 h using the CellTiter96 AQueous Non-Radioactive Cell Proliferation Assay (Promega, Madison, Wis.) as described previously (Mugabe, C.; Hadaschik, B. A.; Kainthan, R. K.; Brooks, D. E.; So, A. I.; Gleave, M. E.; Burt, H. M. *BJU Int.* 2009, 103, 978-986).

Rhodamine Labeling of HPGs

HPG-$C_{8/10}$-MePEG and HPG-$C_{8/10}$-MePEG-$NH_{2(121)}$ polymers were covalently labeled with tetramethyl-rhodamine-carbonyl-azide (TMRCA) as previously reported (Savic, R.; Luo, L.; Eisenberg, A.; Maysinger, D. *Science* 2003, 300, 615-618). Tetramethylrhodamine-carbonyl-azide (TMRCA) was purchased from Invitrogen Canada Inc. (Burlington, ON). Briefly, 500 mg HPGs (HPG-$C_{8/10}$-MePEG or HPG-$C_{8/10}$-MePEG-$NH_{2(121)}$ were dissolved in 5 ml of anhydrous 1,4-dioxane. An appropriate amount of tetramethylrhodamine-5-carbonyl azide (TMRCA, MW 455.47) was dissolved in 2 ml anhydrous 1,4-dioxane to give a final concentration of 1 mg/ml. An aliquot of 675 µl of this fluorescent probe, which corresponds to approximately 20 mol % of HPGs, was added to the HPGs solution and heated at 80° C. in oil bath under nitrogen stream with stirring for 5 h. Unreacted probe was removed by dialysis against DMF (MWCO 12,000-14,000) until the dialysate was colourless and then dialysed against distilled water for 24 h. The fluorescent-labeled polymers (HPGs-TMRCA) were freeze dried and stored at −80° C. in amber vials.

Cell Binding and Uptake

KU7-luc cells were used to assess the binding and uptake of rhodamine labed HPGs. Cells were plated at 10,000 cells/well into 96-well plates in 100 µl volume of McCoy's Medium supplemented with 10% FBS and allowed to equilibrate for 24 h. The media was removed and cells were incubated with rhodamine labeled HPGs (HPG-$C_{8/10}$-MePEG-TMRCA or HPG-$C_{8/10}$-MePEG-$NH_{2(121)}$-TMRCA, 1.56-200 µg/ml) for 2 h. Following incubation period, cell were washed 3 times with PBS and lysed with 200 µl of 0.5% Triton X-100 (pH 8 in PBS) and the amount of cellular fluorescence binding was measured by fluorescence spectroscopy (Synergy 4.0) at excitation/emission of 545/578. Standards were prepared from rhodamine labeled HPGs (0.781-6.25 µg/ml) in Triton X-100 and PBS (pH 8). The amount of rhodamine labeled HPGs taken up into cells or surface bound was expressed as percentage of total amount of polymer added on each well.

Confocal Fluorescence Analysis of Cell Uptake

KU7-luc cells were grown in 10 cm petri dishes with 1 cm×1 cm cover slips on the bottom of the dish for the cells to grow on, until a confluence of ~75% was reached, which corresponded to a cell number of 7×10$^4$ cells. Cell-containing cover slips were then removed and washed 3 times with warmed PBS. Cover slips were then placed cell side up in parafilm lined petri dishes for the duration of the uptake assay. Rhodamine labeled HPG polymers (250 µl of HPG-$C_{8/10}$-MePEG-TMRCA or HPG-$C_{8/10}$-MePEG-$NH_{2(121)}$-TMRCA) were added to the cells on cover slips at a concentration of 1 mg/ml. Cells were incubated for 1, 4, 8 and 24 h. After each time point, cover slips were washed 4 times vigorously in PBS. After gently blotting off excess PBS, 250 µl of 3.7% paraformaldehyde at room temperature was used to fix the cells for 10 minutes. Cover slips were then washed 3 more times in PBS, submerged in water, excess liquid was blotted off and were finally mounted cell side down on glass slides with Prolong gold with 4',6-diamidino-2-phenylindole (DAPI). Clear nail polish was used sparingly around the edges of the cover slip to stop drying out the sample. An overnight incubation ensured proper hardening of the sample which was then ready for imaging. Microscopy studies were performed on Olympus FV-1000 inverted confocal microscope. The laser wavelengths used were 568 nm and 405 nm for imaging of rhodamine and DAPI, respectively. Direct contrast (DIC) was also performed to visualize cell membranes and was activated with the 405 nm laser as well. Laser power and high voltage gain was kept relatively constant within each polymer group to allow for consistent comparison. In order to clearly show that labeled polymer was inside the cell, images were analyzed by fluorescence and DIC.

Cell Proliferation/Binding and Uptake Studies

Figure 21:
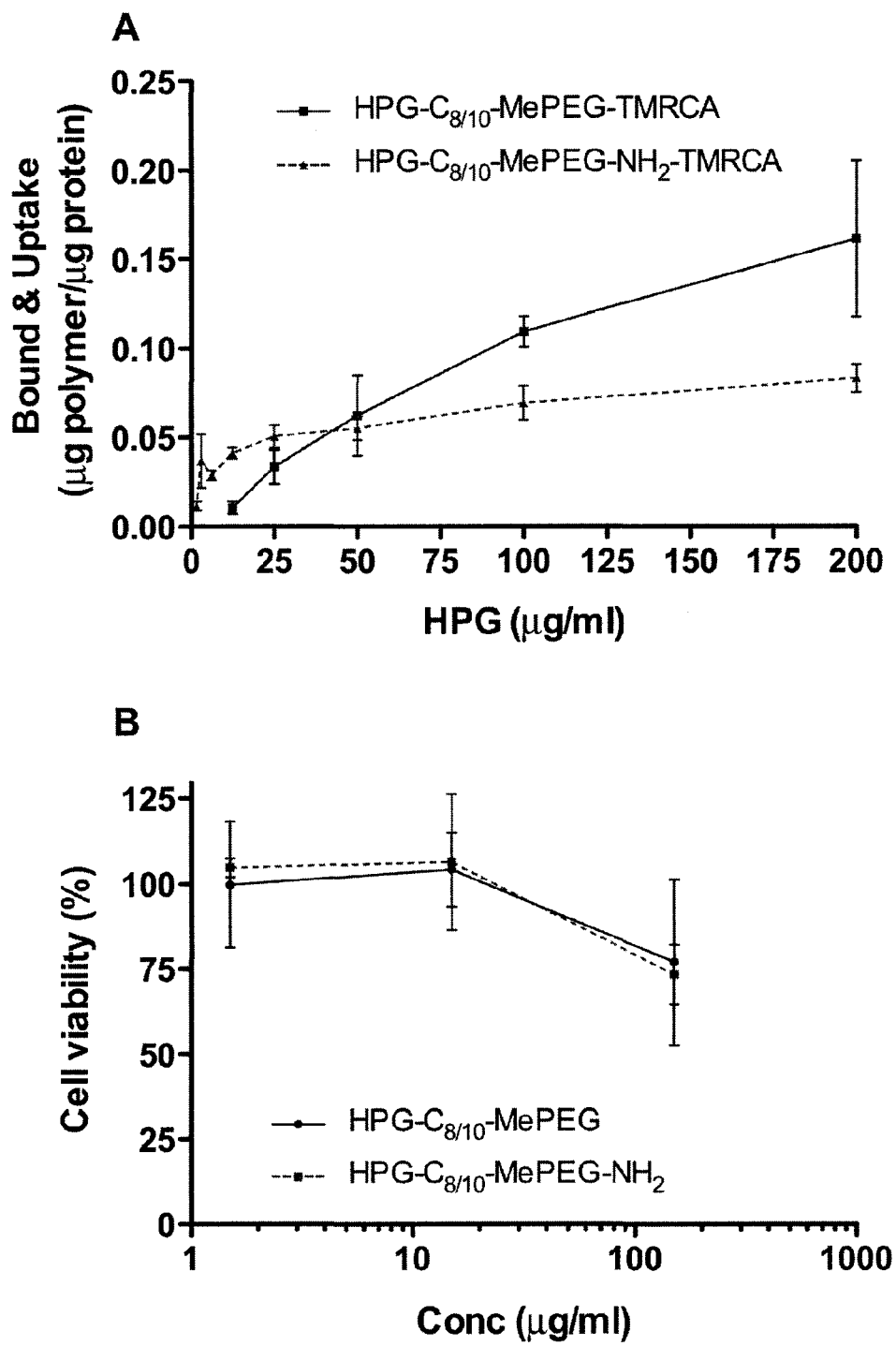
FIG. 21 shows (A) in vitro KU7-luc binding of rhodamine labeled HPGs and (B) cell viability of KU7-luc cells exposed to HPG solutions.

At low concentrations, HPG-$C_{8/10}$-MePEG-$NH_{2(121)}$-TMRCA nanoparticles were extensively bound and internalized into KU7-luc, whereas, no evidence of cell binding or uptake was observed for HPG-$C_{8/10}$-MePEG-TMRCA nanoparticles at concentrations below 12.5 µg/ml (FIG. 21A). The strong binding profile of this polymer is probably due to the electrostatic attraction between the positively charged HPG-$C_{8/10}$-MePEG-$NH_{2(121)}$ polymer and the negatively charged cell membrane of KU7-luc. However, as the concentration of HPGs increased, the cell binding and uptake of HPG-$C_{8/10}$-MePEG-$NH_{2(121)}$-TMRCA nanoparticles reached a saturation point (at 25 µg/ml) while the cell binding and uptake of HPG-$C_{8/10}$-MePEG-TMRCA nanoparticles into KU7-luc was found to be concentration-dependent with linear relationship observed at concentrations between 12.5 and 50 µg/ml, followed by less pronounced binding and uptake at higher polymer concentrations (FIG. 21A). To evaluate whether the saturation behavior of HPG-$C_{8/10}$-MePEG-$NH_{2(121)}$-TMRCA nanoparticles was due to their cytotoxicity effects, we have evaluated the effect of HPG on the proliferation of the KU7-luc cells. Cells were exposed to empty (non drug loaded) HPG-$C_{8/10}$-MePEG and HPG-$C_{8/10}$-MePEG-$NH_2$ nanoparticles (0-150 µg/ml) for 2 h and cell viability was determined by MTS assay. Both HPG-$C_{8/10}$-MePEG and HPG-$C_{8/10}$-MePEG-$NH_2$ nanoparticles exhibited similar proliferation effect and were biocompatible with the KU7-luc cell line at the concentrations tested (FIG. 21B). Therefore, the differences in cell binding and uptake observed for HPG-C$_{8/10}$-MePEG-TMRCA and HPG-C$_{8/10}$-MePEG-NH$_{2(121)}$-TMRCA nanoparticles were likely not due to their cytotoxicity effect on the KU7-luc cell line.

Confocal Fluorescence Analysis of Internalization of Rhodamine Labeled HPGs

Confocal microscopy was used to monitor whether the nanoparticles were internalized by cells or simply bound to the cell membrane of KU7-luc. Both HPG-C$_{8/10}$-MePEG-TMRCA and HPG-C$_{8/10}$-MePEG-NH$_{2(121)}$-TMRCA nanoparticles were rapidly internalized by KU7-luc cells and complete uptake was attained by 1 h of incubation (data not shown). The presence of rhodamine labeled HPGs in the cytoplasm was observed by the fluorescence analysis. The presence of HPG-C$_{8/10}$-MePEG-TMRCA and/or HPG-C$_{8/10}$-MePEG-NH$_{2(121)}$-TMRCA nanoparticles throughout the cytoplasm was observed as opposed to being only adhered to or present in cell membrane. There was no fluorescence from the polymers detected in the nuclear compartment of the KU7-luc cells. The absence of HPG nanoparticles in the nuclear compartment may have been due to their relatively high molecular weights (<80 kDa). Both HPG-C$_{8/10}$-MePEG-TMRCA and HPG-C$_{8/10}$-MePEG-NH$_{2(121)}$-TMRCA nanoparticles have no effect on the viability and prevalence of the KU7-luc cells when compared to the control cells at all time points. Overall, rhodamine labeled HPG nanoparticles were taken up into KU7-luc cells by 1 h of incubation and there were no differences in the images obtained at 1, 4, 8 or 24 h time points.

Example 18

Loading and Quantification of DTX in HPGs and DTX Release from HPGs

Loading and Quantification of DTX in HPGs

DTX was loaded in HPG-C$_{8/10}$-MePEG and HPG-C$_{8/10}$-MePEGNH$_{2(121)}$ by a solvent evaporation method in which the drug and polymer were dissolved in a common organic solvent and the solvent removed. The resulting polymer/drug matrix was reconstituted with 10 mM PBS (pH 7.4). The resulting solutions were generally clear but in cases where white particles were observed, the solutions were centrifuged (18,000 g for 10 min) and supernatants were transferred to new vials.

The amounts of DTX incorporated in HPGs were determined by reversed phase HPLC. Drug content analysis was performed using a symmetry C18 column (Waters Nova-Pak, Milford, Mass.) with a mobile phase containing a mixture of acetonitrile, water, and methanol (58:37:5, v/v/v) at a flow rate of 1 ml/min. Sample injection volumes were 20 µl and detection was performed using UV detection at a wavelength of 232 nm. Total run time was set to 5 min and DTX retention time was 2.9 min. Up to 5% w/w of drug loading was achieved by this method, which corresponds to about 5-6 DTX molecules per HPG molecule. The aqueous solubility of DTX is in the range of 7 µg/ml (Du, W.; Hong, L.; Yao, T.; Yang, X.; He, Q.; Yang, B.; Hu, Y. *Bioorg. Med. Chem.* 2007, 15, 6323-6330; Liggins, R. T.; Hunter, W. L.; Burt, H. M. *J. Pharm. Sci.* 1997, 86, 1458-1463) and incorporation DTX in HPGs resulted in approximately 1,000-fold increase in water solubility of this drug.

DTX Release from HPGs

Figure 22:
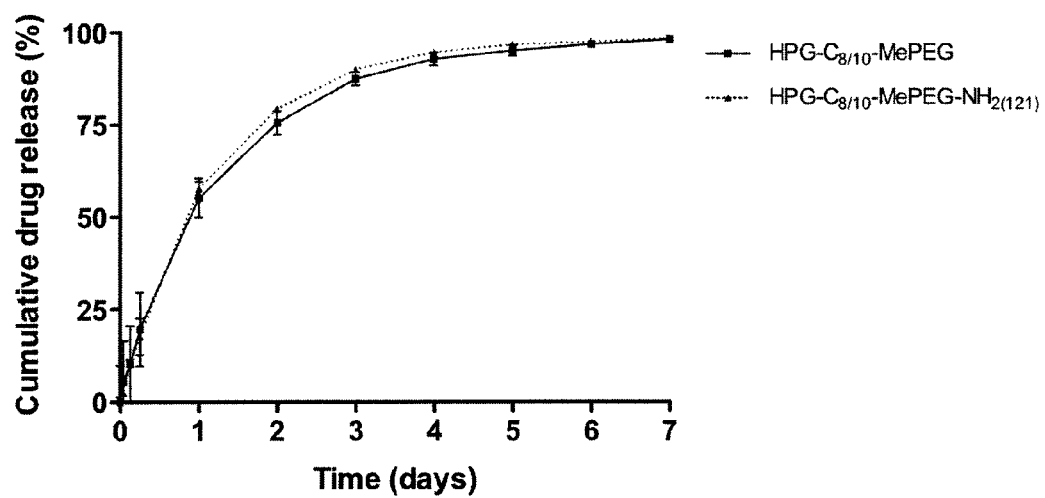
FIG. 22 shows cumulative DTX release from HPG-$C_{8/10}$-MePEG and HPG-$C_{8/10}$-MePEG-$NH_2$ nanoparticles in artificial urine at pH 6.5.

DTX release from HPG nanoparticles (HPG-C$_{8/10}$-MePEG and HPG-C$_{8/10}$-MePEG-NH$_{2(121)}$) was determined by the dialysis method. Briefly, 100 mg of HPG-C$_{8/10}$-MePEG or HPG-C$_{8/10}$-MePEG-NH$_{2(121)}$ were weighed and mixed with 1 mg of DTX in 1 ml acetonitrile solution, spiked with 15 µCi of $^3$H-DTX and then dried under a nitrogen stream to remove the solvent. The HPG/DTX matrix was hydrated with 2 ml of PBS and transferred into the dialysis bags and dialysed against 500 ml of artificial urine (pH 6.5) with shaking at 100 rpm. The pH of the solution was adjusted to 6.5 using 0.1M HCl. The pH 6.5 was chosen because it is the median physiological range for human urine, although it may vary over a wide range (pH 4.5-8). (Brooks, T.; Keevil, C. W. *Lett. Appl. Microbial.* 1997, 24, 203-206.) At different time points, the volumes of the dialysis bags were measured and a 10 µl sample was taken for measurement of the remaining radioactivity in the dialysis bags and the entire external release media was exchanged with fresh media to maintain sink conditions. The concentration of $^3$H-DTX remaining in the dialysis bag at each time point was determined by beta scintillation counting (Beckman Coulter Canada, Mississagua, ON). The cumulative percent drug released was calculated by subtracting the amount of drug remaining at each time point from the initial amount of drug at the beginning of the experiment. The data were expressed as cumulative percentage drug released as a function of time. The release profiles of DTX from HPGs were characterized by a continuous controlled release with little or no burst phase of release (FIG. 22). Approximately 55% of initially encapsulated drug was released within the first 24 h of incubation. The presence of amine groups on the surface of HPGs had no effect on drug release (FIG. 22).

Example 19

Evaluation of Intravesical DTX Formulations in an Orthotopic Bladder Cancer Model Tolerability and efficacy of intravesical DTX loaded HPG formulations in mice bearing orthotopic bladder xenografts were evaluated. The orthotopic mouse model used has been reported (Mugabe, C.; Hadaschik, B. A.; Kainthan, R. K.; Brooks, D. E.; So, A. I.; Gleave, M. E.; Burt, H. M. *BJU Int.* 2009, 103, 978-986; Hadaschik, B. A.; Black, P. C.; Sea, J. C.; Metwalli, A. R.; Fazli, L.; Dinney, C. P.; Gleave, M. E.; So, A. I. *BJU Int* 2007, 100, 1377-1384; Hadaschik, B. A.; ter Borg, M. G.; Jackson, J.; Sowery, R. D.; So, A. I.; Burt, H. M.; Gleave, M. E. *BJU Int.* 2008, 101, 1347-1355). All animal studies were carried out in accordance with the Canadian Council on Animal Care and the animal care protocol has been approved by the Animal Care Committee from our institution (The University of British Columbia). In this model, luciferase expressing KU7-luc cancer cells were used. For tumour inoculation, eight-week-old female nude mice (Harlan, Indianapolis, Ind.) were anaesthetized with isoflurane. A superficial purse-string suture was placed around the urethral meatus before a lubricated 24G Jelco angiocatheter (Medex Medical Ltd., Lancashire, UK) was passed through the urethra into the bladder. After a single irrigation of the bladder with 100 µl PBS, two million KU7-luc cells were instilled as a single cell suspension in 50 µl and the purse-string suture was tied down for a 2.5 h period of time, during which the mice were kept anaesthetized. After removal of the suture mice were placed in cages and monitored until they have regained consciousness and voiding in normal manner. Five days post-tumour inoculation, 26 randomized mice were treated via intravesical instillation (50 µl and 2 h dwell time) according to the following treatment groups: PBS (control); Taxotere® (0.5 and 1.0 mg/ml, DTX in Tween 80); DTX in HPG-C$_{8/10}$-

MePEG (0.5 and 1.0 mg/ml); DTX in HPG-$C_{8/10}$-MePEG-$NH_{2(121)}$ (1.0 mg/ml). Mice were monitored for several hours on the day of treatment and daily thereafter. Any signs of toxicity were reported, in particular, weight loss, change in food and water consumption, lethargy, hunched posture, and/or gross manifestations of stress. Any mouse showing signs of pain or illness which did not recover within 24 h was sacrificed. Tumour burden was monitored by non-invasive imaging of mice on days 2, 8, 12, and 19 with an IVIS 200 Imaging System (Xenogen Corp., Alameda, Calif.). Briefly, mice were injected intraperitoneally with 150 mg/kg luciferin, anaesthetized with isoflurane and imaged in the supine position exactly 15 min after luciferin injection. Data were acquired and analyzed using Living Image software version 2.50 (Xenogen).

Figure 23:
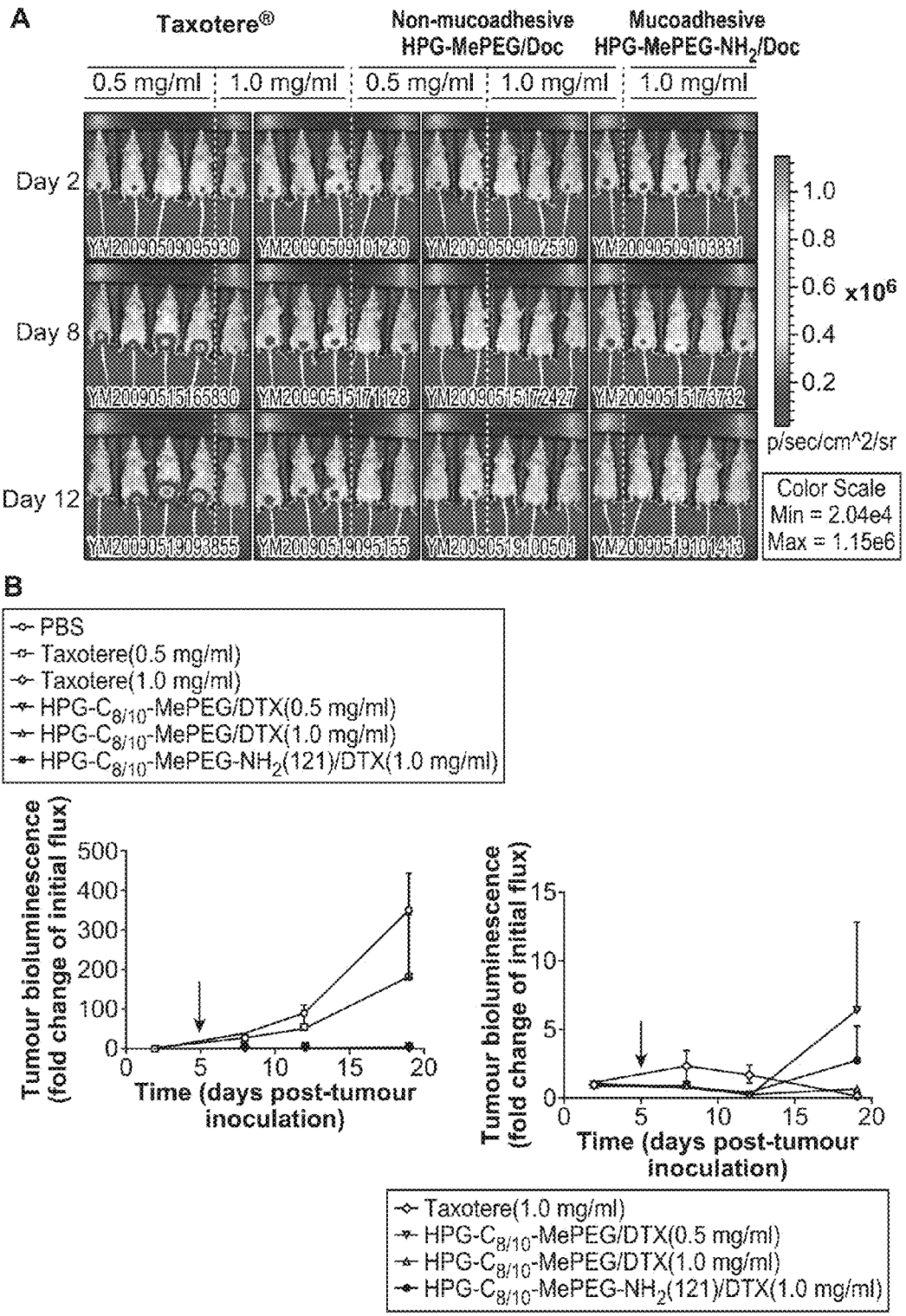
FIG. 23 shows (A) bioluminescence images of mice from each treatment group except PBS control taken on day 2, 8, and 12 post-tumour inoculation and (B) treatment effects of a single intravesical DTX formulations on orthotopic bladder cancer xenografts. Right panel, detailed view of the treatment arms except the PBS and Taxotere® (0.5 mg/ml) groups.

Two days post-tumour inoculation all mice developed bladder tumours, however, 2 mice also developed kidney tumours as demonstrated by bioluminescence imaging (FIG. 23A). Overall, intravesical DTX either the commercial Taxotere® or HPGs formulations were well tolerated by mice. No major toxicities were observed and all mice survived until the end of the study period. However, on day 8 post-tumour inoculation, some mice lost about 5% of their body weight, although, they recovered the following week. Body weight loss might have been a result of intravesical treatment and/or less food and water consumption on the days following treatment. However, there was no significant difference (p>0.05) in body weight loss between different groups.

Doses of 0.5 and 1.0 mg/ml were selected to establish an appropriate dosing regimen for intravesical DTX in mice bearing bladder cancer xenografts. Mice treated with a single dose of either Taxotere® at 1.0 mg/ml, DTX in HPG-$C_{8/10}$-MePEG at 0.5 mg/ml, HPG-$C_{8/10}$-MePEG and/or HPG-$C_{8/10}$-MePEG-$NH_{2(121)}$ at 1 mg/ml strongly inhibited the tumour growth. On day 19 post-tumour inoculation, all treatment groups except that of Taxotere® (0.5 mg/ml) showed statistically significant tumour inhibition compared to PBS control (p<0.001, post-hoc Bonferoni analysis after 2-Way ANOVA). All treatment groups were statistically significantly different compared to the Taxotere® (0.5 mg/ml) group (FIG. 23B, p<0.05, post-hoc Bonferoni analysis after 2-Way ANOVA).

It is believed that mucoadhesive properties of these nanoparticles increase the intimacy of contact with the urothelium leading to enhanced drug permeability and uptake into the bladder wall possibly due to the modulation of tight junctions or desquamation of urothelium. Due to their very small size (Rh<10 nm), HPGs might diffuse through the mucin glycoproteins and interact directly with the umbrella cells of urothelium leading to enhanced endocytosis of these nanoparticles into the bladder wall or tumour tissues.

Figure 24:
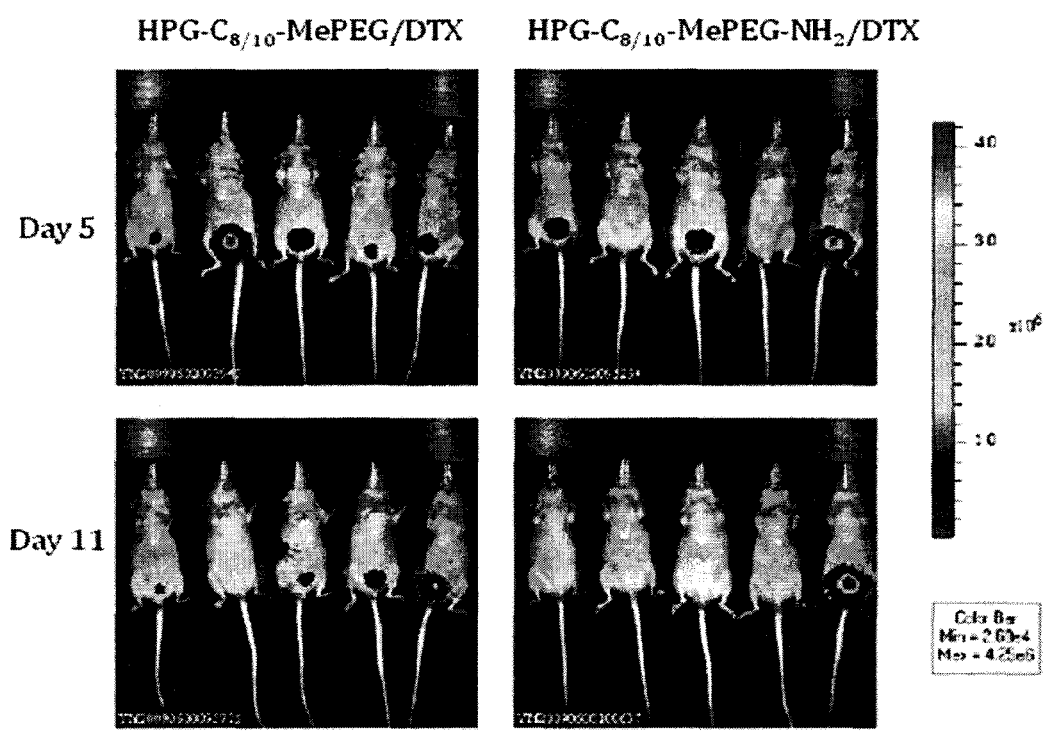
FIG. 24 shows bioluminescence images of mice following a single intravesical treatment with 0.2 mg/ml of DTX loaded HPG-$C_{8/10}$-MePEG and HPG-$C_{8/10}$-MePEG-$NH_{2(121)}$.

A second study was conducted to evaluate the effectiveness of a lower instillation dose of DTX in HPGs. For this study, mice that had no apparent bladder tumours or with low level of bioluminescence as determined by IVIS 200 Imaging System on day 19 were used. In total, 12 mice were found to be suitable for a second tumour re-inoculation as described above. Tumour take was about 75% compared to 100% in previous studies and may be due to an immune response, since the mice were previously inoculated with the same cell line; despite use of athymic immunocompromised mice, these mice still have an inherent local immune system characterized by macrophages and natural killer cells. From the 9 mice that developed bladder tumours after re-inoculation, 2 mice developed even larger (10-100 fold) bladder tumours. On day five post-tumour re-inoculation, mice which developed bladder tumours were randomized in two groups to receive a single 50 µl intravesical DTX (0.2 mg/ml) loaded HPG-$C_{8/10}$-MePEG (n=5) or HPG-$C_{8/10}$-MePEG-$NH_{2(112)}$ (n=4). Mice were imaged on days 5, 11 and 19 post-tumour re-inoculation. Intravesical DTX loaded HPG-$C_{8/10}$-MePEG-$NH_{2(121)}$ inhibited tumour growth in mice while DTX loaded HPG-$C_{8/10}$-MePEG failed to do so at the same concentration. At day 11 and 19 post-tumour re-inoculation, 3 out 4 mice showed no evidence of tumour growth following a single intravesical treatment with DTX (0.2 mg/ml) loaded HPG-$C_{8/10}$ MePEG-$NH_{2(121)}$ nanoparticles whereas, 4 out of 5 mice treated with DTX (0.2 mg/ml) loaded HPG-$C_{8/10}$-MePEG nanoparticles showed evidence of bladder tumour growth and one mouse further developed kidney tumours (FIG. 24). Once again, these formulations were well tolerated by mice no major toxicities or body weight loss occurred during these studies.

Example 20

In Vitro Cytotoxicity Studies

Cytotoxic effects of the commercial formulation of Taxotere® and DTX loaded HPG formulations against the KU7-luc cell line, and both low-grade (RT4, MGHU3) and high-grade (UMUC3) human urothelial carcinoma cell lines were evaluated.

Taxotere® (DTX in Tween 80) was purchased from Sanofi-Aventis Canada Inc. (Laval, Quebec). The human bladder cancer cell lines RT4 and UMUC3 were purchased from the American Type Culture Collection. Cells were maintained in McCoy's medium (Invitrogen, Burlington, ON) containing 10% heat-inactivated fetal bovine serum and kept at 37° C. in a humidified 5% $CO_2$ atmosphere. MGHU3 cells were obtained as a generous gift from Dr. Y. Fradet (L'Hotel-Dieu de Quebec, Quebec, Canada) and maintained in MEM supplemented with 10% fetal bovine serum and 2 mM L-glutamine (Invitrogen). KU7 was kindly provided by Dr. C. Dinney (MD Anderson Cancer Center, Houston, Tex., USA) and maintained in DMEM containing 5% fetal bovine serum. For visualization purposes, KU7 cells were infected with a lentivirus containing the firefly luciferase gene by Dr. Graig Logsdon (M.D. Anderson Cancer Center, Houston, Tex., USA), and these subclones were named KU7-luc as described previously (Hadaschik B A, Black P C, Sea J C, et al. *BJU Int* 2007; 100: 1377-84).

Cells were plated at 5,000 cells/well in 96-well plates in a 100 µl volume of McCoy's Medium supplemented with 10% FBS and allowed to equilibrate for 24 h before freshly prepared solutions of Taxotere®, or DTX in HPG-$C_{8/10}$-MePEG and/or HPG-$C_{8/10}$-MePEG-$NH_2$ (dissolved in PBS, pH 7.4) were added. Cells were exposed to the drug formulations for 2 h, to simulate the current clinical standard for instillation therapy, and cell viability was determined after 72 h using the CellTiter96 AQueous Non-Radioactive Cell Proliferation (MTS) Assay (Promega, Madison, Wis.) as previously reported (Mugabe C, Hadaschik B A, Kainthan R K, et al. *BJU Int* 2009; 103: 978-86). Each experiment was repeated three times and MTS values fell within a linear absorbance range for all cell lines.

Figure 25:
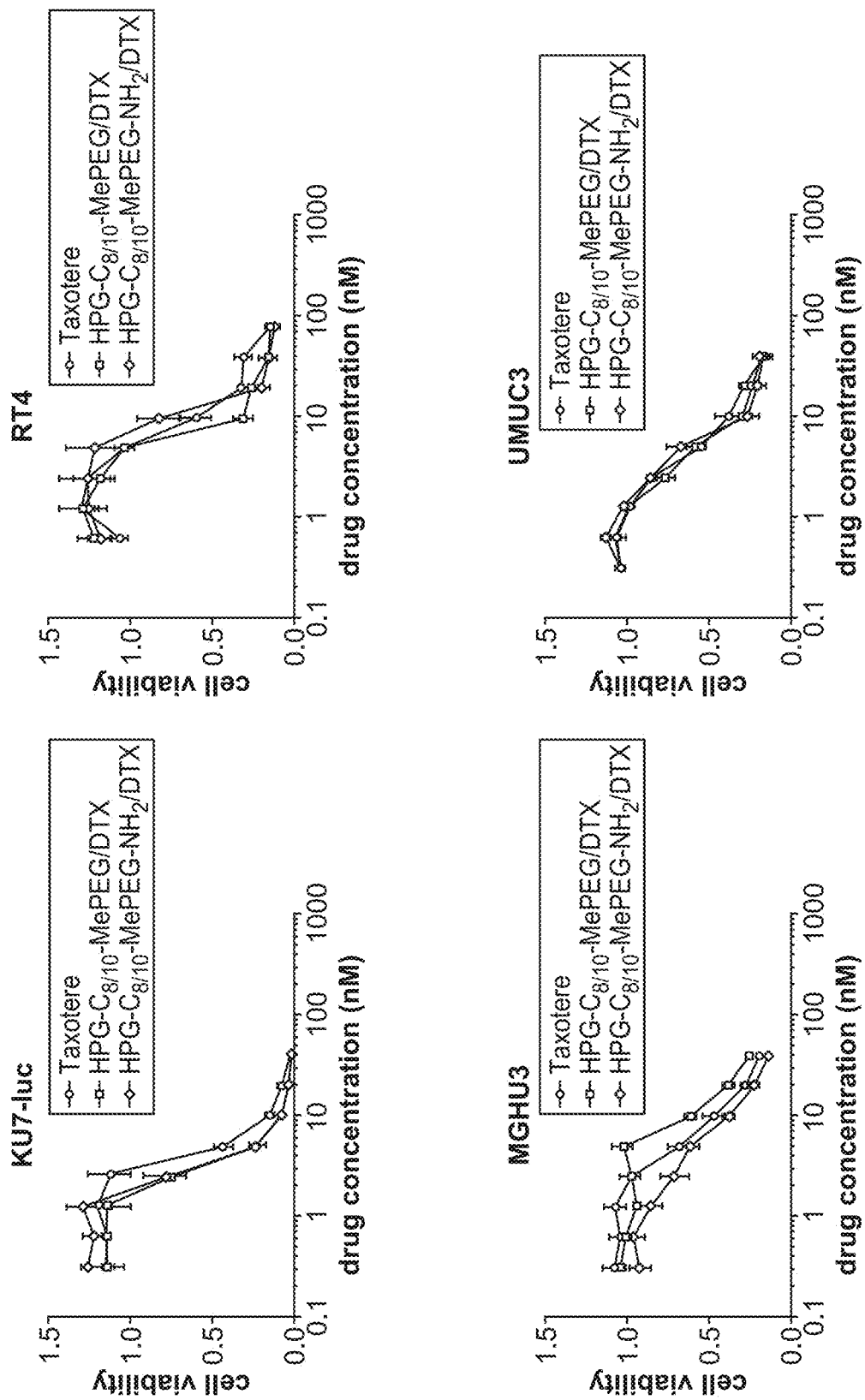
FIG. 25 shows in vitro cytotoxicity of DTX formulations against the KU7-luc cell line, and both lowgrade (RT4, MGHU3) and high-grade (UMUC3) human urothelial carcinoma cell lines.

All DTX formulations resulted in concentration-dependent inhibition of proliferation in all cell lines tested. The more aggressive and fast growing KU7-luc cell line was the most sensitive to DTX formulations DTX loaded HPG-$C_{8/10}$-MePEG or HPG-$C_{8/10}$-MePEG-$NH_2$ were found to be as cytotoxic as the commercial formulation of Taxotere® (FIG. 25). The $IC_{50}$ of DTX formulations were in the low nanomolar range (4-12 nM) for all cell lines tested. Control HPGs nanoparticles (no drug) showed no cytotoxicity across the tested concentration range (15-1,500 nM, data not shown). Loading of DTX in HPGs had no effect on its cytotoxicity.

Example 21

In Vivo Studies

Efficacy of Intravesical DTX in Orthotopic Murine Model of Bladder Cancer

In vivo studies were done in a total of 42 nude mice to evaluate the efficacy of a single intravesical treatment with Taxotere® (0.2 mg/ml) and DTX (0.2 mg/ml) loaded HPG-$C_{8/10}$-MePEG and/or HPG-$C_{8/10}$-MePEG-$NH_2$. The orthotopic mouse model used has been reported (Hadaschik B A, Black P C, Sea J C, et al. *BJU Int* 2007; 100: 1377-84; Mugabe C, Hadaschik B A, Kainthan R K, et al. *BJU Int* 2009; 103: 978-86; Hadaschik B A, ter Borg M G, Jackson J, et al. *BJU Int* 2008; 101: 1347-55; Hadaschik B A, Adomat H, Fazli L, et al. *Clin Cancer Res* 2008; 14: 1510-8; Hadaschik B A, Zhang K, So A I, et al. *Cancer Res* 2008; 68: 4506-10). Animal studies were carried out in accordance with the Canadian Council on Animal Care. Eleven-week-old female nude mice (Harlan, Indianapolis, Ind.) were anaesthetized with isoflurane. A superficial 6-0 polypropylene purse-string suture was placed around the urethral meatus before a lubricated 24 G Jelco angiocatheter (Medex Medical Ltd., Lancashire, UK) was passed through the urethra into the bladder. After a single irrigation of the bladder with PBS, two million KU7-luc cells were instilled as a single cell suspension in 50 µl and the purse-string suture was tied down for 2.5 h. To quantify in vivo tumuor burden, animals were imaged in supine position 15 min after intraperitoneal injection of 150 mg/kg luciferin on days 4, 11, 18, and 25 with an IVIS200 Imaging System (Xenogen/Caliper Life Sciences, Hopkinton, Mass.). Data were acquired and analyzed using Living Image software (Xenogen). On day five post-tumuor inoculation, mice were randomized to receive a single 50 µl intravesical treatment with PBS (control); Taxotere® (0.2 mg/ml); DTX (0.2 mg/ml) loaded HPG-$C_{8/10}$-MePEG; and DTX (0.2 mg/ml) loaded HPG-$C_{8/10}$-MePEG-$NH_2$. Levels of bioluminescence were equivalent among the groups; however, as tumuors varied between individual mice, for statistical analyses, tumuor bioluminescence after treatment was normalized against the initial flux on day four in each mouse. Necropsy was performed on day 25 after tumuor inoculation. The whole bladders were removed, fixed in 10% buffered formalin and embedded in paraffin. 5 µm sections were prepared and stained with H&E using standard techniques. All slides were reviewed and scanned on a BLISS microscope imaging workstation (Bacus Laboratories Inc., Lombard, Ill.).

After intravesical inoculation of KU7-luc cancer cells, all mice developed bladder tumuors. However, one mouse in DTX loaded HPG-$C_{8/10}$-MePEG-$NH_2$ group died unexpectedly on day four post-treatment. Overall, intravesical DTX administered as either the commercial Taxotere® or the HPGs formulations were well tolerated by mice and no major toxicities were observed.

Compared with control mice, DTX loaded HPGs inhibited tumor growth. However, DTX loaded HPG-$C_{8/10}$-MePEG-$NH_2$ was the most effective formulation to inhibit tumor growth in KU7-luc orthotopic bladder cancer xenografts and reached statistical significance compared to either the PBS control or Taxotere® groups (FIG. 26, P<0.01, post-hoc Bonferoni analysis after 2-Way ANOVA). At the end of the study, a single intravesical instillation of DTX loaded HPG-$C_{8/10}$-MePEG-$NH_2$ nanoparticles inhibited tumor growth by 88% compared to the PBS control groups. DTX loaded HPG-$C_{8/10}$-MePEG nanoparticles exhibited a 54% tumor inhibition in this treatment arm. This increase in efficacy likely resulted from enhanced drug uptake in bladder and tumor tissues of mice treated with DTX loaded HPG-$C_{8/10}$-MePEG-$NH_2$ nanoparticles.

Figure 26:
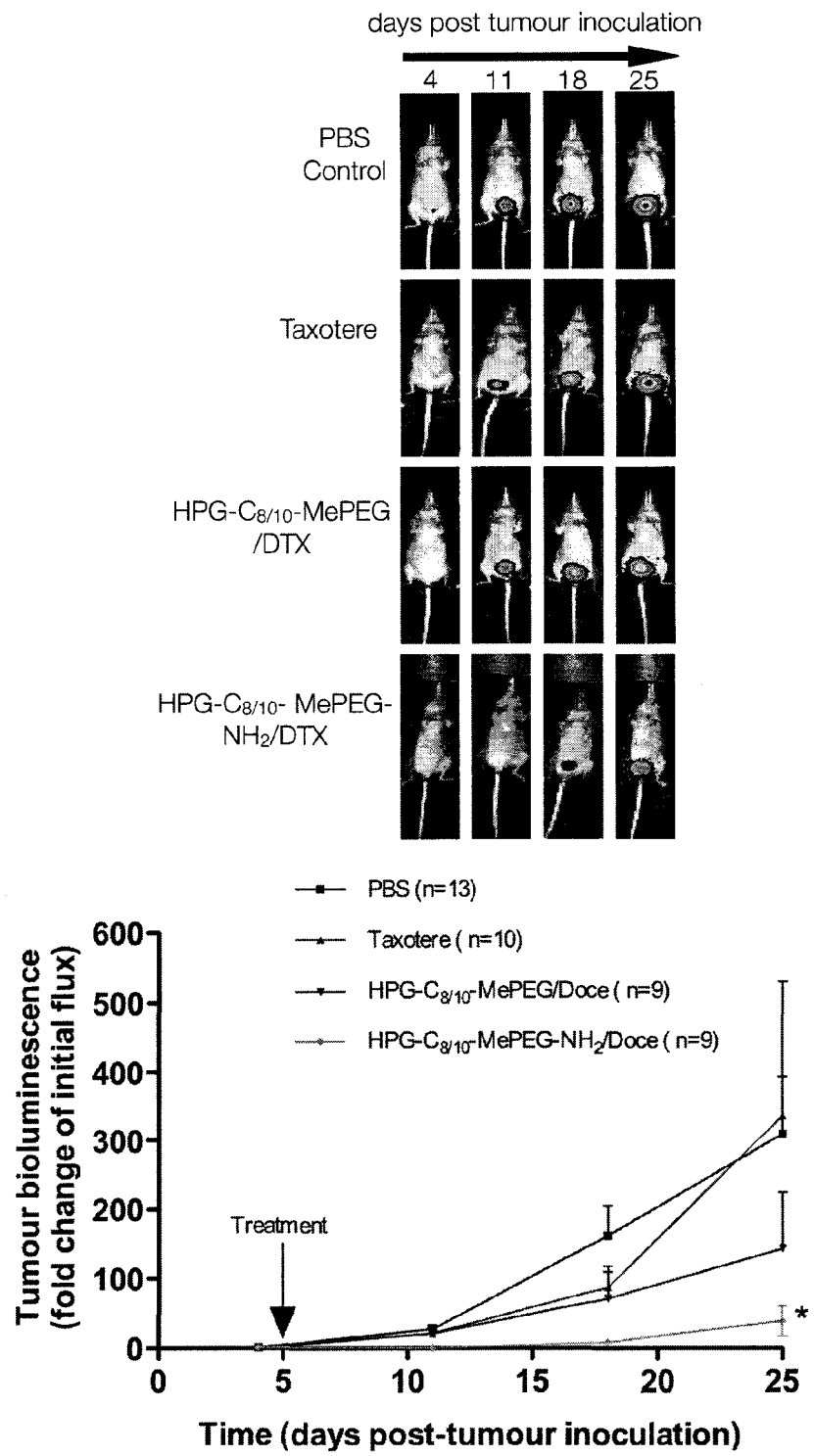
FIG. 26 shows treatment effects of single intravesical DTX formulations on orthotopic bladder cancer xenografts. Bioluminescence imaging of mice is shown on the left panel.
Figure 27:
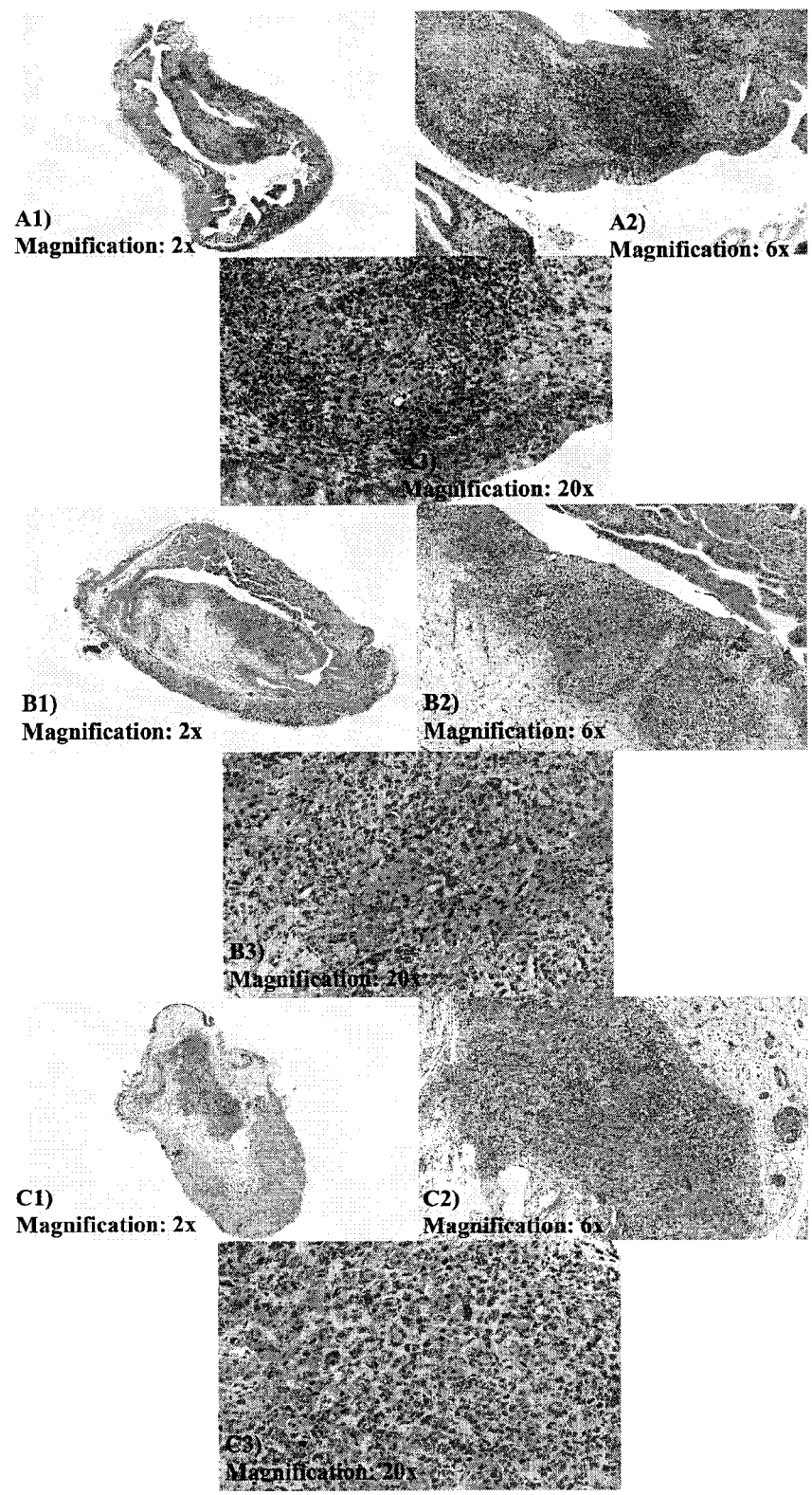
FIG. 27 shows representative histological sections of bladders harvested at the end of study, from mice receiving various formulations of 0.2 mg/ml DTX: (A) HPG-$C_{8/10}$-MePEG-$NH_2$, (B) HPG-$C_{8/10}$-MePEG, (C) Taxotere®. Within treatment groups, A, B, and C, numbers 1-3 designate different magnifications.

The commercial formulation of Taxotere® failed to inhibit tumor growth in this orthotopic xenograft model. Representative bioluminescence images of mice over time in each treatment group are shown in FIG. 26. Histological examination of bladder tissues show that KU7-luc tumors exhibited an aggressive growth pattern and frequent multifocality, but after 25 days post-tumor inoculation, they were generally confined to the lamina propria and correlated with high-grade T1 stage disease (FIG. 27). Although DTX (0.2 mg/ml) did not cause any remarkable histological change in KU7-luc xenograft compared with the PBS treatment, DTX (0.2 mg/ml) loaded HPG-$C_{8/10}$-MePEG and/or HPG-$C_{8/10}$-MePEG-$NH_2$ inhibited tumor growth. Tumors treated by DTX loaded in HPG-$C_{8/10}$-MePEG-$NH_2$ decreased significantly in size, with heterogeneous cellular size, nuclear shape and infiltrating inflammatory cells.

It was also determined that the technique used for loading the biologically active moiety into a dHPG is capable of producing a formulation that can be assayed as having ±20% of the target amount of drug in the delivery system, as determined by HPLC (see Table 11).

TABLE 11

Concentration of DTX formulations in samples analyzed post-treatment by HPLC

| Formulation | Theoretical Concentration of Docetaxel (mg/mL) | Actual Concentration of Docetaxel (mg/mL) |
| --- | --- | --- |
| Taxotere ™ | 0.5 | 0.53 |
|  | 1.0 | 0.81 |
| HPG-$C_{8/10}$—MePEG-$NH_2$ | 0.5 | 0.48 |
|  | 1.0 | 0.94 |
|  | 1.0 | 0.86 |

Figure 28:
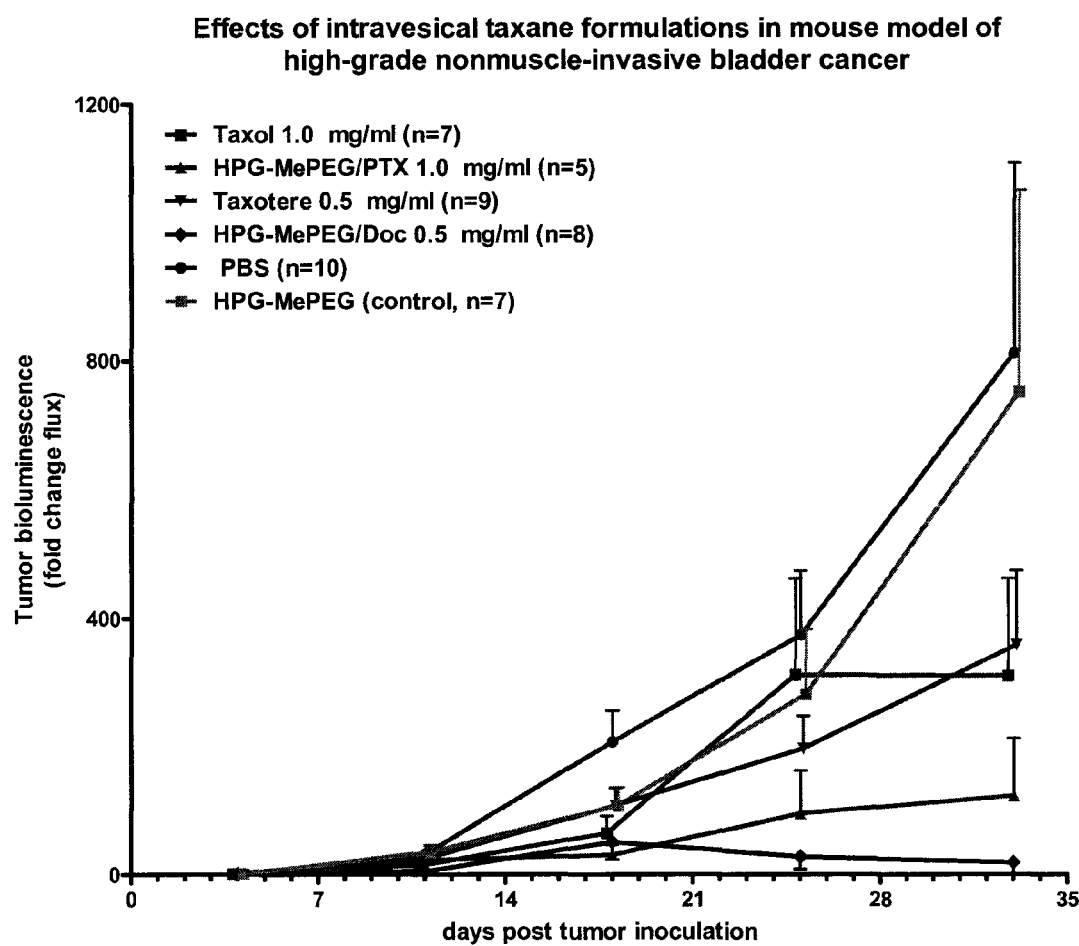
FIG. 28 shows tumour bioluminescence as a function of time for HPG-$C_{8/10}$-MePEG incorporating DTX or paclitaxel (PTX) as compared to the commercial formulations of DTX (Taxotere™) and PTX (Taxol™).

A comparison has been made between formulations incorporating paclitaxel (PTX) and those incorporating DTX, as shown in FIG. 28. For both drugs, incorporating them into a dHPG, such as HPG-$C_{8/10}$-MePEG, results in reduced tumor luminescence, with a dHPG incorporating DTX being more effective than a dHPG incorporating paclitaxel.

Figure 29:
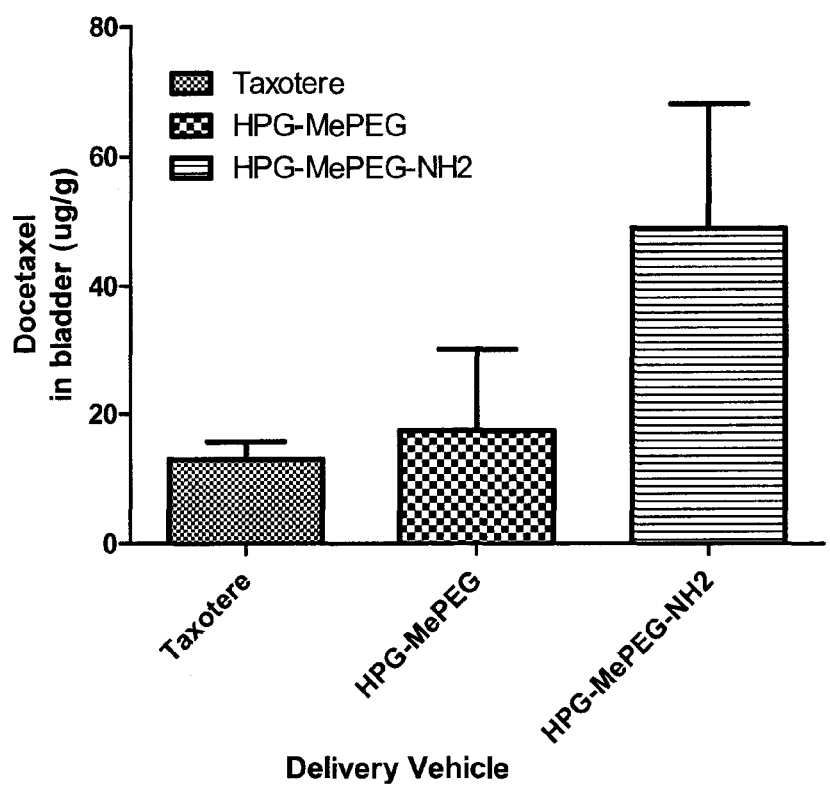
FIG. 29 shows the retention of DTX in the bladder 2 hours after installation of 50 μg of DTX in HPG-$C_{8/10}$-MePEG or HPG-$C_{8/10}$-MePEG-$NH_2$.

A similar experiment has been repeated using two time points and using healthy animals. These data, shown in FIG. 29 demonstrate that in healthy mice, more docetaxel is retained in the bladder over time using HPG-$C_{8/10}$-MePEG-$NH_2$ than when using either HPG-$C_{8/10}$-MePEG or Taxotere™ to deliver the same amount of the drug. Results are semi-quantitative for the HPG-MePEG-$NH_2$ due to exceeding the assays upper limit of quantitation. The results for the Taxotere™ and HPG-$C_{8/10}$-MePEG group are quantitative. Mice were dosed each with 50 µg of drug in a 50 µL volume and 50 mg of dHPG was used (n=3 per group).

Example 22

Drug Uptake Studies

To evaluate the bladder tissue and serum uptake following intravesical DTX formulations, mice with orthotopic bladder tumors were instilled with either Taxotere® (0.2 mg/ml, n=3) or DTX (0.2 mg/ml) loaded HPG-$C_{8/10}$-MePEG (n=4) and/or HPG-$C_{8/10}$-MePEG-$NH_2$ (n=4). The amount of DTX in urine, bladder tissue, and serum were measured two hours post-instillation. Drug uptake studies were conducted in fifteen-week-old female nude mice with established KU7-luc tumors (33 days post-tumor inoculation). Tail blood samples were taken at 0, 30, and 60 min post intravesical instillation. During this period mice were still anaesthetized with isoflurane. After 2 h, all mice were euthanized using $CO_2$ asphyxiation and additional blood was removed by cardiac puncture. Blood samples were centrifuged in micro-haematocrit tubes (Fisher Scientific, Pittsburgh, Pa.) or serum-separator tubes (Becton Dicknson) and the serum was snap-frozen in liquid nitrogen. Urine and bladder of each mouse were also harvested and before freezing, the bladders were cut, opened to expose the lumen and were vigorously washed in five sequential 10 ml PBS washes. All samples were stored at −80° C. The UPLC-MS/MS system used for analysis consisted of an integrated Waters Acquity UPLC separation system (Acquity BEH C18, 1.7 μm, 2.1×50 mm column) coupled to a mass spectometry analysis using Waters TQD mass spectrometer. The system was operated at an electrospray ion source block temperature of 150° C., a desolvation temperature of 350° C., a cone voltage of 14 V, a capillary voltage of 0.70 kV, extractor voltage of 3 kV, RF voltage of 0.1 kV, a cone gas flow at 25 l/h, a desolvation gas flow at 600 l/h and a collision gas flow at 0.2 ml/min. The molecules undergo electron spray ionization in the positive ion mode. DTX was quantified in multiple reaction monitoring with the transition of m/z 808.5→527.2, as previously established (Mugabe C, Liggins R T, Guan D, et al. *Int J Pharm* 2011; 404: 238-49). DTX was extracted from the mouse serum by solvent/solvent extraction method. 50 μl aliquots of the mouse plasma and standards were mixed with 150 μl of 0.1% formic acid in acetonitrile in a 96-well plate and vortexed for 1 min at room temperature. The samples were centrifuged at 5,500 rpm (Allegra™ 25 R centrifuge, Beckman-Coulter) for 10 min at 4° C. Then 100 μl of the supernatant was mixed with 50 μl of distilled water, mixed and vortexed for 30 s. Bladder tissues were weighed and homogenized in 0.1% formic acid/methanol using zirconia beads (Biospec Products) and mini-bead beater equipped with microvial holder (Biospec Products) for 60 s. The samples were centrifuged at 14,000 rpm (Allegra™ 25 R centrifuge, Beckman-Coulter) for 2 min at 4° C. 150 μl of 0.1% trifluoroacetic acid in methanol was added to the samples, mixed and vortexed at 14,000 rpm (Allegra™ 25 R centrifuge, Beckman-Coulter) for 15 min at 4° C. All sample analysis was performed using UPLCMS/MS. The limit of quantification for DTX was 10 ng/ml with a recovery of 97% from spiked control samples. Within run precision (% RSD) was less than 15% in all cases.

Mice instilled with Taxotere® had no detectable DTX in serum at all time points. DTX loaded HPG-$C_{8/10}$-MePEG-$NH_2$ exhibited the highest serum levels at the 2 h time point (150.87±34.98 vs 23.97±16.71 ng/ml, P<0.01, 2-way ANOVA, Bonferroni post-test). However, serum concentrations of DTX were several orders of magnitude lower than the concentrations in urine and bladder tissue (Table 12). DTX loaded HPG-$C_{8/10}$-MePEG-$NH_2$ resulted in significantly higher amounts in bladder tissue accumulation compared to Taxotere® or DTX loaded HPG-$C_{8/10}$-MePEG (P<0.001, 1-way ANOVA, Bonferroni's multiple comparison test). There was no significant difference (P>0.05, 1-way ANOVA) in bladder tissue accumulation between Taxotere® and DTX loaded HPG-$C_{8/10}$-MePEG treatment groups. The final urine concentrations were about 5-7-fold lower than the initial dosing solution. This was due to the urine dilution during the 2 h period of intravesical instillation. However, there was no significant difference (P>0.05, 1-way ANOVA) in the final urine concentrations of DTX between different treatment groups. No local or systemic toxicity was observed in either group.

TABLE 12

Drug uptake of intravesical DTX formulations in orthotopic xenografts

| DTX formulations (No. of mice) | $^1C_{urine}$ (μg/ml) | $^2C_{bladder}$ (μg/g) | $^3C_{serum}$ (ng/ml) 0.5 h | 1 h | 2 h |
|---|---|---|---|---|---|
| Taxotere ® (3) | 31.4 ± 15.5 | 1.24 ± 0.54 | BLOQ | BLOQ | BLOQ |
| DTX/HPG-$C_{8/10}$-MePEG (4) | 53.8 ± 8.1 | 1.09 ± 0.70 | 55.87 | 27.88 | 23.97 ± 16.71 |
| DTX/HPG-$C_{8/10}$-MePEG-$NH_2$ (4) | 27.6 ± 4.0 | 13.07 ± 4.32 | 81.47 ± 23.76 | 88.21 ± 39.42 | 150.87 ± 34.98 |

[1]Final concentration of DTX in mouse urine after 2 h of intravesical instillation measured by HPLC
[2]Concentration of DTX in mouse bladder tissue following a 2 h intravesical instillation measured by LC/MS/MS
[3]Concentration of DTX in mouse serum taken at 0.5, 1, and 2 h post-intravesical instillation measured by LC/MS/MS
BLOQ, below the limit of quantification (lowest limit of quantification was 10 ng/ml)
Data shown are the mean ± SD Example 23

Assessing Tumor Microenvironment and Uptake of Rhodamine Labeled HPGs

Bladder tumor microenvironment and distribution of rhodamine labeled HPGs into tumor tissue was assessed.
Rhodamine Labeling of HPGs HPG-$C_{8/10}$-MePEG and HPG-$C_{8/10}$-MePEG-$NH_2$ polymers were covalently labeled with tetramethyl-rhodamine-carbonyl-azide (TMRCA) as previously reported (Savic R, Luo L, Eisenberg A, Maysinger D. *Science* 2003; 300:615-8; Mugabe C, Liggins R T, Guan D, et al. *Int J Pharm* 2011; 404:238-49). Fifteen-week-old female nude mice with orthotopic bladder tumors (33 days post-tumor inoculation) were anaesthetized with isoflurane. A superficial 6/0 polypropylene purse-string suture was placed around the urethral meatus and the bladder was emptied by manual compression. A lubricated 24-gauge Jelco angiocatheter was passed through the urethra into the bladder and then 50 μl of either PBS, free rhodamine (TMRCA), HPG-$C_{8/10}$-MePEG-TMRCA, and/or HPG-$C_{8/10}$-MePEG-$NH_2$-TMRCA was instilled and the purse-string suture was tied down for a 2-h period, during which the mice were kept anaesthetized. After the 2-h period the purse-string suture was removed, the bladder was emptied by manual compression and washed twice with 150 μl of PBS (pH 6.0). The mice were euthanized and the bladders were excised and frozen on an aluminum block, then embedded in OCT for cryosectioning. 10 μm cryosections were cut at distances of 1, 2, and 3 mm from the bladder edge. Sections were dried at room temperature and imaged for rhodamine fluorescence using 10× objective (0.75 μm/pixel resolution). Slides were fixed in 1:1 acetone: methanol solution for 10 min and stained using a custom capillary-action staining apparatus for CD31 (1:50 hamster anti-CD31 with an anti-hamster Alexa 647 secondary) and Hoechst 33342 (nuclear dye). Following fluorescent imaging of CD31 and Hoechst 33342, sections were counterstained lightly with hematoxylin, mounted & imaged in bright field.

Image analyses: images were reduced to 1.5 μm/pixel resolution to improve manageability in Image J software. With user-supplied algorithms, image stacks were then created, aligned and cropped to tumor tissue boundaries with artifacts removed; necrosis was further cropped based on the hematoxylin image. The bladder lumen was artificially traced along the tumor tissue boundary on Hoechst 33342 images. User-supplied analysis macros were run to generate the following types of data: a) threshold: was manually determined to include positive stain but that does not pick up background outside of necrosis areas; the macro determines the number of positive pixels meeting or exceeding this threshold and was reported as an average for the whole tumor section. b) intensity: was reported as the average intensity of staining for a whole tumor section, or the average intensity of pixels sorted based on their distance from a secondary stain (ie: CD31) or artificially traced boundary (bladder lumen). Calculations to determine averages±standard error were performed and graphic displays created using Microsoft Excel; non-parametric analysis of variance (Kruskal-wallis tests) statistical analyses were performed using Prism v5 for Macs software.

Figure 30:
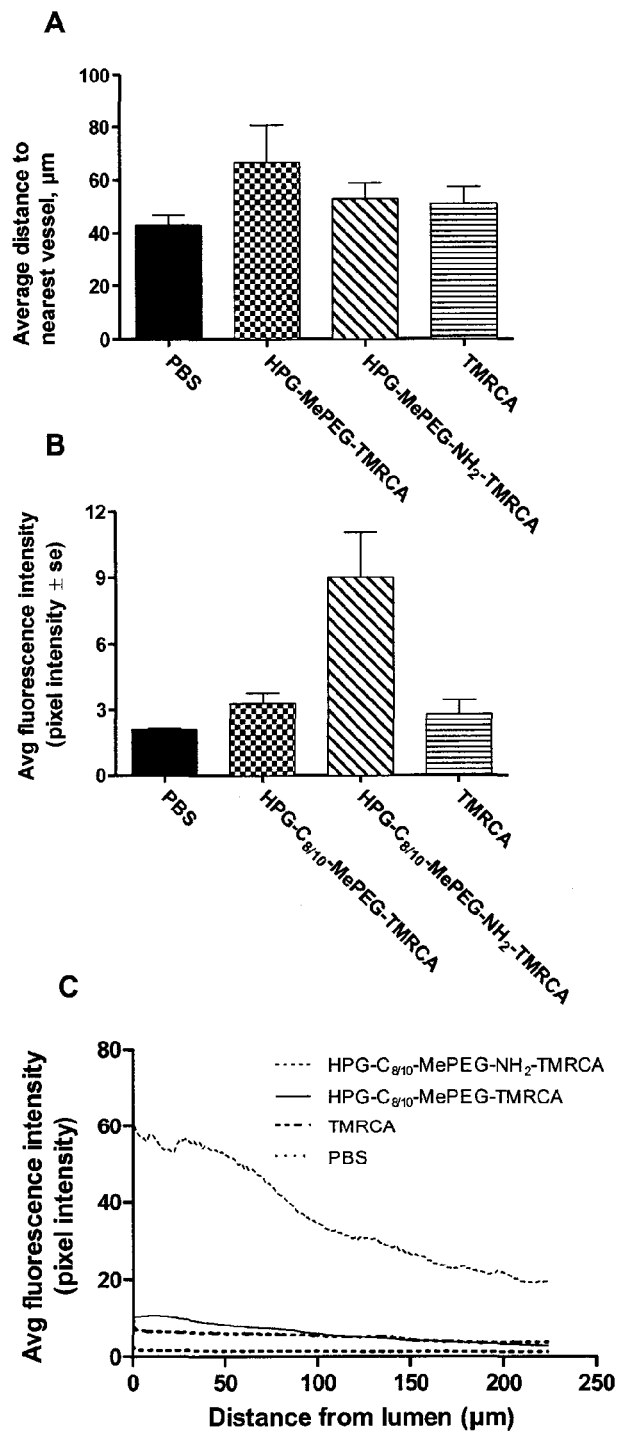
FIG. 30 shows orthotopic bladder carcinoma instilled with PBS; free rhodamine (TMRCA); rhodamine labeled HPG-$C_{8/10}$-MePEG (HPG-$C_{8/10}$-MePEG-TMRCA); rhodamine labeled HPG-$C_{8/10}$-MePEG-$NH_2$ (HPG-$C_{8/10}$-MePEG-$NH_2$-TMRCA). (B) amount of fluorescence inside the bladder tumours, (C) observed rhodamine fluorescence in tumour tissues as a function of distance from bladder lumen.

Bladder tumor microenvironment and distribution of rhodamine labeled HPGs into tumor tissue was assessed. Bladder tumor tissues were highly vascularised with an average distance of 40-60 μm to the nearest blood vessel (FIG. 30A). No significant difference was seen between different groups (P=0.8). The amount of fluorescence inside whole bladder tumors was measured. Rhodamine labeled HPG-$C_{8/10}$-MePEG-$NH_2$ (HPG-$C_{8/10}$-MePEG-$NH_2$-TMRCA) exhibited the highest tumor uptake compared to the other groups (P=0.037). There was no significant difference (P>0.05) in tumor uptake of the bladders instilled with free rhodamine (TMRCA) and rhodamine labeled HPG-$C_{8/10}$-MePEG (FIG. 30B). The depth profile of rhodamine uptake into the tumor tissues was assessed as a function of distance from the bladder lumen. HPG-$C_{8/10}$-MePEG-$NH_2$-TMRCA nanoparticles demonstrated enhanced tumor uptake at all distances from lumen, showing a 5-6-fold increase over HPG-$C_{8/10}$-MePEG-TMRCA nanoparticles (FIG. 30C).

Example 24

Synthesis and Characterization of HPG-$C_{8/10}$-MePEG and HPG-$C_{8/10}$-MePEG-COOH The polymerization of O/DGE core modified HPGs was carried out according to protocols described in our previous report (Kainthan, R. K.; Brooks, D. E. *Bioconjugate Chem.* 2008, 19, 2231-2238). The functionalization of $C_{8/10}$ core-modified HPGs with carboxylic acid groups was carried out according to protocols reported earlier (Haxton, K. J.; Burt, H. M. *Dalton Trans.* 2008, 5872-5875). For a typical reaction, 5.0 g of the HPG-$C_{8/10}$—OH or HPG-$C_{8/10}$-MePEG$_{6.5}$ was dissolved in 100 mL of pyridine, and the solution was kept under a nitrogen atmosphere, followed by the addition of dimethylaminopyridine and succinic anhydride, which were adjusted according to the target amount of carboxylic acid groups on HPGs. For the synthesis of HPG with the highest amount of COOH groups, all available free hydroxyl groups were targeted for modification to carboxylates; therefore, an excess amount of dimethylaminopyridine (0.075 g, 0.61 mmol) and succinic anhydride (4.5 g, 45 mmol) were added to the reaction mixture. Through calculation of the theoretical moles of free hydroxyl groups, it was determined that there were 348 mols of free hydroxyl groups per mole of HPG and, thus, theoretically the same number of carboxyl groups per mole of HPG. Therefore, the resulting HPG was denoted as HPG-$C_{8/10}$-MePEG$_{6.5}$-COOH$_{348}$. The use of lower amounts of dimethylaminopyridine (0.015 g, 0.12 mmol) and of succinic anhydride (0.9 g, 9 mmol) produced HPGs in which not all the free hydroxyls were targeted for modification. The theoretical number of carboxylate groups added to the HPG was determined through the calculation of the number of moles succinic anhydride added to the reaction mixture. Therefore, this low carboxylate containing HPG was denoted as HPG$C_{8/10}$-MePEG$_{6.5}$-COOH$_{113}$. After addition of the dimethylaminopyridine and succinic anhydride, the solution was stirred using a magnetic stir bar overnight at room temperature. Deionized water (100 mL) was added to the flask and the mixture was kept stirring for 30 min. Solvents were removed by rotary evaporation with the periodic addition of water to enable better evaporation of pyridine by azeotropic distillation. The final products were dissolved in methanol and dialyzed against a mixture of 80:20 methanol/deionized water for 3 days using cellulose acetate dialysis tubing (MWCO 10000 g/mol, Spectrum Laboratories Inc., Rancho Domunguez, Calif.). The dialysis medium was changed every 8 h, each time with a lower methanol concentration until during the final three stages, the dialysis medium was 100% water. Polymers were obtained by freeze-drying.

$^{13}$C NMR of HPG-$C_{8/10}$-MePEG-COOH (400 MHz, methanol-$d_4$) $\delta_C$: 0 (tetramethylsilane, internal reference), 14.73 ($CH_3$, alkyl on O/DGE), 23.92-33.24 (C(O)$CH_2CH_2$COOH), 48.51-49.86 (solvent, methanol-$d_4$), 59.29 ($CH_3$O-MePEG), 64.19-65.36 (—$CH_2$OH, unreacted primary alcohol groups in polymer), 69.98-73.74 (—$CH_2$—O—, —CH—O in polymer), 78.93-80.14 (CH in polymer), 173.84-174.16 (C(O)$CH_2CH_2$COOH), 175.92 (C(O)$CH_2CH_2$COOH).

In the preparation of all functionalized HPGs, target amounts of MePEG and COOH groups were added to reaction mixtures. The target amounts of MePEG and COOH of various functionalized HPGs are summarized in Table 13. The reaction yields for the high and low carboxylate functionalized HPGs were 84 and 74%, respectively. HPG polymers are described by the following nomenclature: HPG-$C_{8/10}$-MePEGA-COOHB wherein HPG-$C_{8/10}$ represents the alkyl substituted HPG, A is the target content of MePEG conjugated to the polymer, based on the stoichiometry of reagents (moles of MePEG/mol of TMP initiator), and B is the expected molar content of COOH per mole of HPG polymer, based on the calculated molecular weight of the polymer from GPC data.

TABLE 13

Properties of a Series of Surface-Modified $C_{8/10}$ Alkyl Derivatized Hyperbranched Polyglycerols

| polymer composition[a] | titration data[b] COOH (mol/mol HPG) | molecular weight[c] | | particle size[d] (nm) |
| --- | --- | --- | --- | --- |
| | | Mw (g/mol) | PDI (Mw/Mn) | |
| HPG-$C_{8/10}$-OH | N/A | N/D | N/D | 9.2 ± 3.5 |
| HPG-$C_{8/10}$-MePEG$_{6.5}$ | N/A | 7.6 × 10$^4$ | 1.2 | 8.7 ± 3.8 |
| HPG-$C_{8/10}$-COOH | N/D | N/D | N/D | 5.3 ± 1.8 |
| HPG-$C_{8/10}$-MePEG$_{6.5}$-COOH$_{348}$ | 318 | 1.3 × 10$^5$ | 1.4 | 5.9 ± 2.1 |
| HPG-$C_{8/10}$-MePEG$_{6.5}$-COOH$_{113}$ | 87 | 9.1 × 10$^4$ | 1.3 | 7.4 ± 3.0 |

[a] Nomenclature is designated as follows. HPG-$C_{8/10}$-OH is the "base polymer" and all others were surface modified with MePEG and COOH, expressed as the theoretical number of moles of surface group added in the reaction per mole of HPG.
[b] Moles of COOH groups per mole of HPG as determined by pH titration.
[c] Weight average molecular weight and polydispersity index determined by GPC. Number average molecular weight is calculated by Mw/PDI.
[d] Particle size (diameter), as determined by dynamic light scattering.

NMR Analysis

After purification, all of the HPGs were characterized by NMR analysis. NMR spectra of HPG polymers were acquired using a 400 MHz Bruker Avance II+ spectrometer (Bruker Corporation, Milton, ON). Polymers were dissolved in DMSO-$d_6$ or methanol-$d_4$ (Cambridge Isotope Laboratories, Andover, Mass.). One-dimensional proton and carbon spectra were obtained, as well as two-dimensional, multiplicity-edited heteronuclear single quantum coherence (HSQC), heteronuclear multiple-bond correlation (HMBC), and HSQC-TOCSY (total correlation spectroscopy) NMR experiments. Chemical shifts were referenced to the residual solvent peak. Two-dimensional spectra were analyzed using Sparky (T. D. Goddard and D. G. Kneller, Sparky 3, University of California, San Francisco). The mole fractions of COOH on HPGs were estimated from HSQC data as follows: For each of the modifications, the peak corresponding to the four methylene protons was integrated and its integral corrected for the number of protons. This value was divided by the integral of the TMP methyl group (corrected for proton multiplicity) to yield the mole fraction of COOH.

Figure 31:
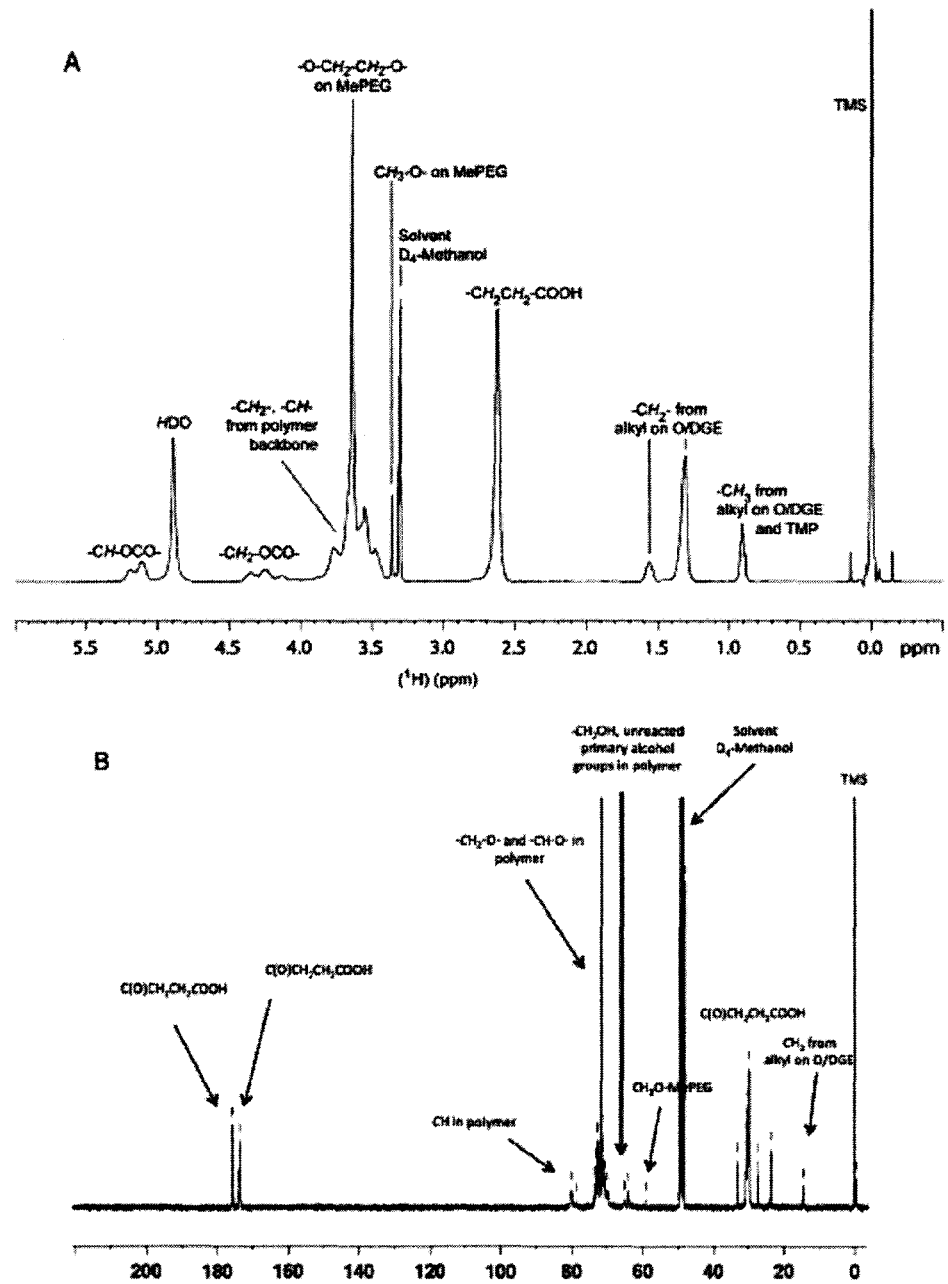
FIG. 31 shows (A) $^1H$ NMR spectrum and (B) $^{13}C$ NMR spectrum of HPG-$C_{8/10}$-MePEG-COOH in methanol-$d_4$.

From FIG. 31 it can be seen that all of the peaks of functionalized HPG-$C_{8/10}$-MePEG$_{6.5}$-COOH polymers were assigned to the structural components of the HPGs and were consistent with previous reports (Kainthan, R. K.; Mugabe, C.; Burt, H. M.; Brooks, D. E. *Biomacromolecules* 2008, 9, 886-895; Kainthan, R. K.; Janzen, J.; Kizhakkedathu, J. N.; Devine, D. V.; Brooks, D. E. *Biomaterials* 2008, 29, 1693-1704; Haxton, K. J.; Burt, H. M. *Dalton Trans.* 2008, 5872-5875). HSQC, HMBC, and HSQC-TOCSY were used to estimate the fractions of the substituents, $C_{8/10}$ alkyl chain, MePEG, and COOH on HPGs using integrated peak volumes.

Degree of Branching and Degree of Polymerization

Figure 32:
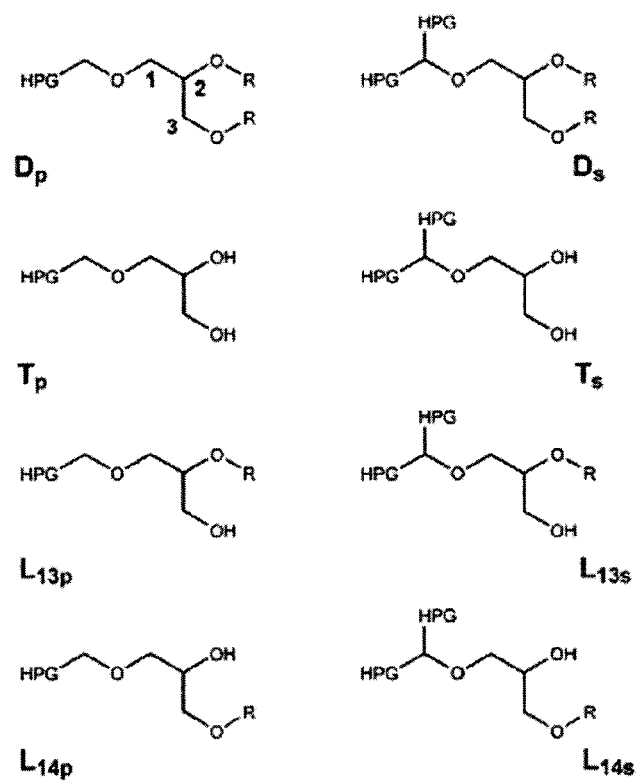
FIG. 32 shows structural units in HPG polymers. Each dendritic, D, terminal, T, and linear, $L_{13}$ or $L_{14}$, unit exists as primary, p, and secondary, s, unit. For unmodified polymers, R) HPG; for modified polymers, R) HPG, $C_{8/10}$, MePEG, or COOH. The numbering scheme is indicated for the Dp unit.

Hyperbranched polymers are typically characterized by the degree of branching (DB) and degree of polymerization (DPn) using the following equations (Holter, D.; Burgath, A.; Frey, H. *Acta Polym.* 1997, 48, 30-35):

$$DB = \frac{2D}{2D + L_{13} + L_{14}}$$

where DB is the degree of branching, D, $L_{13}$, and $L_{14}$ represent the fractions of dendritic, linear 1-3, and linear 1-4 units, respectively. The structures of the dendritic and linear repeat units of glycidol that are present in the hyperbranched structure are summarized in FIG. 32. Furthermore, the degree of polymerization (DPn) for these polymers is calculated as follows (Sunder, A.; Hanselmann, R.; Frey, H.; Mulhaupt, R. *Macromolecules* 1999, 32, 4240-4246):

$$DP_a = \frac{T + L_{13} + L_{14} + D}{T - D} \cdot f_c$$

where D, $L_{13}$, and $L_{14}$ are defined as above, T represents the fraction of terminal units, and $f_c$ is the functionalization of the core molecule (which is 3 for TMP). D is given by the sum of primary and secondary units, Dp and Ds (see FIG. 32), and $L_{13}$, $L_{14}$, and T are defined in an analogous manner.

Figure 33:
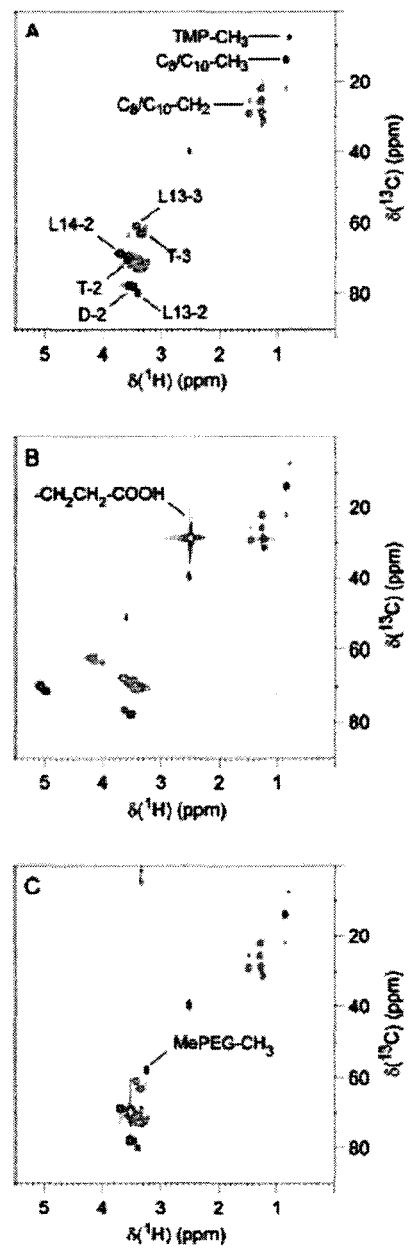
FIG. 33 shows representative multiplicity-edited HSQC spectra of (A) HPG-$C_{8/10}$—OH, (B) HPG-$C_{8/10}$—COOH (high COOH), and (C) HPG$C_{8/10}$-MePEG$_{6.5}$. Representative assignments are indicated in the spectra.

When a combination of 2D HMBC and HSQC-TOCSY experiments is used, a number of peaks corresponding to primary and secondary $L_{13}$, $L_{14}$, T, and D units were assigned for an unmodified HPG polymer (which was synthesized as a reference material, containing no $C_{8/10}$ alkyl component and no MePEG addition or carboxyl modification, data not shown), and peak volumes from a multiplicity-edited HSQC were used to calculate DB and DPn. The results obtained for our unmodified HPG were DB) 0.51 and DPn) 14.83, and the relative abundances for structural units are 39% for linear units, 20% for dendritic units, and 41% for terminal units. These values are in good agreement with literature values (Sunder, A.; Hanselmann, R.; Frey, H.; Mulhaupt, R. *Macromolecules* 1999, 32, 4240-4246; Holter, D.; Burgath, A.; Frey, H. *Acta Polym.* 1997, 48, 30-35). When comparing the HSQC spectrum of HPG modified with $C_{8/10}$ alkyl chains (HPG-$C_{8/10}$—OH), to the HSQC spectrum of unmodified HPG, two new peaks are visible in the spectral region of the polymer core of the former (FIG. 33). One peak was assigned to the R-methylene group of the aliphatic chain, whereas the second peak could not be assigned unambiguously. Based on chemical shifts, this peak may correspond to a T unit with one alkyl chain attached to the secondary hydroxyl group; however, this speculation could not be confirmed. A similar situation was observed for HPG-MePEG$_{6.5}$. The peak from the R-methylene group of the MePEG could be assigned, but the additional, unknown peak could not be assigned unambiguously. Similar to HPG-$C_{8/10}$—OH, the chemical shifts of the new peak are similar to an $L_{14}$-like unit. In summary, DB and DPn could not be calculated from NMR data due to lack of unambiguous signal assignment. NMR data allows for a straightforward characterization of free hydroxyl groups through observation of linear or terminal units and confirmation that all expected branching patterns and modifications (alkyl, MePEG, and carboxyl) are present. FIG. 33 illustrates the various assigned peaks in the NMR spectra, showing the presence of the expected branching pattern, and of MePEG, alkyl chains, and COOH groups.

Mole Fractions of COOH

For all HPG polymers modified with COOH, the mole fractions of COOH were estimated from HSQC NMR spectra. By this method, the number of COON in the HPG polymer is not an absolute number, because it is expressed as relative to the TMP methyl groups present in the sample. Each HPG molecule is assumed to contain only one TMP; however, the amount of TMP per mole of HPG in the various batches of polymer has not been independently quantified. Therefore, these numbers serve as a qualitative indicator of how many hydroxyl groups were capped with COON.

Figure 34:
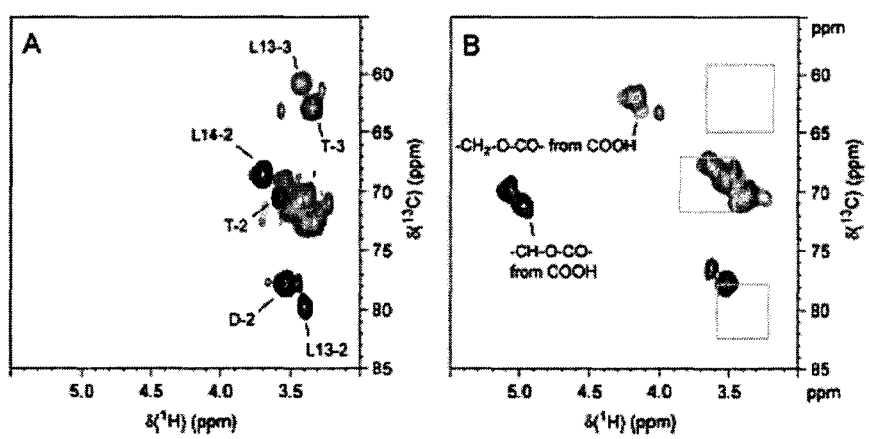
FIG. 34 shows expansions of regions of the HSQC spectra of (A) HPG-$C_{8/10}$—OH and (B) HPG-$C_{8/10}$—COOH. Representative assignments are given.

Furthermore, because the HPG-C$_{8/10}$-MePEG$_{6.5}$-COOH polymers were both synthesized from the same batch of HPGC$_{8/10}$-MePEG$_{6.5}$, the TMP content is expected to be identical and the NMR spectra can be compared to determine the relative amount of COON in the two HPG-C$_{8/10}$-MePEG$_{6.5}$-COOH polymers. The molar ratios indicate that there is a 2.8-fold higher COOH content in HPG-C$_{8/10}$-MePEG$_{6.5}$-COOH$_{348}$ compared with the HPG-C$_{8/10}$-MePEG$_{6.5}$-COOH$_{113}$. This is in good agreement with the 3.1-fold ratio of target COOH content in the two polymers. For HPG-C$_{8/10}$—COOH and the high-carboxyl density HPGC$_{8/10}$-MePEG$_{6.5}$-COOH$_{348}$ polymers, no peaks corresponding to linear or terminal groups were observed, indicating that no hydroxyl groups are present in this polymer (see FIG. 34 for a representative NMR spectrum). For the lower density COON polymer, HPG-C$_{8/10}$-MePEG$_{6.5}$-COOH$_{113}$, peaks of linear and terminal groups were observed in addition to the new peaks, indicating only a partial saturation of hydroxyl groups with carboxylic acids (data not shown).

FT-IR

FT-IR spectra for HPGs were obtained using a Perkin-Elmer FTIR spectrometer (Perkin-Elmer, Woodbridge, ON) with a universal ATR sampling accessory. The scanning range was 4000-650 cm$^{-1}$ with a resolution of 4 cm$^{-1}$.

Figure 35:
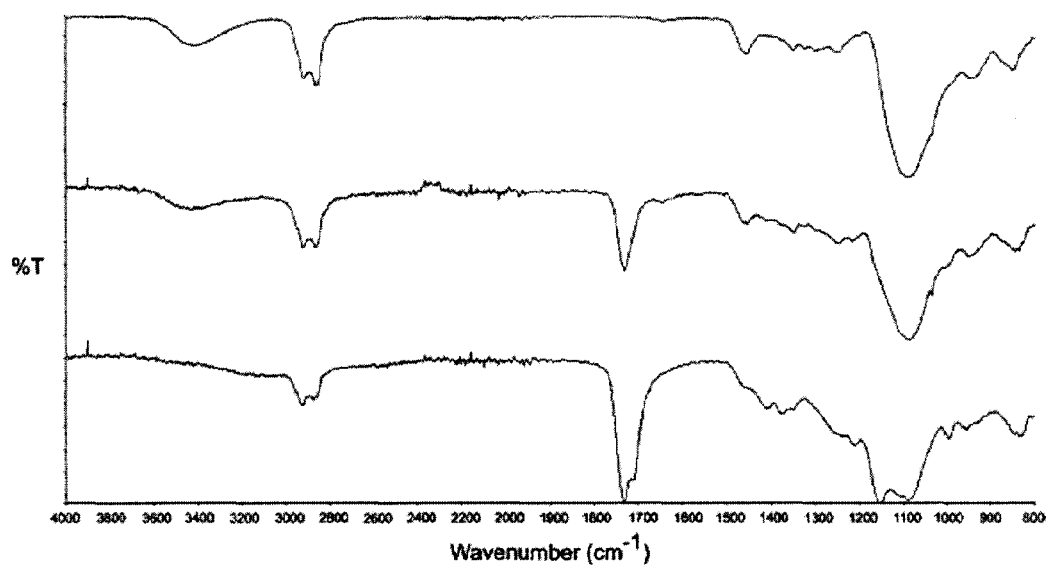
FIG. 35 shows FT-IR spectra of HPG-$C_{8/10}$-MePEG$_{6.5}$ (top), HPG-$C_{8/10}$-MePEG$_{6.5}$-COOH$_{113}$ (center), and HPG-$C_{8/10}$-MePEG$_{6.5}$-COOH$_{348}$ (bottom).

FT-IR spectra of HPG-C$_{8/10}$-MePEG$_{6.5}$, HPG-C$_{8/10}$-MePEG$_{65}$-COOH$_{348}$ and HPG-C$_{8/10}$-MePEG$_{6.5}$-COOH$_{113}$ are shown in FIG. 35. The peak at 2800-3000 cm$^{-1}$ is consistent with C—H vibrations and occurs in all HPGs. The peaks at 1680-1780 cm$^{-1}$ arose from CdO bands, indicating the presence of COOH groups in the HPG-C$_{8/10}$-MePEG-COOH polymers. The peaks at 1200-1400 and 1000-1180 cm$^{-1}$ arise from a C—H bend and C—O vibration, respectively, and therefore, they can be found in all of these polymers. By comparing the FT-IR spectra of the HPG-C$_{8/10}$-MePEG$_{6.5}$, the HPG-C$_{8/10}$-MePEG$_{6.5}$-COOH$_{113}$, and the HPG-C$_{8/10}$-Me-PEG$_{6.5}$-COOH$_{348}$, it can be seen that the OH peak (3300-3500 cm$^{-1}$) decreases and the CdO peak (1680-1780 cm$^{-1}$) in the HPG-C$_{8/10}$-MePEG-COOH appears, indicating the OH groups have been consumed and converted to COOH. The spectrum of the HPG-C$_{8/10}$-MePEG$_{6.5}$-COOH$_{348}$ showed the near elimination of the OH peak, indicating that the OH groups were largely consumed and converted to COOH, whereas the OH peak for HPG-C$_{8/10}$-MePEG$_{6.5}$-COOH$_{113}$ was decreased but still evident, in agreement with the NMR results. Furthermore, the latter HPG also shows a smaller CdO peak, indicating a lower mole ratio of COOH compared to HPG-C$_{8/10}$-MePEG$_{6.5}$-COOH$_{348}$. The FT-IR data showed good evidence to support the changes in the functionalization of the HPGs and also confirmed that unreacted reagents were removed by the purification procedures.

Molecular Weight

Weight average molecular weights (Mw) and polydispersities (PDI) of the HPGs were determined by gel permeation chromatography (GPC) equipped with a DAWN-EOS multiangle laser light scattering (MALLS) detector (GPC-MALLS) and Optilab RI detector (Wyatt Technology Inc., Santa Barbara, Calif.). Aqueous 0.1 N sodium nitrate solution was used as the mobile phase at a flow rate of 0.8 mL/min. The details have been described in a previous report (Kainthan, R. K.; Brooks, D. E. *Bioconjugate Chem.* 2008, 19, 2231-2238; Kumar, K. R.; Kizhakkedathu, J. N.; Brooks, D. E. *Macromol. Chem. Phys.* 2004, 205, 567-573). The dn/dc values for various HPGs were determined to be 0.146, 0.165, and 0.138 for HPGC$_{8/10}$-MePEG$_{6.5}$, HPG-C$_{8/10}$-MePEG$_{6.5}$-COOH$_{348}$, and HPG-C$_{8/10}$-MePEG$_{6.5}$-COOH$_{113}$, respectively, in aqueous 0.1 N NaNO$_3$ solutions and were used for the calculation of molecular weight of polymers. The data were processed using Astra software provided by Wyatt Technology Corp. Number average molecular weights of the polymers were calculated by dividing Mw by PDI.

The molecular weights and polydispersities of these HPGs are shown in Table 13. The functionalized HPGs (HPG-C$_{8/10}$-MePEG$_{6.5}$-COOH) showed increases in molecular weight compared to HPG-C$_{8/10}$-MePEG$_{6.5}$. Furthermore, it was found that after the surface functionalization, the polydispersities of the polymers were not altered greatly, indicating a relatively uniform surface modification. Molecular weight values were similar to those of previously reported HPG-C$_{8/10}$-MePEG (Kainthan, R. K.; Mugabe, C.; Burt, H. M.; Brooks, D. E. *Biomacromolecules* 2008, 9, 886-895; Kainthan, R. K.; Janzen, J.; Kizhakkedathu, J. N.; Devine, D. V.; Brooks, D. E. *Biomaterials* 2008, 29, 1693-1704; Mugabe, C.; Hadaschik, B. A.; Kainthan, R. K.; Brooks, D. E.; So, A. I.; Gleave, M. E.; Burt, H. M. *BJU Int.* 2009, 103, 978-986; Kainthan, R. K.; Brooks, D. E. *Bioconjugate Chem.* 2008, 19, 2231-2238).

Titration of COOH Groups

Potentiometric/pH titrations, to quantify the total concentration of HPGs surface-grafted with COOH, were performed on a T-50 M titrator (Mettler Toledo, Mississauga, ON). HPG-C$_{8/10}$-MePEG$_{6.5}$-COOH$_{348}$ and HPG-C$_{8/10}$-MePEG$_{6.5}$-COOH$_{113}$ samples were dissolved at 0.2 mg/mL in 10 mL of 10 mM NaOH. The pH of each solution was manually increased up to approximately 11 by the addition of 0.1 M NaOH. Samples were then titrated with 0.01 M HCl. Injections were set up in a dynamic range of 10-50 µL and a time interval of 30-60 s between injections was to ensure equilibration was established. Titrations were terminated once the pH reached 3.0. Titration end points were determined using the standard extrapolation/intersection method. The reported COOH titration values represent the mean of three measurements.

The mole ratios of COOH groups conjugated to the HPGs were measured by potentiometric/pH titration (Table 13) and showed good agreement with target mole ratios and the measured molecular weights. For instance, the molecular weight of HPG-C$_{8/10}$-MePEG$_{6.5}$-COOH$_{113}$ can also be calculated by the addition of the number average molecular weight of the HPG-C$_{8/10}$-MePEG$_{6.5}$ (6.3×10$^4$) with the molecular weight ascribed to COOH groups, which equals the number of carboxylate per HPG molecule (87 from titration data) multiplied by the carboxylate molecular weight (101 g/mol). Based on this calculation, the number average molecular weight of HPG-C$_{8/10}$-MePEG$_{6.5}$-COOH$_{113}$ is 7.2×10$^4$ g/mol, in good agreement with the measured value (7.0×10$^4$ g/mol).

Solubility

The solubility characteristics of HPG polymers were assessed by dissolving known weights of the polymer in various aqueous buffers or distilled water. The samples were gently vortexed to speed dissolution. The absorbance of polymer solutions at 550 nm was regularly measured for signs of turbidity for several days to assess whether the polymer remained in solution. For some of the carboxylic acid-derivatized HPG polymers, the pH of the solution was adjusted to facilitate dissolution.

As potential drug nanocarriers, the solubility characteristics in aqueous media of these polymers are critical. It was found that the HPG-C$_{8/10}$-MePEG polymer had good water solubility (greater than 100 mg/mL) in distilled water, PBS buffer (pH of 7.4), and synthetic urine. HPG-C$_{8/10}$—COOH was found to be practically insoluble in aqueous media or PBS (pH 7.4) and only soluble in alkaline solutions such as 0.1 M NaOH, due to decreased ionization at neutral pH. The hydrophobic (alkyl chains) components of the HPG core likely dominated the solubility characteristics. Carboxylate-derivatized HPGs also conjugated with MePEG groups showed increased water solubility. Accordingly, it was found that HPG-C$_{8/10}$-MePEG$_{6.5}$-COOH$_{113}$ could be completely dissolved in 10 mM PBS at a concentration of 100 mg/mL without heating, although the pH of the solution dropped from 7.4 to 4.5. HPG with a higher amount of carboxylate (HPG-C$_{8/10}$-MePEG$_{6.5}$-COOH$_{348}$) was poorly soluble in water or PBS buffer and exceeded the buffering capacity, resulting in acidification of PBS buffer and dropping the pH from 7.4 to approximately 3.8. The solution exhibited significant turbidity as measured by absorbance at 550 nm, demonstrating an insoluble residual fraction of polymer (data not shown). The addition of sodium hydroxide was required to achieve a concentration of 100 mg/mL and a clear solution at pH 4.25.

Particle Size and Zeta Potential

Particle size and zeta-potential analysis were conducted using a Malvern NanoZS Particle Size analyzer (Malvern Instruments Ltd., Malvern, U.K.) using disposable sizing cuvettes. Polymer solutions at a concentration of 15 mg/mL were prepared in 1 mM NaCl at pH 6.0 and filtered with a 0.22 µm syringe filter (Pall Life Sciences, Ann Arbor, Mich.) prior to measurement.

Carboxyl-terminated HPG polymers had particle sizes in the 5-10 nm range (Table 13). Zeta potentials of the nanoparticles were strongly negative at −41.2±3.2 and −60.3±2.1 mV for HPG-C$_{8/10}$-MePEG$_{6.5}$-COOH$_{113}$ and HPG-C$_{8/10}$-MePEG$_{6.5}$-COOH$_{348}$, respectively. The decrease in zeta potential is attributed to the number of carboxyl groups conjugated to the surface of the HPGs.

Example 25

Cisplatin Binding to HPGs

The binding of cisplatin to carboxylate modified HPGs was assessed by preparing 10 mg/mL solutions of the polymers in 0.01 M NaOH. To these solutions, cisplatin was added so that the final concentration of drug ranged from 0.5 to 4 mg/mL. The pH of each solution was adjusted to 6.0 with small volumes of 5 M NaOH. The solutions were incubated overnight at 37° C. with shaking at 50 rpm. Solutions were transferred to Nanosep 3K Omega centrifugal filtration devices (Pall Life Sciences, Ann Arbor, Mich.) and centrifuged at 5000 rpm for 10 min. A small volume of the filtrate (10-40 µL) was diluted to 400 µL with 0.01 M NaOH, and the concentration of unbound cisplatin in the filtrate was assayed by a previously described o-phenylenediamine (OPDA) colorimetric assay (Haxton, K. J.; Burt, H. M. *Dalton Trans*. 2008, 5872-5875). The concentration of cisplatin bound to the HPG was determined by subtracting the concentration of unbound cisplatin found in the filtrate from the initial concentration of drug added to the HPG.

Figure 36:
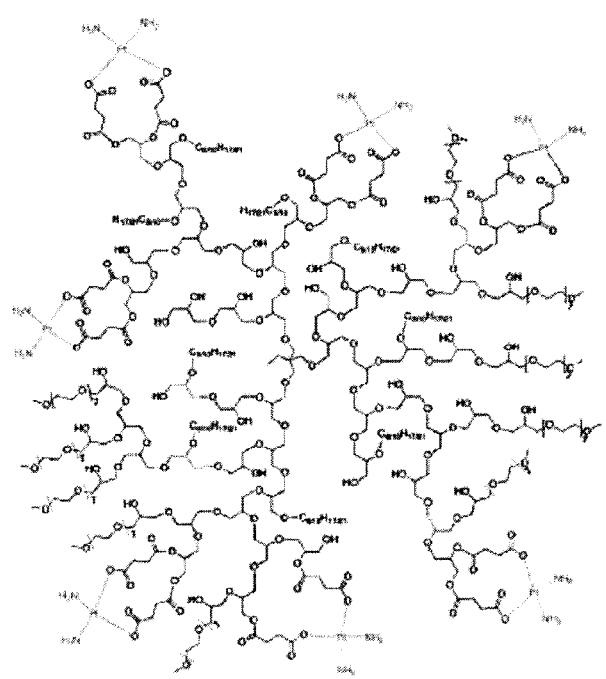
FIG. 36 shows representative structure of HPG-$C_{8/10}$-MePEG-COOH bound to cisplatin.
Figure 37:
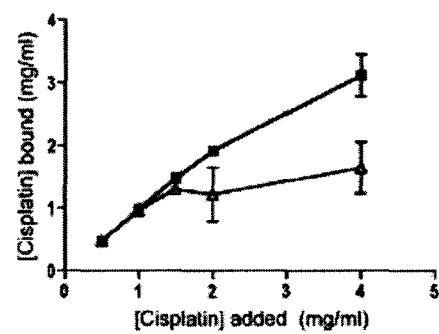
FIG. 37 shows binding of cisplatin to (empty triangle) HPG-$C_{8/10}$-MePEG$_{6.5}$-COOH$_{113}$ or (filled square) HPG-$C_{8/10}$-MePEG$_{6.5}$-COOH$_{348}$ in distilled water adjusted to pH 6.0.

Binding of cisplatin to the HPGs was achieved through coordination of the drug to terminal carboxylate groups on the polymer (FIG. 36). For HPG-C$_{8/10}$-MePEG$_{6.5}$-COOH$_{113}$ cisplatin bound to the polymer with nearly 100% efficiency up to a maximum of 1 mg/mL (10% w/w; FIG. 37). Above this concentration, free drug was detected in the filtrate, indicating saturation of the carboxylate binding sites and the presence of unbound drug in the media. HPG-C$_{8/10}$-MePEG$_{6.5}$-COOH$_{348}$ bound up to 2 mg/mL with 100% efficiency before free drug was detected in the filtrate. This increase in bound drug is attributed to the increased number of carboxylate groups and, thus, number of cisplatin binding sites on HPG-C$_{8/10}$-MePEG$_{6.5}$-COOH$_{348}$ as compared to HPG-C$_{8/10}$-MePEG$_{6.5}$-COOH$_{113}$.

Example 26

In Vitro Cisplatin Release

Cisplatin was bound to the carboxylate modified HPGs as described above with final polymer and cisplatin concentrations of 10 and 1 mg/mL, respectively. Into 7000 MWCO Slide-A-Lyzer mini dialysis units (Thermo Scientific, Rockford, Ill.), 20 µL of cisplatin bound polymer solution, or a 1 mg/mL solution of free cisplatin, were added and the samples were dialyzed at 37° C. with stirring against 4 L of 1 mM PBS adjusted to pHs of 4.5, 6.0, and 7.4 or synthetic urine at pH 7.0. Synthetic urine (Surine) was purchased from Dyna-Tek Industries (Lenexa, Kans.). At predetermined time points, three dialysis units were removed from the release media, and the entire contents were removed with three washings of the dialysis unit followed by dilution to 1 mL with fresh release media. The cisplatin concentration of contents of the dialysis units was determined by OPDA colorimetric assay. The cumulative percent drug released was calculated by subtracting the amount of drug remaining from the initial amount of drug in the dialysis bag at the beginning of the experiment. The data were expressed as cumulative percentage of drug released as a function of time.

Figure 38:
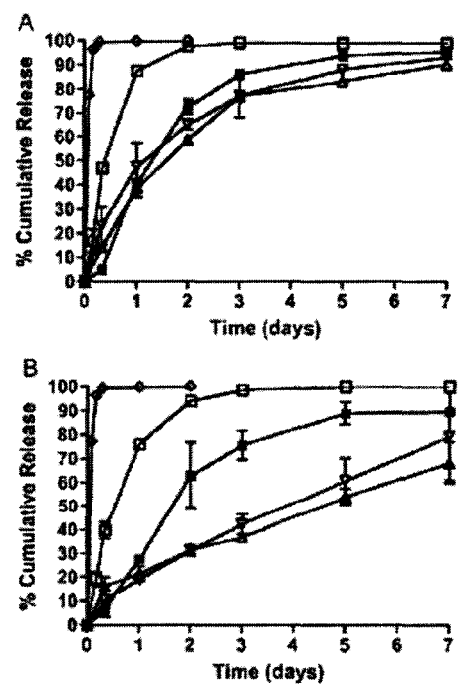
FIG. 38 shows in vitro release of free cisplatin (empty diamond) or cisplatin bound to (A) HPG-$C_{8/10}$-MePEG$_{6.5}$-COOH$_{113}$ or (B) HPG-$C_{8/10}$-MePEG$_{6.5}$-COOH$_{348}$ at a drug concentration of 1 mg/mL and polymer concentration of 10 mg/mL. Release media were 1 mM PBS at pHs of 4.5 (filled square), 6.0 (empty triangle), 7.4 (inverted triangle), or artificial urine (empty square) at 37° C.

Release of free cisplatin in PBS was rapid and 100% complete within 7 h, demonstrating that the membrane did not impede the release of free drug to any great extent (FIG. 38). For all cisplatin-bound HPG samples, the drug was found to release in a controlled fashion, considerably slower than the free drug. In PBS, regardless of the pH, cisplatin bound to HPG-C$_{8/10}$-MePEG$_{6.5}$-COOH$_{113}$ was released at nearly the same rate in PBS with approximately 5% released in the first 2 h, 40% release after 1 day, and up to 90% released after 7 days. Cisplatin bound to HPG-C$_{8/10}$-MePEG$_{6.5}$-COOH$_{348}$ at pHs of 6.0 and 7.4 released the drug in PBS at similar rates, in a nearly linear manner, with approximately 3% of bound cisplatin released in 2 h, 20% released in 1 day, and up to 70% over 7 days. The release rate for cisplatin bound to HPG-C$_{8/10}$-MePEG$_{6.5}$-COOH$_{348}$ at pH 4.5 was faster than its higher pH counterparts, with a release profile similar to those of HPG-C$_{8/10}$-MePEG$_{6.5}$-COOH$_{113}$. The release rate of cisplatin was considerably faster in the presence of urine, with just over 10% of the dose released in 2 h and complete drug release by 2 days for HPG-C$_{8/10}$-MePEG$_{6.5}$-COOH$_{113}$ and 3 days for HPG-C$_{8/10}$-MePEG$_{6.5}$-COOH$_{348}$. Similar to release in PBS, the difference in cisplatin release between the two HPGs may be attributed to the increased number of carboxylate groups present on HPG-C$_{8/10}$-MePEG$_{6.5}$-COOH$_{348}$. As urine is a complex mixture made up of several components, it is uncertain which compounds are responsible for the increased release of the cisplatin from the HPGs; however, this increased release rate may be advantageous, providing a mechanism by which the drug release increases upon dilution with urine. Upon displacement of cisplatin from the HPG it is possible that nitrogen containing compounds in urine, such as urea, uric acid and creatinine, may bind and inactivate cisplatin. Although cisplatin has been shown to complex with these compounds to some degree, it has been determined that the majority of cisplatin present in urine after IV administration is in the originally administered form and the highly active monoaqua hydrolysis product (Tang, X.; Hayes Ii, J. W.; Schroder, L.; Cacini, W.; Dorsey, J.; Elder, R. C.; Tepperman, K. *Met. Based Drugs* 1997, 4, 97-109). In light of this finding, it is likely that the majority of the cisplatin released in from the HPGs in urine is in a pharmacologically active form.

Example 27

Cytotoxicity Evaluation

Cytotoxicity studies were performed using the MTS cell proliferation assay (Promega, Madison, Wis.). This assay does not measure immediate cytolytic effects of agents but measures the effect of the polymer on cellular proliferation over long time periods. In this study, KU-7-luc bladder cancer cells, kindly provided by Dr. M. Tachibana (Keio University, Tokyo, Japan). The cells were plated at 5000 cells/well into 96-well plates in 180 µL of Dulbecco's modified Eagle (DMEM) medium (Invitrogen Canada, Inc., Burlington, ON) supplemented with 10% fetal bovine serum (FBS) (Invitrogen Canada, Inc., Burlington, ON), 1% penicillin-streptomycin, and 1% L-glutamine and allowed to grow for 24 h at 37° C. in 5% $CO_2$ to reach approximately 80% confluence for cytotoxicity assays. Cells were then incubated for 2 or 72 h with HPGs alone, ranging from 0.01-100 mg/mL, or free cisplatin or cisplatin-loaded HPGs with drug concentrations ranging from 0.01-100 µg/mL. After treatment, the cells were washed twice with Hank's balanced salt solution (HBSS) and 180 µL of fresh culture media was added into each well and cells were allowed to grow for 72 h. Proliferation of these cells was measured using a CellTiter 96 aqueous non-radioactive cell proliferation assay (Promega, Madison, Wis.) as described previously (Mugabe, C.; Hadaschik, B. A.; Kainthan, R. K.; Brooks, D. E.; So, A. I.; Gleave, M. E.; Burt, H. M. *BJU Int.* 2009, 103, 978-986). Briefly, 180 µL of a 10% v/v solution of 3-(4,5-dimethythiazol-2-yl)-5-(3-carboxylmethonyphenol)-2-(4-sulfophenyl)-2H-tetrazolium in HBSS was added to each well and the cells were incubated for 2 h. The absorbance was measured at 490 nm with a reference of 620 nm using a microplate reader.

Figure 39:
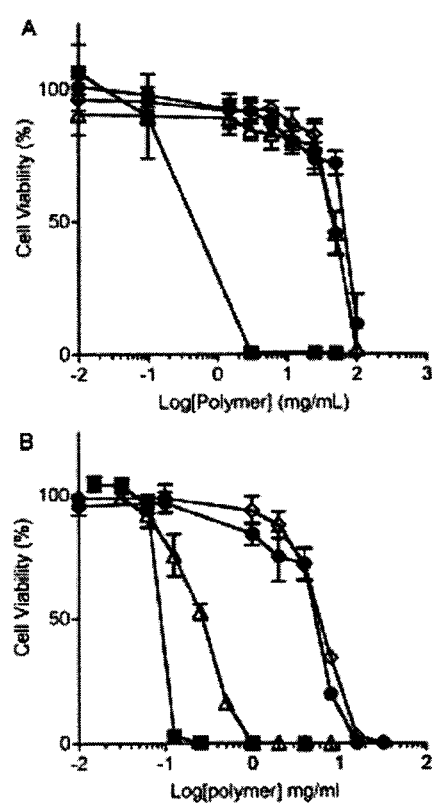
FIG. 39 shows cell viability of KU-7-luc cells after (A) 2 and (B) 72 h of incubation with HPG-$C_{8/10}$—OH (filled square), HPG-$C_{8/10}$-MePEG$_{6.5}$ (empty triangle), HPG$C_{8/10}$-MePEG$_{6.5}$-COOH$_{113}$ (filled circle), and HPG-$C_{8/10}$-MePEG$_{6.5}$-COOH$_{348}$ (empty diamond).
Figure 40:
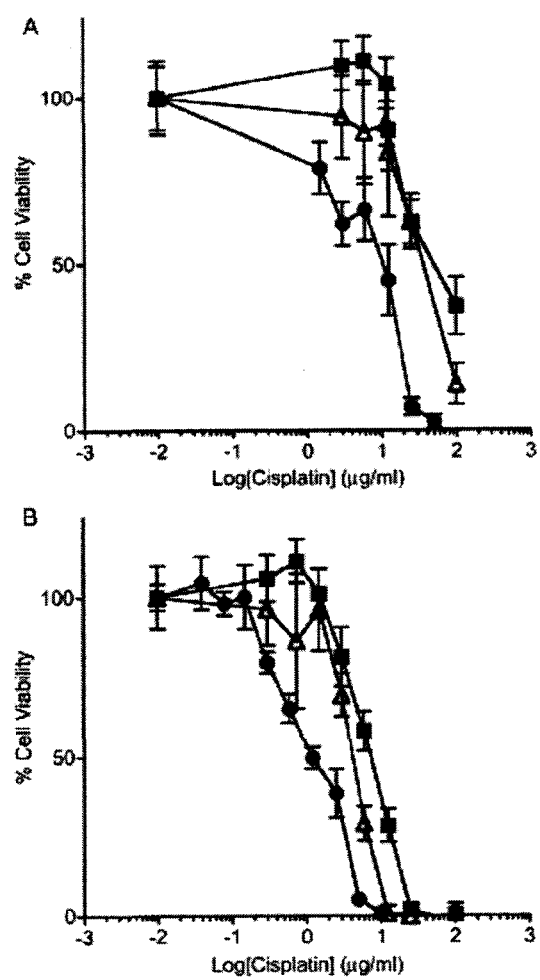
FIG. 40 shows viability of KU-7-luc cells after (A) 2 and (B) 72 h incubation with free cisplatin (filled circle), cisplatin-loaded HPG-$C_{8/10}$-MePEG$_{6.5}$-COOH$_{113}$ (empty triangle), and HPG-$C_{8/10}$-MePEG$_{6.5}$-COOH$_{348}$ (filled square).

The inhibition effects of nondrug-loaded HPGs and cisplatin-loaded HPGs on KU-7-luc bladder cancer cells were investigated for incubation times of 2 and 72 h (FIG. 39). These incubation times were chosen to allow for imitation of the typical intravesical instillation period as well as to compare against previously determined inhibitory concentrations for cisplatin Inhibitory concentrations at 50% ($IC_{50}$) for 2 h incubations were determined to be 1.3, 45.7, 47.0, and 63.0 mg/mL for $HPG-C_{8/10}$—OH, $HPG-C_{8/10}$-$MePEG_{6.5}$, $HPGC_{8/10}$-$MePEG_{6.5}$-$COOH_{348}$, and $HPG-C_{8/10}$-$MePEG_{6.5}$-$COOH_{113}$, respectively. When a 72 h incubation was used, the polymers inhibited cell proliferation to a greater degree than those found with a 2 h incubation. The $HPG-C_{8/10}$—OH and $HPG-C_{8/10}$-$MePEG_{6.5}$ had $IC_{50}$s of 0.1 and 0.2 mg/mL, respectively. The $IC_{50}$ for the carboxylate-modified HPGs decreased approximately 10-fold; however, these polymers still exhibited a high degree of cellular compatibility with $IC_{50}$ values of approximately 5 mg/mL. The overall excellent biocompatibility of the $HPG-C_{8/10}$-MePEG and $HPG-C_{8/10}$-MePEG-COOH probably arises from the known cellular compatibility of MePEG surfaces ensuring little interaction with the plasma membrane of the cells. The added benefit of carboxylation may arise from the net negative charge of this moiety at a pH of 7.4, establishing a slight repulsive force with the negatively charged cell surface. Following a 72 h incubation, free cisplatin inhibited KU-7-luc cell proliferation with an $IC_{50}$ of 1 µg/mL (FIG. 40A), consistent with previous reports for this drug and cell combination (Hadaschik, B. A.; ter Borg, M. G.; Jackson, J.; Sowery, R. D.; So, A. I.; Burt, H. M.; Gleave, M. E. *BJU Int.* 2008, 101, 1347-1355). With a 2 h incubation, this $IC_{50}$ value increased to approximately 10 µg/mL (FIG. 40B). When bound to $HPG-C_{8/10}$-$MePEG_{6.5}$-COOH polymers, the complexed form of cisplatin also inhibited KU-7-luc proliferation with higher $IC_{50}$ values observed for the 2 h incubation (approximately 50 µg/mL) as compared to the 72 incubation values (approximately 5 µg/mL). Clearly, for both 2 and 72 h incubations, the complexed form of cisplatin inhibited cell proliferation less than the free drug by a factor of almost 5. This increase in the $IC_{50}$ for the drug complexed to the HPGs is likely due to the slow release rate of the drug from the polymer.

Example 28

Penetration of DTX and Mitomycin F from Different Formulations into Pig Bladder Tissue with or without Pre-Treatment Penetration of DTX from DTX formulations and penetration of mitomycin F from mitomycin F formulations into porcine bladder tissue were evaluated. Freshly excised porcine bladder tissue sections were mounted on Franz diffusion cells and treated with anticancer drug DTX formulated in Tween 80, $HPG-C_{8/10}$-MePEG, or $HPG-C_{8/10}$-MePEG-$NH_2$ for 2 hours. In some experiments, the porcine bladder tissue was pretreated with chitosan solution (without drug) or $HPG-C_{8/10}$-MePEG-$NH_2$ solution (without drug) for 1 hour before being treated with DTX formulated in Tween 80, $HPG-C_{8/10}$-MePEG or $HPG-C_{8/10}$-MePEG-$NH_2$. For mitomycin F penetration studies, freshly excised porcine bladder tissue sections were mounted on Franz diffusion cells and treated with anticancer drug mitomycin F formulations for 2 hours. The porcine bladder tissue was pretreated with $HPG-C_{8/10}$-MePEG-$NH_2$ solution (without drug) for 1 hour before being treated with mitomycin F formulations. Tissue concentration versus tissue depth profiles were obtained and drug exposures were obtained from area-under-the-curve (AUC) calculations.

HPLC-grade acetonitrile and dichloromethane were obtained from Fisher Scientific (Fairlawn, N.J.). Liquid scintillation fluid, CytoScint™ES, was purchased from MP Biomedicals (Irvine, Calif.). Tyrode salts were purchased from Sigma-Aldrich (St. Louis, Mo.) (Tyrodes contains the following in g/L: NaCl: 8.0, KCl: 0.3, $NaH_2PO_4.5H_2O$: 0.093, $KH_2PO_4$: 0.025, $NaHCO_3$: 1.0, Glucose: 2.0). Docetaxel was obtained from Natural Pharma (Langley BC. Canada). Commercial Taxotere® 20 mg/0.5 mL (Sanofi Aventis, Laval, QC) was purchased from the BC Cancer Agency at the Vancouver General Hospital. Tritium labeled DTX in ethanol was purchased from Moravek Biochemicals (Brea, Calif.) with a specific activity of 23.2 Ci/mmol. $HPG-C_{8/10}$-MePEG was prepared by adapting the protocol described in Example 10 and $HPG-C_{8/10}$-MePEG-$NH_2$ was prepared by adapting the protocol described in Example 18. Chitosan was supplied by Novamatrix FMC. Porcine bladders were purchased from Britco Inc. (Langley, BC). Freshly excised urinary bladders were removed on-site from 6-10 month old male pigs weighing between 90-113 kg.

The mols of amine per mol of HPG-MePEG-$NH_2$ was measured for the HPG-MePEG-$NH_2$ polymers using different methods, including a forward titration method, a back titration method and a fluorescamine assay (Table 14).

TABLE 14

Mol of amine per mol of HPG-MePEG-NH$_2$ measurements

| Sample | Forward titration method[a] (mol amine/ mol HPG) | Back titration method[b] (mol amine/ mol HPG) | Fluorescamine derivatization method[c] (mol amine/ mol HPG) |
|---|---|---|---|
| HPG-MePEG-NH$_2$ (low) | 6.7 | 10.3 | 10.3 |
| HPG-MePEG-NH$_2$ (high) | 25.2 | Not done | 37.6 |

[a]Forward titration method - titrated against HCl
[b]Back titration method - titrated against NaOH after addition of a known amount of HCl
[c]Fluorescence quantitation after derivatization with fluorescamine (fluorescamine assay described in Example 15)

Preparation of DTX Loaded HPG-C$_{8/10}$-MePEG, HPG-C$_{8/10}$-MePEG-NH$_2$ and Tween 80 Formulations HPG-C$_{8/10}$-MePEG and HPG-C$_{8/10}$-MePEG-NH$_2$ loaded with DTX were prepared using the solvent evaporation technique. DTX and HPG-C$_{8/10}$-MePEG or HPG-C$_{8/10}$-MePEG-NH$_2$ were dissolved in acetonitrile and dried in an oven at 60° C. for 1 h and flashed with nitrogen to eliminate traces of the organic solvent. Prior to drying, the polymer/drug solution was spiked with a small aliquot of $^3$H DTX. The resulting polymer/drug matrix was reconstituted with 60° C. tyrode buffer (pH 7.4) and vortexed for 2 min. The final concentration of drug was 0.5 mg/mL and was used at 37° C. DTX was prepared in Tween 80 by diluting Taxotere® concentrated solution (containing 40 mg of DTX and 1040 mg of Tween 80 per mL) with tyrode buffer to yield a final concentration of 0.5 mg/mL DTX. Solutions were doped with a small amount of $^3$H DTX prior to dilution.

Preparation of Mitomycin F Formulations

The mitomycin F (MW=363.4) was prepared in Tyrode's buffer. It was received from American Radiolabeled Chemicals Inc. (St Louis, Mo.) Cat # ART-1689. The activity was 1-10 Ci/mmol, 1 mCi/mL in ethanol. The solution was prepared by dissolving 50 uL of the ethanolic stock into 3 mL of buffer, a 300× dilution.

Preparation of Chitosan Solution and HPG-C$_{8/10}$-MePEG-NH$_2$ Solution for Use as a Pretreatment Chitosan used to prepare the chitosan solutions is PROTASAN™ UP CL 213 (Product#: 4210106) and is based on a chitosan where between 75-90% of the acetyl groups are removed. The cationic polymer is a highly purified and well-characterized water-soluble chloride salt. Typically, the molecular weight for PROTASAN™ UP CL 213 is in the 150000-400000 g/mol range (measured as a chitosan acetate). The chitosan solution was prepared by dissolving it in water to a solution concentration of 0.5% w/v.

The HPG-C$_{8/10}$-MePEG-NH$_2$ solution for use as a pretreatment was prepared by dissolving HPG-C$_{8/10}$-MePEG-NH$_2$ in acetonitrile. The resulting solution was dried in an oven at 60° C. for 1 h and flashed with nitrogen to eliminate traces of the organic solvent. The resulting polymer was reconstituted with 60° C. tyrode buffer (pH 7.4) and vortexed for 2 min.

Tissue Preparation

Freshly excised porcine bladders were removed of excess adipose tissue on the exterior wall and opened longitudinally into left and right lateral sides and cut into pieces approximately 2 cm×2 cm in a shallow bath of 37° C. tyrode buffer bubbled with carbogen (95% O$_2$/5% CO$_2$). All studies were performed within 5 h after sacrifice. Bladder pieces were mounted onto a Franz diffusion cell apparatus, such that the luminal side of the bladder wall was exposed to the drug solution. These tissue sections were not stretched and measured approximately 2-3 mm thick. Receptor chambers were filled with 10 mL of 37° C. tyrode buffer (pH 7.4). Excess tissue was trimmed around the perimeter of the diffusion cell. The donor chamber of the diffusion cell was filled with 1 mL of 0.5 mg/ml drug solution and the tissue exposure area was 0.64 cm$^2$. Each diffusion cell was set into a shallow water bath and incubated at 37° C. for 2 hours. For some experiments, tissues samples were pre-treated with a chitosan solution (without drug) or a HPG-C$_{8/10}$-MePEG-NH$_2$ solution (without drug) for 1 hour before being treated with the DTX or mitomycin F loaded formulations. Tissue samples were washed three times with tyrode buffer to remove all unbound drug. Tissue samples were trimmed and rapidly frozen on metal plates with liquid nitrogen on a bed of dry ice.

Cryotome Sectioning of Tissue

Frozen bladder tissue was mounted with Shandon Cryomatrix™ (Themo Scientific, Pittsburgh, Pa.) onto a cryotome object holder. Bladder tissue was sectioned with Shandon MB35 Premier Low Grade Microtome Blades (Themo Scientific, Pittsburgh, Pa.) at −20° C. on a Shandon Cryotome Electronic (Thermo Electron Corporation, Cheshire, England) with a R404A refrigeration system. Tissues were sectioned. Tissue sections were placed in pre-weighed 1.5 mL eppendorf tubes and stored frozen at −20° C.

Quantification of Drug in Tissue

Two hundred μL of acetonitrile was added to the weighed tissue slices for drug extraction. Samples were vortexed until all tissue slices were freely submerged in acetonitrile and left at room temperature for 24 hours to ensure complete extraction of drug. The extracted samples including all tissue slices were transferred to scintillation vials and 5 mL of scintillation fluid was added. Counts of $^3$H DTX or $^3$H mitomycin F were measured by liquid scintillation counting and quantitated using calibration graphs from the original stock solution.

Analysis of Tissue Level-Depth Profiles

The tissue level-depth profiles were analyzed for average DTX or mitomycin F concentrations in all layers of the bladder wall down to the muscle, for example, urothelium, lamina propria, and muscularis. The average tissue levels were determined as the total amount of drug found in the tissue layer divided by the total tissue weight for that layer. The area under the tissue-level depth profile (AUC) was calculated using the linear trapezoid rule, as follows:

$$AUC_0^t = \sum_{i=0}^{N-1} \frac{(t_{i+1} - t_i)}{2} \times (C_1 + C_{i+1})$$

Where, t is tissue depth in μm and C is concentration in μg/g
An estimation by extrapolation of the drug concentration (μg/g) at 0 μm was required in order to calculate the AUC.

Figure 41:
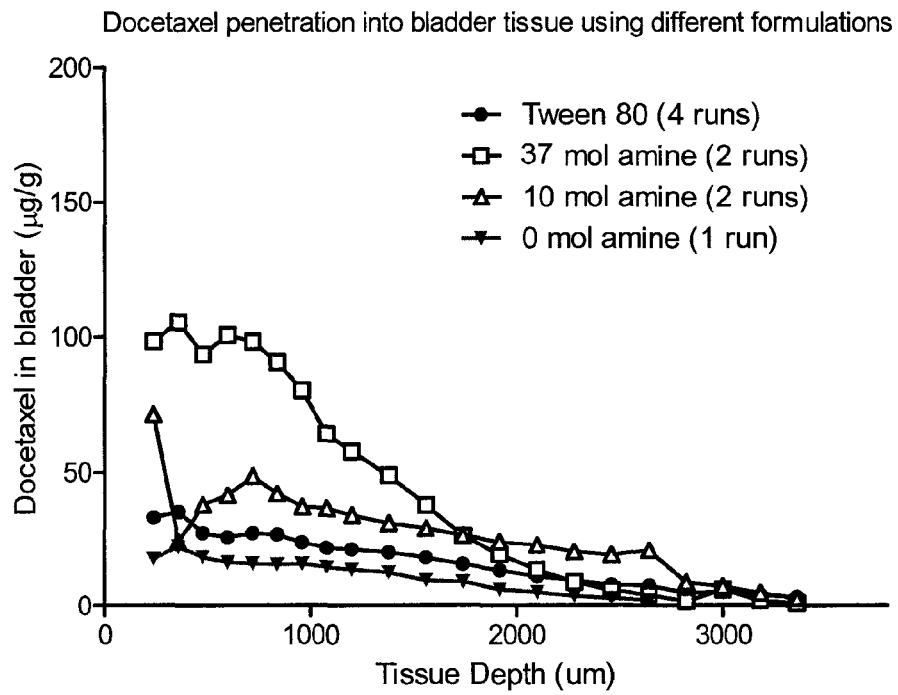
FIG. 41 shows tissue level-depth profiles of DTX in porcine bladder tissue following exposure to 0.5 mg/ml DTX in Tween 80 (filled circle), 0.5 mg/ml DTX in HPG-$C_{8/10}$-MePEG-$NH_2$ (37 mole amine/mole polymer) (empty square), 0.5 mg/ml DTX in HPG-$C_{8/10}$-MePEG-$NH_2$ (10 mole amine/mole polymer) (empty triangle), 0.5 mg/ml DTX in HPG-$C_{8/10}$-MePEG (filled inverted triangle). Average values for repeated runs of four formulations, comparing the penetration using HPG polymer with increasing amine content, compared with Tween 80 (eg the Taxotere formulation). Within each run, 5-6 replicates were run.

Data for DTX penetration into porcine bladder tissue from DTX formulations without pretreatment are shown in FIG. 41. Both dHPGs evaluated that contained amine resulted in higher drug concentration to depths of about 1500 μm, compared with formulations without amine, including the Tween 80 formulation (Taxotere®) and a dHPG that contained no amine functionality. The effect of adding amine was observed to be concentration dependent. FIG. 41 shows that the highest concentration of drug in tissue, in particular at depths to about 1500 μm was obtained using the dHPG formulation that contained the highest amine content (37 mol/mol). AUCs at the indicated tissue depth ranges have been calculated (Tables 15a and 15b), showing improvement of dHPG formulations over Taxotere in the range of 1.3 to 2.4 fold. Cavg and Cmax values at the indicated tissue depth ranges have been calculated (Table 15c).

TABLE 15a

AUC (180-2640 um) calculated for penetration of docetaxel with delivery in various vehicles without pretreatment

|  | Tween 80 | HPG-MePEG (0 mol) | HPG-MePEG-NH2 (10 mol) | HPG-MePEG-NH2 (37 mol) |
|---|---|---|---|---|
| AUC (180-2640) | 46642 | 26589 | 60207 | 100353 |
| Fold Change of Taxotere | 1 | 0.6 | 1.3 | 2.2 |
| SD | 5735 | N/A | 30088 | 21652 |
| N of Runs | 4 | 1 | 2 | 2 |

TABLE 15b

AUC(180-1560 um) calculated for penetration of docetaxel with delivery in various vehicles without pretreatment

|  | Tween 80 | HPG-MePEG (0 mol) | HPG-MePEG-NH2 (10 mol) | HPG-MePEG-NH2 (37 mol) |
|---|---|---|---|---|
| AUC(180-1560) | 35874 | 21983 | 43768 | 86899 |
| Fold Change | 1 | 0.6 | 1.2 | 2.4 |
| SD | 3053 | N/A | 20542 | 23196 |
| N of Runs | 4 | 1 | 2 | 2 |

TABLE 15c

Cavg and Cmax values calculated for the ranges of 180-2640 and 180-1560 tissue depth (um), for penetration of docetaxel with delivery in various vehicles without pretreatment

|  | Tween 80 | HPG-MePEG (0 mol) | HPG-MePEG-NH2 (10 mol) | HPG-MePEG-NH2 (37 mol) |
|---|---|---|---|---|
| C max/avg values (180-2640) |  |  |  |  |
| C(max) | 35.2 | 105.6 | 71.5 | 22.2 |
| C(avg) | 20.3 | 56.1 | 33.3 | 11.8 |
| Fold Change | 1.0 | 2.8 | 1.6 | 0.6 |
| St Dev. C(avg) | 8.5 | 38.1 | 13.2 | 6.1 |
| C max/avg values (180-1560) |  |  |  |  |
| C(max) | 35.2 | 105.6 | 71.5 | 22.2 |
| C(avg) | 25.4 | 79.6 | 39.4 | 15.5 |
| Fold Change | 1.0 | 3.1 | 1.5 | 0.6 |
| St Dev. C(avg) | 5.3 | 23.6 | 12.6 | 3.3 |

Figure 42:
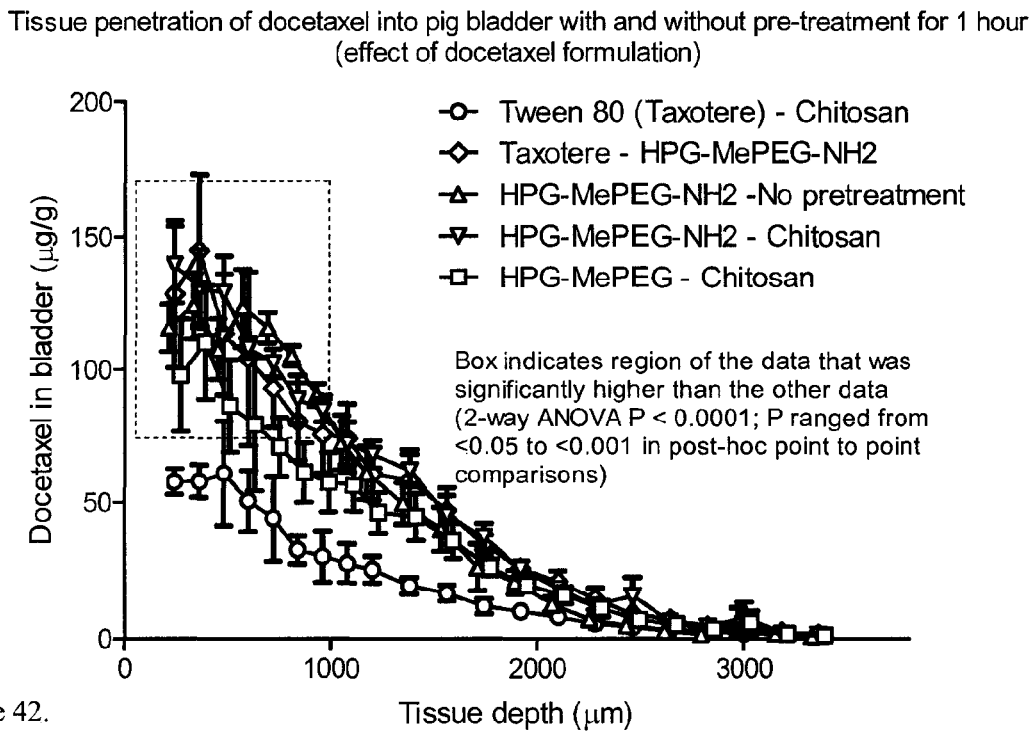
FIG. 42 shows tissue level-depth profiles of DTX in porcine bladder tissue following exposure to different DTX formulations with and without pre-treatment for 1 hour. 0.5 mg/ml DTX in Tween 80 with chitosan pretreatment (empty circle), 0.5 mg/ml DTX in Tween 80 with HPG-$C_{8/10}$-MePEG-$NH_2$ pretreatment (empty diamond), 0.5 mg/ml DTX in HPG-$C_{8/10}$-MePEG-$NH_2$ without pretreatment (empty triangle), 0.5 mg/ml DTX in HPG-$C_{8/10}$-MePEG-$NH_2$ with chitosan pretreatment (empty inverted triangle), and 0.5 mg/ml DTX in HPG-$C_{8/10}$-MePEG with chitosan pretreatment.
Figure 43:
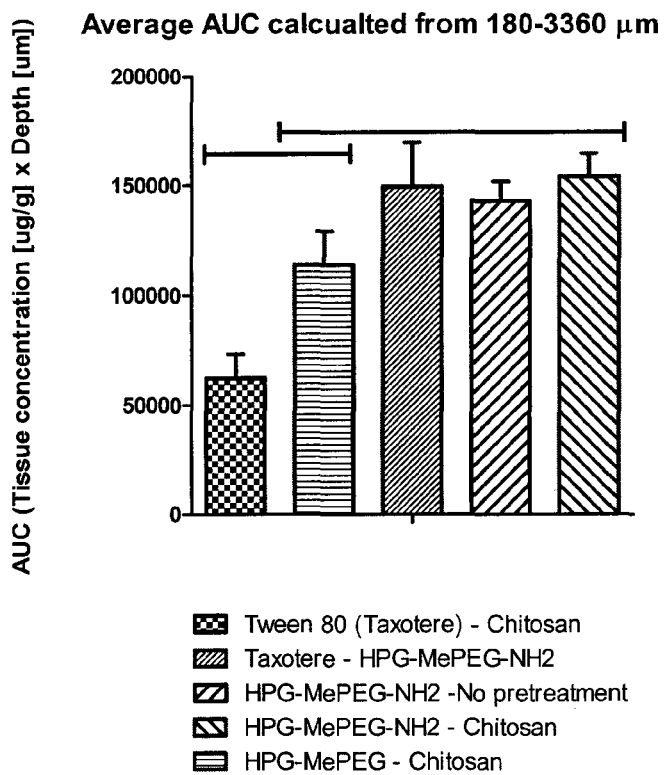
FIG. 43 shows AUCs of DTX for different DTX formulations with and without pre-treatment for 1 hour. 0.5 mg/ml of DTX in Tween 80 with chitosan pretreatment, 0.5 mg/ml of DTX in Tween 80 with HPG-$C_{8/10}$-MePEG-$NH_2$ pretreatment, 0.5 mg/ml of DTX in HPG-$C_{8/10}$-MePEG-$NH_2$ without pretreatment, 0.5 mg/ml of DTX in HPG-$C_{8/10}$-MePEG-$NH_2$ with chitosan pretreatment, and 0.5 mg/ml DTX in HPG-$C_{8/10}$-MePEG with chitosan pretreatment. Lines indicate lack of significant difference (p>0.05) between groups in post-hoc Tukey analysis after a significant 1-way ANOVA result, p=0.0007. Error bars indicate S.E.M.

Data for DTX penetration into porcine bladder tissue from DTX formulations with chitosan or HPG-$C_{8/10}$-MePEG-$NH_2$ pretreatment are shown in FIGS. 42 and 43. The goal of the experiment was to differentiate the dHPG polymer's function from chitosan, which is also a polymer containing amine functions. Chitosan has been contemplated as a polymer for use in intravesical delivery; however in the context of a pre-treatment to facilitate drug uptake into tissues, it is demonstrated that dHPGs of certain composition are superior. The data show that with chitosan pretreatment, the Tween 80 formulation (Taxotere®) provides relatively little tissue penetration, providing the lowest tissue concentration for docetaxel in bladder at all tissue depths. Similarly, pre-treatment with chitosan resulted in a modest improvement in tissue penetration of docetaxel when the drug was administered in the HPG-$C_{8/10}$-MePEG (no amine) vehicle, however, this was only superior to the Taxotere-treated (chitosan pre-treated) group. A superior effect in docetaxel tissue penetration was observed when dHPGs containing amines (37 mol amine/mol polymer) (called HPG-$C_{8/10}$-MePEG-$NH_2$ in FIGS. 42 and 43). As well, chitosan provided no benefit to delivery when it was used as a pre-treatment for the docetaxel loaded HPG-$C_{8/10}$-MePEG-NH2 formulation. The performance of each was compared by measuring the area under the curve (AUC, FIG. 43) of tissue concentration over tissue depth (FIG. 42), which is a measure of total drug exposure. The results show that the greatest exposure was obtained when pre-treatment or treatment utilized the dHPG containing amine. AUC values calculated for the range of 180-3360 tissue depth (um), and Cavg and Cmax values calculated for the ranges of 180-1560 and 180-3360 tissue depth (um), for penetration of docetaxel from various formulations after various pretreatment regimens are shown in Tables 15d and 15e.

TABLE 15d

AUC(180-3360 um) calculated for penetration of docetaxel with delivery in various vehicles after various pre-treatment regimens

| Group: | Taxotere-No Pretreatment (average of 4 runs) | Tween 80 (Taxotere)-Chitosan | HPG-MePEG-Chitosan | Taxotere-HPG-MePEG-NH2 | HPG-MePEG-NH2-No pretreatment | HPG-MePEG-NH2-Chitosan |
|---|---|---|---|---|---|---|
| Pre-Treatment | None | Chitosan | Chitosan | HPG-MePEG-NH2 | None | Chitosan |
| Delivery Vehicle | Taxotere | Taxotere | HPG-MePEG | Taxotere | HPG-MePEG-NH2 | HPG-MePEG-NH2 |
| Number of values | 4 × 5 replicates | 5 | 5 | 5 | 5 | 5 |
| Mean | 46642 | 62282 | 113817 | 149441 | 142930 | 154003 |
| Fold Increase Over "Taxotere-Chitosan" | 0.8 | 1 | 1.8 | 2.4 | 2.3 | 2.5 |

TABLE 15d-continued

AUC(180-3360 um) calculated for penetration of docetaxel with delivery in various vehicles after various pre-treatment regimens

| Group: | Taxotere-No Pretreatment (average of 4 runs) | Tween 80 (Taxotere)-Chitosan | HPG-MePEG-Chitosan | Taxotere-HPG-MePEG-NH2 | HPG-MePEG-NH2-No pretreatment | HPG-MePEG-NH2-Chitosan |
|---|---|---|---|---|---|---|
| Fold Increase Over "Taxotere-No Pretreat" | 1 | 1.3 | 2.3 | 3.0 | 2.9 | 3.1 |
| Std. Deviation | | 24996 | 34271 | 44998 | 19627 | 23451 |
| Std. Error | | 11178 | 15327 | 20124 | 8778 | 10488 |

TABLE 15e

Cavg and Cmax values calculated for the ranges of 180-1560 and 180-3360 tissue depth (um), for penetration of docetaxel with delivery in various vehicles after various pre-treatment regimens

| | | Tween 80 (Taxotere) - Chitosan | Taxotere - HPG-MePEG-NH$_2$ | HPG-MePEG-NH$_2$ -No pretreatment | HPG-MePEG-NH$_2$ - Chitosan | HPG-MePEG - Chitosan |
|---|---|---|---|---|---|---|
| Values for Depth Range: 180-1560 um | | | | | | |
| C(avg) | Values | 38.47 | 89.08 | 91.39 | 93.64 | 67.85 |
| | Fold increase over Taxotere-Chitosan Group | 1 | 2.3 | 2.4 | 2.4 | 1.8 |
| | St. Deviation | 16.33 | 30.78 | 30.58 | 30.94 | 23.44 |
| C(max) | Values | 61 | 144.8 | 123.9 | 139.5 | 110.3 |
| | Fold increase over Taxotere-Chitosan Group | 1 | 2.4 | 2.0 | 2.3 | 1.8 |
| Values for Depth Range: 180-3360 um | | | | | | |
| C(avg) | Values | 22.55 | 52.76 | 51.94 | 55.07 | 40.18 |
| | Fold increase over Taxotere-Chitosan Group | 1 | 2.3 | 2.3 | 2.4 | 1.8 |
| | St. Deviation | 20.79 | 45.28 | 47.95 | 47.53 | 34.49 |
| C(max) | Values | 61 | 144.8 | 123.9 | 139.5 | 110.3 |
| | Fold increase over Taxotere-Chitosan Group | 1 | 2.4 | 2.0 | 2.3 | 1.8 |

Figure 44:
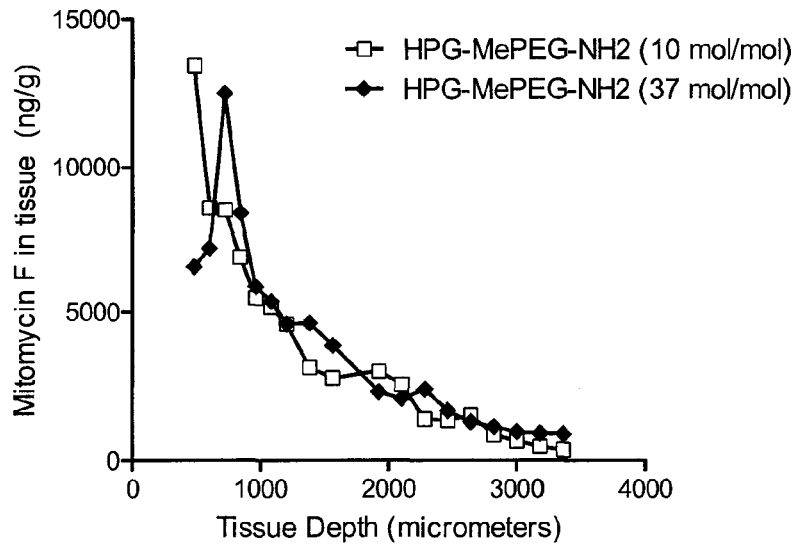
FIG. 44 shows tissue level-depth profiles of mitomycin F in porcine bladder tissue following exposure to mitomycin formulations with pre-treatment for 1 hour. Mitomycin F with HPG-$C_{8/10}$-MePEG-$NH_2$ (10 mol amine/mol HPG) pre-treatment (empty square), and mg/ml mitomycin F with HPG-$C_{8/10}$-MePEG-$NH_2$ (37 mol amine/mol HPG) pre-treatment (filled diamond).

Data for mitomycin F penetration into porcine bladder tissue with HPG-C$_{8/10}$-MePEG-NH$_2$ pretreatment are shown in FIG. 44.

SEM Images of Ex Vivo Penetration Studies of Pig Bladders

The effects of drug penetration observed in Example 28 above were correlated with the appearance of the bladder tissue after exposure to the various treatments. For these experiments, no drug was used and only a single exposure to a single vehicle per bladder was used. After the 2 h exposure time, bladder tissue was harvested, rinsed with buffer and fixed overnight with 4% paraformaldehyde and 2% glutaraldehyde, post-fixed with 1% OsO$_4$, dehydrated in ethanol and critical point dried. Whole bladders were divided in two and sputter coated with gold. The entire surface inspected by SEM (Hitachi 54700, 3-5 kV) and representative images were recorded (minimum 3 fields per sample). Representative images are shown (approximately 130 μm wide×100 μm tall).

Figure 45:
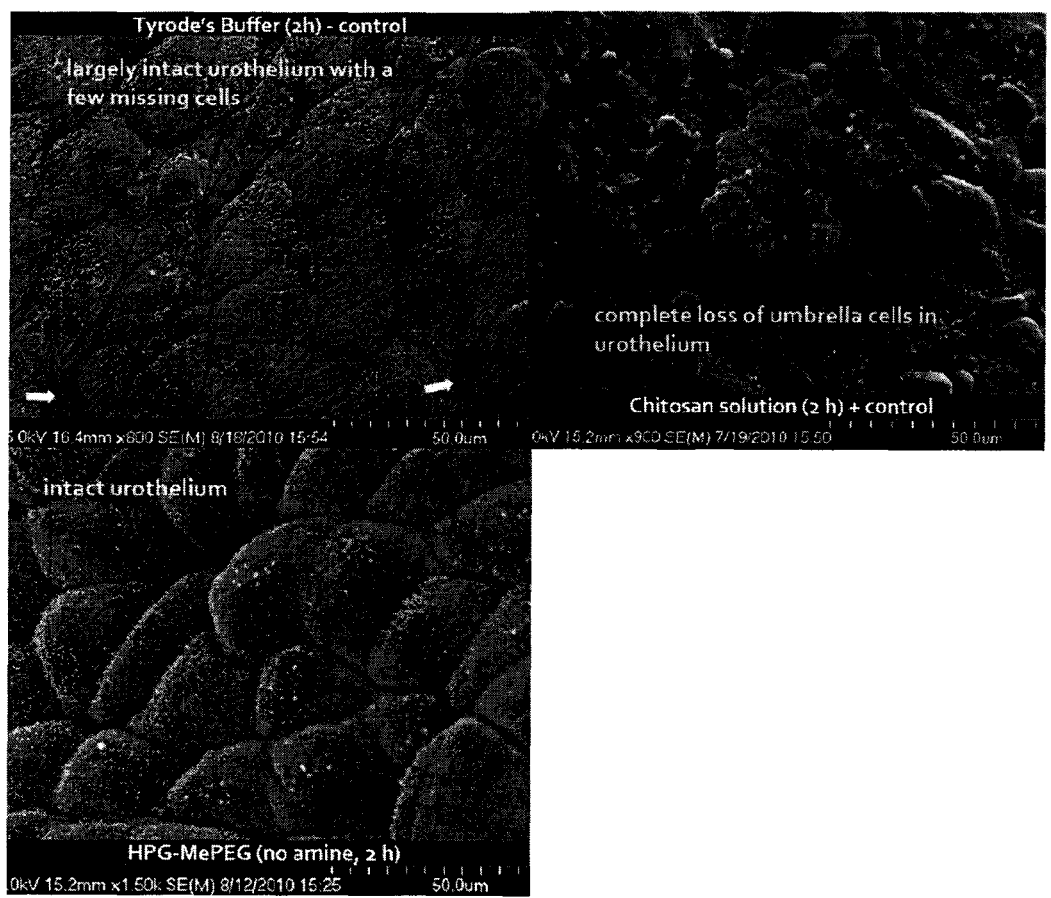
FIG. 45 shows SEM images of pig bladders treated ex vivo with HPG delivery vehicles:controls (Tyrode's buffer, chitosan & HPG-$C_{8/10}$-MePEG with 0 mol amine/mol polymer).
Figure 46:
FIG. 46 shows SEM images of pig bladders treated ex vivo with HPG delivery vehicles: HPG-$C_{8/10}$-MePEG-$NH_2$ 10 & 37 mol amine/mol polymer, 0.1, 1 & 10% w/v solution.

The SEM images reveal that the urothelium of bladders treated with only buffer, and also bladders treated with HPG-C$_{8/10}$-MePEG (no amine) showed intact or largely intact urothelium, eg no loss of umbrella cells. In contrast, after exposure to the chitosan pre-treatment vehicle, the surface of the bladder was quite different in appearance, with the urothelium having lost its top layer of umbrella cells (FIG. 45). After exposure to HPG-C$_{8/10}$-MePEG-NH$_2$ having 10 mol amine/mol HPG at solution concentrations of 1 and 10% w/v, partial loss of umbrella cells from the urothelium was observed (FIG. 46). In contrast, when a HPG-C$_{8/10}$-MePEG-NH$_2$ with higher amine content (37 mol/mol) was used more umbrella cell loss could be seen. The effect was observed to be concentration dependent. A solution concentration of 0.1% w/v resulted in little or no change in appearance of the bladder surface, whereas as partial and complete loss of umbrella cells was observed after treatment with solutions having concentrations of 1 and 10% w/v respectively (FIG. 46). Without being bound by theory, it is believed that the effect of the amine may be to alter the surface of the bladder, effecting a change in its permeability to the drug. The effect was shown to be dependent on amine content and on polymer concentration.

Example 29

In Vivo Penetration Studies of Mouse Bladders

The effect of exposure of different formulations (without drug) on mouse bladders was evaluated. Eight-eleven week old female athymic nude mice (Harlan, Indianapolis, Ind.) were anesthetised to a deep plane using 4% isoflurane and 2 L/min $O_2$. The bladder was fully expressed and formulations were instilled via a surgically implanted catheter. A polypropylene purse-string suture was placed around the urethral meatus before a lubricated 24-gauge Jelco angiocatheter (BDickenson) was passed through the urethra into the bladder. A volume of 50 µL was injected, the animals were slightly inverted (cranially) and the purse-string suture was tied off while the catheter was removed in one quick motion. Mice remained anesthetised (at 1.5-2% isoflurane 2 L/min $O_2$) until the 2 hour installation was completed. The purse-string suture was removed, and the animals were allowed to recover.

Dosing solutions prepared were clear colorless to slightly amber solutions. The polymer solution concentration was either 1 or 10% w/v. HPG-MePEG polymer was used, which had no amine content, and two HPG-MePEG-NH2 polymers were used with 8-10 (low) and 37 mol (high) of amine per mole of HPG (based on a nominal HPG molecular weight of 65 k g/mol). The dosing concentration results are summarized in Table 16.

TABLE 16

Formulation concentration summary

| Dosing Solution | Polymer concentration | Appearance | Amine content |
|---|---|---|---|
| PBS | 0 | Clear, colorless | NT[†] |
| HPG-MePEG | 10 | Clear, colorless | NT (0) |
| HPG-MePEG-NH$_2$ (10) | 10 | | |
| HPG-MePEG-NH$_2$ (37) | 1 | | |
| HPG-MePEG-NH$_2$ (37) | 10 | | |

[†]NT means not tested.

Bladders were excised from each mouse for SEM and histology. All animals were observed post-administration for 2 hours and prior to each tissue collection for mortality and morbidity. No signs of mortality or morbidity were noted, with the exception of some small amount of blood at the installation site.

SEM Analysis

Tissues were washed 3 times with PBS, fixed overnight in 2% paraformaldehyde then transferred in 0.1 M cacodylate buffer. Tissues were postfixed in 1% osmium tetroxide for 1 h at room temperature then dehydrated in ethanol mixed with water, in increasing percentage of ethanol in the mixture, starting at 30 and increasing to 100%. Samples were dried by critical point dehydration and then sputter-coated with gold-palladium twice (once at 90° and second time at 45°). Samples were examined in scanning electron microscopy with Hitachi S4700 at Bioimaging Facility. Each bladder was visualized at low magnification and then the entire surface examined again at high magnification. Multiple (9-10 images) were taken at various magnifications

TABLE 17

Formulation concentration summary

| Formulation | Amine Density (mol/mol HPG) | Polymer Concentration (% w/v) | Hours post-instillation 2 | 6 | 24 |
|---|---|---|---|---|---|
| PBS | N/A[†] | N/A | Intact | NT[††] | NT |
| HPG-MePEG | 0 | 10 | Intact | Intact | Intact |
| HPG-MePEG-NH$_2$ | 10 (low) | 10 | Intact | + | Intact |
| | 37 (high) | 1 | ++ | Intact | + |
| | 37 (high) | 10 | ++ | ++ | Intact |

Figure 47:
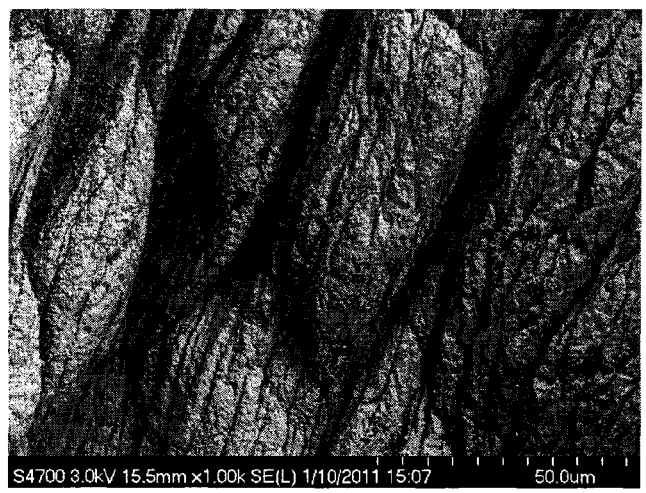
FIG. 47 shows an SEM image of the surface of a mouse bladder treated with a 2 hour installation of PBS. The image was taken of a bladder harvested immediately after the 2 hour installation period.
Figure 48:
FIG. 48 shows SEM images of the surface of a mouse bladder treated with a 2 hour installation of HPG-MePEG 10% solution. The image was taken of a bladder harvested A) immediately after the 2 hour installation period, B) 6 and C) 24 h after the installation.
Figure 49:
FIG. 49 shows SEM images of the surface of a mouse bladder treated with a 2 hour installation of HPG-MePEG-$NH_2$ (10 mol/mol) 10% solution. The image was taken of a bladder harvested A) immediately after the 2 hour installation period, B) 6 and C) 24 h after the installation. Arrow shows loss of a single umbrella cell, exposing lower layers of epithelium.
Figure 50:
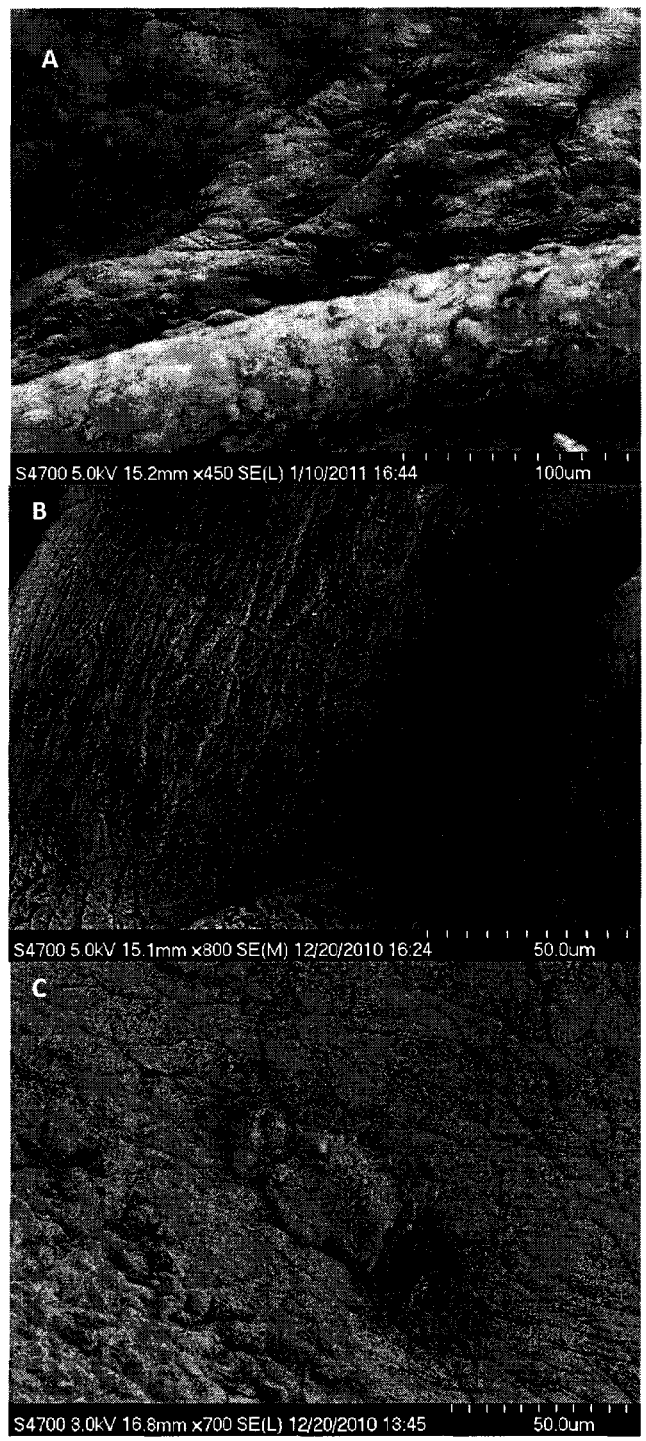
FIG. 50 shows SEM images of the surface of a mouse bladder treated with a 2 hour installation of HPG-MePEG-$NH_2$ (37 mol/mol) 1% solution. The image was taken of a bladder harvested A) immediately after the 2 hour installation period, B) and C) 24 h after the installation.
Figure 51:
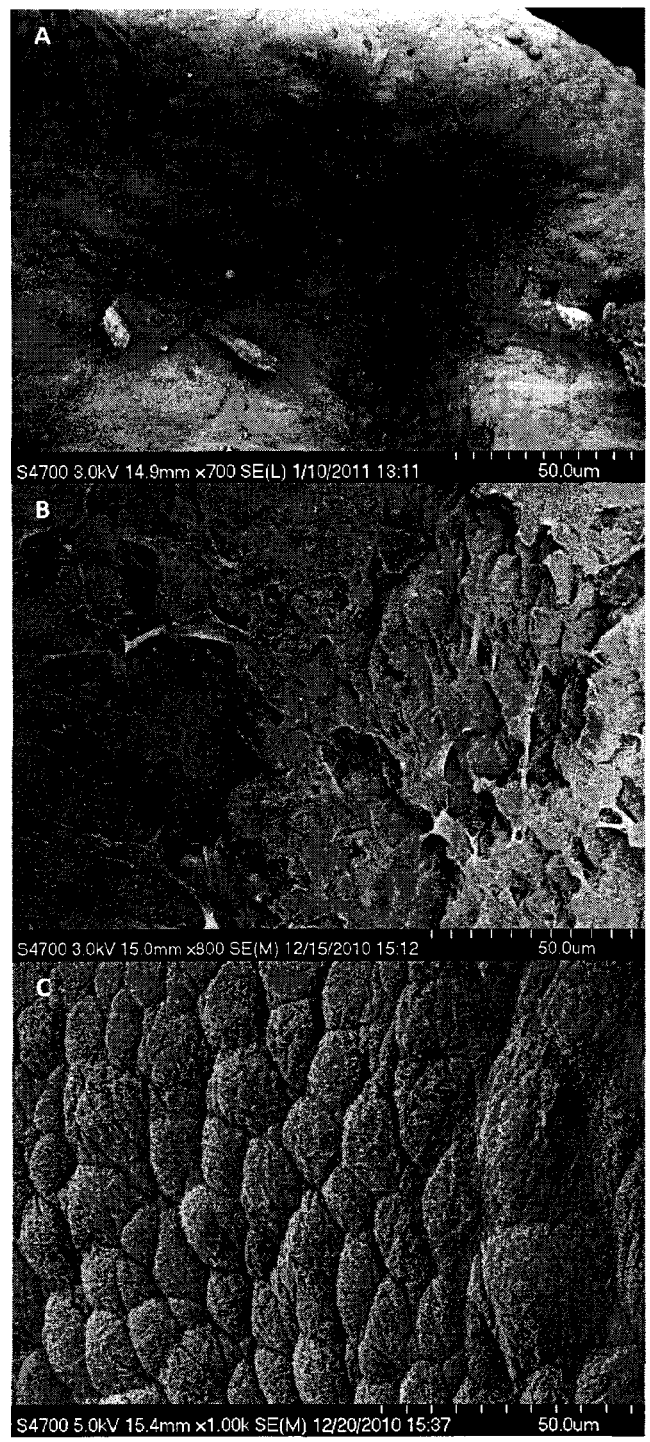
FIG. 51 shows SEM images of the surface of a mouse bladder treated with a 2 hour installation of HPG-MePEG-$NH_2$ (37 mol/mol) 10% solution. The image was taken of a bladder harvested A) immediately after the 2 hour installation period, B) and C) 24 h after the installation.

[†]N/A means not applicable.
[††]NT means not tested.
Intact: no signs of umbrella cell loss
+: very little or partial loss of umbrella cells
++: substantial or complete loss of umbrella cells The mouse bladder surface treated with a 2 hour instillation of PBS had an intact umbrella cell layer and had a folded appearance as seen in the SEM image of the mouse bladder surface in FIG. 47. The mouse bladder surface treated with a 2 hour instillation of HPG-MePEG solution at 10% w/v had an intact umbrella cell layer immediately after the 2 hour instillation period. An intact umbrella cell layer was also observed at 6 hours and 24 hours after the HPG-MePEG solution instillation (FIG. 48). As shown in FIG. 48, the surface cells had a flat appearance. The mouse bladder surface treated with a 2 hour instillation of the HPG-MePEG-NH$_2$ (10 mol/mol) 10% w/v solution had an intact umbrella cell layer immediately after the 2 hour instillation period (FIG. 49). At 6 hours after the HPG-MePEG-NH$_2$ (10 mol/mol) 10% w/v solution instillation, the mouse bladder surface exhibited loss of a single umbrella cell, exposing lower layers of epithelium. At 24 hours after the same instillation, the mouse bladder surface had an intact umbrella surface layer (FIG. 49). The mouse bladder surface treated with a 2 hour instillation of the HPG-MePEG-NH$_2$ (37 mol/mol) 1% w/v solution exhibited complete loss of umbrella cells, exposing lower layers of epithelium immediately after the 2 hour instillation period as shown in FIG. 50. At 6 hours after the HPG-MePEG-NH$_2$ (37 mol/mol) 1% w/v solution instillation, the mouse bladder surface still exhibited substantial loss of umbrella cells. At 24 hours after the HPG-MePEG-NH$_2$ (37 mol/mol) 1% w/v solution instillation, the mouse bladder surface had a partially intact surface (upper section of FIG. 50C) with significant loss of umbrella cells (lower left of FIG. 50C). The mouse bladder surface treated with the 2 hour instillation of HPG-MePEG-NH$_2$ (37 mol/mol) 10% solution exhibited a complete loss of umbrella cells, exposing lower layers of epithelium immediately after the 2 hour instillation period as shown in FIG. 51. At 6 hours after the HPG-MePEG-NH$_2$ (37 mol/mol) 10% solution instillation, the mouse bladder surface also exhibited complete loss of umbrella cells. At 24 hours after the instillation. The mouse bladder surface had an intact umbrella cell layer; however, the surface cells appeared smaller and less flat in appearance than other observed intact layers (FIG. 51). The effect of the formulations on umbrella cell loss was observed to be dependent on amine content of the dHPG and on dHPG concentration.

Histology

Tissues were evaluated for changes in tight junctions, exfoliation of cells, and infiltration of inflammatory cells. Histological analysis results are summarized in Table 18. As can be seen from the histology results, signs of inflammation and necrosis were not observed in the mouse bladder surface after exposure to the dHPG formulations.

TABLE 18

Histology of Mice Bladder Surface

| Formulation | Amine content (mol/mol) | Solution Concentration (% w/v) | Sample time (h) | Neutrophil infiltration | Signs of inflammation | Signs of necrosis |
|---|---|---|---|---|---|---|
| Untreated | N/A | N/A | 2 | No | No | No |
| PBS | N/A | N/A | 2 | No | No | No |
| HPG-MePEG | 0 | 10 | 2 | No | No | No |
|  |  |  | 6 | No | No | No |
|  |  |  | 24 | No | No | No |
| HPG-MePEG-NH$_2$ | 10 (Low) | 10 | 2 | No | No | No |
|  |  |  | 6 | No | No | No |
|  |  |  | 24 | No | No | No |
|  |  |  | 24 | No | No | No |
|  | 37 (High) | 1 | 2 | No | No | No |
|  |  |  | 6 | No | No | No |
|  |  |  | 24 | No | No | No |
|  |  |  | 24 | No | No | No |
|  |  | 10 | 6 | No | No | No |
|  |  |  | 6 | No | No | No |
|  |  |  | 24 | No | No | No |

Urine Analysis

Figure 52:
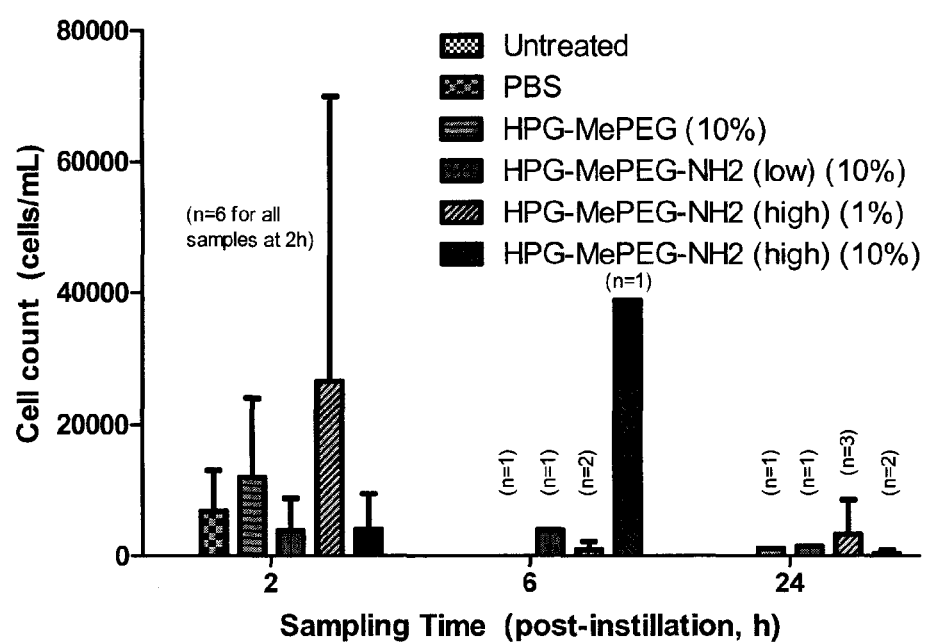
FIG. 52 shows cell counts in urine harvested from mice at the point of removing the installation catheter (2 h, N=6 for all groups) and at the time of bladder harvest (2, 6, 24 h, n=1-3 for 6 and 24 h sampling times).

Urine was collected at the time of sacrifice. After euthanizing the animal, the bladder was exposed and its contents removed by bladder puncture and withdrawal through a 25 G needle. The urine was stored on ice (but not frozen) and transported for evaluation. Urine was analyzed for the presence of cells. A few drops of urine was placed onto a microscope slide and observed by microscope for the presence of cells. Any cells present were counted with a hemocytometer slide. Cells counts in urine harvested from mice immediately after the 2 hour instillation, and at the time of bladder harvest (2, 6, 24 hours), are shown in FIG. 52.

Blood Analysis

Figure 53:
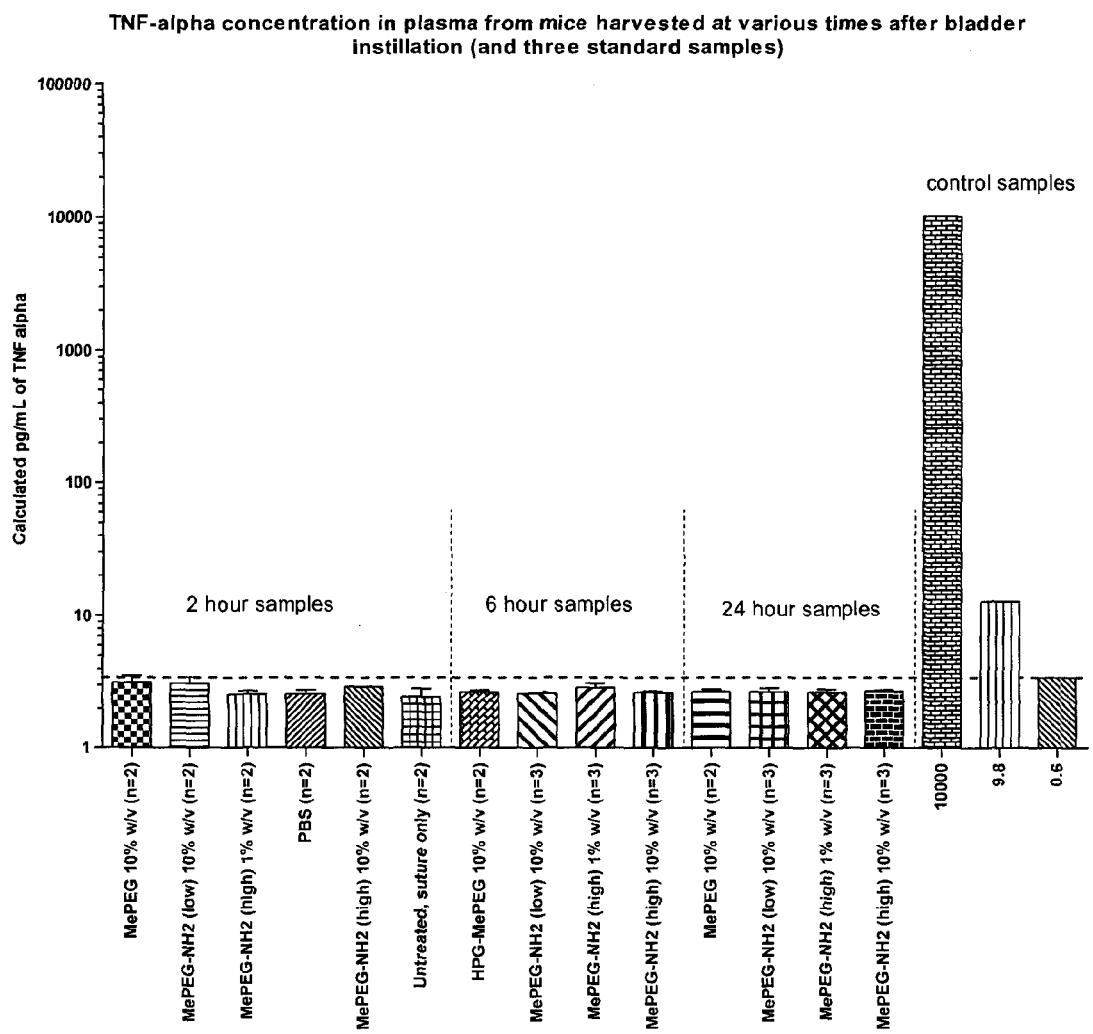
FIG. 53 shows circulating TNFα levels in mouse blood at 2, 6 and 24 h after installation of A) HPG-MePEG 10% solution, B) HPG-MePEG-$NH_2$ (low) 10% solution, C) HPG-MePEG-$NH_2$ (high) 1% solution, D) HPG-MePEG- NH$_2$ (high) 10% solution, CN) PBS buffer (control), and in U) untreated animals. Results are shown with standards used to construct the standard curve. The dashed line represents the signal of the lowest standard (0.6 pg/mL standard concentration).

Blood was collected upon termination by CO$_2$ inhalation by cardiac puncture upon last breath, approximately 500-700 μL was placed into EDTA microtainer tubes. Each tube was inverted several times to ensure even mixing of blood and EDTA to prevent coagulation. Blood samples were stored on ice until all samples were collected for a particular time point and then processed to generate plasma. Plasma was generated by centrifuging samples at 2500 rpm for 15 minutes at 4° C. (rpm based on Beckman GH 3.8A rotor, RCF$_{avg}$ 200×g). The plasma supernatant was pipetted off and placed into labelled vials and stored at −80° C. Blood was analyzed for TNFα levels using the MesoScale platform and standard assay kits. Circulating TNFα levels in the mouse blood at 2, 6 and 24 h after instillation with the various formulations are shown in FIG. 53. No TNFα was detected in any of the samples.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as any open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing.

Citation of references herein is not an admission that such references are prior art to the present invention nor does it constitute any admission as to the contents or date of these documents. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A hyperbranched polyglycerol comprising:
   a core comprising hyperbranched polyglycerol derivatized with C$_8$ alkyl chains, C$_{10}$ alkyl chains, or a combination thereof; and
   a shell comprising at least one hydrophilic substituent and at least one functional group, wherein the at least one hydrophilic substituent comprises methoxypolyethylene glycol (MePEG) and the at least one functional group comprises —NH$_2$.

2. The hyperbranched polyglycerol according to claim 1, wherein the hyperbranched polyglycerol comprises from about 1 to about 200 moles of the at least one functional group per mole of the hyperbranched polyglycerol.

3. The hyperbranched polyglycerol according to claim 2, wherein the hyperbranched polyglycerol comprises from about 30 to about 100 moles of the at least one functional group per mole of the hyperbranched polyglycerol.

4. The hyperbranched polyglycerol according to claim 2, wherein the hyperbranched polyglycerol comprises about 37 moles of the at least one functional group per mole of the hyperbranched polyglycerol.

5. The hyperbranched polyglycerol according to claim 1, wherein the core comprises hyperbranched polyglycerol derivatized with a combination of C$_8$ alkyl chains and C$_{10}$ alkyl chains.

6. The hyperbranched polyglycerol according to claim 1, wherein the ratio of alkyl chains to glycerol units is greater at a centre of the core compared to a periphery of the core.

7. The hyperbranched polyglycerol according to claim 1, further comprising a biologically active moiety.

8. The hyperbranched polyglycerol according to claim 7, wherein the biologically active moiety is a hydrophobic drug.

9. The hyperbranched polyglycerol according to claim 7, wherein the biologically active moiety is a taxane or derivative thereof.

10. The hyperbranched polyglycerol according to claim 9, wherein the taxane or derivative thereof is docetaxel or a derivative thereof.

11. The hyperbranched polyglycerol according to claim 9, wherein the taxane or derivative thereof is paclitaxel or a derivative thereof.

12. The hyperbranched polyglycerol according to claim 7, wherein the biologically active molecule is selected from the group consisting of valrubicin, vinblastine, mitomycin, cisplatin, methotrexate, doxorubicin, epirubicin, gemcitabine, everolimus, suramin, and analogs thereof.

13. The hyperbranched polyglycerol according to claim 7, wherein the biologically active moiety is a combination of moieties.

14. The hyperbranched polyglycerol according to claim 13, wherein the combination of moieties is methotrexate, vinblastine and doxorubicin (M-VAC), or M-VAC and cisplatin.

15. A pharmaceutical composition comprising the hyperbranched polyglycerol according to claim 7 and a pharmaceutically acceptable carrier.

16. A method of treating a cancer in a subject in need thereof, the method comprising administering a pharmaceutical composition according to claim 15 to the subject, wherein the administering is effective to treat a cancer in the subject, wherein the cancer is a bladder cancer.

17. The method according to claim 16, wherein the cancer is non-muscle invasive bladder cancer.

18. The method according to claim 16, wherein the administering comprises intravesical administration of the pharmaceutical composition.

19. The method according to claim 16, wherein the subject is a human.

20. A method of delivering a biologically active moiety to a biological tissue of a patient, the method comprising administering a hyperbranched polyglycerol according to claim 7 to the patient, wherein the administering is effective to increase uptake of the biologically active moiety by the biological tissue of the patient.

21. A method of increasing permeability of a biological tissue of a patient to a biologically active moiety, the method comprising administering a hyperbranched polyglycerol according to claim 1 to the patient, wherein the administering is effective to increase permeability of the biological tissue of the patient to the biologically active moiety.

22. A pharmaceutical composition comprising the hyperbranched polyglycerol according to claim 1 and a pharmaceutically acceptable carrier.

23. The pharmaceutical composition according to claim 22, further comprising a biologically active moiety.

24. The pharmaceutical composition according to claim 23, wherein the biologically active moiety is a hydrophobic drug.

25. The pharmaceutical composition according to claim 23, wherein the biologically active moiety is a taxane or derivative thereof.

26. The pharmaceutical composition according to claim 25, wherein the taxane or derivative thereof is docetaxel or a derivative thereof.

27. The pharmaceutical composition according to claim 25, wherein the taxane or derivative thereof is paclitaxel or a derivative thereof.

28. The pharmaceutical composition according to claim 23, wherein the biologically active molecule is selected from the group consisting of valrubicin, vinblastine, mitomycin, cisplatin, methotrexate, doxorubicin, epirubicin, gemcitabine, everolimus, suramin, and analogs thereof.

29. The pharmaceutical composition according to claim 23, wherein the biologically active moiety is a combination of moieties.

30. The pharmaceutical composition according to claim 29, wherein the combination of moieties is methotrexate, vinblastine and doxorubicin (M-VAC), or M-VAC and cisplatin.

31. A method of treating a cancer in a subject in need thereof, the method comprising administering a pharmaceutical composition according to claim 23 to the subject, wherein the administering is effective to treat a cancer in the subject, wherein the cancer is a bladder cancer.

32. The method according to claim 31, wherein the cancer is non-muscle invasive bladder cancer.

33. The method according to claim 31, wherein the administering comprises intravesical administration of the pharmaceutical composition.

34. The method according to claim 31, wherein the subject is a human.

35. A method of pre-treating or co-treating a biological tissue to increase uptake of a drug by the biological tissue of a patient, the method comprising administering a pharmaceutical composition according to claim 22 to the patient before or during administration of the drug to the patient.

36. A method of delivering a biologically active moiety to a biological tissue of a patient, the method comprising administering a hyperbranched polyglycerol according to claim 1 and a biologically active moiety to the patient, wherein the administering is effective to increase uptake of the biologically active moiety by the biological tissue of the patient.

37. The method according to claim 36, wherein the administering comprises pre-treating the biological tissue by administering the hyperbranched polyglycerol to the patient before administering the biologically active moiety to the patient.

38. The method according to claim 36, wherein the administering comprises co-treating the biological tissue by administering the hyperbranched polyglycerol to the patient during administration of the biologically active moiety to the patient.

* * * * *